(12) United States Patent
Merla et al.

(10) Patent No.: US 8,178,535 B2
(45) Date of Patent: May 15, 2012

(54) SUBSTITUTED SULFONAMIDE COMPOUNDS HAVING BRADYKININ 1 RECEPTOR ACTIVITY AND USE THEREOF AS MEDICAMENTS

(75) Inventors: Beatrix Merla, Aachen (DE); Stefan Oberboersch, Aachen (DE); Ruth Jostock, Solberg (DE); Michael Engels, Turnhout (BE); Stefan Schunk, Aachen (DE); Melanie Reich, Aachen (DE); Sabine Hees, Aachen (DE)

(73) Assignee: Gruenenthal GmbH, Aachen (DE)

( * ) Notice: Subject to any disclaimer, the term of this patent is extended or adjusted under 35 U.S.C. 154(b) by 57 days.

(21) Appl. No.: 12/354,818

(22) Filed: Jan. 16, 2009

(65) Prior Publication Data

US 2009/0203672 A1 Aug. 13, 2009

Related U.S. Application Data

(60) Provisional application No. 61/021,802, filed on Jan. 17, 2008.

(30) Foreign Application Priority Data

Jan. 17, 2008 (EP) ..................... 08000839

(51) Int. Cl.
*A61K 31/495* (2006.01)
*A61K 31/40* (2006.01)

(52) U.S. Cl. ........ 514/249; 514/413; 540/567; 544/111; 544/350; 544/359; 546/152; 546/208; 546/268.1; 548/518; 549/59

(58) Field of Classification Search .................. 514/249, 514/413; 540/567; 544/111, 350, 359; 546/152, 546/208, 268.1; 548/518; 549/59
See application file for complete search history.

(56) References Cited

FOREIGN PATENT DOCUMENTS

| WO | WO 2004/092164 A1 | 10/2004 |
|---|---|---|
| WO | WO 2007/101007 A2 | 9/2007 |
| WO | WO 2008/040492 A1 | 4/2008 |
| WO | WO 2009/090055 | * 7/2009 |

OTHER PUBLICATIONS

Jordan, V. C. Nature Reviews: Drug Discovery, 2, 2003, 205.*
Hackam, et al. JAMA, 296(14), 2006, 1731-1732.*
Robert W. Colman, "Regulation of angiogenesis by the kallikrein-kinin system", Current Pharmaceutical Design, vol. 12, No. 21, pp. 2599-2607, 2006 ("Colman").
Parenti et al., "The bradykinin/B1 receptor promotes angiogenesis by up-regulation of endogenous FGF-2 in endothelium via the nitric oxide synthase pathway", FASEB J 2001; 15: 1497-1489 ("Parenti et al.").
Göbel et al., Blockade of the kinin receptor B1 protects from autoimmune CNS disease by reducing leukocyte trafficking, Journal of Autoimmunity, 2010, 1-9 ("Göbel et al.").

Rodi et al, "Targeting kinin receptors for the treatment of neurological diseases," Current Pharmacuetical Design, 2005, 11, 1313-1326 ("Rodi et al.").
Austinat et al., "Blockade of bradykinin receptor B1 but not bradykinin receptor B2 provides protection from cerebral infarction and brain edema", Stroke, 2009, 40(1), 285-293 ("Austinat et al.").
Sara H. Bengtson, et al, "Kinin Receptor Expression during *Staphylococcus aureus* Infection", Blood, Sep. 15, 2006, pp. 2055-2063, vol. 108, No. 6, The American Society of Hematology, Washington, DC, USA.
Gabra et al., The kinin system mediates hyperalgesia through the inducible bradykinin B1 receptor subtype: evidence in various experimental animal models of type 1 and type 2 diabetic neuropathy, *Biol. Chem.* vol. 387, pp. 127-143, Feb. 2006.
Joao B. Calixto, et al., "Kinin $B_1$ Receptors: Key G-Protein-Coupled Receptors and their Role in Inflammatory and Painful Processes", British Journal of Pharmacology, 2004, pp. 803-818, vol. 143, Nature Publishing Group.
R. Hayashi et al., "Bradykinin Stimulates IL-6 and IL-8 Production by Human Lung Fibroblasts through ERK- and p38 MAPK-dependent Mechanisms", European Respiratory Journal, 2000, pp. 452-458, vol. 16, ERS Journals Ltd.
L.M. Fredrik Leeb-Lundberg et al., "International Union of Pharmacology. XLV. Classification of the Kinin Receptor Family: from Molecular Mechanisms to Pathophysiological Consequences", Pharmacological Reviews, 2005, pp. 27-77, vol. 57, No. 1, The American Society for Pharmacology and Experimental Therapeutics, USA.
Hess et al., Generation and characterization of a humanized bradykinin B1 receptor mouse, *Biol. Chem.*, vol. 387, pp. 195-201, Feb. 2006.
Joao B. Pesquero et al., "Genetically Altered Animal Models in the Kallikrein-Kinin System", Biol. Chem., Feb. 2006, pp. 119-126, vol. 387.
Joao B. Pesquero et al., "Hypoalgesia and Altered Inflammatory Responses in Mice Lacking Kinin B1 Receptors", PNAS, Jul. 5, 2000, pp. 8140-8145, vol. 97, No. 14.

(Continued)

*Primary Examiner* — James O Wilson
*Assistant Examiner* — Douglas M Willis
(74) *Attorney, Agent, or Firm* — Crowell & Moring LLP

(57) ABSTRACT

Substituted sulfonamide compounds corresponding to the formula I'

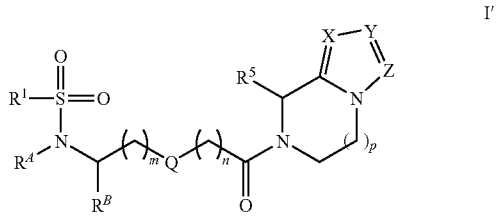

wherein m, n, p, X, Y, Z, R1, RA and RB have specified meanings, processes for their preparation, pharmaceutical compositions containing these compounds, and the use of these substituted sulfonamide compounds for the treatment and/or inhibition of pain or other conditions.

27 Claims, No Drawings

OTHER PUBLICATIONS

A. Prat et al, "Bradykinin $B_1$ Receptor Expression and Function on T Lymphocytes in Active Multiple Sclerosis", Neurology, Dec. 10, 1999, pp. 2087-2092, vol. 53, No. 9, 1999 American Academy of Neurology.

Antoni Stadnicki et al., "Immunolocalization and Expression of Kinin $B_1R$ and $B_2R$ Receptors in Human inflammatory Bowel Disease", Am. J. Physiol. Gastrointest. Liver Physiol., Mar. 31, 2005, pp. G361-G366, vol. 289, American Physiological Society.

Giselle F. Passos et al., "Kinin $B_1$ Receptor Up-Regulation after Lipopolysaccharide Administration: Role of Proinflammatory Cytokines and Neutrophil Influx[1]", The Journal of Immunology, 2004, pp. 1839-1847, vol. 172, The American Association of Immunologists, Inc.

Cuadro A.M. et al, "Synthesis of N-(Aminoethyl) Azoles Under Phase Transfer Catalysis," *Synthetic Communications*, 1991, 21(4), 535-544.

G. Kienast et al., "Eine neue Variante der Mannich-Reaktion", *Chemie* 1976, 88, 8, 261-262.

I. Jirkovski, et al., "A Facile, Large-Scale Preparation of 1H-Pyrrole-1-ethanamine and Syntheses of Substituted Pyrrolo[1,2-a]pyrazines and Hydro Derivatives thereof," *Synthesis* 1981, 481-483.

International Search Report and Written Opinion, mailed May 6, 2009.

European Search Report mailed Aug. 6, 2008.

* cited by examiner

SUBSTITUTED SULFONAMIDE COMPOUNDS HAVING BRADYKININ 1 RECEPTOR ACTIVITY AND USE THEREOF AS MEDICAMENTS

CROSS REFERENCE TO RELATED APPLICATIONS

This application claims priority from U.S. provisional patent application No. 61/021,802, filed Jan. 17, 2008 and European patent application no. EP 08000839, also filed Jan. 17, 2008, the entire disclosures of which are incorporated herein by reference.

BACKGROUND OF THE INVENTION

The present invention relates to substituted sulfonamide compounds, processes for their preparation, medicaments containing these compounds, and the use of substituted sulfonamide compounds for the preparation of medicaments.

In contrast to the constitutive expression of the bradykinin 2 receptor (B2R), the bradykinin 1 receptor (B1R) is not expressed or is only weakly expressed in most tissues. However, the expression of B1R[2] can be induced in various cells. For example, in the course of inflammatory reactions there is a rapid and pronounced induction of B1R on neuronal cells but also on various peripheral cells such as fibroblasts, endothelial cells, granulocytes, macrophages and lymphocytes. In the course of inflammatory reactions there is thus a switch from a B2R to a B1R dominance on the involved cells. The cytokines interleukin-1 (IL-1) and tumour necrosis factor alpha (TNFα) (Passos et al. J. Immunol. 2004, 172, 1839-1847) are significantly involved in this B1R up-regulation. After activation with specific ligands, B1R-expressing cells can then themselves secrete inflammation-promoting cytokines such as IL-6 and IL-8 (Hayashi et al. Eur. Respir. J. 2000, 16, 452-458). This leads to the inflow of further inflammatory cells, e.g. neutrophilic granulocytes (Pesquero et al. PNAS 2000, 97, 8140-8145). Via these mechanisms the bradykinin B1R system can contribute to the chronic state of diseases. This is confirmed by a number of animal experiment investigations (reviews in Leeb-Lundberg et al., Pharmacol Rev. 2005, 57, 27-77 and Pesquero et al., Biol. Chem., 2006, 387, 119-126). An enhanced expression of B1R is also found in humans, for example on enterocytes and macrophages in the affected tissue of patients suffering from inflammatory intestinal diseases (Stadnicki et al. Am. J. Physio. Gastrointest. Liver Physiol. 2005, 289, G361-366) and on T lymphocytes of patients suffering from multiple sclerosis (Pratet et al., Neurology, 1999, 53, 2087-2092) or an activation of the bradykinin B2R-B1R system during infections with *Staphyloccocus aureus* (Bengtson et al., Blood 2006, 108, 2055-2063). Infections with *Staphyloccocus aureus* are responsible for clinical conditions ranging from surface infections of the skin up to septic shock.

Due to the pathophysiological relationships outlined above there is therefore a great therapeutic potential for the use of B1R antagonists in acute and in particular chronic-inflammatory diseases. These include diseases of the respiratory tract (bronchial asthma, allergies, COPD (chronic obstructive pulmonary disease), cystic fibrosis, etc.), inflammatory intestinal diseases (ulcerative colitis, CD (Crohn's disease), etc.), neurological diseases (multiple sclerosis, neurodegeneration, etc.), inflammations of the skin (atopic dermatitis, psoriasis, bacterial infections, etc.) and mucous membranes (M. Behcet, pelvitis, prostatitis), rheumatic diseases (rheumatoid arthritis, osteoarthritis, etc.), septic shock, and reperfusion syndrome (after heart attacks and strokes).

In addition the bradykinin (receptor) system is also involved in the regulation of angiogenesis (potential as an angiogenesis inhibitor in cancer and also macular degeneration of the eye) and B1R knockout mice are protected against the danger of becoming overweight due to a particularly fat-rich diet (Pesquero et al., Biol. Chem. 2006, 387, 119-126). B1R antagonists are therefore also suitable for treating obesity.

B1R antagonists are particularly suitable for treating pain, in particular inflammatory pain and neuropathic pain (Calixto et al. Br. J. Pharmacol 2004, 1-16), in this connection in particular diabetic neuropathy (Gabra et al., Biol. Chem. 2006, 387, 127-143). Furthermore they are suitable for the treatment of migraine.

In the development of B1R modulators there is the problem however that the human and rat B1R receptors differ so greatly that many compounds that are good B1R modulators on the human receptor have only a poor affinity or no affinity at all for the rat receptor. This significantly complicates animal pharmacological investigations since many investigations are normally carried out on rats. If however a compound has no effect on the rat receptor, then neither the action nor side effects on rats can be investigated. This has already led to the creation of transgenic animals with human B1 receptors for animal pharmacological investigations (Hess et al., Biol. Chem. 2006; 387(2): 195-201). Working with transgenic animals is however more costly than working with unaltered animals. Since long-term toxicity investigations on rats are in particular part of the routine investigations in drug research and development however, these are not practicable if the compound is ineffective on the receptor, and an important established tool for checking safety is therefore lacking in the development of such compounds. There is therefore a need for new B1R modulators, in which connection B1R modulators that bind to the rat receptor as well as to the human receptor offer particular advantages.

SUMMARY OF THE INVENTION

An object of the present invention was accordingly to provide new compounds that are suitable in particular as pharmacological active constituents in medicaments.

A particular object of the invention was to provide new pharmaceutically active compounds useful for treating disorders or diseases that are at least partially mediated by B1R receptors.

These and other objects have been achieved by providing the substituted sulfonamide compounds according to the invention.

The present invention thus relates to substituted sulfonamide compounds corresponding to formula I':

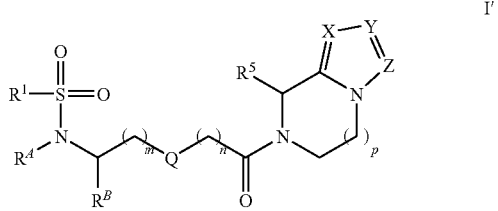

wherein
m and n each independently denote 0, 1 or 2;
p denotes 1 or 2;
Q denotes —O— or —CH$_2$—;

X denotes N or CR$^6$;

Y denotes N or CR$^7$;

Z denotes N or CR$^8$;

R$^A$ and R$^B$ together with their linking group —N—CH— form a 4-, 5-, 6- or 7-membered heterocycle, wherein said heterocycle:

may be substituted on one or more of its carbon ring members with one or more substituents independently selected from the group consisting of halogen, O—CF$_3$, methyl, ethyl, n-propyl, iso-propyl, and cyclopropyl, wherein methyl, ethyl, n-propyl, iso-propyl, and cyclopropyl may be unsubstituted or substituted with one or more halogens which may be identical or different;

optionally may be annelated with at least one ring;

wherein said ring is 4-, 5-, 6- or 7-membered and saturated, unsaturated or aromatic and unsubstituted or monosubstituted or polysubstituted with identical or different groups independently selected from the group consisting of C$_{1-6}$-alkyl, —O—C$_{1-16}$-alkyl, CF$_3$, OCF$_3$ and halogen, may be saturated or at least mono-unsaturated, but not aromatic, and may comprise one or more heteroatoms or heteroatom groups independently selected from the group consisting of N, NR$^{50}$, O, S, S=O and S(=O)$_2$ in addition to the nitrogen atom to which R$^A$ is attached, and wherein R$^{50}$ represents H, C$_{1-6}$-alkyl, —C(=O)—R$^{51}$, C$_{3-8}$-cycloalkyl, aryl, heteroaryl or C$_{3-8}$-cycloalkyl, aryl or heteroaryl bonded via a C$_{1-6}$-alkylene group, wherein R$^{51}$ represents C$_{1-6}$-alkyl, C$_{3-8}$-cycloalkyl, aryl, heteroaryl or C$_{3-8}$-cycloalkyl, aryl or heteroaryl bonded via a C$_{1-6}$-alkylene group;

R$^1$ denotes aryl or heteroaryl; or denotes an aryl or heteroaryl bonded via a C$_{1-6}$-alkylene group;

R$^5$ denotes H, halogen, CN, NO$_2$, C$_{1-6}$-alkyl, C$_{2-6}$-alkenyl, aryl or heteroaryl; or denotes an aryl or heteroaryl bonded via a C$_{1-6}$-alkylene group, C$_{2-6}$-alkenylene group or C$_{2-6}$-alkynylene group;

R$^6$, R$^7$ and R$^8$ each independently denote H, halogen, CN, C$_{1-6}$-alkyl, —NH(C$_{1-6}$-alkyl), —N(C$_{1-6}$-alkyl)$_2$, —C$_{1-6}$-alkylene-NH(C$_{1-6}$-alkyl), —C$_{1-6}$-alkylene-N(C$_{1-6}$-alkyl)$_2$, C$_{3-8}$-cycloalkyl, heterocyclyl, aryl or heteroaryl; or denote a C$_{3-8}$-cycloalkyl, heterocyclyl, aryl or heteroaryl bonded via a C$_{1-6}$-alkylene group, C$_{2-6}$-alkenylene group or C$_{2-6}$-alkynylene group;

wherein the aforementioned C$_{1-6}$-alkyl, C$_{1-6}$-alkylene, C$_{2-6}$-alkenyl, C$_{2-6}$-alkenylene, C$_{2-6}$-alkynylene, C$_{3-8}$-cycloalkyl, heterocyclyl, aryl and heteroaryl groups may in each case be unsubstituted or monosubstituted or polysubstituted with identical or different groups, and the abovementioned C$_{1-16}$-alkyl, C$_{1-16}$-alkylene, C$_{2-6}$-alkenyl, C$_{2-6}$-alkenylene, and C$_{2-6}$-alkynylene groups can in each case be branched or unbranched;

in the form of an individual enantiomer or an individual diastereomer, in the form of the racemate, enantiomers, diastereomers, mixtures of the enantiomers and/or diastereomers, as well as in each case in the form of their bases and/or physiologically compatible salts.

In one specific embodiment the present invention provides substituted sulfonamide compounds corresponding to formula I

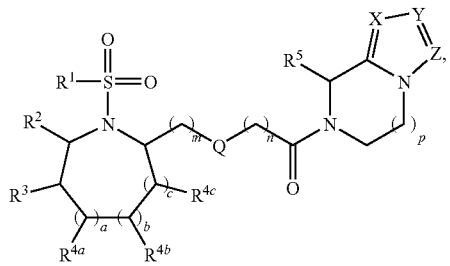

wherein a, b and c each independently denote 0 or 1;

m and n each independently denote 0, 1 or 2;

p denotes 1 or 2;

Q denotes —O— or —CH$_2$—;

X denotes N or CR$^6$;

Y denotes N or CR$^7$;

Z denotes N or CR$^8$;

R$^1$ denotes aryl or heteroaryl; or denotes an aryl or heteroaryl bonded via a C$_{1-6}$-alkylene group;

R$^2$, R$^3$, R$^{4a}$, R$^{4b}$ and R$^{4c}$ each independently denote H, or two adjacent groups selected from the group consisting of R$^2$, R$^3$, R$^{4a}$, R$^{4b}$ and R$^{4c}$ form a 5- or 6-membered ring, which may be saturated, unsaturated or aromatic and unsubstituted or monosubstituted or polysubstituted with identical or different groups;

R$^5$ denotes H, halogen, CN, NO$_2$, C$_{1-6}$-alkyl, C$_{2-6}$-alkenyl, aryl or heteroaryl; or denotes an aryl or heteroaryl group bonded via a C$_{1-6}$-alkylene group, C$_{2-6}$-alkenylene group or C$_{2-6}$-alkynylene group;

R$^6$, R$^7$ and R$^8$ each independently denote H, halogen, CN, C$_{1-6}$-alkyl, —NH(C$_{1-6}$-alkyl), —N(C$_{1-6}$-alkyl)$_2$, —C$_{1-6}$-alkylene-NH(C$_{1-6}$-alkyl), —C$_{1-6}$-alkylene-N(C$_{1-6}$-alkyl)$_2$, C$_{3-8}$-cycloalkyl, heterocyclyl, aryl or heteroaryl; or denote a C$_{3-8}$-cycloalkyl, heterocyclyl, aryl or heteroaryl bonded via a C$_{1-6}$-alkylene group, C$_{2-6}$-alkenylene group or C$_{2-6}$-alkynylene group;

wherein the aforementioned C$_{1-6}$-alkyl, C$_{1-6}$-alkylene, C$_{2-6}$-alkenyl, C$_{2-6}$-alkenylene, C$_{2-6}$-alkynylene, C$_{3-8}$-cycloalkyl, heterocyclyl, aryl and heteroaryl groups may in each case be unsubstituted or monosubstituted or polysubstituted with identical or different groups, and the abovementioned C$_{1-6}$-alkyl, C$_{1-6}$-alkylene, C$_{2-6}$-alkenyl, C$_{2-6}$-alkenylene, and C$_{2-6}$-alkynylene groups may in each case be branched or unbranched;

in the form of an individual enantiomer or an individual diastereomer, in the form of the racemate, enantiomers, diastereomers, mixtures of the enantiomers and/or diastereomers, as well as in each case in the form of their bases and/or physiologically compatible salts.

In the context of the present invention the term "halogen" preferably denotes the groups F, Cl, Br and I, and particularly preferably the denotes groups F, Cl and Br.

In the context of the present invention the expression "C$_{1-6}$-alkyl" includes acyclic saturated hydrocarbon groups with 1, 2, 3, 4, 5 or 6 carbon atoms, which may be branched or straight-chain (unbranched) as well as unsubstituted or monosubstituted or polysubstituted, for example 2, 3, 4 or 5 times, with identical or different groups. Preferably the alkyl groups can be selected from the group consisting of methyl, ethyl, n-propyl, iso-propyl, n-butyl, iso-butyl, sec-butyl, tert-butyl, n-pentyl, iso-pentyl, neo-pentyl and hexyl. Particularly preferred alkyl groups can be selected from the group consisting of methyl, ethyl, n-propyl, iso-propyl, n-butyl, sec-butyl, iso-butyl and tert-butyl.

In the context of the present invention, the expression "$C_{2-6}$-alkenyl" includes acyclic unsaturated hydrocarbon groups with 2, 3, 4, 5 or 6 carbon atoms, which may be branched or straight-chain (unbranched) as well as unsubstituted or monosubstituted or polysubstituted, for example 2, 3, 4 or 5 times, with identical or different substituents. In this connection the alkenyl groups contain at least one C═C double bond. Preferably alkenyl groups can be selected from the group consisting of vinyl, prop-1-enyl, allyl, 2-methyl-prop-1-enyl, but-1-enyl, but-2-enyl, but-3-enyl, but-1,3-dienyl, 2-methylprop-1-enyl, but-2-en-2-yl, but-1-en-2-yl, pentenyl and hexenyl. Particularly preferred alkenyl groups can be selected from the group consisting of vinyl, prop-1-enyl, allyl, 2-methylprop-1-enyl, but-1-enyl, but-2-enyl, but-1,3-dienyl, 2-methylprop-1-enyl, but-2-en-2-yl and but-1-en-2-yl.

In the context of the present invention the expression "$C_{3-8}$-cycloalkyl" denotes cyclic saturated hydrocarbons with 3, 4, 5, 6, 7 or 8 carbon atoms, which may be unsubstituted or monosubstituted or polysubstituted on one or more ring members, for example with 2, 3, 4 or 5 identical or different substituents. Preferably $C_{3-8}$-cycloalkyl can be selected from the group consisting of cyclopropyl, cyclobutyl, cyclopentyl, cyclohexyl, cycloheptyl and cyclooctyl.

In the context of the present invention the expression "heterocyclyl" denotes monocyclic or polycyclic, in particular mono-, bi- or tricyclic organic groups, in which at least one cycle contains 1 heteroatom or 2, 3, 4 or 5 identical or different heteroatoms, which is/are preferably selected from the group consisting of N, O and S. Each heterocyclyl group can be unsubstituted or monosubstituted or polysubstituted on one or more ring members, for example with 2, 3, 4 or 5 identical or different substituents. Saturated or unsaturated heterocyclyl are understood in particular to denote monocyclic 5-membered or 6-membered groups with at least one heteroatom selected from the group consisting of N, O and S, wherein a further 5-membered or 6-membered, saturated, unsaturated or aromatic cycle, which likewise can contain at least one heteroatom selected from the group consisting of N, O and S, may be condensed onto these groups. Examples are the benzo-condensed or pyridino-condensed analogs of the aforementioned monocyclic 5- or 6-membered compounds. Preferably a saturated or unsaturated heterocyclyl group can be selected from the group consisting of azetidinyl, pyrrolidinyl, piperidinyl, piperazinyl, pyrazolinyl, morpholinyl, tetrahydropyranyl, dioxanyl, dioxolanyl, indolinyl, isoindolinyl and

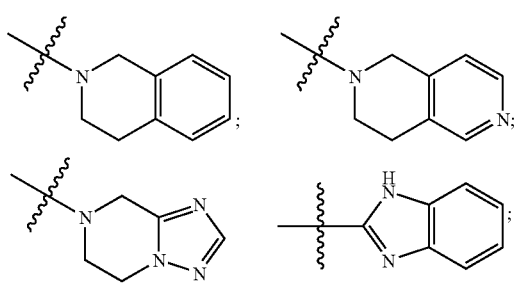

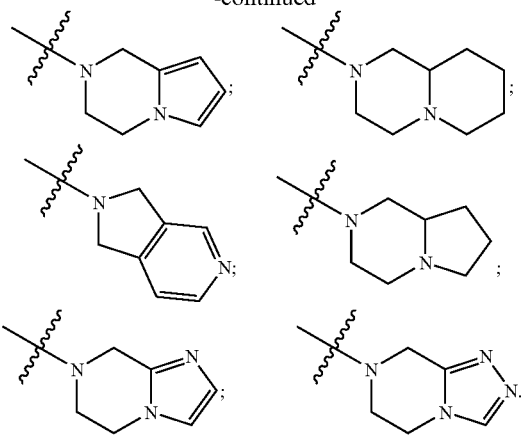

Unless otherwise specified, the substitution with a heterocyclyl group can take place at any suitable position of the heterocyclyl group.

In the context of the present invention, the expression "aryl" denotes aromatic hydrocarbons, in particular phenyl and naphthyl groups. The aryl groups can also be condensed with further saturated, (partially) unsaturated or aromatic ring systems. Each aryl group can be unsubstituted or monosubstituted or polysubstituted, for example 2, 3, 4 or 5 times, in which the aryl substituents can be identical or different and can be in any arbitrary and possible position of the aryl group. Preferably aryl can be selected from the group consisting of phenyl, 1-naphthyl and 2-naphthyl, which can in each case be unsubstituted or monosubstituted or polysubstituted, for example with 2, 3, 4 or 5 groups.

In the context of the present invention, the expression "heteroaryl" denotes a 5-, 6- or 7-membered cyclic aromatic group, which contains at least 1 heteroatom, and optionally 2, 3, 4 or 5 heteroatoms, in which the heteroatoms may be identical or different and the heteroaryl may be unsubstituted or monosubstituted or polysubstituted, for example 2, 3, 4 or 5 times, with identical or different groups. The substituents can be bonded in any desired and possible position of the heteroaryl. The heterocycle can also be part of a bicyclic or polycyclic ring system, in particular of a monocyclic, bicyclic or tricyclic system, which can then overall contain more than 7 members, preferably up to 14 members. Preferred heteroatoms are selected from the group consisting of N, O and S. The heteroaryl group can preferably be selected from the group consisting of pyrrolyl, indolyl, furyl, (furanyl), benzofuranyl, thienyl (thiophenyl), benzothienyl, benzothiadiazolyl, benzothiazolyl, benzotriazolyl, benzodioxolanyl, benzodioxanyl, benzooxazolyl, benzooxadiazolyl, imidazothiazolyl, dibenzofuranyl, dibenzothienyl, phthalazinyl, pyrazolyl, imidazolyl, thiazolyl, oxadiazolyl, isoxazoyl, pyridinyl (pyridyl), pyridazinyl, pyrimidinyl, pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl, wherein the bonding to the general structure I can take place via any desired and possible ring member of the heteroaryl group. Particularly preferably the heteroaryl group may be selected from the group consisting of furyl, thienyl and pyridinyl.

The expression "$C_{1-6}$-alkylene group" includes in the context of the present invention acyclic saturated hydrocarbon groups with 1, 2, 3, 4, 5 or 6 carbon atoms, which can be branched or straight-chain (unbranched) as well as unsubstituted or monosubstituted or polysubstituted, for example 2, 3, 4 or 5 times, with identical or different substituents, and which connect a corresponding group to the overall general structure. Preferably the alkylene groups can be selected from the group consisting of —CH$_2$—, —CH$_2$—CH$_2$—, —CH(CH$_3$), —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$, —CH(CH$_2$CH$_2$CH$_3$)—, —C(CH$_3$)(CH$_2$CH$_3$)—, —CH$_2$—(CH$_2$)$_3$—CH$_2$—, —CH(CH$_3$)—CH$_2$—CH$_2$—CH$_2$—, —CH$_2$—CH(CH$_3$)—CH$_2$—CH$_2$—, —CH(CH$_3$)—CH$_2$—CH(CH$_3$)—, —CH(CH$_3$)—CH—(CH$_3$)—CH$_2$—, —C(CH$_3$)$_2$—CH$_2$—CH$_2$—, —CH$_2$—C(CH$_3$)$_2$—CH$_2$—, —CH(CH$_2$CH$_3$)—CH$_2$—CH$_2$, —CH$_2$—CH(CH$_2$CH$_3$)—CH$_2$—, —C(CH$_3$)$_2$—CH(CH$_3$)—, —CH(CH$_2$CH$_3$)—CH(CH$_3$)—, —C(CH$_3$)(CH$_2$CH$_3$)—CH$_2$—, —CH(CH$_2$CH$_2$CH$_3$)—CH$_2$—, —C(CH$_2$CH$_2$CH$_3$)—CH$_2$—, —CH(CH$_2$CH$_2$CH$_2$CH$_3$)—, —C(CH$_3$)(CH$_2$CH$_2$CH$_3$)—, —C(CH$_2$CH$_3$)$_2$— and —CH$_2$—(CH$_2$)$_4$—CH$_2$—. Particularly preferably the alkylene groups can be selected from the group consisting of —CH$_2$—, —CH$_2$—CH$_2$— and —CH$_2$—CH$_2$—CH$_2$—.

In the context of the present invention, the expression "C$_{2-6}$-alkenylene group" includes acyclic, monosubstituted or polysubstituted, for example 2, 3 or 4 times, unsaturated hydrocarbon groups with 2, 3, 4, 5 or 6 carbon atoms, which may be branched or straight-chain (unbranched) as well as unsubstituted or monosubstituted or polysubstituted, for example 2, 3, 4 or 5 times, with identical or different substituents, and which connect a corresponding group to the overall general structure. In this regard, the alkenylene groups contain at least one C═C double bond. Preferably the alkenylene groups can be selected from the list consisting of —CH═CH—, CH═CH—CH$_2$—, —C(CH$_3$)═CH$_2$—, —CH═CH—CH$_2$—CH$_2$—, —CH$_2$—CH═CH—CH$_2$—, —CH═CH—CH═CH—, —C(CH$_3$)═CH—CH$_2$—, —CH═C(CH$_3$)—CH$_2$—, —C(CH$_3$)═C(CH$_3$)—, —C(CH$_2$CH$_3$)═CH—, —CH═CH—CH$_2$—CH$_2$—CH$_2$—, —CH$_2$CH═CH$_2$—CH$_2$—CH$_2$—, —CH═CH—CH═CH—CH$_2$— and —CH═CH$_2$—CH—CH═CH$_2$—.

In the context of the present invention, the expression "C$_{2-6}$-alkynylene group" includes acyclic, monosubstituted or polysubstituted, for example 2, 3 or 4 times, unsaturated hydrocarbon groups with 2, 3, 4, 5 or 6 carbon atoms, which can be branched or straight-chain (unbranched) as well as unsubstituted or monosubstituted or polysubstituted, for example 2, 3, 4 or 5 times, with identical or different substituents, and which connect a corresponding group to the overall general structure. In this connection the alkynylene groups contain at least one C≡C triple bond. Preferably the alkynylene groups can be selected from the group consisting of —C≡C—, —C≡C—CH$_2$—, —C≡C—CH$_2$—CH$_2$—, —C≡C—CH(CH$_3$)—, —CH$_2$—C≡C—CH$_2$—, —C≡C—C≡C—, —C≡C—C(CH$_3$)$_2$—, —C≡C—CH$_2$—CH$_2$—CH$_2$—, —CH$_2$—C≡C—CH$_2$—CH$_2$—, —C≡C—C≡C—CH$_2$— and —C≡C—CH$_2$—C≡C—.

In the context of the present invention, the expression "aryl or heteroaryl bonded via a C$_{1-6}$-alkylene group, C$_{2-6}$-alkenylene group or C$_{2-6}$-alkynylene group" denotes that the C$_{1-6}$-alkylene groups, C$_{2-6}$-alkenylene groups or C$_{2-6}$-alkynylene groups as well as aryl and/or heteroaryl have the meanings given above, and the aryl and/or heteroaryl is/are bonded via a C$_{1-6}$-alkylene group, C$_{2-6}$-alkenylene group or C$_{2-6}$-alkynylene group to the overall general structure. Examples of such groups include benzyl, phenethyl and phenylpropyl groups.

In the context of the present invention, the expression "C$_{3-8}$-cycloalkyl and heterocyclyl bonded via a C$_{1-6}$-alkylene group, C$_{2-6}$-alkenylene group or C$_{2-6}$-alkynylene group" denotes that the C$_{1-6}$-alkylene group, C$_{2-6}$-alkenylene group, C$_{2-6}$-alkynylene group, C$_{3-8}$-cycloalkyl and heterocyclyl have the meanings given above, and the C$_{3-8}$-cycloalkyl and heterocyclyl are bonded via a C$_{1-6}$-alkylene group, C$_{2-6}$-alkenylene group or C$_{2-6}$-alkynylene group to the overall general structure.

In connection with "alkyl", "alkenyl", "alkylene", "alkenylene", "alkynylene" and "cycloalkyl" the term "substituted" is understood in the context of the present invention to denote the substitution of a hydrogen atom by F, Cl, Br, I, CN, NH$_2$, NH—C$_{1-6}$-alkyl, NHC$_{1-6}$-alkylene-OH, C$_{1-6}$-alkyl, N(C$_{1-6}$-alkyl)$_2$, N(C$_{1-6}$-alkylene-OH)$_2$, NO$_2$, SH, S—C$_{1-6}$-alkyl, S-benzyl, O—C$_{1-6}$-alkyl, OH, O—C$_{1-6}$-alkylene-OH, ═O, O-benzyl, C(═O)C$_{1-6}$-alkyl, CO$_2$H, CO$_2$—C$_{1-6}$-alkyl, or benzyl. Polysubstituted groups are understood to be those groups that are substituted several times, for example twice or three times, either on different or on the same atoms, for example three times on the same carbon atom as in the case of CF$_3$ or CH$_2$CF$_3$, or at different sites as in the case of CH(Cl)—CH═CH—CHCl$_2$. The polysubstitution can be carried out with identical or different substituents, as for example in the case of CH(OH)—CH═CH—CHCl$_2$.

In connection with "heterocyclyl" the term "substituted" is understood to denote the replacement of a hydrogen atom on one or more ring members by F, Cl, Br, I, —CN, NH$_2$, NH—C$_{1-6}$-alkyl, NH—C$_{1-6}$-alkylene-OH, C$_{1-6}$-alkyl, N(C$_{1-6}$-alkyl)$_2$, N(C$_{1-6}$-alkylene-OH)$_2$, pyrrolinyl, piperazinyl, morpholinyl, NO$_2$, SH, S—C$_{1-6}$-alkyl, S-benzyl, O—C$_{1-6}$-alkyl, OH, O—C$_{1-6}$-alkylene-OH, ═O, O-benzyl, C(═O)C$_{1-6}$-alkyl, CO$_2$H, CO$_2$—C$_{1-6}$-alkyl or benzyl. The polysubstitution can be carried out with identical or different substituents. In particular the hydrogen bonded to a N-heteroatom can be substituted by a C$_{1-6}$-alkyl group.

With regard to "aryl" and "heteroaryl", in the context of the present invention the term "substituted" is understood to denote monosubstitution or polysubstitution, for example 2, 3, 4 or 5 times, of one or more hydrogen atoms of the corresponding ring system by F, Cl, Br, I, CN, NH$_2$, NH—C$_{1-6}$-alkyl, NH—C$_{1-6}$-alkylene-OH, N(C$_{1-6}$-alkyl)$_2$, N(C$_{1-6}$-alkylene-OH)$_2$, NH-aryl$^1$, N(aryl$^1$)$_2$, N(C$_{1-6}$-alkyl)aryl$^1$, pyrrolinyl, piperazinyl, morpholinyl, NO$_2$, SH, S—C$_{1-6}$-alkyl, OH, O—C$_{1-6}$-alkyl, O—C$_{1-6}$-alkyl-OH, C(═O)C$_{1-6}$-alkyl, NHSO$_2$C$_{1-6}$-alkyl, NHCOC$_{1-6}$-alkyl, CO$_2$H, CH$_2$SO$_2$-phenyl, CO$_2$—C$_{1-6}$-alkyl, OCF$_3$, CF$_3$, —O—CH$_2$—O—, —O—CH$_2$—CH$_2$—O—, —O—C(CH$_3$)$_2$—CH$_2$—, unsubstituted C$_{1-6}$-alkyl, pyrrolidinyl, imidazolyl, piperidinyl, benzyloxy, phenoxy, phenyl, naphthyl, pyridinyl, —C$_{1-3}$-alkylene-aryl$^1$, benzyl, thienyl, furyl, wherein aryl$^1$ denotes phenyl, furyl, thienyl or pyridinyl, on one or various atoms, wherein the aforementioned substituents—unless otherwise specified—may optionally for their part be substituted by the aforementioned substituents. The polysubstitution of aryl and heteroaryl groups can take place with identical or different substituents. Preferred substituents for aryl and heteroaryl may be selected from the group consisting of —O—C$_{1-3}$-alkyl, unsubstituted C$_{1-6}$-alkyl, F, Cl, Br, I, CF$_3$, OCF$_3$, OH, SH, phenyl, naphthyl, furyl, thienyl and pyridinyl, in particular from the group consisting of F, Cl, Br, CF$_3$, CH$_3$ and OCH$_3$.

If in the substituted sulfonamide compounds according to the invention two adjacent groups selected from R$^2$, R$^3$, R$^{4a}$, R$^{4b}$ and R$^{4c}$ form a 5- or 6-membered aromatic ring, preferably a 6-membered aromatic ring (benzo group), which is monosubstituted or polysubstituted, for example 2, 3 or 4 times with identical or different substituents, then the substituents can preferably be selected from the group consisting of $C_{1-6}$-alkyl, —O—$C_{1-6}$-alkyl, $CF_3$, F, Cl, and Br, in particular from the group consisting of methyl, methoxy, $CF_3$, F, Cl and Br.

Those skilled in the art will understand that the following partial structure of formula I

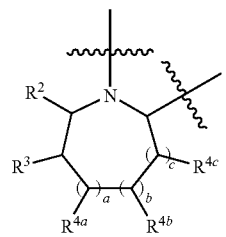

can adopt the following forms for the respective values 0 and 1 of the indices a, b and c:

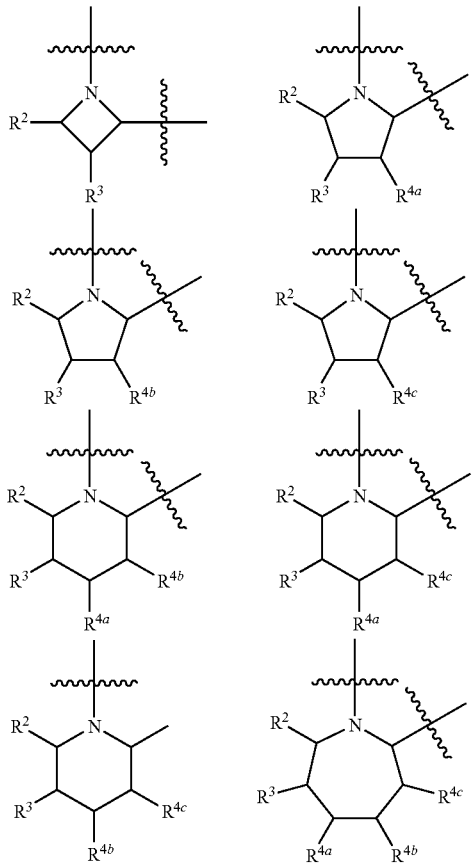

Those skilled in the art also understand that if two adjacent groups selected from $R^2$, $R^3$, $R^{4a}$, $R^{4b}$ and $R^{4c}$ form an (annelated) ring which is aromatic or is unsaturated on one or both of the carbon atoms that are coupled to the vicinal groups, then this or these carbon atom(s) can no longer carry a hydrogen.

For example, for a partial structure in which one of the indices a, b or c=0 and the other two are each 1 and the adjacent groups $R^2$ and $R^3$ form an annelated benzene ring, the following structure is obtained:

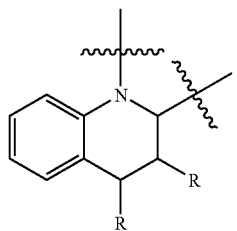

wherein R denotes the corresponding group from $R^{4a}$, $R^{4b}$ or $R^{4c}$.

For a partial structure in which one of the indices a, b or c=0 and the other two are each 1 and the adjacent groups $R^3$ and $R^{4a}$ or $R^{4b}$ form an annelated benzene ring, then the following structure is obtained:

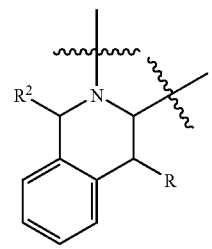

wherein R denotes the corresponding group from $R^{4b}$ or $R^{4c}$.

For a partial structure in which one of the indices a, b or c=0 and the other two are each 1 and two adjacent groups from $R^{4a}$, $R^{4b}$ and/or $R^{4c}$ form an annelated benzene ring, then the following structure is obtained:

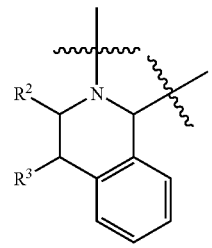

If the ring size of the partial structures identified above so permits, i.e. for compounds in which a+b+c=2 or 3, then two pairs of adjacent groups each can form an annelated ring, for example:

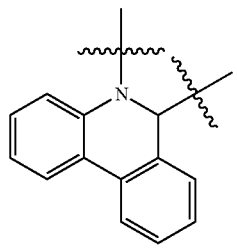

In the context of the present invention the symbol:

used in the formulas denotes a coupling of a corresponding group to the respective overall general structure.

The expression "physiologically compatible salt" is understood in the context of the present invention to denote salts of the compounds according to the invention with inorganic or organic acids that are physiologically compatible, especially when used in humans and/or mammals. Examples of suitable acids include hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro1λ$^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, hippuric acid, phosphoric acid and/or aspartic acid. Particularly preferred are the salts of hydrochloric acid (hydrochlorides) as well as of citric acid (citrates).

In the substituted sulfonamide compounds according to one preferred embodiment of the present invention, the group $R^1$ denotes phenyl, naphthyl, indolyl, benzofuranyl, benzothiophenyl (benzothienyl); benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl or dibenzothiophenyl (dibenzothienyl), more preferably denotes phenyl, naphthyl, benzothiophenyl, benzooxadiazolyl, thiophenyl, pyridinyl, imidazothiazolyl or dibenzofuranyl, and particularly preferably denotes phenyl or naphthyl, in each case unsubstituted or monosubstituted or polysubstituted with identical or different substituents, wherein the substituents are preferably selected from the group consisting of —O—$C_{1-3}$-alkyl, $C_{1-6}$-alkyl, F, Cl, Br, I, $CF_3$, $OCF_3$, OH, SH, phenyl, naphthyl, furyl, thienyl and pyridinyl.

In the substituted sulfonamide compounds according to a further preferred embodiment of the present invention, the group $R^1$ denotes phenyl or naphthyl, wherein the phenyl or naphthyl is unsubstituted or monosubstituted or polysubstituted, for example 2, 3, 4 or 5 times, with identical or different substituents selected from the group consisting of methyl, methoxy, $CF_3$, $OCF_3$, F, Cl and Br.

In a further preferred embodiment the group $R^1$ in the sulfonamide compounds according to the invention is selected from the group consisting of 4-methoxy-2,3,6-trimethylphenyl, 4-methoxy-2,6-dimethylphenyl, 4-methoxy-2,3,5-trimethylphenyl, 2,4,6-trimethylphenyl, 2-chloro-6-methylphenyl, 2,4,6-trichlorophenyl, 2-chloro-6-(trifluoromethyl)phenyl, 2,6-dichloro-4-methoxyphenyl, 2-methylnaphthyl, 2-chloronaphthyl, 2-fluoronaphthyl, 2-chloro-4-(trifluoromethoxy)phenyl, 4-chloro-2,5-dimethylphenyl, 2,3-dichlorophenyl, 3,4-dichlorophenyl, 2(trifluoromethyl)phenyl, 3-(trifluoromethyl)phenyl, 4-(trifluoromethyl)phenyl, 1-naphthyl and 2-naphthyl.

In another preferred embodiment the group $R^1$ in the sulfonamide compounds according to the invention is selected from the group consisting of 4-methoxy-2,3,6-trimethylphenyl, 4-methoxy-2,6-dimethylphenyl, 4-methoxy-2,3,5-trimethylphenyl, 2,4,6-trimethylphenyl, 4-chloro-2,5-dimethylphenyl, 2,3-dichlorophenyl, 3,4-dichlorophenyl, 2-(trifluoromethyl)phenyl, 3-(trifluoromethyl)phenyl, 4-(trifluoromethyl)phenyl, 1-naphthyl and 2-naphthyl.

In yet another preferred embodiment the group $R^1$ in the sulfonamide compounds according to the invention is 4-methoxy-2,6-dimethylphenyl or 2,4,6-trimethylphenyl, preferably 4-methoxy-2,6-dimethylphenyl.

In still another preferred embodiment of the present invention, in the substituted sulfonamide compounds according to the invention the groups $R^2$, $R^3$, $R^{4a}$, $R^{4b}$ and $R^{4c}$ independently of one another denote in each case H, or two vicinal groups from $R^2$, $R^3$, $R^{4a}$, $R^{4b}$ and $R^{4c}$ form a 5- or 6-membered aromatic ring, preferably a 6-membered aromatic ring (benzo group), which is unsubstituted or monosubstituted or polysubstituted, for example 2, 3 or 4 times, with identical or different groups selected from the group consisting of methyl, methoxy, $CF_3$, F, Cl and Br.

In a further preferred embodiment of the present invention, in the substituted sulfonamide compounds according to the invention the groups $R^2$, $R^3$, possibly $R^{4a}$, possibly $R^{4b}$ and possibly $R^{4c}$ in each case denote H.

In a further preferred embodiment of the present invention, in the substituted sulfonamide compounds according to the invention the sum of a+b+c=2.

Preferably m and n in the substituted sulfonamide compounds according to the invention can each independently denote 0 or 1.

In a further preferred embodiment of the present invention, if Q=-O—, then m and n each denote 1, and if Q=-$CH_2$—, then the sum of m+n=0, 1 or 2.

In yet a further preferred embodiment of the substituted sulfonamide compounds of the present invention, the following partial structures

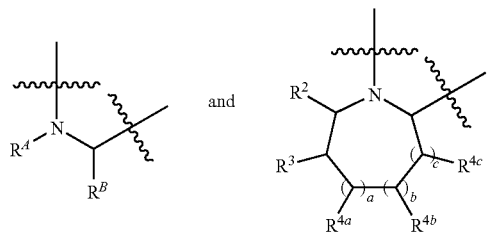

and are selected from the group consisting of:

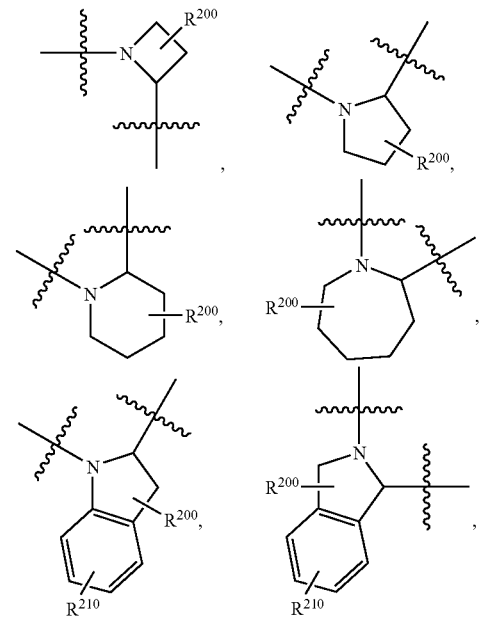

-continued

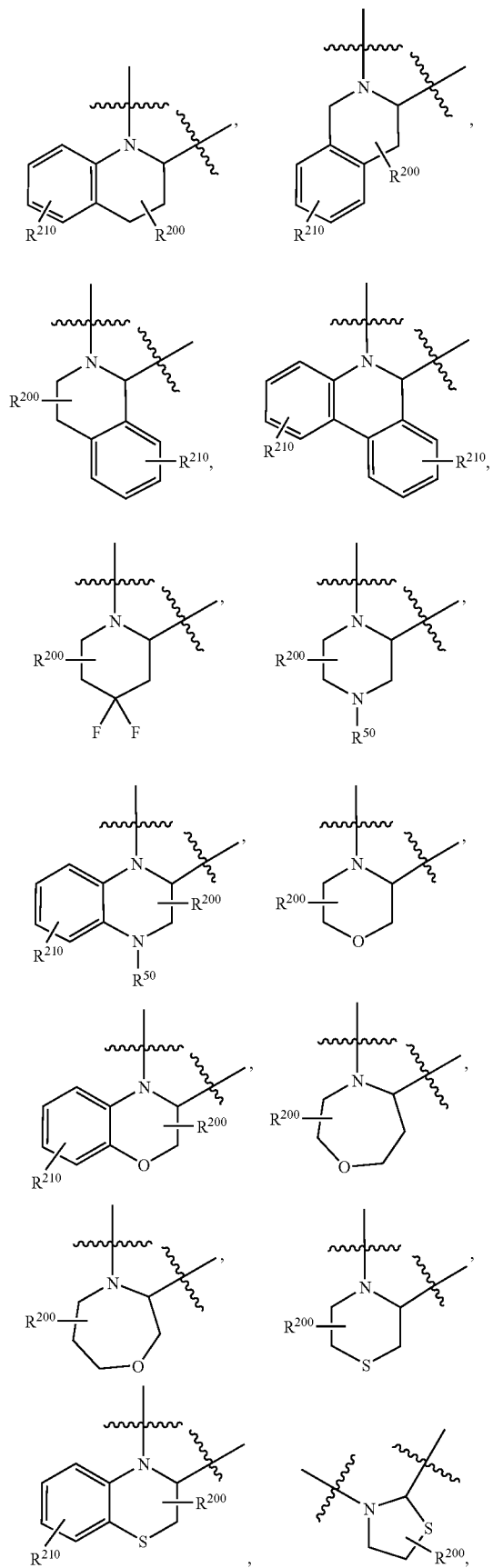

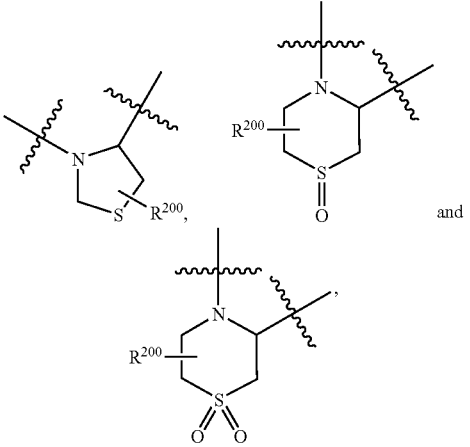

wherein
R²⁰⁰ represents 1, 2, 3 or 4 substituents, independently selected from the group consisting of H, halogen, O—CF₃, CF₃, methyl, ethyl, n-propyl, iso-propyl, and cyclopropyl;
R²¹⁰ represents 1, 2, 3 or 4 substituents, independently selected from the group consisting of H, methoxy, methyl, ethyl, n-propyl, iso-propyl, halogen, CF₃ and OCF₃, and
R⁵⁰ represents H, methyl, ethyl, n-propyl, iso-propyl, C₃₋₈-cycloalkyl, aryl, heteroaryl or a C₃₋₈-cycloalkyl, aryl or heteroaryl bonded via a C₁₋₃-alkylene group.

In the substituted sulfonamide compounds according to another preferred embodiment of the present invention, p is 1.

The group R⁵ in the substituted sulfonamide compounds according to the invention denotes, according to a further preferred embodiment of the present invention, H, C₁₋₆-alkyl, 5- or 6-membered aryl or heteroaryl; or denotes a 5- or 6-membered aryl or heteroaryl bonded via a C₁₋₆-alkylene group, C₂₋₆-alkenylene group or C₂₋₆-alkynylene group, wherein the aryl or heteroaryl is in each case unsubstituted, or is monosubstituted or polysubstituted, for example 2, 3, 4 or 5 times, with identical or different substituents selected from the group consisting of O—C₁₋₃-alkyl, unsubstituted C₁₋₆-alkyl, F, Cl, Br, I, CF₃, OCF₃, OH and SH. Preferably the aryl or heteroaryl is selected from the group consisting of phenyl, naphthyl, pyridinyl, thienyl and furyl.

In a further preferred embodiment of the substituted sulfonamide compounds according to the invention R⁵ denotes a group selected from the group consisting of H, methyl, ethyl, n-propyl, iso-propyl, n-butyl, sec-butyl, iso-butyl, tert-butyl, phenyl, 2,3,4-dimethylphenyl, 2-tert-butylphenyl, 3-tert-butylphenyl, 4-tert-butylphenyl, 2-methoxyphenyl, 3-methoxyphenyl, 4-methoxyphenyl, 2-fluorophenyl, 3-fluorophenyl, 4-fluorophenyl, 2,3-difluorophenyl, 3,4-difluorophenyl, 2(trifluoromethyl)phenyl, 3-(trifluoromethyl)phenyl, 4-(trifluoromethyl)phenyl, 2-fluoro-4(trifluoromethyl)phenyl, 3-fluoro-4-(trifluoromethyl)phenyl, benzyl, phenethyl, thienyl, pyridinyl and 6-chloropyridin-3-yl.

In the substituted sulfonamide compounds according to a further embodiment of the present invention, X denotes N, Y denotes N, and Z denotes CR⁸.

In the substituted sulfonamide compounds according to another preferred embodiment of the present invention X denotes N, Y denotes CR⁷ and Z denotes CR⁸.

In a further embodiment of the present invention, in the substituted sulfonamide compounds according to the invention X denotes N, Y denotes CR⁷ and Z denotes N.

In the substituted sulfonamide compounds according to still another preferred embodiment of the invention, X denotes $CR^6$, Y denotes $CR^7$, and Z denotes $CR^8$.

In the substituted sulfonamide compounds according to a yet further preferred embodiment of the invention, the groups $R^6$, $R^7$ and $R^8$ each independently denote H, halogen, $C_{1-6}$-alkyl, —$N(C_{1-6}$-alkyl$)_2$, —$C_{1-6}$-alkylene-$N(C_{1-6}$-Alkyl$)_2$, 5-, 6- or 7-membered heterocyclyl, 5- or 6-membered heteroaryl or denote a 5- or 6-membered heteroaryl or a 5-, 6- or 7-membered heterocyclyl bonded via a $C_{1-6}$-alkylene group, wherein heterocyclyl comprises one or two identical or different heteroatoms selected from the group consisting of N and O and is unsubstituted or monosubstituted or polysubstituted, identically or differently, with $C_{1-6}$-alkyl.

In the sulfonamide compounds according to still another preferred embodiment of the present invention, the groups $R^6$, $R^7$ and $R^8$ each independently denote H, F, Cl, Br, I, methyl, ethyl, n-propyl, iso-propyl, n-butyl, iso-butyl, sec-butyl, tert-butyl or denote a group that is selected from the group consisting of

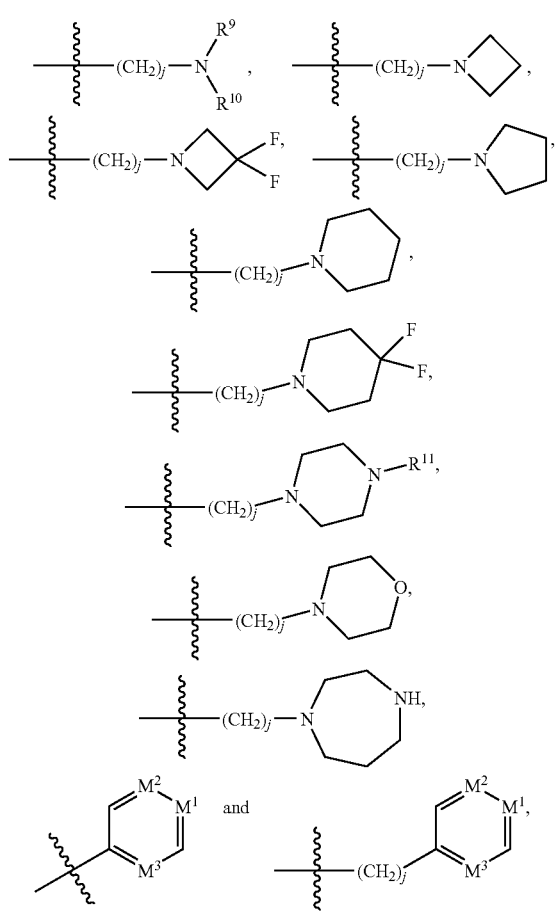

wherein $R^9$ and $R^{10}$ each independently denote a $C_{1-6}$-alkyl group; j is 1, 2 or 3; $R^{11}$ denotes a group selected from the group consisting of H, methyl, ethy, n-propyl, iso-propyl, n-butyl, iso-butyl, sec-butyl, tert-butyl, cyclopropyl, cyclobutyl, cyclopentyl and cyclohexyl; and $M^1$, $M^2$ and $M^3$ each independently denote N or CH, wherein one of $M^1$, $M^2$ and $M^3$ represents N, and the other two of $M^1$, $M^2$ and $M^3$ each represent CH.

In a further preferred embodiment of the compounds according to the invention $R^6$ denotes H.

In a further preferred embodiment of the compounds according to the invention $R^7$ denotes H or a group selected from the group consisting of:

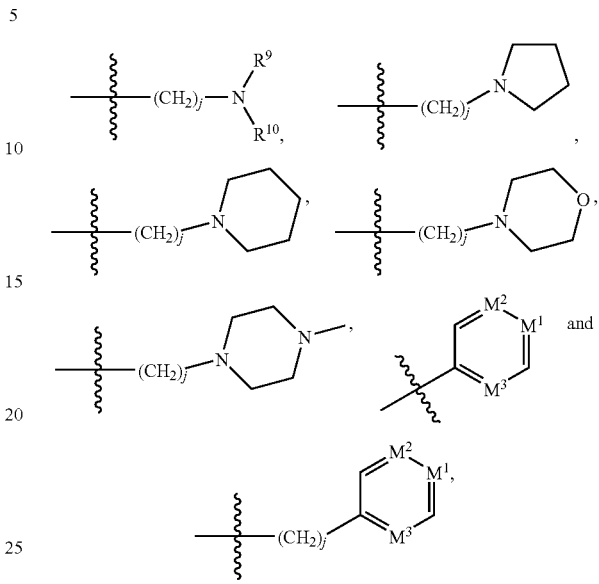

wherein $R^9$ and $R^{10}$ each independently denote a $C_{1-6}$-alkyl group; j is 1, 2 or 3; and $M^1$, $M^2$ and $M^3$ each independently denote N or CH, wherein one of $M^1$, $M^2$ and $M^3$ represents N, and the other two of $M^1$, $M^2$ and $M^3$ each represent CH.

In the compounds according to a further preferred embodiment of the invention, $R^8$ denotes H, F, Cl, Br, I, $C_{1-6}$-alkyl or a group selected from the group consisting of:

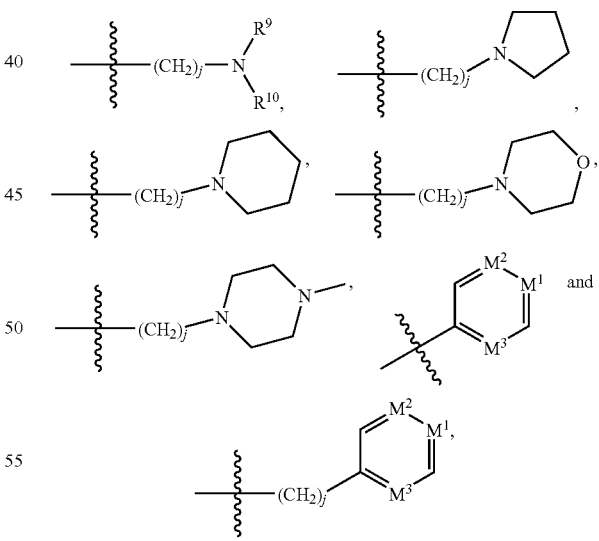

wherein $R^9$ and $R^{10}$ each independently denote a $C_{1-6}$-alkyl group; j is 1, 2 or 3; and $M^1$, $M^2$ and $M^3$ each independently denote N or CH, wherein one of $M^1$, $M^2$ and $M^3$ represents N, and the other two of $M^1$, $M^2$ and $M^3$ each represent CH.

Also preferred are substituted sulfonamide compounds according to the invention corresponding to the following formula Ia:

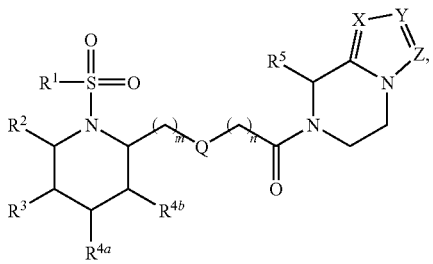

Ia wherein m and n each independently denote 0, 1 or 2;

Q denotes —O— or —CH$_2$—;

X denotes N or CR$^6$;

Y denotes N or CR$^7$;

Z denotes N or CR$^8$;

R$^1$ denotes aryl, heteroaryl, or an aryl or heteroaryl bonded via a C$_{1-6}$-alkylene group;

R$^2$, R$^3$, R$^{4a}$ and R$^{4b}$ each independently denote H, or two adjacent groups selected from R$^2$, R$^3$, R$^{4a}$ and R$^{4b}$ form a 5- or 6-membered ring that is saturated, unsaturated or aromatic and may be unsubstituted or monosubstituted or polysubstituted with identical or different substituents;

R$^5$ denotes H, halogen, CN, NO$_2$, C$_{1-6}$-alkyl, C$_{2-6}$-alkenyl, aryl, heteroaryl, or an aryl or heteroaryl bonded via a C$_{1-6}$-alkylene group, C$_{2-6}$-alkenylene group or C$_{2-6}$-alkynylene group;

R$^6$, R$^7$ and R$^8$ each independently denote H, halogen, CN, C$_{1-6}$-alkyl, —NH(C$_{1-6}$-alkyl), —N(C$_{1-6}$-alkyl)$_2$, —C$_{1-6}$-alkylene-NH(C$_{1-6}$-alkyl), —C$_{1-6}$-alkylene-N(C$_{1-6}$-alkyl)$_2$, C$_{3-8}$-cycloalkyl, heterocyclyl, aryl or heteroaryl; or denote a C$_{3-8}$-cycloalkyl, heterocyclyl, aryl or heteroaryl bonded via a C$_{1-6}$-alkylene group, C$_{2-6}$-alkenylene group or C$_{2-6}$-alkynylene group;

wherein the aforementioned C$_{1-6}$-alkyl, C$_{1-6}$-alkylene, C$_{2-6}$-alkenyl, C$_{2-6}$-alkenylene, C$_{2-6}$-alkynylene, C$_{3-8}$-cycloalkyl, heterocyclyl, aryl and heteroaryl groups each may be unsubstituted or monosubstituted or polysubstituted with identical or different substituents, and the aforementioned C$_{1-6}$-alkyl, C$_{1-6}$-alkylene, C$_{2-6}$-alkenyl, C$_{2-6}$-alkenylene and C$_{2-6}$-alkynylene groups each may be branched or unbranched, in the form of an individual enantiomer or of an individual diastereomer, or in the form of the racemate, enantiomers, diastereomers, mixtures of the enantiomers and/or diastereomers, as well as in each case in the form of their bases and/or physiologically compatible salts, wherein a substituted alkyl, alkenyl, alkylene, alkenylene, alkynylene or cycloalkyl is monosubstituted or polysubstituted identically or differently with substituents selected from the group consisting of F, Cl, Br, I, CN, NH$_2$, NH—C$_{1-6}$-alkyl, NH—C$_{1-6}$-alkylene-OH, C$_{1-6}$-alkyl, N(C$_{1-6}$-alkyl)$_2$, N(C$_{1-6}$-alkylene-OH)$_2$, NO$_2$, SH, S—C$_{1-6}$-alkyl, S-benzyl, O—C$_{1-6}$-alkyl, OH, O—C$_{1-6}$-alkylene-OH, =O, O-benzyl, C(=O)C$_{1-6}$-alkyl, CO$_2$H, CO$_2$—C$_{1-6}$-alkyl and benzyl;

a substituted heterocyclyl is monosubstituted or polysubstituted, identically or differently, with substituents selected from the group consisting of F, Cl, Br, I, —CN, NH$_2$, NH—C$_{1-6}$-alkyl, NH—C$_{1-6}$-alkylene-OH, C$_{1-6}$-alkyl, N(C$_{1-6}$-alkyl)$_2$, N(C$_{1-6}$-alkylene-OH)$_2$, pyrrolinyl, piperazinyl, morpholinyl, NO$_2$, SH, S—C$_{1-6}$-alkyl, S-benzyl, O—C$_{1-6}$-alkyl, OH, O—C$_{1-6}$-alkylene-OH, =O, O-benzyl, C(=O)C$_{1-6}$-alkyl, CO$_2$H, CO$_2$—C$_{1-6}$-alkyl and benzyl; and a substituted aryl or heteroaryl group is monosubstituted or polysubstituted, identically or differently, with substituents selected from the group consisting of F, Cl, Br, I, CN, NH$_2$, NH—C$_{1-6}$-alkyl, NH—C$_{1-6}$-alkylene-OH, N(C$_{1-6}$-alkyl)$_2$, N(C$_{1-6}$-alkylene-OH)$_2$, NH-aryl$^1$, N(aryl$^1$)$_2$, N(C$_{1-6}$-alkyl)aryl$^1$, pyrrolinyl, piperazinyl, morpholinyl, NO$_2$, SH, S—C$_{1-6}$-alkyl, OH, O—C$_{1-6}$-alkyl, O—C$_{1-6}$-alkyl-OH, C(=O)C$_{1-6}$-alkyl, NHSO$_2$C$_{1-6}$-alkyl, NHCOC$_{1-6}$-alkyl, CO$_2$H, CH$_2$SO$_2$-phenyl, CO$_2$—C$_{1-6}$-alkyl, OCF$_3$, CF$_3$, —O—CH$_2$—O—, —O—CH$_2$—CH$_2$—O—, —O—C(CH$_3$)$_2$—CH$_2$—, unsubstituted C$_{1-6}$-alkyl, pyrrolidinyl, imidazolyl, piperidinyl, benzyloxy, phenoxy, phenyl, pyridinyl, —C$_{1-3}$-alkylene-aryl$^1$, benzyl, thienyl and furyl, wherein aryl$^1$ denotes phenyl, furyl, thienyl or pyridinyl.

Also preferred are substituted sulfonamide compounds according to the invention corresponding to formula Ia, in which m and n each independently denote 0 or 1;

Q denotes —O— or —CH$_2$—;

X denotes N or CR$^6$;

Y denotes N or CR$^7$;

Z denotes N or CR$^8$;

R$^1$ denotes phenyl, naphthyl, indolyl, benzofuranyl, benzothiophenyl (benzothienyl); benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl or dibenzothiophenyl (dibenzothienyl), preferably phenyl, naphthyl, benzothiophenyl, benzooxadiazolyl, thiophenyl, pyridinyl, imidazothiazolyl or dibenzofuranyl, and particularly preferably denotes phenyl or naphthyl, in each case unsubstituted or monosubstituted or polysubstituted with identical or different substituents, wherein the substituents are preferably selected from the group consisting of —O—C$_{1-3}$-alkyl, C$_{1-6}$-alkyl, F, Cl, Br, I, CF$_3$, OCF$_3$, OH, SH, phenyl, naphthyl, furyl, thienyl and pyridinyl;

R$^2$, R$^3$, R$^{4a}$ and R$^{4b}$ each independently denote H, or two adjacent groups selected from R$^2$, R$^3$, R$^{4a}$, R$^{4b}$ form a 5- or 6-membered aromatic ring, preferably a 6-membered aromatic ring (benzo group), which may be unsubstituted or monosubstituted or polysubstituted, identically or differently, wherein the substituents are selected from the group consisting of methyl, methoxy, CF$_3$, Cl, Br and F;

R$^5$ denotes H, C$_{1-6}$-alkyl, a 5- or 6-membered aryl or heteroaryl group, or a 5-membered or 6-membered aryl or heteroaryl bonded via a C$_{1-6}$-alkylene group, C$_{2-6}$-alkenylene group or C$_{2-6}$-alkynylene group, wherein the aryl or heteroaryl is preferably selected from the group consisting of phenyl, naphthyl, pyridinyl, thienyl and furyl, and the aryl or heteroaryl may in each case be unsubstituted or monosubstituted or polysubstituted, identically or differently, with substituents selected from the group consisting of O—C$_{1-3}$-alkyl, unsubstituted C$_{1-6}$-alkyl, F, Cl, Br, I, CF$_3$, OCF$_3$, OH and SH;

R$^6$, R$^7$ and R$^8$ each independently denote H, halogen, C$_{1-6}$-alkyl, —N(C$_{1-6}$-alkyl)$_2$, —C$_{1-6}$-alkylene-N(C$_{1-6}$-alkyl)$_2$, 5- or 6-membered heterocyclyl or denote a 5- or 6-membered heterocyclyl bonded via a C$_{1-6}$-alkylene group, wherein heterocyclyl comprises 1 or 2 identical or different heteroatoms selected from the group consisting of N and O and is unsubstituted or is monosubstituted or identically or differently polysubstituted with C$_{1-6}$-alkyl; or denote a 5- or 6-membered heteroaryl or a 5- or 6-membered heteroaryl bonded via a C$_{1-6}$-alkylene group, wherein said heteroaryl is unsubstituted, monosubstituted or polysubstituted and wherein said heteroaryl comprises 1 or 2 nitrogen atoms;

in the form of an individual enantiomer or an individual diastereomer, in the form of the racemate, enantiomers, diastereomers, mixtures of the enantiomers and/or diastereomers, as well as in the form of their bases and/or physiologically compatible salts.

Also preferred are substituted sulfonamide compounds according to the invention corresponding to formula Ia, wherein:

m and n each independently denote 0 or 1;

Q denotes —O— or —CH$_2$—;

X denotes N or CR$^6$;

Y denotes N or CR$^7$;

Z denotes N or CR$^8$;

R$^1$ denotes phenyl or naphthyl, in each case unsubstituted or monosubstituted or polysubstituted, identically or differently, with substituents selected from the group consisting of methyl, methoxy, CF$_3$, F, Cl and Br;

R$^2$, R$^3$, R$^{4a}$ and R$^{4b}$ each independently denote H, or two adjacent groups selected from R$^2$, R$^3$, R$^{4a}$, and R$^{4b}$ form a 6-membered aromatic ring (benzo group), which may be unsubstituted or monosubstituted or polysubstituted, identically or differently, with substituents selected from the group consisting of methyl, methoxy, CF$_3$, Cl, Br and F;

R$^5$ denotes H, a C$_{1-6}$-alkyl, phenyl, furyl, thienyl or pyridinyl group, or a phenyl, furyl, thienyl or pyridinyl group bonded via a C$_{1-3}$-alkylene group, wherein the phenyl, furyl, thienyl or pyridinyl group may be unsubstituted or monosubstituted or identically or differently polysubstituted with substituents selected from the group consisting of —O—C$_{1-3}$-alkyl, unsubstituted C$_{1-6}$-alkyl, Br, Cl, F, I, CF$_3$, OCF$_3$, OH, SH;

R$^6$ denotes H;

R$^7$ denotes H or a group selected from the group consisting of:

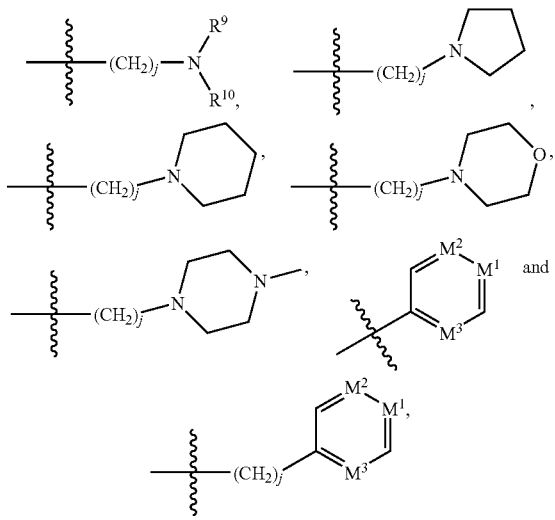

wherein R$^9$ and R$^{10}$ each independently denote a C$_{1-6}$-alkyl group; j is 1, 2 or 3; and M$^1$, M$^2$ and M$^3$ each independently denote N or CH, wherein one of M$^1$, M$^2$ and M$^3$ represents N, and the other two of M$^1$, M$^2$ and M$^3$ each represent CH;

R$^8$ denotes H, F, Cl, Br, I, C$_{1-6}$-alkyl, or a group selected from the group consisting of

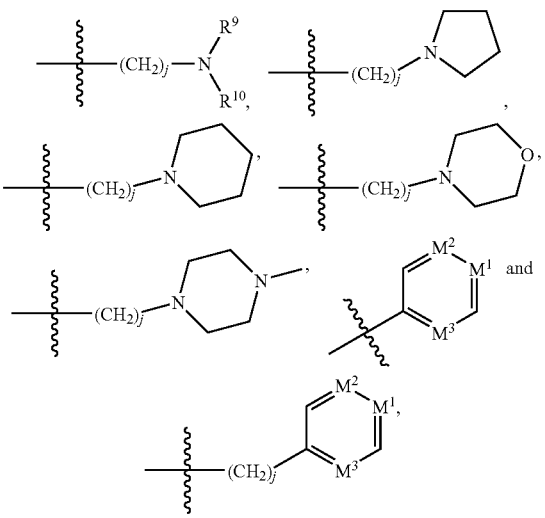

wherein R$^9$ and R$^{10}$ each independently denote a C$_{1-6}$-alkyl group; j is 1, 2 or 3; and M$^1$, M$^2$ and M$^3$ each independently denote N or CH, wherein one of M$^1$, M$^2$ and M$^3$ represents N, and the other two of M$^1$, M$^2$ and M$^3$ each represent CH.

Also preferred are substituted sulfonamide compounds according to the invention corresponding to formula Ia, wherein m=1, n=1 and Q denotes —O—, m=1, n=1 and Q denotes —CH$_2$—, m=1, n=0 and Q denotes —CH$_2$—, m=0, n=1 and Q denotes —CH$_2$— or m=0, n=0 and Q denotes —CH$_2$—;

X denotes N or CR$^6$;

Y denotes N or CR$^7$;

Z denotes N or CR$^8$;

R$^1$ denotes phenyl or naphthyl, which may be unsubstituted or monosubstituted or identically or differently disubstituted, trisubstituted, tetrasubstituted or pentasubstituted, with substituents selected from the group consisting of methyl, methoxy, CF$_3$, Cl, Br and F;

R$^2$, R$^3$, R$^{4a}$, and R$^{4b}$ each independently denote H, or two adjacent groups selected from R$^2$, R$^{4a}$ and R$^{4b}$ form an unsubstituted 6-membered aromatic ring (benzo group);

R$^5$ denotes H, methyl, ethyl, n-propyl, iso-propyl, n-butyl, iso-butyl, sec-butyl, tert-butyl, phenyl, furyl, thienyl or pyridinyl; or denotes a phenyl, furyl, thienyl or pyridinyl bonded via a —(CH$_2$)—, —(CH$_2$)$_2$— or —(CH$_2$)$_3$— group, wherein the phenyl, furyl, thienyl or pyridinyl may in each case be unsubstituted or monosubstituted, disubstituted or trisubstituted identically or differently with substituents selected independently of one another from the group consisting of methoxy, ethoxy, n-propoxy, iso-propoxy, methyl, ethyl, n-propyl, iso-propyl, n-butyl, iso-butyl, sec-butyl, tert-butyl, Br, Cl, F, I, CF$_3$, OCF$_3$, OH and SH;

R$^6$ denotes H;

R$^7$ denotes H or a group that is selected from the group consisting of

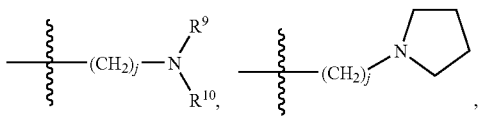

-continued

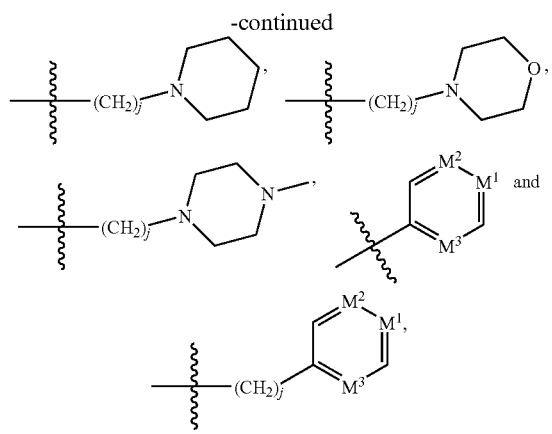

wherein R⁹ and R¹⁰ each independently denote a methyl group; j is 1, 2 or 3; and M¹, M² and M³ each independently denote N or CH, wherein one of M¹, M² and M³ represents N, and the other two of M¹, M² and M³ each represent CH;

R⁸ denotes H, F, Cl, Br, I, methyl, ethyl, n-propyl, iso-propyl, n-butyl, iso-butyl, sec-butyl, tert-butyl or a group selected from the group consisting of:

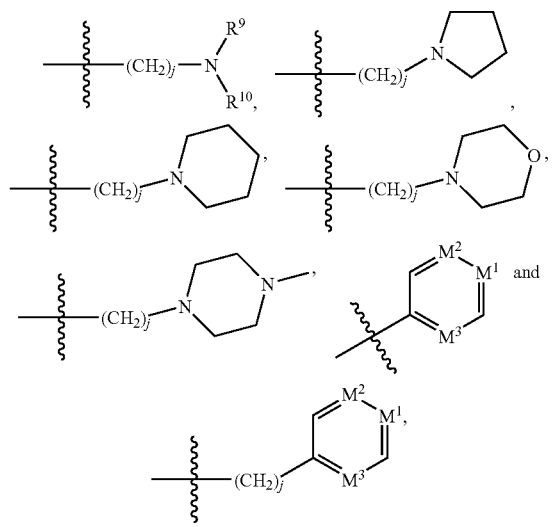

wherein R⁹ and R¹⁰ each independently denote a methyl group; j is 1, 2 or 3; and M¹, M² and M³ each independently denote N or CH, wherein one of M¹, M² and M³ represents N, and the other two of M¹, M² and M³ each represent CH.

Also preferred are sulfonamide compounds according to the invention corresponding to formula Ib:

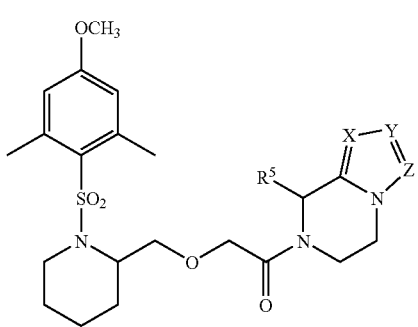

wherein

X denotes N or CR⁶;

Y denotes N or CR⁷;

Z denotes N or CR⁸;

R⁵ denotes H, methyl, ethyl, n-propyl, iso-propyl, n-butyl, iso-butyl, sec-butyl, tert-butyl, phenyl, furyl, thienyl or pyridinyl; or a phenyl group bonded via a —(CH₂)—, —(CH₂)₂— or —(CH₂)₃— group, wherein the phenyl, furyl, thienyl or pyridinyl may in each case be unsubstituted, or monosubstituted or identically or differently disubstituted or trisubstituted with substituents selected independently of one another from the group consisting of methoxy, ethoxy, n-propoxy, iso-propoxy, methyl, ethyl, n-propyl, iso-propyl, n-butyl, sec-butyl, tert-butyl, Br, Cl, F, I, CF₃, OCF₃, OH and SH;

R⁶ denotes H;

R⁷ denotes H or a group selected from the group consisting of:

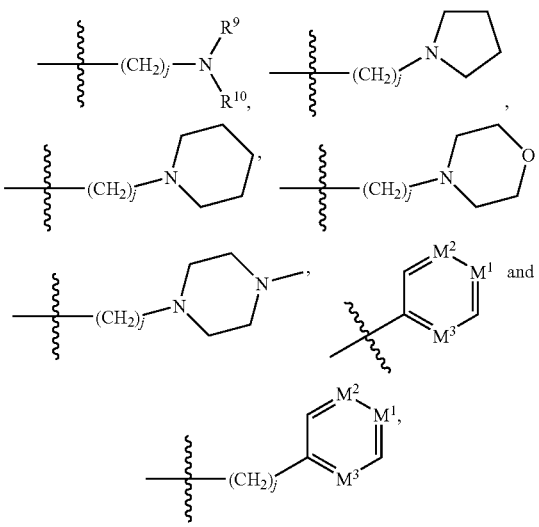

wherein R⁹ and R¹⁰ each independently denote a methyl group; j is 1, 2 or 3; and M¹, M² and M³ each independently denote N or CH, wherein one of M¹, M² and M³ represents N, and the other two of M¹, M² and M³ each represent CH;

R⁸ denotes H, F, Cl, Br, I, methyl, ethyl, n-propyl, iso-propyl, n-butyl, sec-butyl, tert-butyl or a group selected from the group consisting of:

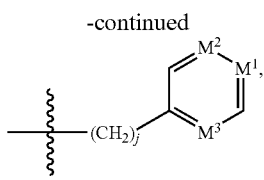

wherein R[9] and R[10] each independently denote a methyl group; j is 1, 2 or 3; and M[1], M[2] and M[3] each independently denote N or CH, wherein one of M[1], M[2] and M[3] represents N, and the other two of M[1], M[2] and M[3] each represent CH. Particularly preferred are sulfonamide compounds according to the invention selected from the group consisting of (1) 1-(5,6-dihydro-[1,2,4]triazolo[4,3-a]pyrazin-7(8H)-yl)-2-((1-(4-methoxy-2,6-dimethylphenylsulfonyl)piperidin-2-yl)methoxy)ethanone,
(2) 2-((1-(4-methoxy-2,6-dimethylphenylsulfonyl)piperidin-2-yl)methoxy)-1-(2-(piperidin-1-ylmethyl)-5,6-dihydroimidazo[1,2-a]pyrazin-7(8H)-yl)ethanone,
(3) 1-(3-chloro-2-(piperidin-1-ylmethyl)-5,6-dihydroimidazo[1,2-a]pyrazin-7(8H)-yl)-2-((1-(4-methoxy-2,6-dimethylphenylsulfonyl)piperidin-2-yl)methoxy)ethanone,
(4) 2-((1-(4-methoxy-2,6-dimethylphenylsulfonyl)piperidin-2-yl)methoxy)-1-(6-((4-methylpiperazin-1-yl)methyl)-3,4-dihydropyrrolo[1,2-a]pyrazin-2(1H)-yl)ethanone,
(5) 3-(1-(4-chloro-2,5-dimethylphenylsulfonyl)piperidin-2-yl)-1-(6-((4-methyl-piperazin-1-yl)methyl)-3,4-dihydropyrrolo[1,2-a]pyrazin-2(1H)-yl)propan-1-one,
(6) 2-((1-(4-methoxy-2,6-dimethylphenylsulfonyl)piperidin-2-yl)methoxy)-1-(6-(morpholinomethyl)-3,4-dihydropyrrolo[1,2-a]pyrazin-2(1H)-yl)ethanone,
(7) 1-(6-((4-methylpiperazin-1-yl)methyl)-3,4-dihydropyrrolo[1,2-a]pyrazin-2(1H)-yl)-2-(1-(3-(trifluoromethyl)phenylsulfonyl)piperidin-2-yl)ethanone,
(8) 1-(6-(pyrrolidin-1-ylmethyl)-3,4-dihydropyrrolo[1,2-a]pyrazin-2(1H)-yl)-2-(1-(3-(trifluoromethyl)phenylsulfonyl)piperidin-2-yl)ethanone,
(9) 3-(1-(4-chloro-2,5-dimethylphenylsulfonyl)piperidin-2-yl)-1-(6-(pyrrolidin-1-yl methyl)-3,4-dihydropyrrolo[1,2-a]pyrazin-2(1H)-yl)propan-1-one,
(10) 2-((1-(3,4-dichlorophenylsulfonyl)-1,2,3,4-tetrahydroquinolin-2-yl)methoxy)-1-(6-(pyrrolidin-1-ylmethyl)-3,4-dihydropyrrolo[1,2-a]pyrazin-2(1H)-yl)ethanone,
(11) 2-((1-(3,4-dichlorophenylsulfonyl)-1,2,3,4-tetrahydroquinolin-2-yl)methoxy)-1-(6-((4-methylpiperazin-1-yl)methyl)-3,4-dihydropyrrolo[1,2-a]pyrazin-2(1H)-yl)ethanone,
(12) 3-(1-(4-chloro-2,5-dimethylphenylsulfonyl)piperidin-2-yl)-1-(6-(morpholino-methyl)-3,4-dihydropyrrolo[1,2-a]pyrazin-2(1H)-yl)propan-1-one,
(13) 2-((1-(4-methoxy-2,6-dimethylphenylsulfonyl)piperidin-2-yl)methoxy)-1-(6-(pyrrolidin-1-ylmethyl)-3,4-dihydropyrrolo[1,2-a]pyrazin-2(1H)-yl)ethanone,
(14) 2-((1-(4-methoxy-2,6-dimethylphenylsulfonyl)piperidin-2-yl)methoxy)-1-(6-(3-(4-methylpiperazin-1-yl)propyl)-3,4-dihydropyrrolo[1,2-a]pyrazin-2(1H)-yl)ethanone,
(15) 1-(6-(3-(4-methylpiperazin-1-yl)propyl)-3,4-dihydropyrrolo[1,2-a]pyrazin-2(1H)-yl)-2-(1-(3-(trifluoromethyl)phenylsulfonyl)piperidin-2-yl)ethanone,
(16) 2-((1-(3,4-dichlorophenylsulfonyl)-1,2,3,4-tetrahydroquinolin-2-yl)methoxy)-1-(6-(3-(4-methylpiperazin-1-yl)propyl)-3,4-dihydropyrrolo[1,2-a]pyrazin-2(1H)-yl)ethanone,
(17) 1-(6-(3-(pyrrolidin-1-yl)propyl)-3,4-dihydropyrrolo[1,2-a]pyrazin-2(1H)-yl)-2-(1-(3-(trifluoromethyl)phenylsulfonyl)piperidin-2-yl)ethanone,
(18) 3-(1-(4-chloro-2,5-dimethylphenylsulfonyl)piperidin-2-yl)-1-(6-(3-(pyrrolidin-1-yl)propyl)-3,4-dihydropyrrolo[1,2-a]pyrazin-2(1H)-yl)propan-1-one,
(19) 1-(1-tert-butyl-3,4-dihydropyrrolo[1,2-a]pyrazin-2(1H)-yl)-2-((1-(4-methoxy-2,6-dimethyl-phenylsulfonyl)piperidin-2-yl)methoxy)ethanone,
(20) 2-((1-(4-methoxy-2,6-dimethylphenylsulfonyl)piperidin-2-yl)methoxy)-1-(1-methyl-3,4-dihydropyrrolo[1,2-a]pyrazin-2(1H)-yl)ethanone,
(21) 2-((1-(4-methoxy-2,6-dimethylphenylsulfonyl)piperidin-2-yl)methoxy)-1-(1-(pyridin-3-yl)-3,4-dihydropyrrolo[1,2-a]pyrazin-2(1H)-yl)ethanone,
(22) 1-(1-(6-chloropyridin-3-yl)-3,4-dihydropyrrolo[1,2-a]pyrazin-2(1H)-yl)-2-((1-(4-methoxy-2,6-dimethyl phenylsulfonyl)piperidin-2-yl)methoxy)ethanone,
(23) 1-(5,6-dihydroimidazo[1,2-a]pyrazin-7(8H)-yl)-2-((1-(4-methoxy-2,6-dimethyl-phenylsulfonyl)piperidin-2-yl)methoxy)ethanone,
(24) 2-((1-(4-methoxy-2,6-dimethylphenylsulfonyl)piperidin-2-yl)methoxy)-1-(1-(4-methoxyphenyl)-3,4-dihydropyrrolo[1,2-a]pyrazin-2(1H)-yl)ethanone,
(25) 2-((1-(4-methoxy-2,6-dimethylphenylsulfonyl)piperidin-2-yl)methoxy)-1-(1-phenyl-3,4-dihydropyrrolo[1,2-a]pyrazin-2(1H)-yl)ethanone,
(26) 1-(1-(3,4-difluorophenyl)-3,4-dihydropyrrolo[1,2-a]pyrazin-2(1H)-yl)-2-((1-(4-methoxy-2,6-dimethyl phenylsulfonyl)piperidin-2-yl)methoxy)ethanone,
(27) 1-(1-(3,4-dimethylphenyl)-3,4-dihydropyrrolo[1,2-a]pyrazin-2(1H)-yl)-2-((1-(4-methoxy-2,6-dimethyl phenylsulfonyl)piperidin-2-yl)methoxy)ethanone,
(28) 1-(1-(3-fluorophenyl)-3,4-dihydropyrrolo[1,2-a]pyrazin-2(1H)-yl)-2-((1-(4-methoxy-2,6-dimethylphenylsulfonyl)piperidin-2-yl)methoxy)ethanone,
(29) 2-((1-(4-methoxy-2,6-dimethylphenylsulfonyl)piperidin-2-yl)methoxy)-1-(1-(thiophen-2-yl)-3,4-dihydropyrrolo[1,2-a]pyrazin-2(1H)-yl)ethanone,
(30) 2-((1-(4-methoxy-2,6-dimethylphenylsulfonyl)piperidin-2-yl)methoxy)-1-(1-(3-(trifluoromethyl)phenyl)-3,4-dihydropyrrolo[1,2-a]pyrazin-2(1H)-yl)ethanone,
(31) 2-((1-(4-methoxy-2,6-dimethylphenylsulfonyl)piperidin-2-yl)methoxy)-1-(1-(3-methoxyphenyl)-3,4-dihydropyrrolo[1,2-a]pyrazin-2(1H)-yl)ethanone,
(32) 1-(1-(2-fluoro-4-(trifluoromethyl)phenyl)-3,4-dihydropyrrolo[1,2-a]pyrazin-2(1H)-yl)-2-((1-(4-methoxy-2,6-dimethylphenylsulfonyl)piperidin-2-yl)methoxy)ethanone,
(33) 1-(1-tert-butyl-3,4-dihydropyrrolo[1,2-a]pyrazin-2(1H)-yl)-2-((1-(mesitylsulfonyl)piperidin-2-yl)methoxy)ethanone,
(34) 2-((1-(mesitylsulfonyl)piperidin-2-yl)methoxy)-1-(1-methyl-3,4-dehydro-pyrrolo[1,2-a]pyrazin-2(1H)-yl)ethanone,
(35) 2-((1-(mesitylsulfonyl)piperidin-2-yl)methoxy)-1-(1-(pyridin-3-yl)-3,4-dihydropyrrolo[1,2-a]pyrazin-2(1H)-yl)ethanone,
(36) 1-(1-(6-chloropyridin-3-yl)-3,4-dihydropyrrolo[1,2-a]pyrazin-2(1H)-yl)-2-((1-(mesitylsulfonyl)piperidin-2-yl)methoxy)ethanone,
(37) 1-(5,6-dihydroimidazo[1,2-a]pyrazin-7(8H)-yl)-2-((1-(mesitylsulfonyl)piperidin-2-yl)methoxy)ethanone,
(38) 2-((1-(mesitylsulfonyl)piperidin-2-yl)methoxy)-1-(1-(4-methoxyphenyl)-3,4-dihydropyrrolo[1,2-a]pyrazin-2(1H)-yl)ethanone,

(39) 2-((1-(mesitylsulfonyl)piperidin-2-yl)methoxy)-1-(1-phenyl-3,4-dihydropyrrolo[1,2-a]pyrazin-2(1H)-yl)ethanone,
(40) 1-(1-(3,4-difluorophenyl)-3,4-dihydropyrrolo[1,2-a]pyrazin-2(1H)-yl)-2-((1-(mesitylsulfonyl)piperidin-2-yl)methoxy)ethanone,
(41) 1-(1-(3,4-dimethylphenyl)-3,4-dihydropyrrolo[1,2-a]pyrazin-2(1H)-yl)-2-((1-(mesitylsulfonyl)piperidin-2-yl)methoxy)ethanone,
(42) 1-(1-(3-fluorophenyl)-3,4-dihydropyrrolo[1,2-a]pyrazin-2(1H)-yl)-2-((1-(mesitylsulfonyl)piperidin-2-yl)methoxy)ethanone,
(43) 2-((1-(mesitylsulfonyl)piperidin-2-yl)methoxy)-1-(1-(thiophen-2-yl)-3,4-dihydropyrrolo[1,2-a]pyrazin-2(1H)-yl)ethanone,
(44) 2-((1-(mesitylsulfonyl)piperidin-2-yl)methoxy)-1-(1-(3-(trifluoromethyl)phenyl)-3,4-dihydropyrrolo[1,2-a]pyrazin-2(1H)-yl)ethanone,
(45) 2-((1-(mesitylsulfonyl)piperidin-2-yl)methoxy)-1-(1-phenethyl-3,4-dihydro-pyrrolo[1,2-a]pyrazin-2(1H)-yl)ethanone,
(46) 1-(6-((dimethylamino)methyl)-1-phenyl-3,4-dihydropyrrolo[1,2-a]pyrazin-2(1H)-yl)-2-((1-(mesitylsulfonyl)piperidin-2-yl)methoxy)ethanone,
(47) 2-((1-(mesitylsulfonyl)piperidin-2-yl)methoxy)-1-(1-phenyl-6-(pyrrolidin-1-yl-methyl)-3,4-dihydropyrrolo[1,2-a]pyrazin-2(1H)-yl)ethanone,
(48) 2-((1-(mesitylsulfonyl)piperidin-2-yl)methoxy)-1-(1-phenyl-6-(piperidin-1-yl-methyl)-3,4-dihydropyrrolo[1,2-a]pyrazin-2(1H)-yl)ethanone,
(49) 2-((1-(mesitylsulfonyl)piperidin-2-yl)methoxy)-1-(6-(morpholinomethyl)-1-phenyl-3,4-dihydropyrrolo[1,2-a]pyrazin-2(1H)-yl)ethanone,
(50) 1-(1-benzyl-6-((dimethylamino)methyl)-3,4-dihydropyrrolo[1,2-a]pyrazin-2(1H)-yl)-2-((1-(mesitylsulfonyl)piperidin-2-yl)methoxy)ethanone,
(51) 1-(6-((dimethylamino)methyl)-1-phenethyl-3,4-dihydropyrrolo[1,2-a]pyrazin-2(1H)-yl)-2-((1-(mesitylsulfonyl)piperidin-2-yl)methoxy)ethanone,
(52) 1-(1-butyl-6-((dimethylamino)methyl)-3,4-dihydropyrrolo[1,2-a]pyrazin-2(1H)-yl)-2-((1-(mesitylsulfonyl)piperidin-2-yl)methoxy)ethanone,
(53) 1-(6-((dimethylamino)methyl)-1-(thiophen-2-yl)-3,4-dihydropyrrolo[1,2-a]pyrazin-2(1H)-yl)-2-((1-(mesitylsulfonyl)piperidin-2-yl)methoxy)ethanone,
(54) 1-(6-((dimethylamino)methyl)-1-ethyl-3,4-dihydropyrrolo[1,2-a]pyrazin-2(1H)-yl)-2-((1-(mesitylsulfonyl)piperidin-2-yl)methoxy)ethanone,
(55) 1-(1-ethyl-3,4-dihydropyrrolo[1,2-a]pyrazin-2(1H)-yl)-2-((1-(mesitylsulfonyl)piperidin-2-yl)methoxy)ethanone,
(56) 2-((1-(mesitylsulfonyl)piperidin-2-yl)methoxy)-1-(1-propyl-3,4-dihydropyrrolo[1,2-a]pyrazin-2(1H)-yl)ethanone,
(57) 1-(1-isopropyl-3,4-dihydropyrrolo[1,2-a]pyrazin-2(1H)-yl)-2-((1-(mesitylsulfonyl)piperidin-2-yl)methoxy)ethanone,
(58) 1-(1-ethyl-6-methyl-3,4-dihydropyrrolo[1,2-a]pyrazin-2(1H)-yl)-2-((1-(mesitylsulfonyl)piperidin-2-yl)methoxy)ethanone
(59) 1-(1-isopropyl-6-methyl-3,4-dihydropyrrolo[1,2-a]pyrazin-2(1H)-yl)-2-((1-(mesitylsulfonyl)piperidin-2-yl)methoxy)ethanone,
(60) 2-((1-(4-methoxy-2,6-dimethylphenylsulfonyl)piperidin-2-yl)methoxy)-1-(1-phenethyl-3,4-dihydropyrrolo[1,2-a]pyrazin-2(1H)-yl)ethanone,
(61) 1-(6-((dimethylamino)methyl)-1-phenyl-3,4-dihydropyrrolo[1,2-a]pyrazin-2(1H)-yl)-2-((1-(4-methoxy-2,6-dimethylphenylsulfonyl)piperidin-2-yl)methoxy)ethanone,
(62) 2-((1-(4-methoxy-2,6-dimethylphenylsulfonyl)piperidin-2-yl)methoxy)-1-(1-phenyl-6-(pyrrolidin-1-ylmethyl)-3,4-dihydropyrrolo[1,2-a]pyrazin-2(1H)-yl)ethanone,
(63) 2-((1-(4-methoxy-2,6-dimethylphenylsulfonyl)piperidin-2-yl)methoxy)-1-(1-phenyl-6-(piperidin-1-ylmethyl)-3,4-dihydropyrrolo[1,2-a]pyrazin-2(1H)-yl)ethanone,
(64) 2-((1-(4-methoxy-2,6-dimethylphenylsulfonyl)piperidin-2-yl)methoxy)-1-(6-(morpholinomethyl)-1-phenyl-3,4-dihydropyrrolo[1,2-a]pyrazin-2(1H)-yl)ethanone,
(65) 1-(1-benzyl-6-((dimethylamino)methyl)-3,4-dihydropyrrolo[1,2-a]pyrazin-2(1H)-yl)-2-((1-(4-methoxy-2,6-dimethylphenylsulfonyl)piperidin-2-yl)methoxy)ethanone,
(66) 1-(6-((dimethylamino)methyl)-1-phenethyl-3,4-dihydropyrrolo[1,2-a]pyrazin-2(1H)-yl)-2-((1-(4-methoxy-2,6-dimethylphenylsulfonyl)piperidin-2-yl)methoxy)ethanone,
(67) 1-(1-butyl-6-((dimethylamino)methyl)-3,4-dihydropyrrolo[1,2-a]pyrazin-2(1H)-yl)-2-((1-(4-methoxy-2,6-dimethylphenylsulfonyl)piperidin-2-yl)methoxy)ethanone,
(68) 1-(6-((dimethylamino)methyl)-1-(thiophen-2-yl)-3,4-dihydropyrrolo[1,2-a]pyrazin-2(1H)-yl)-2-((1-(4-methoxy-2,6-dimethylphenylsulfonyl)piperidin-2-yl)methoxy)ethanone,
(69) 1-(6-((dimethylamino)methyl)-1-ethyl-3,4-dihydropyrrolo[1,2-a]pyrazin-2(1H)-yl)-2-((1-(4-methoxy-2,6-dimethylphenylsulfonyl)piperidin-2-yl)methoxy)ethanone,
(70) 1-(1-ethyl-3,4-dihydropyrrolo[1,2-a]pyrazin-2(1H)-yl)-2-((1-(4-methoxy-2,6-dimethylphenylsulfonyl)piperidin-2-yl)methoxy)ethanone,
(71) 2-((1-(4-methoxy-2,6-dimethylphenylsulfonyl)piperidin-2-yl)methoxy)-1-(1-propyl-3,4-dihydropyrrolo[1,2-a]pyrazin-2(1H)-yl)ethanone,
(72) 1-(1-isopropyl-3,4-dihydropyrrolo[1,2-a]pyrazin-2(1H)-yl)-2-((1-(4-methoxy-2,6-dimethylphenylsulfonyl)piperidin-2-yl)methoxy)ethanone,
(73) 1-(5,6-dihydro-[1,2,4]triazolo[1,5-a]pyrazin-7(8H)-yl)-2-((1-(4-methoxy-2,6-dimethylphenylsulfonyl)piperidin-2-yl)methoxy)ethanone,
(74) 2-((1-(4-methoxy-2,6-dimethylphenylsulfonyl)piperidin-2-yl)methoxy)-1-(6-(2-(4-methylpiperazin-1-yl)ethyl)-3,4-dihydropyrrolo[1,2-a]pyrazin-2(1H)-yl)ethanone,
(75) 1-(6-(2-(4-methylpiperazin-1-yl)ethyl)-3,4-dihydropyrrolo[1,2-a]pyrazin-2(1H)-yl)-2-(1-(3-(trifluoromethyl)phenylsulfonyl)piperidin-2-yl)ethanone,
(76) 1-(6-(2-morpholinoethyl)-3,4-dihydropyrrolo[1,2-a]pyrazin-2(1H)-yl)-2-(1-(3-(trifluoromethyl)phenylsulfonyl)piperidin-2-yl)ethanone,
(77) 3-(1-(4-chloro-2,5-dimethylphenylsulfonyl)piperidin-2-yl)-1-(6-(2-morpholinoethyl)-3,4-dihydropyrrolo[1,2-a]pyrazin-2(1H)-yl)propan-1-one,
(78) 2-((1-(3,4-dichlorophenylsulfonyl)-1,2,3,4-tetrahydroquinolin-2-yl)methoxy)-1-(6-(2-morpholinoethyl)-3,4-dihydropyrrolo[1,2-a]pyrazin-2(1H)-yl)ethanone,
(79) 3-(1-(4-chloro-2,5-dimethylphenylsulfonyl)piperidin-2-yl)-1-(6-(2-(pyrrolidin-1-yl)ethyl)-3,4-dihydropyrrolo[1,2-a]pyrazin-2(1H)-yl)propan-1-one,
(80) 2-((1-(4-methoxy-2,6-dimethylphenylsulfonyl)piperidin-2-yl)methoxy)-1-(6-(2-(pyrrolidin-1-yl)ethyl)-3,4-dihydropyrrolo[1,2-a]pyrazin-2(1H)-yl)ethanone,

(81) 1-(6-(2-(pyrrolidin-1-yl)ethyl)-3,4-dihydropyrrolo[1,2-a]pyrazin-2(1H)-yl)-2-(1-(3-(trifluoromethyl)phenylsulfonyl)piperidin-2-yl)ethanone,
(82) 2-((1-(3,4-dichlorophenylsulfonyl)-1,2,3,4-tetrahydroquinolin-2-yl)methoxy)-1-(6-(2-(pyrrolidin-1-yl)ethyl)-3,4-dihydropyrrolo[1,2-a]pyrazin-2(1H)-yl)ethanone,
(83) 3-(1-(4-chloro-2,5-dimethylphenylsulfonyl)piperidin-2-yl)-1-(6-(2-(4-methylpiperazin-1-yl)ethyl)-3,4-dihydropyrrolo[1,2-a]pyrazin-2(1H)-yl)propan-1-one,
(84) 2-((1-(4-methoxy-2,6-dimethylphenylsulfonyl)piperidin-2-yl)methoxy)-1-(6-(2-morpholinoethyl)-3,4-dihydropyrrolo[1,2-a]pyrazin-2(1H)-yl)ethanone,
(85) 1-(1-ethyl-3,4-dihydropyrrolo[1,2-a]pyrazin-2(1H)-yl)-3-(1-(4-methoxy-2,6-dimethylphenylsulfonyl)piperidin-2-yl)propan-1-one,
(86) 1-(1-ethyl-3,4-dihydropyrrolo[1,2-a]pyrazin-2(1H)-yl)-2-(((S)-1-(4-methoxy-2,6-dimethylphenylsulfonyl)piperidin-2-yl)methoxy)ethanone,
(87) 2-((1-(4-Methoxy-2,6-dimethylphenylsulfonyl)piperidin-2-yl)methoxy)-1-(3-(piperidin-1-ylmethyl)-5,6-dihydro-[1,2,4]triazolo[4,3-a]pyrazin-7(8H)-yl)ethanone,
(88) 2-((1-(4-Methoxy-2,6-dimethylphenylsulfonyl)piperidin-2-yl)methoxy)-1-(6-(pyridin-4-ylmethyl)-3,4-dihydropyrrolo[1,2-a]pyrazin-2(1H)-yl)ethanone,
(89) 2-((1-(4-Methoxy-2,6-dimethylphenylsulfonyl)piperidin-2-yl)methoxy)-1-(6-(pyridin-3-yl)-3,4-dihydropyrrolo[1,2-a]pyrazin-2(1H)-yl)ethanone,
(90) 1-(6-(Pyridin-4-ylmethyl)-3,4-dihydropyrrolo[1,2-a]pyrazin-2(1H)-yl)-2-(1-(3-(trifluoromethyl)phenylsulfonyl)piperidin-2-yl)ethanone,
(91) 4-(1-(4-Methoxy-2,6-dimethylphenylsulfonyl)piperidin-2-yl)-1-(6-(pyridin-4-ylmethyl)-3,4-dihydropyrrolo[1,2-a]pyrazin-2(1H)-yl)butan-1-one,
(92) 4-(1-(4-Methoxy-2,6-dimethylphenylsulfonyl)piperidin-2-yl)-1-(6-(pyridin-3-yl)-3,4-dihydropyrrolo[1,2-a]pyrazin-2(1H)-yl)butan-1-one,
(93) 1-(6-(Pyridin-3-yl)-3,4-dihydropyrrolo[1,2-a]pyrazin-2(1H)-yl)-2-(1-(3-(trifluoromethyl)phenylsulfonyl)piperidin-2-yl)ethanone,
(94) 3-(1-(4-Methoxy-2,6-dimethylphenylsulfonyl)piperidin-2-yl)-1-(6-(pyridin-3-yl)-3,4-dihydropyrrolo[1,2-a]pyrazin-2(1H)-yl)propan-1-one,
(95) 2-((1-(4-Methoxy-2,6-dimethylphenylsulfonyl)piperidin-2-yl)methoxy)-1-(6-(pyridin-4-yl)-3,4-dihydropyrrolo[1,2-a]pyrazin-2(1H)-yl)ethanone,
(96) 3-(1-(4-Methoxy-2,6-dimethylphenylsulfonyl)piperidin-2-yl)-1-(6-(pyridin-4-yl)-3,4-dihydropyrrolo[1,2-a]pyrazin-2(1H)-yl)propan-1-one,
(97) 1-(6-(Pyridin-3-ylmethyl)-3,4-dihydropyrrolo[1,2-a]pyrazin-2(1H)-yl)-2-(1-(3-(trifluoromethyl)phenylsulfonyl)piperidin-2-yl)ethanone,
(98) 1-(6-(2-(Pyridin-3-yl)ethyl)-3,4-dihydropyrrolo[1,2-a]pyrazin-2(1H)-yl)-2-(1-(3-(trifluoromethyl)phenylsulfonyl)piperidin-2-yl)ethanone,
(99) 3-(1-(4-Methoxy-2,6-dimethylphenylsulfonyl)piperidin-2-yl)-1-(6-(pyridin-4-ylmethyl)-3,4-dihydropyrrolo[1,2-a]pyrazin-2(1H)-yl)propan-1-one,
(100) 4-(1-(4-Methoxy-2,6-dimethylphenylsulfonyl)piperidin-2-yl)-1-(2-(pyridin-4-yl)-5,6-dihydroimidazo[1,2-a]pyrazin-7(8H)-yl)butan-1-one,
(101) 2-((1-(4-Methoxy-2,6-dimethylphenylsulfonyl)piperidin-2-yl)methoxy)-1-(6-(2-(pyridin-3-yl)ethyl)-3,4-dihydropyrrolo[1,2-a]pyrazin-2(1H)-yl)ethanone,
(102) 3-(1-(4-Methoxy-2,6-dimethylphenylsulfonyl)piperidin-2-yl)-1-(6-(2-(pyridin-3-yl)ethyl)-3,4-dihydropyrrolo[1,2-a]pyrazin-2(1H)-yl)propan-1-one,
(103) 4-(1-(4-Methoxy-2,6-dimethylphenylsulfonyl)piperidin-2-yl)-1-(6-(2-(pyridin-3-yl)ethyl)-3,4-dihydropyrrolo[1,2-a]pyrazin-2(1H)-yl)butan-1-one,
(104) 1-(2-(Pyridin-4-yl)-5,6-dihydroimidazo[1,2-a]pyrazin-7(8H)-yl)-2-(1-(3-(trifluoromethyl)phenylsulfonyl)piperidin-2-yl)ethanone,
(105) 4-(1-(4-Methoxy-2,6-dimethylphenylsulfonyl)piperidin-2-yl)-1-(6-(pyridin-3-ylmethyl)-3,4-dihydropyrrolo[1,2-a]pyrazin-2(1H)-yl)butan-1-one,
(106) 2-((1-(4-Methoxy-2,6-dimethylphenylsulfonyl)piperidin-2-yl)methoxy)-1-(6-(2-(pyridin-4-yl)ethyl)-3,4-dihydropyrrolo[1,2-a]pyrazin-2(1H)-yl)ethanone,
(107) 1-(6-(2-(Pyridin-4-yl)ethyl)-3,4-dihydropyrrolo[1,2-a]pyrazin-2(1H)-yl)-2-(1-(3-(trifluoromethyl)phenylsulfonyl)piperidin-2-yl)ethanone,
(108) 3-(1-(4-Methoxy-2,6-dimethylphenylsulfonyl)piperidin-2-yl)-1-(6-(2-(pyridin-4-yl)ethyl)-3,4-dihydropyrrolo[1,2-a]pyrazin-2(1H)-yl)propan-1-one,
(109) 4-(1-(4-Methoxy-2,6-dimethylphenylsulfonyl)piperidin-2-yl)-1-(6-(2-(pyridin-4-yl)ethyl)-3,4-dihydropyrrolo[1,2-a]pyrazin-2(1H)-yl)butan-1-one,
(110) 4-(1-(4-Methoxy-2,6-dimethylphenylsulfonyl)piperidin-2-yl)-1-(6-(pyridin-4-yl)-3,4-dihydropyrrolo[1,2-a]pyrazin-2(1H)-yl)butan-1-one,
(111) 2-((1-(4-Methoxy-2,6-dimethylphenylsulfonyl)piperidin-2-yl)methoxy)-1-(6-(pyridin-3-ylmethyl)-3,4-dihydropyrrolo[1,2-a]pyrazin-2(1H)-yl)ethanone,
(112) 2-((1-(4-Methoxy-2,6-dimethylphenylsulfonyl)piperidin-2-yl)methoxy)-1-(2-(pyridin-4-yl)-5,6-dihydroimidazo[1,2-a]pyrazin-7(8H)-yl)ethanone,
(113) 3-(1-(4-Methoxy-2,6-dimethylphenylsulfonyl)piperidin-2-yl)-1-(6-(pyridin-3-ylmethyl)-3,4-dihydropyrrolo[1,2-a]pyrazin-2(1H)-yl)propan-1-one,
(114) 3-(1-(4-Methoxy-2,6-dimethylphenylsulfonyl)piperidin-2-yl)-1-(2-(pyridin-4-yl)-5,6-dihydroimidazo[1,2-a]pyrazin-7(8H)-yl)propan-1-one,
(115) 2-((1-(4-Methoxy-2,6-dimethylphenylsulfonyl)piperidin-2-yl)methoxy)-1-(2-(2-(pyridin-4-yl)ethyl)-5,6-dihydroimidazo[1,2-a]pyrazin-7(8H)-yl)ethanone,
(116) 1-(2-(2-(pyridin-4-yl)ethyl)-5,6-dihydroimidazo[1,2-a]pyrazin-7(8H)-yl)-2-(1-(3-(trifluoromethyl)phenylsulfonyl)piperidin-2-yl)ethanone,
(117) 3-(1-(4-Methoxy-2,6-dimethylphenylsulfonyl)piperidin-2-yl)-1-(2-(2-(pyridin-4-yl)ethyl)-5,6-dihydroimidazo[1,2-a]pyrazin-7(8H)-yl)propan-1-one,
(118) 4-(1-(4-Methoxy-2,6-dimethylphenylsulfonyl)piperidin-2-yl)-1-(2-(2-(pyridin-4-yl)ethyl)-5,6-dihydroimidazo[1,2-a]pyrazin-7(8H)-yl)butan-1-one,
(119) 4-(1-(4-Methoxy-2,6-dimethylphenylsulfonyl)piperidin-2-yl)-1-(2-(pyridin-4-ylmethyl)-5,6-dihydroimidazo[1,2-a]pyrazin-7(8H)-yl)butan-1-one,
(120) 2-((1-(4-Methoxy-2,6-dimethylphenylsulfonyl)piperidin-2-yl)methoxy)-1-(2-(pyridin-4-ylmethyl)-5,6-dihydroimidazo[1,2-a]pyrazin-7(8H)-yl)ethanone, and
(121) 3-(1-(4-Methoxy-2,6-dimethylphenylsulfonyl)piperidin-2-yl)-1-(2-(pyridin-4-ylmethyl)-5,6-dihydroimidazo[1,2-a]pyrazin-7(8H)-yl)propan-1-one, in the form of an individual enantiomer or an individual diastereomer, in the form of the racemate, enantiomers, diastereomers, mixtures of the enantiomers or diastereomers, bases and/or salts of physiologically compatible acids.

The foregoing numbering of the individual species of the compounds of the present invention is retained in the following discussion of the invention, in particular in the description of the examples.

The compounds according to the invention exhibit an antagonistic action on the human B1R receptor or on the B1R receptor of rats. In one preferred embodiment of the invention, the compounds according to the invention exhibit an antagonistic action on both the human B1R receptor (hB1R) and the B1R receptor of rats (rB1R).

Particularly preferred are compounds which at a concentration of 10 µM in the FLIPR assay exhibit an inhibition on the human B1R receptor and/or on the B1R receptor of rats of at least 15%, 25%, 50%, 70%, 80% or 90%. Most particularly preferred are compounds which in a concentration of 10 µM exhibit an inhibition of at least 70%, especially at least 80%, and particularly preferably at least 90% on the human B1R receptor and on the B1R receptor of rats.

The agonistic or antagonistic action of compounds can be quantified on the bradykinin 1 receptor (B1R) of humans and rats with ectopically expressing cell lines (CHO K1 cells) and with the aid of a $Ca^{2+}$-sensitive dye (Fluo-4) in the fluorescent imaging plate reader (FLIPR). The figure in percent activation refers to the $Ca^{2+}$ signal after addition of Lys-Des-$Arg^9$-bradykinin (0.5 nM) and Des-$Arg^9$-bradykinin (100 nM). Antagonists result in a suppression of the $Ca^{2+}$ inflow after the addition of the agonist. Percent inhibition values are given in comparison to the maximum achievable inhibition. The compounds according to the invention act, for example, on the B1R which is implicated in various disease states. This means that the compounds of the invention are useful as pharmaceutically active substances in medicaments for the treatment and/or inhibition of such disease states.

The present invention therefore also relates to pharmaceutical compositions containing at least one substituted sulfonamide derivative according to the invention as well as optionally suitable additives and/or auxiliary substances and/or optionally further active substances. These pharmaceutical compositions are particularly suitable for treating pain, in particular acute, visceral, neuropathic, chronic pain and/or inflammatory pain. Moreover, these medicaments are also suitable for treating diabetes, diseases of the respiratory tract, inflammatory intestinal diseases, neurological diseases, inflammation of the skin, rheumatic diseases, septic shock, reperfusion syndrome, obesity, and as an angiogenesis inhibitor.

The pharmaceutical compositions according to the invention optionally also may contain suitable additives and/or auxiliary substances in addition to at least one substituted sulfonamide derivative according to the invention. Thus, carrier materials, fillers, solvents, diluents, coloring agents and/or binders, and can be administered as part of liquid pharmaceutical compositions in the form of injections for solution, drops or juices, or as part of solid or semi-solid pharmaceutical compositions in the form of granules, tablets, pellets, patches, capsules, plasters/spray plasters or aerosols. The choice of the auxiliary substances, etc. as well as the amounts thereof to be used, depend on whether the medicament is to be administered orally, parenterally, intravenously, intraperitoneally, intradermally, intramuscularly, nasally, buccally, rectally or topically, for example to the skin, mucous membranes or to the eyes. Suitable preparations for oral administration include tablets, pills, capsules, granules, drops, juices and syrups, while suitable preparations for parenteral, topical and inhalative administration include solutions, suspensions, easily reconstitutable dry preparations as well as sprays. Sulfonamide compounds according to the invention in depot form, in dissolved form or in a plaster, optionally with the addition of agents promoting penetration of the skin, are suitable for use in dosage forms intended for percutaneous administration. Orally or percutaneously administerable preparation forms may provide for delayed release of the substituted sulfonamide compounds according to the invention. The substituted sulfonamide compounds according to the invention also can be used in parenteral long-term depot forms, such as for example implants or implanted pumps. In principle other active constituents known to persons skilled in the art can be added to the pharmaceutical compositions according to the invention.

The amount of active constituent to be administered to the patient varies depending on the patient's weight, manner of administration, medical indications and the severity of the illness. Normally 0.00005 to 50 mg/kg, preferably 0.01 to 5 mg/kg of at least one substituted sulfonamide derivative according to the invention are administered.

In one preferred form of the pharmaceutical composition of the invention, the substituted sulfonamide derivative according to the invention is present in the form of an isolated stereoisomer (e.g., diastereomer or enantiomer), a racemate, or a non-equimolar or equimolar mixture of diastereomers and/or enantiomers.

B1R is involved in particular in the phenomenon of pain. Accordingly, the substituted sulfonamide compounds according to the invention can be used for the preparation of a medicament for treating pain, in particular acute, visceral, neuropathic or chronic pain. The invention accordingly also provides the use of a substituted sulfonamide derivative according to the invention for the preparation of a medicament for treating pain, in particular acute, visceral, neuropathic, chronic pain and/or inflammatory pain.

The present invention also provides the use of a substituted sulfonamide derivative according to the invention for the preparation of a medicament for treating diabetes, diseases of the respiratory tract, inflammatory intestinal diseases, neurological diseases, inflammation of the skin, rheumatic diseases, septic shock, reperfusion syndrome, obesity, and as an angiogenesis inhibitor.

In this connection it may be preferred in one of the above uses if a substituted sulfonamide derivative is present as an isolated diastereomer and/or enantiomer, as a racemate, or as a non-equimolar or equimolar mixture of the diastereomers and/or enantiomers.

The invention also provides a method for treating, in particular in one of the aforementioned medical indications, a non-human mammal or a person that requires treatment for pain, in particular chronic pain, by administration of a therapeutically effective dose of a substituted sulfonamide derivative according to the invention or a medicament according to the invention.

The invention further provides a method for treating pain, in particular one or more types of pain selected from the group consisting of acute, visceral, neuropathic, chronic and inflammatory pain, in a non-human mammal or a person that requires treatment, by administration of a therapeutically effective dose of a substituted sulfonamide derivative according to the invention or a medicament according to the invention.

The invention further provides a method for treating pain, in particular one or more types of pain selected from the group consisting of diabetes, diseases of the respiratory tract, inflammatory intestinal diseases, neurological diseases, inflammation of the skin, rheumatic diseases, septic shock, reperfusion syndrome, obesity and angiogenesis, in a non-human mammal or a person that requires treatment, by administration of a therapeutically effective dose of a substituted sulfonamide compound according to the invention or a medicament according to the invention.

The invention also provides a method for the preparation of the substituted sulfonamide compounds according to the invention as explained and illustrated in the following description and examples.

General Process for Preparing Substituted Sulfonamide Compounds of the Invention:

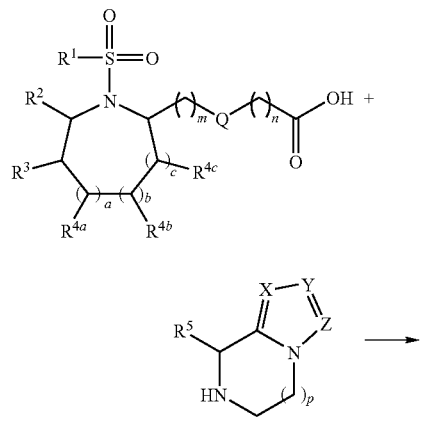

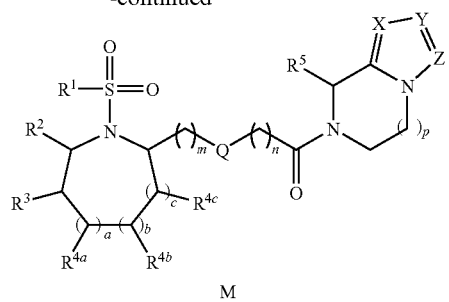

M

The carboxylic acids are reacted in an amide formation using primary or secondary amines in the presence of water-removing agents such as sodium or magnesium sulfate, phosphorus oxide or reagents such as for example CDI, DCC (optionally polymer-bound), TBTU, EDCI, PyBOP or PFPTFA, also in the presence of HOAt or HOBt and an organic base, for example DIPEA or pyridine, in an organic solvent such as THF, dichloromethane, diethyl ether, dioxane, DMF or acetonitrile, at temperatures from 0° C. to the reflux temperature, to form the final products of the general formula M.

General Process for the Preparation of the Acids:

Method I

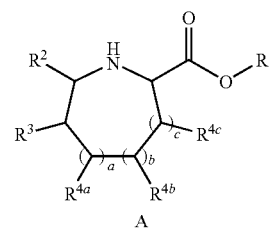

A

Method II

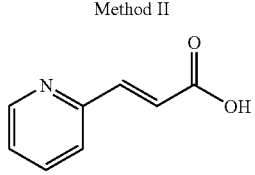

E

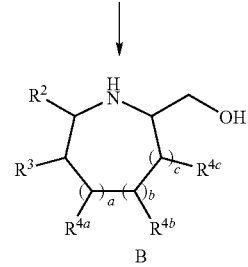

B

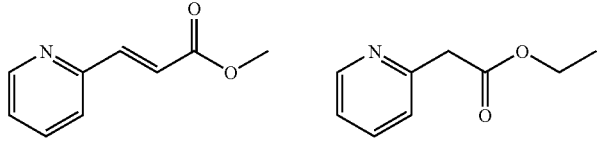

F     Method III     G

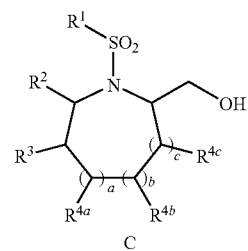

C

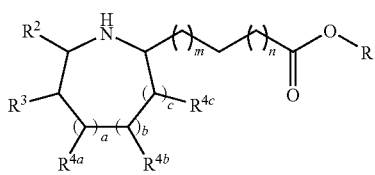

H

-continued

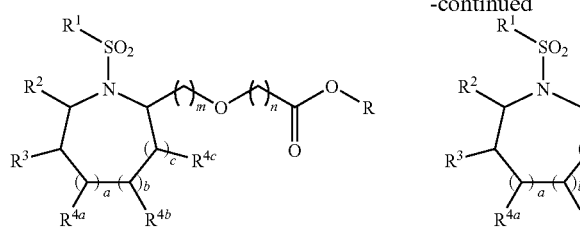

D

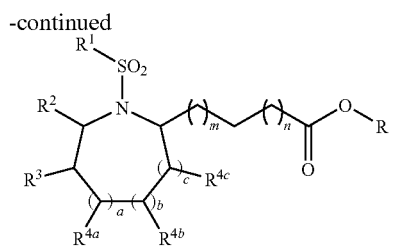

I

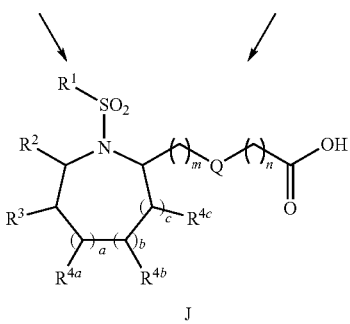

J

In Method I the racemic (R and S configuration) or enantiomer-pure (R or S configuration) amino acid esters A are reduced to an amino alcohol B using metal hydrides as reducing agents, for example $LiAlH_4$, $BH_3 \times DMS$ or $NaBH_4$ in an organic solvent such as THF or diethyl ether, at temperatures from 0° C. to the reflux temperature. The amino alcohols B are reacted further in a sulfonylation with sulfonyl chlorides, bromides or pentafluorophenolate $R^1SO_2X$ (X=Cl, Br, OPFP), optionally in the presence of an organic or inorganic base, for example potassium carbonate, sodium carbonate, sodium hydrogen carbonate, diisopropylethylamine, triethylamine, pyridine, dimethylaminopyridine, diethylamine or DBU, preferably in an organic solvent, for example acetone, acetonitrile, dichloromethane or tetrahydrofuran and at a temperature from 0° to the reflux temperature, to form the sulfonylated aminoalcohols C.

The sulfonylated aminoalcohols C are reacted in an alkylation reaction with halogenated ester derivatives using tetrobutylammonium chloride or bromide or tetrabutylammonium hydrogen sulfate in a phase transfer reaction using an organic solvent such as THF, toluene, benzene or xylene and inorganic bases such as potassium hydroxide, sodium hydroxide, sodium carbonate, sodium hydrogen carbonate, potassium carbonate or in the presence of an organic or inorganic base, conventional inorganic bases being metal alcoholates such as sodium methanolate, sodium ethanolate, potassium tert-butylate, lithium or sodium bases such as lithium diisopropylamide, butyllithium, tert-butyllithium, sodium methylate or metal hydrides such as potassium hydride, lithium hydride, sodium hydride, conventional organic bases being diisopropylethylamine, triethylamine, in an organic solvent such as dichloromethane, THF or diethyl ether, at 0° C. to the reflux temperature, to form the products of the general structure D.

In Method II 3-(pyridin-2-yl)acrylic acid E is esterified using water-extracting reagents, for example inorganic acids such as $H_2SO_4$ or phosphorus oxides or organic reagents such as thionyl chloride, in organic solvents such as THF, diethyl ether, methanol, ethanol or dichloromethane to the stage F, at temperatures from room temperature to the reflux temperature.

In Methods II and III the ester stages F and G are hydrogenated with hydrogen under normal pressure or excess pressure under conditions known to the person skilled in the art in organic solvents such as THF, chloroform and in the presence of catalysts such as platinum oxides, to form the intermediates H.

In Methods II-III the stage H is reacted further in a sulfonylation with sulfonyl chlorides, bromides or pentofluorophenolate $R^1SO_2X$ (X=Cl, Br, OPFP), optionally in the presence of an organic or inorganic base, for example potassium carbonate, sodium carbonate, sodium hydrogen carbonate, diisopropylethylamine, triethylamine, pyridine, diethylamine or DBU, preferably in an organic solvent, for example acetonitrile, dichloromethane or tetrahydrafuran, at 0° C. to the reflux temperature, to form the sulfonylated amino esters I.

In Methods I-III the ester derivatives D and I are reacted in an ester cleavage using organic acids such as trifluoroacetic acid or aqueous inorganic acids such as hydrochloric acid, or using aqueous inorganic bases such as lithium hydroxide, potassium hydroxide, sodium hydroxide, sodium carbonate, sodium hydrogen carbonate, potassium carbonate in organic solvents such as methanol, dioxane, dichloromethane, THF, diethyl ether or mixtures of these solvents, at 0° C. to room temperature, to form the acid stages of the general formula J.

General Process for Preparing the Amines:

Method I

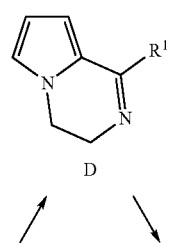

D

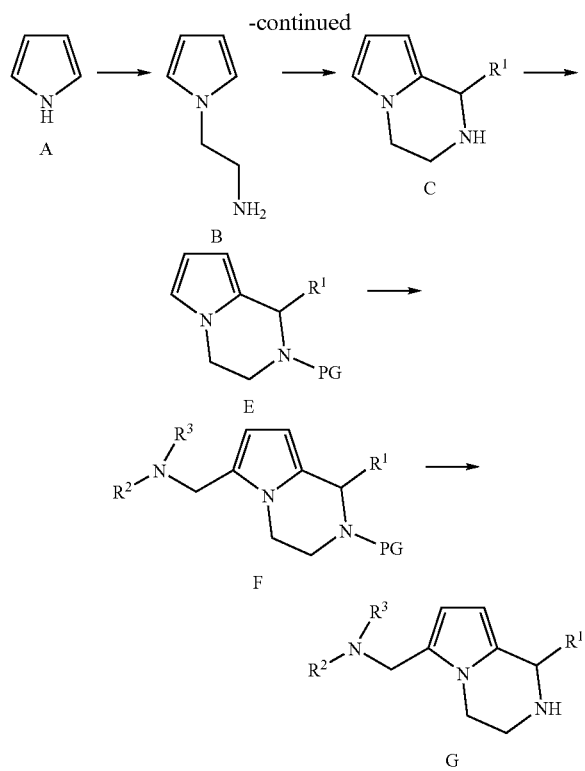

Pyrrole A is dissolved in a suitable solvent, such as for example ethanol, methanol, 2-butanone, DMSO, diethyl ether, water, benzene, toluene, THF, DCM, acetonitrile, acetone, DMF or pentane or a mixture of these solvents, and a suitable base is added, such as for example potassium hydroxide, sodium hydroxide, optionally in aqueous or alcoholic solution, potassium carbonate, potassium hexamethyldisilazane, sodium hydride, potassium hydride, sodium methanolate, sodium ethanolate, sodium tert.butylate or diisopropylethylamine, optionally with the addition of an auxiliary substance such as for example 18-crown-6,15-crown-5, tetrabutylammonium bromide or sulfate, benzyltriethylammonium chloride, 1-n-butyl-3-methylimidazolium tetrafluoroborate or DMAP, followed by reaction with the corresponding iodide, bromide or chloride compound to form the stage B.

The ring closure to form the 1,2,3,4-tetrahydropyrrolo[1,2-a]pyrazine C is carried out by reacting the 2-(1H-pyrrol-1-yl)ethanamine with the corresponding aldehyde in solvents such as acetic acid, ethanol, methanol, pyridine, benzene, toluene, DCM or a mixture of these solvents, optionally with the addition of benzotriazole, aluminium trichloride or p-toluenesulfonic acid and optionally with removal by azeotropic distillation of the water formed in the reaction. The reaction times can be between 1 and 48 hours and the reaction temperature can vary between 20° C. and 110° C.

The ring closure to form the 1,2,3,4-tetrahydropyrrolo[1,2-a]pyrazine stage C can however also be achieved by reacting the 2-(1H-pyrrol-1-yl)ethanamine with the corresponding carboxylic acid followed by reduction of the primarily formed cyclic imine D with reducing agents, such as for example sodium boron hydride.

Starting from 1,2,3,4-tetrahydropyrrolo[1,2-a]pyrazines, for further derivatisations on the pyrrole part the nitrogen in the piperidine part must if necessary be protected. Various protective groups are suitable for this purpose, such as for example butyloxycarbonyl (BOC), Cbz or Fmoc protective groups.

The introduction of the BOC protective group by means of di-tert.-butyl dicarbonate can be carried out in solvents such as for example dioxane, DCM, THF, DMF, water, benzene, toluene, methanol, acetonitrile or mixtures of these solvents, optionally with the addition of sodium hydroxide, triethylamine, diisopropylethylamine, sodium hydrogen carbonate, sodium carbonate or DMAP at temperatures between 0° C. and 100° C.

The Cbz protective group can be introduced by reacting benzyl chloroformate in solvents such as for example diethyl ether, THF, DMF, benzene, toluene, dioxane, water, acetone, ethyl acetate, DCM or chloroform, optionally with the addition of a base such as for example sodium carbonate, sodium hydrogen carbonate, potassium carbonate, sodium hydroxide or triethylamine, optionally with the addition of a coupling reagent, such as for example HOBt.

The Fmoc protective group is introduced by reacting 9H-fluoren-9-yl methyl-chloroformate in solvents such as for example DCM, DCE, diethyl ether, THF, dioxane, acetone, acetonitrile, DMF or water, optionally with the addition of a base, such as for example diisopropylethylamine, triethylamine, pyridine, N-methylmorpholine, sodium carbonate or sodium hydrogen carbonate and optionally under microwave irradiation.

The introduction of the aminomethyl substituent on the pyrrole ring is carried out via an aminoalkylation to form the stages F. For the aminoalkylation the corresponding aromatic compound can be reacted with formaldehyde and the corresponding amine in ethanol or methanol. A variant of this process uses the reaction of an iminium salt with the corresponding aromatic system to form the stage E. The iminium salt is obtained for example by cleavage of the corresponding aminal.

The aminal is formed by reacting the corresponding amine with formaldehyde. The reaction can be carried out in solvents such as for example water, methanol, ethanol, tert.-butanol, benzene, toluene, diethyl ether, dioxane, THF, chloroform, DCM, DMF, acetonitrile, dilute aqueous HCl solution or mixtures of these solvents, optionally with the addition of a base, such as for example potassium carbonate or sodium hydroxide.

The iminium salt is obtained by reacting the aminal with for example acetyl or benzoyl chloride, mesyl chloride, trimethylsilyl chloride or iodide, tetrachlorosilane or boron trifluoride etherate, in solvents such as for example carbon tetrachloride, chloroform, DCM, diethyl ether, DMF, acetonitrile, hexane or DME at a temperature between −80° C. and +25° C.

The subsequent aminoalkylation to the stages F can be carried out in solvents such as for example acetonitrile, THF, DCM, diethyl ether, toluene or benzene at temperatures between −78° C. and room temperature.

The aminoalkylated 5,6,7,8-tetrahydropyrrolo[1,2-a]pyrazine derivative G used as building block is obtained by cleavage of the corresponding protective group.

BOC protective groups can be split off for example by reaction with HCl in organic solvents such as dioxane, methanol, ethanol, acetonitrile or ethyl acetate, or by reaction with TFA or methanesulfonic acid in dichloromethane or THF, at a temperature from 0° C. to 110° C. (66) and a reaction time of 0.5 to 20 hours.

The Cbz protective group can be split off for example under acidic conditions. This acidic cleavage can be carried out for example by reaction with an HBr/glacial acetic acid mixture, a mixture of TFA in dioxane/water or HCl in methanol or ethanol. Also suitable however are reagents such as for example Me₃Sil in solvents such as for example DCM, chloroform or acetonitrile, BF₃ etherate with the addition of ethanethiol or Me₂S in solvents such as for example DCM, a mixture of aluminium chloride/anisole in a mixture of DCM and nitromethane, or triethylsilane/PdCl₂ in methanol with the addition of triethylamine. A further method is the hydrogenolytic cleavage of the protective group at elevated pressure or without the use of pressure, by means of catalysts such as for example Pd on charcoal, Pd(OH)₂, PdCl₂, Raney nickel or PtO₂ in solvents such as for example methanol, ethanol, 2-propanol, THF, acetic acid, ethyl acetate, chloroform, optionally with the addition of HCl, formic acid or TFA.

The Fmoc protective group is as a rule split off under basic conditions in solvents such as for example acetonitrile, DMF, THF, diethyl ether, methanol, ethanol, 1-octanethiol, DMC or chloroform. Suitable bases are for example diethylamine, piperidine, 4-aminomethylpiperidine, pyrrolidine, DBU, NaOH or LiOH. Reagents such as for example Ag₂O/MeI can however also be used.

Method II

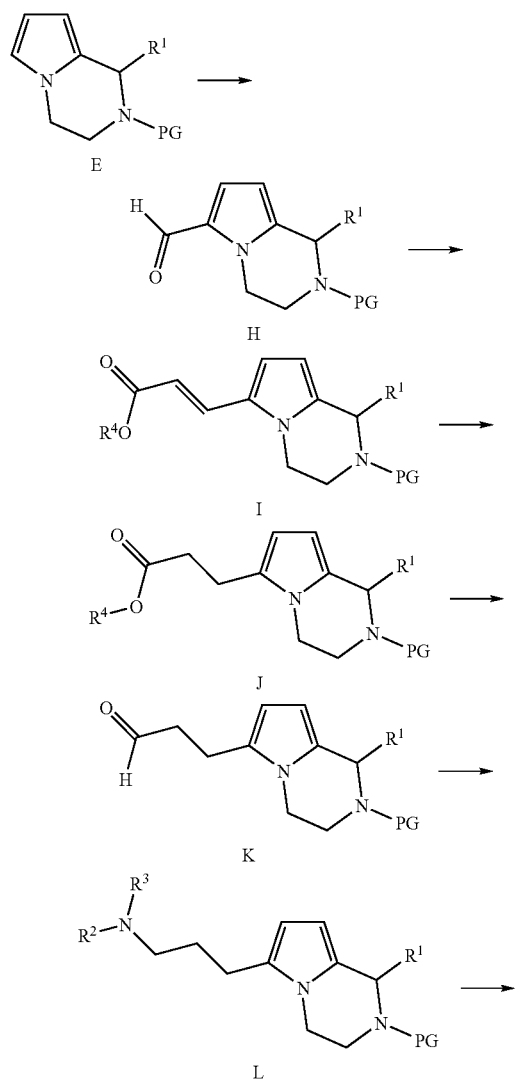

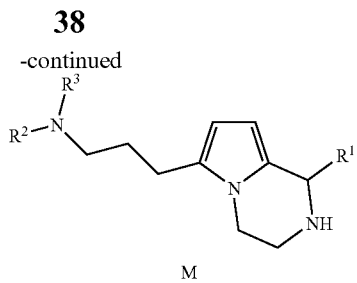

Starting from the protected 1,2,3,4-tetrahydropyrrolo[1,2] a]pyrazine E an aldehyde function is first of all introduced in the pyrrole ring in a Vilsmeier reaction. The Vilsmeier reaction is carried out by reacting HCN and HCl in CHCl₃ or diethyl ether or a mixture of these solvents. Further suitable reagents for the Vilsmeier reaction are DMF and oxalyl chloride or POCl₃ in solvents such as for example DCM or DCE, but also for example trimethoxyethane and TiCl₄ in DCM. N-(chloromethylene)-N-methylmethane aminium chloride with the addition of NaOH can also be used.

The subsequent Wittig reaction to the stages I, using phosphorylidene and a strong base, for example potassium tert.-butylate, n-butyllithium, s-butyllithium, phenyllithium, lithium diisopropylamide or lithium hexamethyldisilazide in organic solvents such as THF, diethyl ether, cyclohexane, toluene or a mixture of these solvents at a temperature from −78° C. to +30° C. yields the corresponding unsaturated esters.

The reduction of the double bond can be carried out hydrogenolytically or by adding suitable reducing agents. Heterogeneous catalysts as well as homogeneous catalysts can be used in the hydrogenolysis. Suitable heterogeneous catalysts are for example Pd on charcoal or Raney nickel in solvents such as for example methanol, ethanol, toluene, THF, ethyl acetate, acetic acid or in mixtures of these solvents, optionally with the addition of bases such as for example triethylamine. The reaction can be carried out at atmospheric pressure or at elevated pressure. A suitable homogeneous catalyst is for example (PPh₃)₃RhCl in benzene or toluene. A suitable reducing agent is for example NaBH₄ with the addition of NiCl₂ in solvents such as for example methanol, ethanol, THF or mixtures of these solvents.

The reduction of the ester group for the preparation of the stages K can be carried out by reduction with reducing agents such as for example DIBAHL-H in solvents such as for example THF, DCM, toluene or hexane at temperatures between −78° C. and room temperature.

In the subsequent reductive amination to the stages L the aldehyde is reacted with an amine and the imine thereby formed is then reduced to the amine. Suitable reducing agents are for example NaBH₄, NaBH(OAc)₃, NaCNBH₃, NH₄CNBH₃, polymer-bound cyanoboron hydride, borane-pyridine complex or triethylsilane. The reaction can be carried out in solvents such as for example methanol, ethanol, DCM, DCE, acetonitrile, THF, toluene, water, DMSO, DMF, 1-methyl-2-pyrrolidin-2-one or mixtures of these solvents. Auxiliary reagents such as for example HCl (gaseous or as an aqueous solution), acetic acid, TFA, ZnCl₂, 1,3-dimethyl-2-imidazolidine, MgSO₄, Na₂SO₄ or molecular sieves are also used. The imine that is formed can however also be converted to the amine by catalytic hydrogenation on catalysts such as for example PtO₂ or Pd/C in solvents such as for example methanol or ethanol.

The derivative M used as building block is obtained by cleavage of the corresponding protective group. BOC protective groups can be split off for example by reaction with HCl in organic solvents such as dioxane, methanol, ethanol, acetonitrile or ethyl acetate, or by reaction with TFA or methanesulfonic acid in dichloromethane or THF at a temperature from 0° C. to 110° C. and a reaction time of 0.5 to 20 hours. The Cbz protective group can be split off for example under acidic conditions. This acidic cleavage can be carried out for example by reaction with an HBr/glacial acetic acid mixture, a mixture of TFA in dioxane/water or HCl in methanol or ethanol. Also suitable however are reagents such as for example Me$_3$SiI in solvents such as for example DCM, chloroform or acetonitrile, BF$_3$ etherate with the addition of ethanethiol or Me$_2$S in solvents such as for example DCM, a mixture of aluminium chloride/anisole in a mixture of DCM and nitromethane or triethylsilane/PdCl$_2$ in methanol with the addition of triethylamine. A further method is the hydrogenolytic cleavage of the protective group at elevated pressure or without the use of pressure with the aid of catalysts such as for example Pd on charcoal, Pd(OH)$_2$ PdCl$_2$, Raney nickel or PtO$_2$ in solvents such as for example methanol, ethanol, 2-propanol, THF, acetic acid, ethyl acetate, chloroform, optionally with the addition of HCl, formic acid or TFA. The Fmoc protective group is as a rule split off under basic conditions in solvents such as for example acetonitrile, DMF, THF, diethyl ether, methanol, ethanol, 1-octanethiol, DCM or chloroform. Suitable bases are for example diethylamine, piperidine, 4-aminomethylpiperidine, pyrrolidine, DBU, NaOH or LiOH. Reagents such as for example Ag$_2$O/MeI can however also be used.

Method III

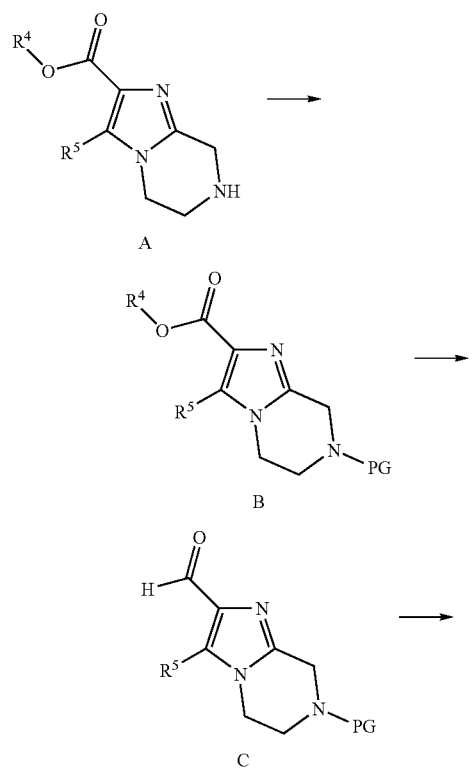

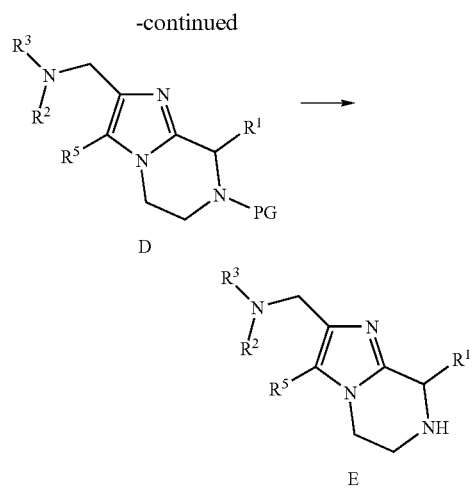

The nitrogen on the piperidine part of the alkyl 5,6,7,8-tetrahydroimidazo[1,2]a]-pyrazin-2-carboxylate of stage A first of all has to be protected for further reactions. Various protective groups, such as for example the BOC, Cbz or Fmoc protective group, are suitable for this purpose. The introduction of the BOC protective group by means of di-tert.-butyl dicarbonate can be carried out in solvents such as for example dioxane, DCM, THF, DMF, water, benzene, toluene, methanol, acetonitrile or mixtures of these solvents, optionally with the addition of sodium hydroxide, triethylamine, diisopropylethylamine, sodium hydrogen carbonate, sodium carbonate or DMAP at temperatures between 0° C. and 100° C. The Cbz protective group can be introduced by the reaction of benzyl chloroformate in solvents such as for example diethyl ether, THF, DMF, benzene, toluene, dioxane, water, acetone, ethyl acetate, DCM or chloroform, optionally with the addition of a base, such as for example sodium carbonate, sodium hydrogen carbonate, potassium carbonate, sodium hydroxide or triethylamine, optionally with the addition of a coupling reagent such as for example HOBt. The Fmoc protective group is introduced by reacting 9H-fluoren-9-yl methylchloroformate in solvents such as for example DCM, DCE, diethyl ether, THF, dioxane, acetone, acetonitrile, DMF or water, optionally with the addition of a base, such as for example diisopropylethylamine, triethylamine, pyridine, N-methylmorpholine, sodium carbonate or sodium hydrogen carbonate and optionally under microwave irradiation.

The reduction of the ester group for the preparation of the stages C can be carried out by reduction with reducing agents such as for example DIBAHL-H in solvents such as for example THF, DCM, toluene or hexane at temperatures between −78° C. and room temperature.

In the subsequent reductive amination for the preparation of the stages D, the aldehyde is reacted with an amine and the formed imine is then reduced to the amine. Suitable reducing agents are for example NaBH$_4$, NaBH(OAc)$_3$, NaCNBH$_3$, NH$_4$CNBH$_3$, polymer-bound cyano boron hydride, borane-pyridine complex or triethylsilane. The reaction can be carried out in solvents such as for example methanol, ethanol, DCM, DCE, acetonitrile, THF, toluene, water, DMSO, DMF, 1-methyl-2-pyrrolidin-2-one or mixtures of these solvents. Often auxiliary reagents such as for example HCl (gaseous or as an aqueous solution), acetic acid, TFA, ZnCl$_2$, 1,3-dimethyl-2-imidazolidine, MgSO$_4$, Na$_2$SO$_4$ or molecular sieves are also used. The formed imine can however also be converted to the amine by catalytic hydrogenation on catalysts such as for example $PtO_2$ or Pd/C in solvents such as for example methanol or ethanol.

The aminoalkylated derivative E used as building block is obtained by cleavage of the corresponding protective group. BOC protective groups can be split off for example by reaction with HCl in organic solvents such as dioxane, methanol, ethanol, acetonitrile or ethyl acetate, or by reaction with TFA or methanesulfonic acid in dichloromethane or THF at a temperature from 0° C. to 110° C. and a reaction time of 0.5 to 20 hours. The Cbz protective group can be split off for example under acidic conditions. This acidic cleavage can be carried out for example by reaction with an HBr/glacial acetic acid mixture, a mixture of TFA in dioxane/water or HCl in methanol or ethanol. Also suitable however are reagents such as for example $Me_3Sil$ in solvents such as for example DCM, chloroform or acetonitrile, $BF_3$ etherate with addition of ethanethiol or $Me_2S$ in solvents such as for example DCM, a mixture of aluminium chloride/anisole in a mixture of DMC and nitromethane, or triethylsilane/$PdCl_2$ in methanol with the addition of triethylamine. A further method is the hydrogenolytic cleavage of the protective group at elevated pressure or without pressure with the aid of catalysts such as for example Pd on charcoal, $Pd(OH)_2$, $PdCl_2$, Raney nickel or $PtO_2$ in solvents such as for example methanol, ethanol, 2-propanol, THF, acetic acid, ethyl acetate, chloroform, optionally with the addition of HCl, formic acid or TFA. The Fmoc protective group is as a rule split off under basic conditions in solvents such as for example acetonitrile, DMF, THF, diethyl ether, methanol, ethanol, 1-octanethiol, DCM or chloroform. Suitable bases are for example diethylamine, piperidine, 4-aminomethylpiperidine, pyrrolidine, DBU, NaOH or LiOH. Reagents such as for example $Ag_2O$/MeI can however also be used.

The invention is described in further detail hereinafter with reference to illustrative examples, which do not, however, limit the scope of the invention.

Pharmacological Investigations

1. Functional Investigation on the Bradykinin 1 Receptor (B1R)

The agonistic or antagonistic action of substances can be determined on the bradykinin 1 receptor (B1R) of humans and rats by means of the following assay. According to this assay the $Ca^{2+}$ inflow through the channel is quantified by means of a $Ca^{2+}$-sensitive dye (Fluo-4 type, Molecular Probes Europe BV, Leiden, Netherlands), in a Fluorescent Imaging Plate Reader (FLIPR, Molecular Devices, Sunnyvale, USA).

Method:

Chinese hamster ovary cells (CHO K1 cells) are used, which are stably transfected with the human B1R gene (hB1R cells, Euroscreen s.a., Gosselies, Belgium), or with the B1R gene of rats (rB1R cells, Axxam, Milan, Italy). For functional investigations these cells are plated out on black 96-well plates with a clear floor (BD Biosciences, Heidelberg, Germany) in a density of 20,000/25,000 cells/well. The cells are incubated overnight with 10 vol. % FBS (foetal bovine serum, Gibco Invitrogen GmbH, Karlsruhe, Germany) at 37° C. and 5% $CO_2$ in a culture medium (hB1R cells: Nutrient Mixture Ham's F12, Gibco Invitrogen GmbH, Karlsruhe, Germany; rB1R cells: D-MEM/F12, Gibco Invitrogen GmbH, Karlsruhe, Germany). The following day the cells are charged for 60 minutes at 37° C. with 2.13 µM Fluo-4 (Molecular Probes Europe BV, Leiden, Netherlands) in HBSS buffer (Hank's buffered saline solution, Gibco Invitrogen GmbH, Karlsruhe, Germany) together with 2.5 M probenecid (Sigma-Aldrich, Taufkirchen, Germany) and 10 mM HEPES (Sigma-Aldrich, Taufkirchen, Germany).

The plates are then washed twice with HBSS buffer and HBSS buffer is added which additionally contains 0.1% BSA (bovine serum albumin; Sigma-Aldrich, Taufkirchen, Germany), 5.6 mM glucose and 0.05% gelatin (Merck KGaA, Darmstadt, Germany). After further incubation for 20 minutes at room temperature the plates are used for the $Ca^{2+}$ measurement in the FLIPR. The $Ca^{2+}$-dependent fluorescence is measured both before and after the addition of substances ($\lambda_{ex}$=488 nm, $\lambda_{em}$=540 nm). The quantification is carried out by measuring the highest fluorescence intensity (FC, fluorescence counts) over time.

FLIPR Assay:

The FLIPR protocol consists of two substance additions. First, test substances (10 µM) are pipetted onto the cells and the $Ca^{2+}$ inflow is compared with the control (hB1R: Lys-Des-Arg9-bradykinin 0.5 nM; rB1R: Des-Arg9-bradykinin 100 nM). This gives the result in percent activation referred to the $Ca^{2+}$ signal after addition of Lys-Des-Arg9-bradykinin (0.5 nM), bzw. Des-Arg9-bradykinin (100 nM). After 10 minutes' incubation 0.5 nM Lys-Des-Arg9-bradykinin (hB1R) and 100 nM Des-$Arg^9$-bradykinin (rB1R) are applied and the inflow of $Ca^{2+}$ is likewise determined. Antagonists lead to a suppression of the $Ca^{2+}$ inflow. The percent inhibition compared to the maximum achievable inhibition is calculated. The compounds show a good activity on both human and rat receptors.

EXAMPLES

List of Abbreviations

Eq. Equivalent(s)
$Boc_2O$ Di-tert.-butyl dicarbonate
CDI 1,1'-carbonyl diimidazole
d Day(s)
DCE 1,2-dichloroethane
DCM Dichloromethane
DIBAL-H Diisobutyl aluminium hydride
DIPEA Diisopropylethylamine
DMF Dimethylformamide
DMAP 4-dimethylaminopyridine
DME 1,2-dimethoxyethane
wt. % Weight percent
h Hour(s)
HOAt 1-hydroxy-7-azabenzotriazole
HOBt 1-hydroxy-1H-benzotriazole
LAH Lithium aluminium hydride
M Molar
mbar Millibar
N Normal
NaOH Sodium hydroxide
RT Room temperature
B.p. Boiling point
THF Tetrahydrofuran
TFA Trifluoroacetic acid
Ms Methanesulfonyl Acid Building Blocks The following acid building blocks were synthesized and used for the synthesis of the compounds according to the invention:

| Acid building block | Structure | Name |
| --- | --- | --- |
| S1 | 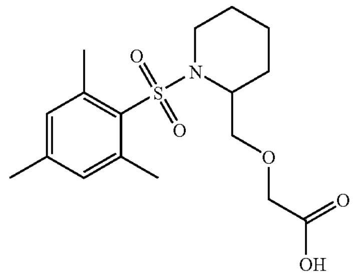 | (2-((1-mesitylsulfonyl)piperidin-2-yl)methoxy)acetic acid |
| S2 | 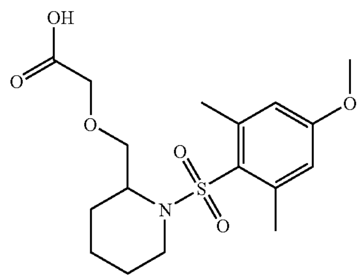 | 2-((1-(4-methoxy-2,6-dimethylphenylsulfonyl)piperidin-2-yl)methoxy)acetic acid |
| S3 | 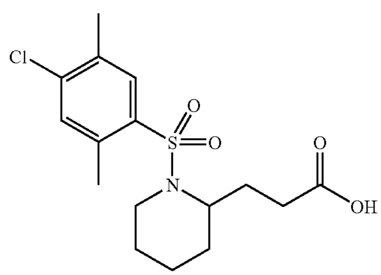 | 3-(1-(4-chloro-2,5-dimethylphenylsulfonyl)piperidin-2-yl)propionic acid |
| S4 | 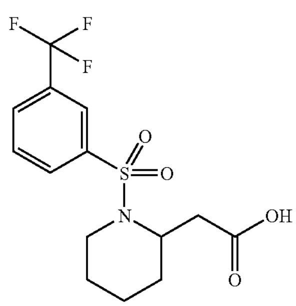 | 2-(1-3-(trifluoromethyl)phenylsulfonyl)piperidin-2-yl)acetic acid |
| S5 | 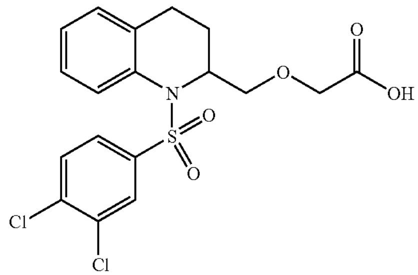 | 2-((1-(3,4-dichlorophenylsulfonyl)-1,2,3,4-tetrahydroquinolin-2-yl)methoxy)acetic acid |

-continued

| Acid building block | Structure | Name |
|---|---|---|
| S6 | 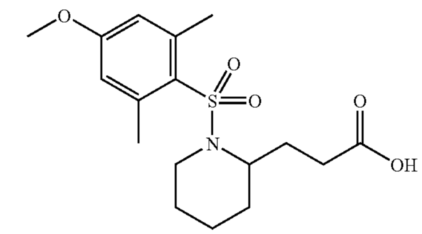 | 3-(1-(4-Methoxy-2,6-dimethylphenylsulfonyl)piperidin-2-yl)propanoic acid |
| S7 | 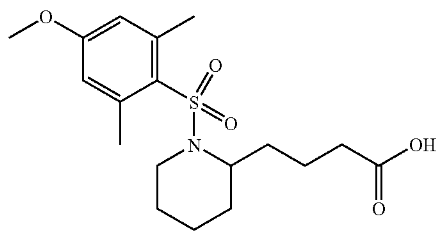 | 4-(1-(4-Methoxy-2,6-dimethylphenylsulfonyl)piperidin-2-yl)butanoic acid |
| S8 | 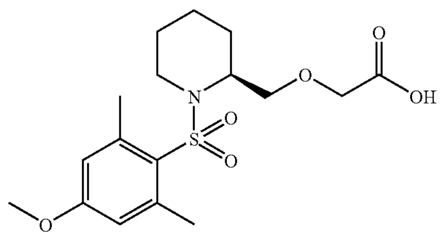 | (S)-2-((1-(4-Methoxy-2,6-dimethylphenylsulfonyl)piperidin-2-yl)methoxy)acetic acid |

Preparation of 2-((1-mesitylsulfonyl)piperidin-2-yl)methoxy)acetic acid S1

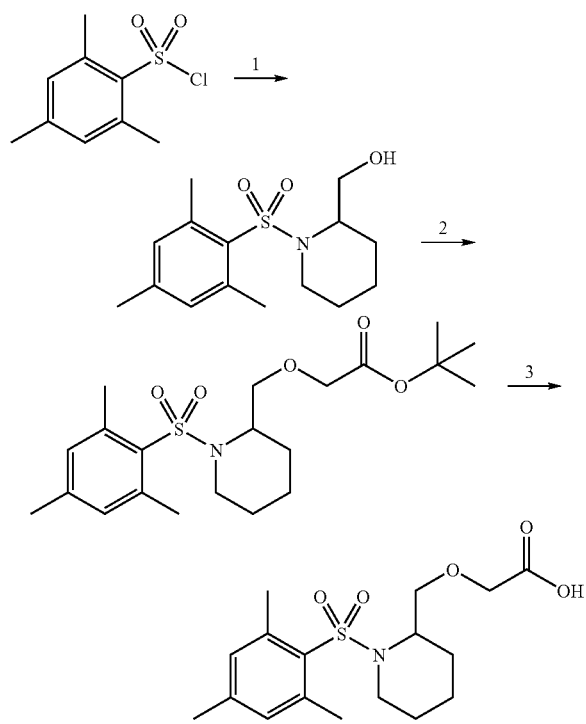

Stage 1. Triethylamine (14.4 ml, 104.2 mmole) was added to a solution of the 2-(hydroxymethyl)-piperidine (10 g, 86.8 mmole) in DCM (400 ml) and cooled using an ice bath. 2,4,6-trimethylbenzene-1-sulfonyl chloride (22.8 g, 104.2 mmole) dissolved in DCM (90 ml) was then added and the mixture was stirred for 4 hours at RT. The mixture was first hydrolysed with water and then made alkaline with sodium hydrogen carbonate solution. The organic phase was separated and the aqueous phase was extracted with DCM. The combined organic phases were dried over sodium sulfate, filtered, and the solvent was distilled off. The crude product was purified by column chromatography (silica gel, hexane/diethyl ether 9:1→1:1)

Stage 2. n-Bu$_4$NHSO$_4$ (1.5 g, 6.4 mmole) was added to a solution of tert.-butyl bromoacetate (13.62 ml, 93 mmole) in toluene (300 ml), cooled to 0° C., following which aqueous 50% NaOH (300 ml) and then 1-(mesitylsulfonyl)piperidin-2-yl)methanol (13.15 g, 44.2 mmole) were added. The reaction mixture was vigorously stirred for 3 hours at RT. The phases were separated and the aqueous phase was extracted twice more with diethyl ether (200 ml). The combined organic phases were dried with sodium sulfate and the organic solvent was distilled off. The crude product was purified by column chromatography (silica gel, hexane→hexane/diethyl ether 2:1). Yield: 15.4 g, 84%.

Stage 3. The tert.-butyl 2-((1-(mesitylsulfonyl)piperidin-2-yl)methoxy)acetate (15.4 g, 37.4 mmole) in a solution of TFA (57.7 ml) and DCM (265 ml) was stirred for 4 hours at RT. After completion of the reaction the solvent was distilled off on a rotary evaporator and the remaining TFA was removed by evaporating twice with toluene (200 ml). The residue was washed with diisopropyl ether. Yield: 11.5 g, 86.4%.

Preparation of 2-((1-(4-methoxy-2,6-dimethylphenyl-sulfonyl)piperidin-2-yl)methoxy)acetic acid S2

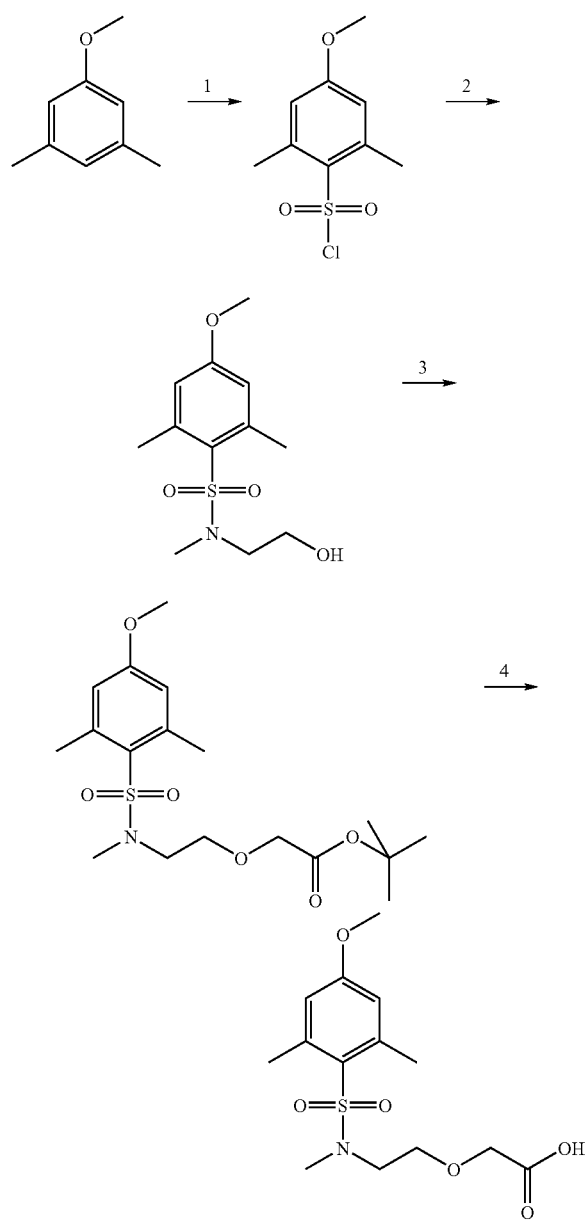

Stage 1. A solution of 3,5-dimethylanisole (102.5 g, 753 mmole) in DCM (1000 ml) was cooled to 0° C. A solution of chlorosulfonic acid (251 ml, 3763 mmole) in DCM (250 ml) was added dropwise to this solution. After 10 minutes' reaction time the reaction solution was added to an ice bath (1 litre), and the phases were separated and extracted once more with DCM (250 ml). The combined organic phases were washed with water (1000 ml) and saturated sodium chloride solution (1 litre), dried over $Na_2SO_4$ and concentrated. The product was purified by column chromatography on silica gel (heptane/DCM 5:1). Yield: 63.5 g, 36%.

Stage 2. 2-piperidinemethanol (8.50 g, 73.8 mmole) was suspended in acetone (350 ml), $K_2CO_3$ (20.40 g, 147.6 mmole) and 4-methoxy-2,6-dimethylbenzene-1-sulfonyl chloride (19.05 g, 81.2 mmole) were added in succession, and the reaction solution was stirred overnight at 50° C. After cooling to RT, the reaction solution was filtered and the filtrate was concentrated by evaporation to dryness under reduced pressure. The crude product was used without further purification in the next stage. Yield: 27.25 g, >100%.

Stage 3. n-$Bu_4NCl$ (7.52 g, 27.1 mmole) was added to a solution of (1-(4-methoxy-2,6-dimethylphenylsulfonyl)piperidin-2-yl)methanol (27.2 g, max. 73.8 mmole) in toluene (150 ml) and DCM (150 ml). The reaction solution was cooled to 0° C. and NaOH solution (35%, 300 ml) was added. Tert.-butyl bromoacetate (17.8 ml, 122 mmole) was added dropwise to this solution and then stirred for 3 hours at RT. The organic phase was separated and washed three times with water (300 ml), dried over sodium sulfate, and concentrated. The crude product was purified by column chromatography on silica gel (heptane/ethyl acetate 3:1). Yield: 26.8 g, 85% over 2 stages.

Stage 4. NaOH (6 M, 200 ml, 1200 mmole) was added to a solution of tert.-butyl 2-((1-(4-methoxy-2,6-dimethylphenyl-sulfonyl)piperidin-2-yl)methoxy)acetate (26.8 g, 62.7 mmole) in THF (200 ml) and methanol (200 ml). The reaction mixture was stirred at RT. After 1 hour the organic solvent was distilled off on a rotary evaporator and HCl (6 M, 210 ml) was added at 0° C. The aqueous phase was extracted with DCM (200 ml) and ethyl acetate (200 ml). The combined organic phases were dried over sodium sulfate and concentrated. Diisopropyl ether was added twice and evaporated. Yield: 21.92 g, 94%.

Preparation of 3-(1-(4-chloro-2,5-dimethylphenylsulfonyl)piperidin-2-yl)propionic acid S3

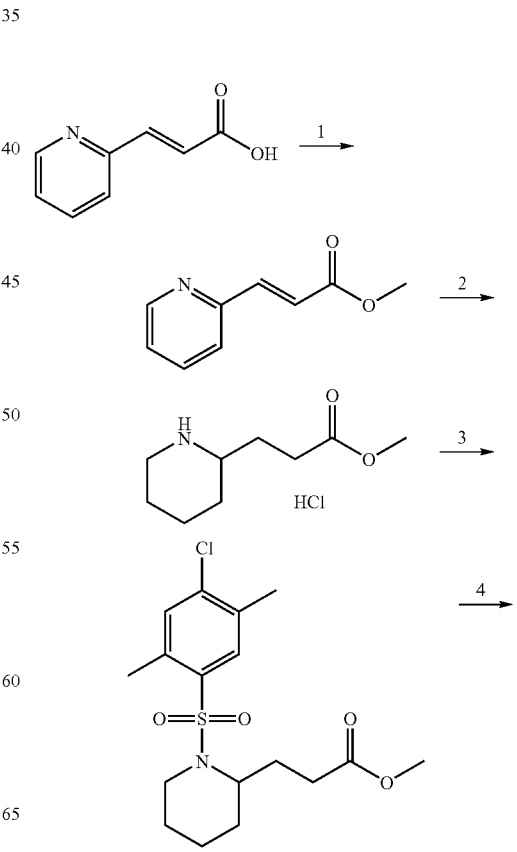

Preparation of 2-(1-(3-trifluoromethyl)phenyl-sulfonyl)piperidin-2-yl)acetic acid S4

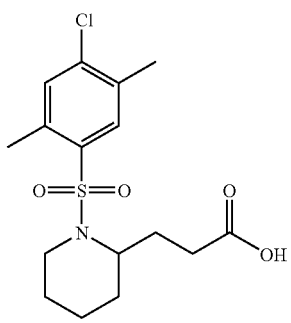

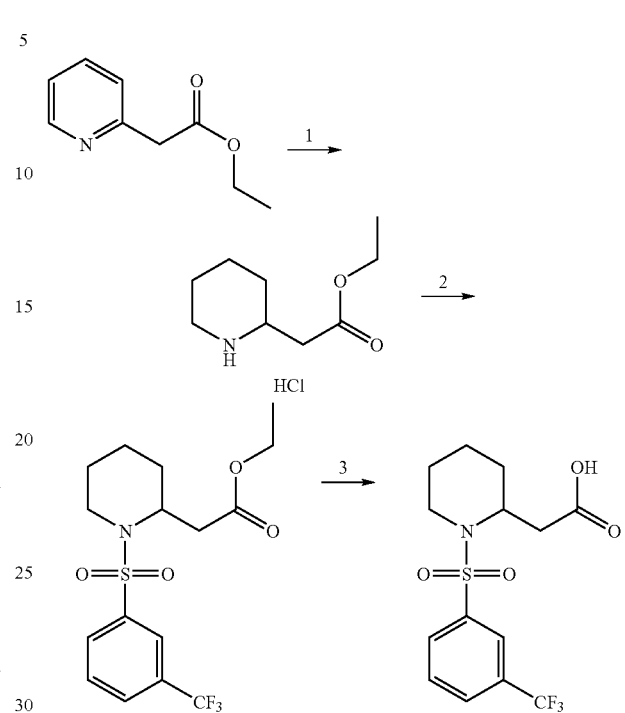

Stage 1. H$_2$SO$_4$ (12.8 ml, 240 mmole) was added to a solution of 3-(2-pyridyl)-acrylic acid (23.88 g, 160 mmole) in methanol (750 ml). The reaction mixture was heated overnight under reflux and, after cooling to RT, was poured into saturated aqueous NaHCO$_3$ solution (1 ml). The methanol was removed on a rotary evaporator and the aqueous phase was extracted twice with ethyl acetate (400 ml). The organic phase was washed with saturated sodium chloride solution (500 ml), dried over sodium sulfate, and concentrated. The crude product was used without further purification in the next stage. Yield: 22.19 g, 85%.

Stage 2. Methyl-3-(pyridin-2-yl)acrylate (22.15 g, 136 mmole) was dissolved in THF (300 ml) and chloroform (10.9 ml), and PtO$_2$ (3.08 g, 13.6 mmole, 0.1 equiv.) was added under a nitrogen atmosphere. The solution was first flushed for 10 minutes with nitrogen and then stirred overnight under a H$_2$ atmosphere (8 bar). The solution was cooled, first of all flushed again with nitrogen, the catalyst was removed by filtration through filter earth, flushed further with DCM, and the filtrate was concentrated by evaporation to dryness in vacuo. The methyl 3-(piperidin-2-yl)propionate hydrochloride was used without further purification in the next stage. Yield: 27.95 g, 99%.

Stage 3. A solution of triethylamine (14.7 ml, 104.5 mmole) dissolved in DCM (150 ml) was added to a solution of methyl 3-(piperidin-2-yl)propionate hydrochloride (8.69 g, 41.8 mmole) and 4-chloro-2,5-dimethylbenzenesulfonyl chloride (10 g, 41.8 mmole) in DCM. The reaction mixture was stirred overnight at RT and then washed with HCl (1 M, 300 ml). The organic phase was dried over sodium sulfate and concentrated. The crude product was purified by column chromatography on silica gel (heptane/ethyl acetate 6:1 to 3:1). Yield: 12.82 g, 82%.

Stage 4. Aqueous NaOH solution (6 M, 100 ml) was added to a solution of methyl 3-(1-(4-chloro-2,5-dimethylphenyl-sulfonyl)piperidin-2-yl)propionate (12.82 g, 34.3 mmole) in THF (100 ml). After 1 hour's reaction time the solvent was removed on a rotary evaporator and the solution was cooled to 0° C. HCl (6 M, 100 ml) was added and the mixture was extracted with ethyl acetate. The organic phase was dried over sodium sulfate and concentrated. Yield: 12.36 g, 100%.

Stage 1. Ethyl 2-(pyridin-2-yl)acetate (24.51 g, 148.4 mmole) was dissolved in ethanol (130 ml) and PtO$_2$ (3.37 g, 14.84 mmole, 0.1 equiv.) and chloroform (20 ml) were added. The suspension was stirred overnight at 40° C. under a H$_2$ atmosphere (8 bar). According to a DC check (silica gel, DCM/methanol 95:5) the reaction had not gone to completion, so that further chloroform (15 ml) was added and the mixture was stirred at 40° C. for a further 2 days under a H$_2$ atmosphere (8 bar) (DC check). After cooling the mixture, the catalyst was removed by filtering through filter earth and the filtrate was concentrated by evaporation to dryness in vacuo. The ethyl 2-(piperidin-2-yl)acetate hydrochloride was used without further purification in the next stage. Yield: 31.51 g>100%.

Stage 2. The ethyl 2-(piperidin-2-yl)acetate hydrochloride (7.5 g, max. 36.1 mmole) was dissolved in DCM (225 ml) and triethylamine (11 ml, 78.3 mmole) was added. 3-(trifluoromethyl)benzene-1-sulfonyl chloride (9.72 g, 39.7 mmole) was then added dropwise and stirred overnight at RT. After completion of the reaction (DC check, DCM/methanol 98:2) the reaction mixture was diluted with DCM (275 ml) and washed successively with KHSO$_4$ solution (0.5 M, 500 ml) and saturated sodium chloride solution (500 ml). The organic phase was dried over sodium sulfate and concentrated. The crude product was purified by column chromatography on silica gel (DCM). Yield: 10.45 g, 76% over 2 stages.

Stage 3. The ethyl-2-(1-(3-trifluoromethyl)phenylsulfonyl)piperidin-2-yl)acetate (10.45 g, 27.5 mmole) was dissolved in a mixture of methanol (150 ml), dioxane (40 ml) and aqueous NaOH solution (4 M, 41.3 ml, 165.2 mmole, 6 equiv.) and stirred overnight. After completion of the reaction (DC check, DCM/methanol 95:5) the solution was concentrated. The crude product was taken up in ethyl acetate (600 ml) and KHSO$_4$ solution (0.5 M, 600 ml) was added. The aqueous phase was extracted once more with ethyl acetate (100 ml) and the combined organic phases were washed with saturated sodium chloride solution (500 ml), dried over sodium sulfate and concentrated. Yield: 9.4 g, 97%.

Preparation of 2-((1-(3,4-dichlorophenylsulfonyl)-1,2,3,4-tetrahydroquinolin-2-yl)methoxy)acetic acid S5

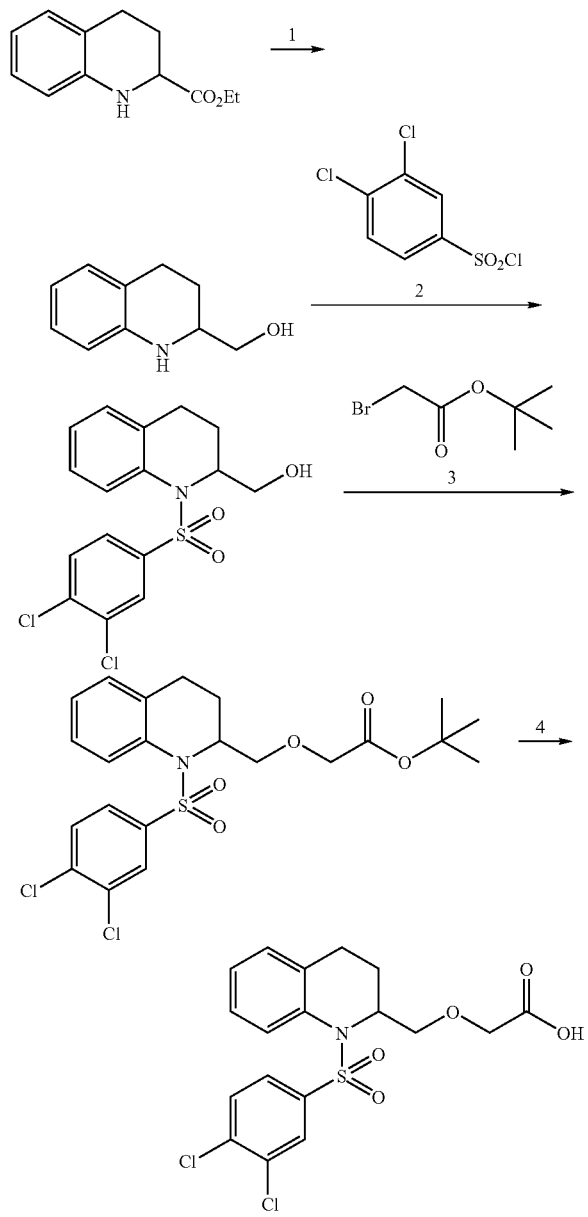

Stage 1. Ethyl 1,2,3,4-tetrahydroquinoline-2-carboxylate (25 mmole) in THF (5 ml/mole) was added dropwise at 0° C. to a suspension of LAH (2 equiv.) in THF (50 ml). The reaction mixture was stirred for 1 hour at RT and then heated for 4 hours under reflux. After adding aqueous saturated sodium sulfate solution the mixture was filtered and the organic solvent was removed in vacuo. The product was purified by column chromatography (3:7 ethyl acetate/hexane). Yield: 50%.

Stage 2. Pyridine (5 equiv.) DMAP (0.5 equiv.) and 3,4-dichlorobenzenesulfonyl chloride (1.2 equiv.) dissolved in DCM (50 ml) were added to a suspension, cooled to 0° C., of the alcohol (16 mmole) in DCM (5 ml/mmole). After stirring at 0° C. for 5 hours, DCM was added and the mixture was washed with aqueous copper sulfate solution, water and saturated sodium chloride solution. After drying over sodium sulfate and filtration, the solvent was removed in vacuo. The product was purified by column chromatography (5:95 ethyl acetate/DCM). Yield: 80%.

Stage 3. A solution of the sulfonamide (16 mmole) dissolved in THF (100 ml) was added dropwise while stirring to a suspension, cooled to 0° C., of NaH (2 equiv.) in THF (300 ml). After stirring for 45 minutes at this temperature, a solution of tert.-butyl bromoacetate (1.5 equiv.) in THF (50 ml) was added. The reaction mixture was heated for 20 hours at 50° C. The reaction mixture was then cooled to 0° C., ice was added, and the mixture was extracted with ethyl acetate. The organic phase was washed with aqueous saturated sodium chloride solution and dried over sodium sulfate. After filtration the solvent was removed in vacuo. The product was purified by column chromatography (1:9 ethyl acetate/hexane). Yield: 50%.

Stage 4. TFA (13 equiv.) was added at a temperature of 0° C. while stirring to a solution of the tert.-butyl ester (1 equiv.) in DCM (10 ml/mmole). After stirring the mixture for 3 hours at 0° C. the solvent was removed in vacuo. The crude product was used without further working-up.

Preparation of 3-(1-(4-Methoxy-2,6-dimethylphenylsulfonyl)piperidin-2-yl)propanoic acid S6

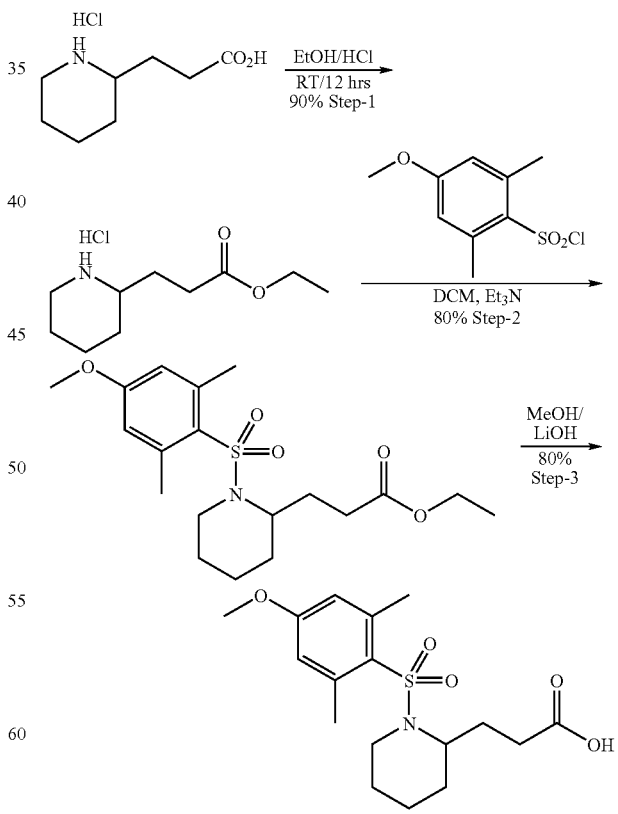

Procedure for Step-1:
3-Piperidin-2-yl-propionic acid hydrochloride (5 g) was treated with ethanol (200 ml) saturated with HCl gas at 0° C.

and the resulting reaction mixture was stirred at ambient temperature for 16 hrs (monitored by LCMS). Solvent was completely evaporated under reduced pressure and the crude material was used directly in the next step without any further purification. Yield: 90%

Procedure for Step-2:

To a dichloromethane solution (60 ml) of the ester (20 mmol) was added 4-Methoxy-2,6-dimethylbenzenesulfonyl chloride (25 mmol) and the resulting reaction mixture was cooled to 0° C. To this cold reaction mixture was added triethyl amine (60 mmol) dropwise over a period of 15 minutes. The reaction was stirred at this temperature for 4 hrs (monitored by TLC). After complete consumption of starting material, reaction mixture was diluted with DCM, washed successively with water and brine and finally dried over sodium sulfate. Evaporation of the organic layer under reduced pressure gave the crude sulfonamide which was purified by column chromatography (9:1 Ethyl acetate in hexane). Yield: 80%

Procedure for Step-3:

To the ester (9 mmol) obtained from step-2 was added a mixture of methanol-$H_2O$ (3:1, 90 ml) at R.T and the reaction mixture was cooled to 0° C. To this cold reaction mixture was added LiOH (2 eqv) and the resulting solution was stirred at ambient temperature for 16 hrs. Solvent was completely evaporated under reduced pressure, residue dissolved in water, washed with dichloromethane and the aqueous layer was acidified carefully with 1(N)HCl. It was extracted with ethyl acetate, washed successively with water and brine and finally dried over sodium sulfate. Evaporation of the organic layer gave the pure acid. Yield: 80%

Preparation of 4-(1-(4-Methoxy-2,6-dimethylphenylsulfonyl)piperidin-2-yl)butanoic acid S7

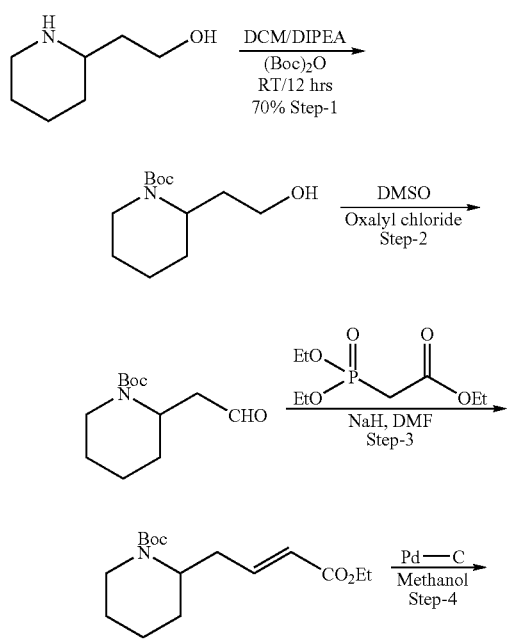

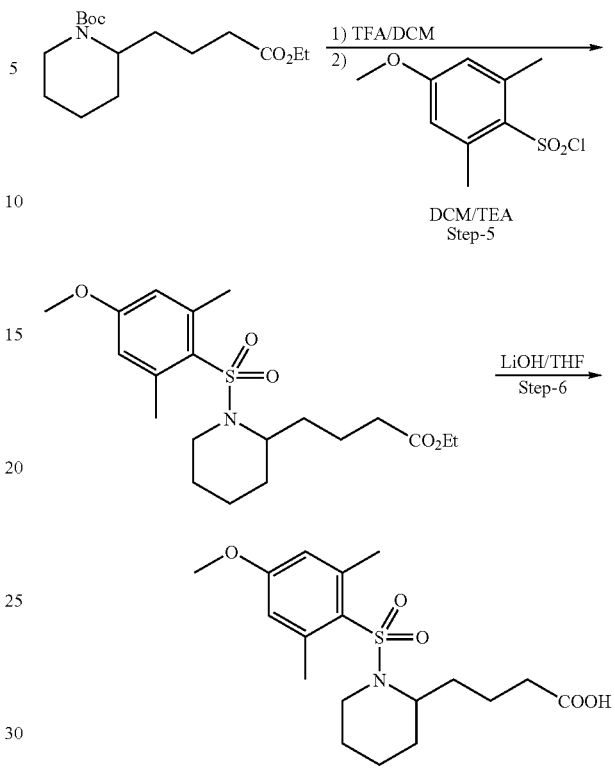

Procedure for Step-1:

To a dichloromethane solution (5 ml/mmol) of piperidine-2-ethanol (1 eqv) was added DIPEA (1.5 eqv) and boc-anhydride (1.2 eqv) at 0° C. and the resulting reaction mixture was stirred at 25° C. for 12 hrs. Reaction mixture was diluted with dichloromethane, organic layer was washed successively with water and brine and finally dried over sodium sulfate. Organic layer was evaporated under reduced pressure to get the crude product which was purified by column chromatography. Yield: 70%

Procedure for Step-2:

To a dichloromethane solution (3 ml/mmol) of oxalyl chloride (1.1 eqv) was added DMSO (2 eqv) at −78° C. under argon atmosphere and the resulting reaction mixture was stirred at this temperature for 15 minutes. To this cold reaction mixture was added boc-protected alcohol (1 eqv) obtained from step-1 in DCM (3 ml/mmol) dropwise and it was stirred at this temperature for further 1 hr. Triethyl amine (5 eqv) was added to the reaction, it was slowly brought to ambient temperature and was stirred at this temperature for 1 hr. Reaction mixture was diluted with DCM, organic layer was washed successively with saturated aqueous ammonium chloride, water, brine and finally dried over sodium sulfate. Evaporation of organic layer under reduced pressure gave the crude product which was used directly in the next step without any further purification. Yield: 80% (crude)

Procedure for Step-3:

To a cold (0° C.) suspension of 60% NaH (1.1 eqv) in dry THF (5 ml/mmol) was added slowly a solution of triethyl phosphonoacetate (11 eqv) in THF (5 ml/mmol) and the resulting reaction mixture was stirred at 25° C. for 30 minutes. It was then cooled to 0° C. and the aldehyde obtained from step-2 (1 eqv) in dry THF (5 ml/mmol) was added dropwise maintaining the same temperature and the reaction mixture was stirred at 25° C. for 16 hrs by which time starting material was completely consumed. It was quenched with ice and brine solution, aqueous layer was extracted with ethyl acetate and the organic layer was washed successively with water and brine. It was dried over sodium sulfate and evaporated under reduced pressure to get the crude product which was purified by column chromatography (50% ethyl acetate in hexane). Yield: 51%

Procedure for Step-4:

A solution of the ester (1 eqv) obtained from step-3 in MeOH (5 ml/mmol) was deoxygenated with argon for 15 minutes followed by the addition of 10% Pd/C (50% by weight) and the resulting reaction mixture was hydrogenated under atmospheric pressure for 1 hr (monitored by LCMS). It was filtered through celite bed, residue washed with methanol mixture was cooled to 0° C. To this cold reaction mixture was added LiOH (2 eqv), and the resulting solution was stirred at ambient temperature for 16 hrs. The solvent was completely evaporated under reduced pressure, the residue was dissolved in water, washed with dichloromethane, and the aqueous layer was acidified carefully with 1(N)HCl. It was extracted with ethyl acetate, washed successively with water and brine and finally dried over sodium sulfate. Evaporation of the organic layer gave acid which was finally purified by column chromatography. Yield: 60% (crude)

Preparation of (S)-2-((1-(4-Methoxy-2,6-dimethylphenylsulfonyl)piperidin-2-yl)methoxy)acetic acid S8

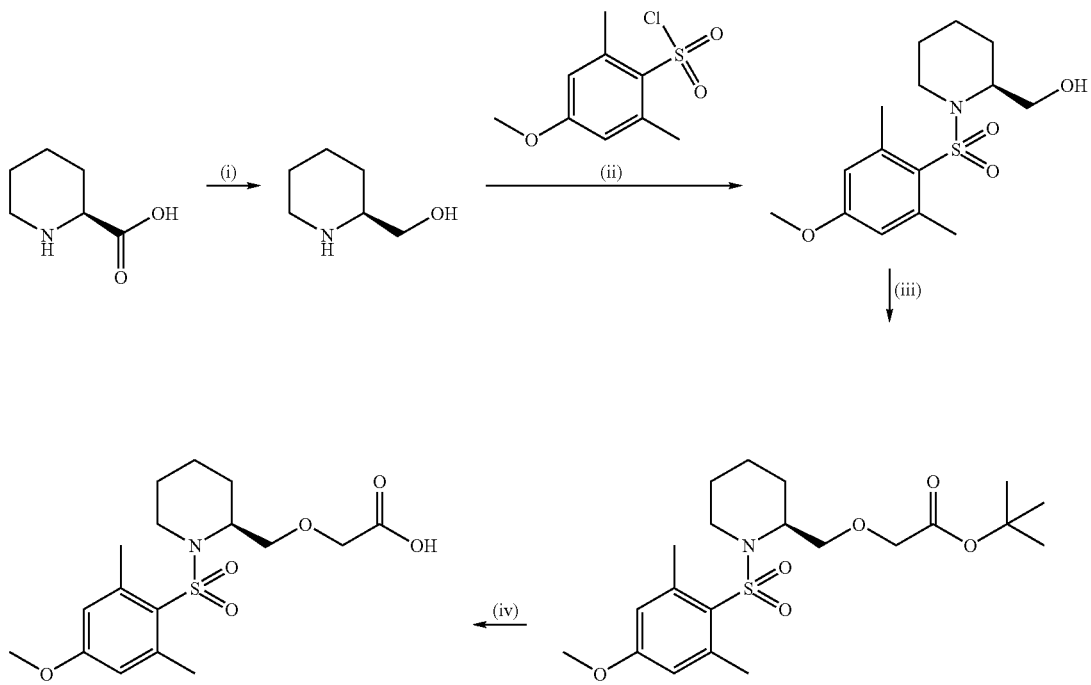

and the combined organic layer was evaporated completely to get the crude product which was used directly in the next step without any further purification. Yield: 90% (crude)

Procedure for Step-5:

To a dichloromethane solution of BOC-protected ester (1 eqv) obtained from step-4 was added with 20% TFA in DCM (5 ml/mol) at 0° C. and the resulting reaction mixture was stirred at 25° C. for 3 hrs (monitored by TLC). Solvent was completely evaporated, dried properly to remove traces of TFA and the crude material was again taken in dichloromethane and cooled to 0° C. To this cold reaction mixture was added TEA (4 eqv), 4-Methoxy-2,6-dimethylbenzenesulfonyl chloride and the resulting reaction mixture was stirred at 25° C. for 3 hrs (monitored by TLC). It was diluted with dichloromethane, the organic layer was successively washed with water and brine and finally dried over sodium sulfate. Evaporation of the organic layer under reduced pressure gave the crude product which was purified by column chromatography. Yield: 60% (crude)

Procedure for Step-6

To the ester (12 mmol) obtained from step-5 was added a mixture of THF-H$_2$O (8:2, 220 ml) at RT, and the reaction Step (i): (S)-Piperidin-2-ylmethanol To a stirred solution of L-Pipecolinic acid (2 g, 15.5 mmol) in dry tetrahydrofuran (20 ml) was added boron trifluoride etherate (2.1 ml, 117.1 mmol) followed by the dropwise addition of borane dimethyl sulfide in THF (3 ml, 30.9 mmol) and the mixture refluxed for 16 h. The reaction mixture was quenched with methanol (10 ml) in ice cold condition, then conc. HCl (3 ml) was added dropwise, and the mixture heated to reflux for 30 min. After cooling to 25° C. it was basified with 4% NaOH solution, extracted with dichloromethane (3×50 ml), washed with brine, dried over sodium sulphate, filtered and concentrated to dryness under reduced pressure to get the crude alcohol, which was used for the next step without further purification. Yield: 44%

Steps (ii) to (iv) were carried out closely analogously to the synthetic procedures employed in the synthesis of carboxylic acid S2.

[step (ii) yield: 20%; step (iii): yield: 64%; step (iv): yield: quantitative]

Amine Building Blocks

The following amine building blocks were used for the synthesis of the sulfonamide compounds according to the invention:

| Amine building block | Structure | Name |
|---|---|---|
| A1 | 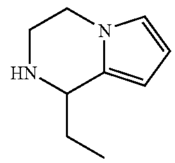 | 1-ethyl-1,2,3,4-tetrahydropyrrolo[1,2]a]pyrazine |
| A2 | 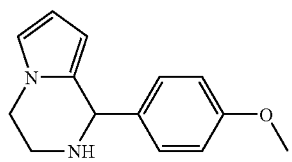 | 1-(4-methoxyphenyl)-1,2,3,4-tetrahydropyrrolo[1,2]a]pyrazine |
| A3 | 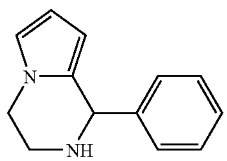 | 1-phenyl-1,2,3,4-tetrahydropyrrolo[1,2]a]pyrazine |
| A4 | 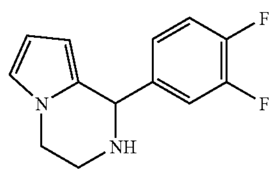 | 1-(3,4-difluorophenyl)-1,2,3,4-tetrahydropyrrolo[1,2-a]pyrazine |
| A5 | 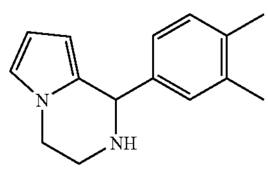 | 1-(3,4-dimethylphenyl)-1,2,3,4-tetrahydropyrrolo[1,2-a]pyrazine |
| A6 | 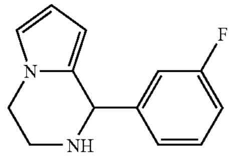 | 1-(3-fluorophenyl)-1,2,3,4-tetrahydropyrrolo[1,2-a]pyrazine |
| A7 | 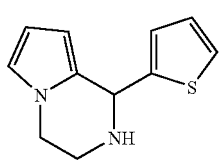 | 1-(thiophen-2-yl)-1,2,3,4-tetrahydropyrrolo[1,2-a]pyrazine |
| A8 | 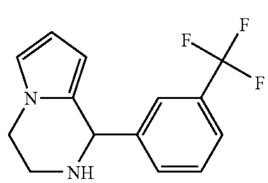 | 1-(3-(trifluoromethyl)-1,2,3,4-tetrahydropyrrolo[1,2-a]pyrazine |
| A9 | 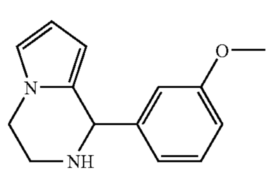 | 1-(3-methoxyphenyl)-1,2,3,4-tetrahydropyrrolo[1,2-a]pyrazine |

-continued

| Amine building block | Structure | Name |
|---|---|---|
| A10 | 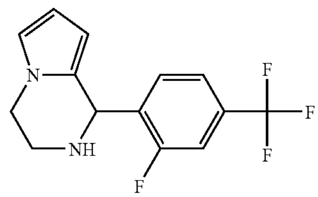 | 1-(2-fluoro-4-(trifluoromethyl)phenyl)-1,2,3,4-tetrahydropyrrolo[1,2-a]pyrazine |
| A11 | 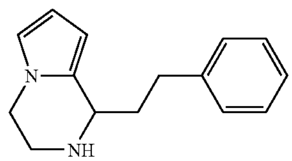 | 1-phenethyl-1,2,3,4-tetrahydropyrrolo[1,2-a]pyrazine |
| A12 | 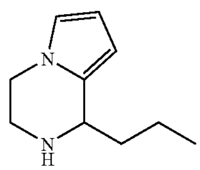 | 1-propyl-1,2,3,4-tetrahydropyrrolo[1,2-a]pyrazine |
| A13 | 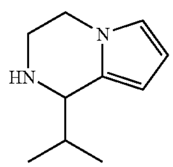 | 1-isopropyl-1,2,3,4-tetrahydropyrrolo[1,2-a]pyrazine |
| A14 | 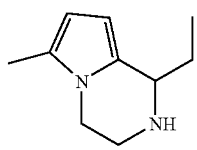 | 1-ethyl-6-methyl-1,2,3,4-tetrahydropyrrolo[1,2-a]pyrazine |
| A15 | 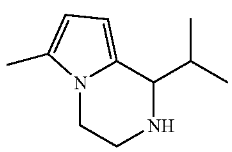 | 1-isopropyl-6-methyl-1,2,3,4-tetrahydropyrrolo[1,2-a]pyrazine |
| A16 | 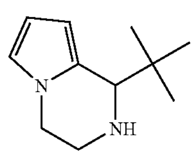 | 1-tert-butyl-1,2,3,4-tetrahydropyrrolo[1,2-a]pyrazine |
| A17 | 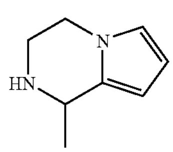 | 1-methyl-1,2,3,4-tetrahydropyrrolo[1,2-a]pyrazine |
| A18 | 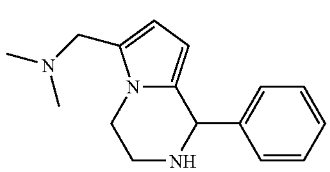 | N,N-dimethyl-1-(1-phenyl-1,2,3,4-tetrahydropyrrolo[1,2-a]pyrazin-6-yl)methanamine |

-continued

| Amine building block | Structure | Name |
|---|---|---|
| A19 | 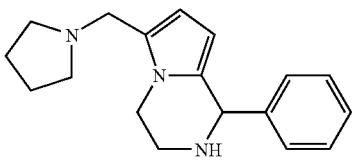 | 1-phenyl-6-(pyrrolodin-1-ylmethyl)-1,2,3,4-tetrahydropyrrolo[1,2-a]pyrazine |
| A20 | 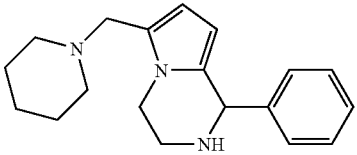 | 1-phenyl-6-(piperidin-1-ylmethyl)-1,2,3,4-tetrahydropyrrolo[1,2-a]pyrazine |
| A21 | 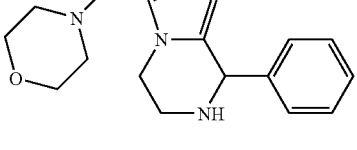 | 4-((1-phenyl-1,2,3,4-tetrahydropyrrolo[1,2-a]pyrazin-6-yl)methyl)morpholine |
| A22 | 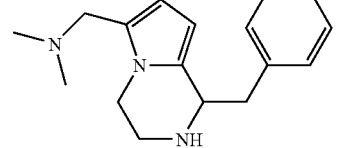 | 1-(1-benzyl-1,2,3,4-tetrahydropyrrolo[1,2-a]pyrazin-6-yl)-N,N-dimethylmethanamine |
| A23 | 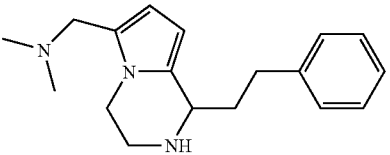 | N,N-dimethyl(1-phenethyl-1,2,3,4-tetrahydropyrrolo[1,2-a]pyrazln-6-yl)methanamine |
| A24 | 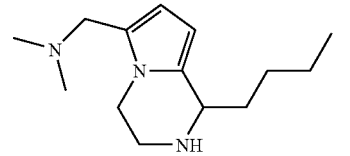 | 1-(1-butyl-1,2,3,4-tetrahydropyrrolo[1,2-a]pyrazin-6-yl)-N,N-dimethylmethanamine |
| A25 | 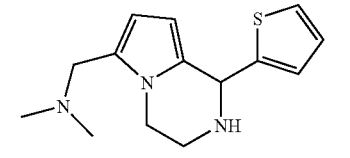 | N,N-dimethyl(1-thiophen-2-yl)-1,2,3,4-tetrahydropyrrolo[1,2-a]pyrazin-6-yl)methanamine |
| A26 | 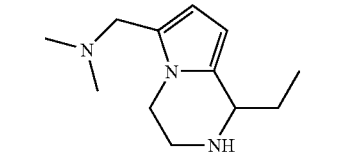 | 1-(1-ethyl-1,2,3,4-tetrahydropyrrolo[1,2-a]pyrazin-6-yl)-N,N,-dimethylmethanamine |
| A27 | 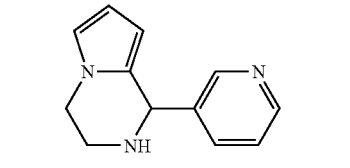 | 1-(pyridine-3-yl)-1,2,3,4-tetrahydropyrrolo[1,2-a]pyrazine |

-continued

| Amine building block | Structure | Name |
|---|---|---|
| A28 | 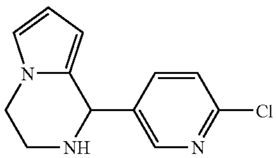 | 1-(6-chloropyridin-3-yl)-1,2,3,4-tetrahydropyrrolo[1,2-a]pyrazine |
| A29 | 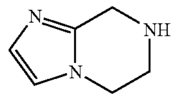 | 5,6,7,8-tetrahydroimidazo[1,2-a]pyrazine |
| A30 | 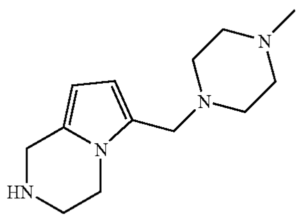 | 6-((4-methylpiperazin-1-yl)methyl)-1,2,3,4-tetrahydropyrrolo[1,2-a]pyrazine |
| A31 | 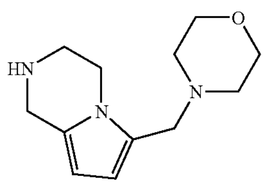 | 4-((1,2,3,4-tetrahydropyrrolo[1,2-a]pyrazin-6-yl)methyl)morpholine |
| A32 | 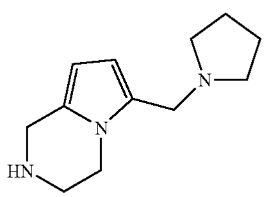 | 6-(pyrrolidin-1-ylmethyl)-1,2,3,4-tetrahydropyrrolo[1,2-a]pyrazine |
| A33 | 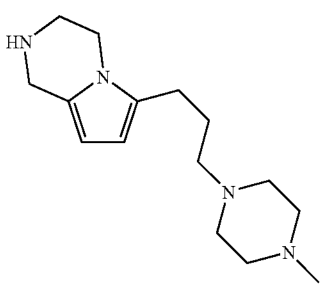 | 6-(3-(4-methylpiperazin-1-yl)propyl)-1,2,3,4-tetrahydropyrrolo[1,2-a]pyrazine |
| A34 | 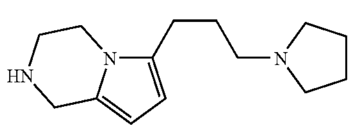 | 6-3-(pyrrolidin-1-yl)propyl)-1,2,3,4-tetrahydropyrrolo[1,2-a]pyrazine |
| A35 | 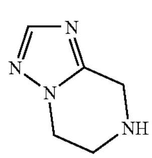 | 5,6,7,8-tetrahydro-[1,2,4]triazolo[1,5-a]pyrazine |

| Amine building block | Structure | Name |
|---|---|---|
| A36 | 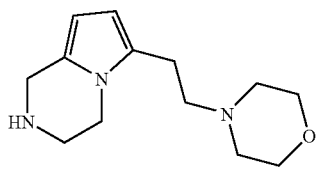 | 4-(2-(1,2,3,4-tetrahydropyrrolo[1,2-a]pyrazin-6-yl)ethyl)morpholine |
| A37 | 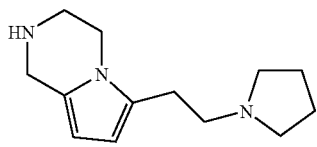 | 6-(2-(pyrrolidin-1-yl)ethyl)-1,2,3,4-tetrahydropyrrolo[1,2-a]pyrazine |
| A38 | 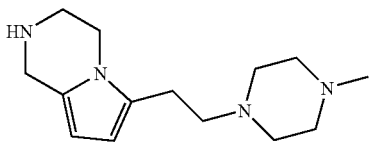 | 6-(2-(4-methylpiperazin-1-yl)ethyl)-1,2,3,4-tetrahydropyrrolo[1,2-a]pyrazine |
| A39 | 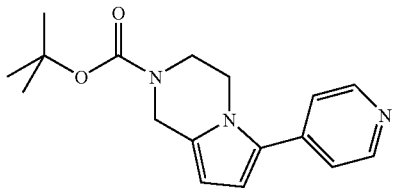 | tert-Butyl 6-(pyridin-4-yl)-3,4-dihydropyrrolo[1,2-a]pyrazine-2(1H)-carboxylate |
| A40 | 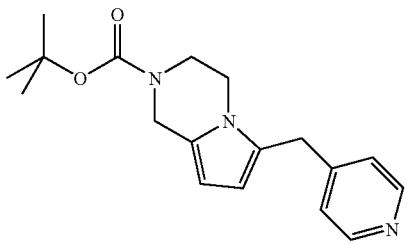 | tert-Butyl 6-(pyridin-4-ylmethyl)-3,4-dihydropyrrolo[1,2-a]pyrazine-2(1H)-carboxylate |
| A41 | 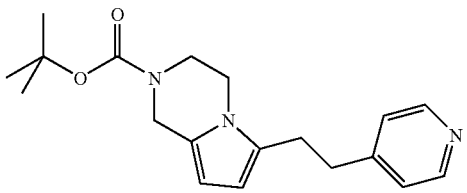 | tert-Butyl 6-(2-(pyridin-4-yl)ethyl)-3,4-dihydropyrrolo[1,2-a]pyrazine-2(1H)-carboxylate |
| A42 | 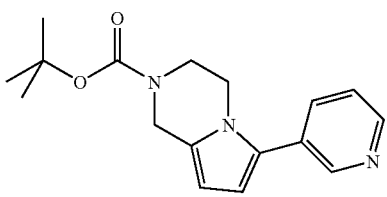 | tert-Butyl 6-(pyridin-3-yl)-3,4-dihydropyrrolo[1,2-a]pyrazine-2(1H)-carboxylate |

| Amine building block | Structure | Name |
|---|---|---|
| A43 | 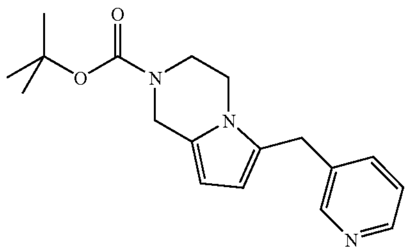 | tert-Butyl 6-(pyridin-3-ylmethyl)-3,4-dihydropyrrolo[1,2-a]pyrazine-2(1H)-carboxylate |
| A44 | 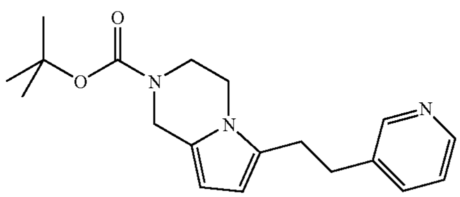 | tert-Butyl 6-(2-(pyridin-3-yl)ethyl)-3,4-dihydropyrrolo[1,2-a]pyrazine-2(1H)-carboxylate |
| A45 | 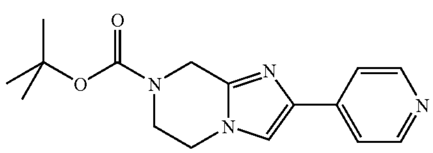 | tert-Butyl 2-(pyridin-4-yl)-5,6-dihydroimidazo[1,2-a]pyrazine-7(8H)-carboxylate |
| A46 | 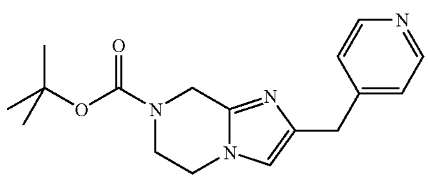 | tert-Butyl 2-(pyridin-4-ylmethyl)-5,6-dihydroimidazo[1,2-a]pyrazine-7(8H)-carboxylate |
| A47 | 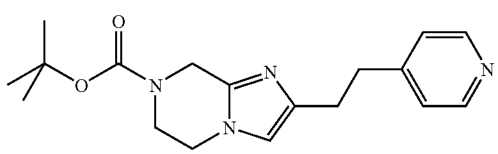 | tert-Butyl 2-(2-(pyridin-4-yl)ethyl)-5,6-dihydroimidazo[1,2-a]pyrazine-7(8H)-carboxylate |
| A48 | 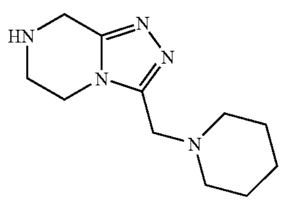 | 3-(Piperidin-1-ylmethyl)-5,6,7,8-tetrahydro-[1,2,4]triazolo[4,3-a]pyrazine |

Synthesis of the Amine Building Blocks A1-17, A27-28

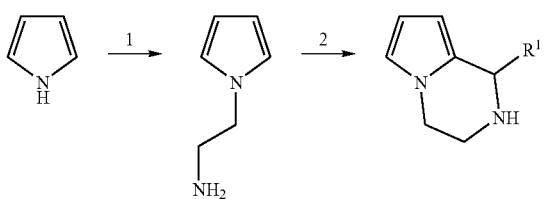

Stage 1. NaOH (9.4 g, 0.23 mole) and tetrabutylammonium hydrogen sulfate (0.8 g, 2.36 mmole) were added to a solution of the corresponding pyrrole (0.06 mmole) in acetonitrile (33 ml) and stirred for 30 minutes at RT. After the addition of 2-chloroethylamine hydrochloride (8.2 g, 0.07 mole) the reaction mixture was heated for 24 hours under reflux. After the reaction mixture had cooled the insoluble inorganic residue was filtered out, and the solvent was removed under reduced pressure. The crude product was distilled in vacuo (35°-37° C., 0.037 mbar).

$^1$H NMR (400 MHz, CDCl$_3$) δ ppm 2.95-3.15 (m, 1H) 3.89-4.00 (m, 1H) 6.12-6.21 (m, 1H) 6.64-6.73 (m, 1H)

Literature: Cuadro A. M., Matia M. P., Garcia J. L., Vaquero J. J. and Alvarez-Builla J.: *Synth. Commun.*, 1991, 21(4), 535-544.

Stage 2 Method A. A solution of the 2-(1H-pyrrol-1-yl) ethanamine (0.1 mole) and the corresponding aldehyde (0.1 mole) in acetic acid (250 ml) was stirred for 48 hours at RT. After completion of the reaction the solvent was removed on a rotary evaporator and the residue was taken up in aqueous sodium carbonate solution (10%) and extracted with DCM. The organic phase was then dried over MgSO$_4$ and concentrated by evaporation in vacuo. Purification was carried out by column chromatography on neutral Al$_2$O$_3$ or silica gel or by washing with 2-propanol or by crystallising from ethanol or 2-propanol/n-hexane.

Literature: I. Jirkovski, R. Baudy, *Synthesis* 1981, 481-483

Stage 2 Method B. Acetic acid (0.3 ml) was added to a solution of the 2-(1H-pyrrol-1-yl)ethanamine (0.05 mole) and the corresponding aldehyde (0.05 mole) in ethanol (25 ml) and heated for 10 minutes under reflux. The reaction mixture was then stirred for a further hour at RT. The reaction mixture was concentrated by evaporation on a rotary evaporator and taken up in ethyl acetate. The organic phase was washed with NaHCO$_3$ solution, dried over MgSO$_4$ and concentrated by evaporation. Purification was carried out if necessary by column chromatography on neutral Al$_2$O$_3$ or silica gel.

Stage 2 Method C. Benzotriazole (54.5 mmole) and a spatula tip amount of p-toluenesulfonic acid were added to a solution of the 2-(1H-pyrrol-1-yl)ethanamine (54.5 mmole) and corresponding aldehyde (54.5 mmole) in toluene (500 ml). The reaction mixture was heated overnight on a Dean-Stark water separator. After completion of the reaction first of all the solvent was removed on a rotary evaporator and the residue was taken up in ethyl acetate. The organic phase was washed firstly with 1 M NaOH and then with saturated NaCl solution. The organic phase was dried over sodium sulfate and then concentrated by evaporation to dryness. Purification was carried out if necessary by column chromatography by neutral Al$_2$O$_3$ or silica gel.

5,6,7,8-tetrahydroimidazo[1,2-a]pyrazine A29

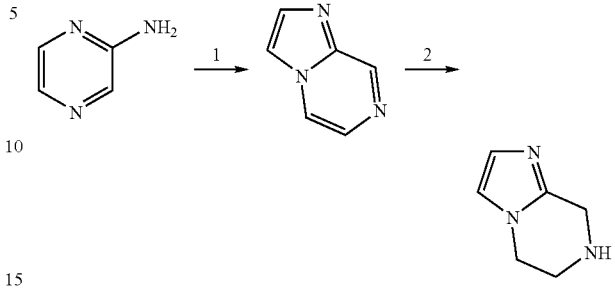

Stage 1. was added to a mixture of 2-aminopyrazin (25 g, 262.9 mmole), chloroacetaldehyde (50% in water, 50 ml, 394 mmole) and NaHCO$_3$ (33.1 g, 394 mmole) and heated for 2 days at 100° C. The reaction mixture was then cooled to RT, saturated K$_2$CO$_3$ solution (100 ml) was added, and the mixture was washed with DCM. The organic phase was dried over sodium sulfate and then concentrated by evaporation to dryness. Purification was carried out by column chromatography on silica gel (DCM/methanol, 95:5+5% NH$_4$OH [35%].

Stage 2. The imidazo[1,2-a]pyrazine (7.2 g, 60.44 mmole) was dissolved in 2-methoxyethanol (100 ml) and PtO$_2$ (1.2 g, 5.13 mmole) was added. The reaction mixture was stirred overnight at RT in an autoclave under a hydrogen atmosphere (4 bar). The autoclave was then flushed with nitrogen, the reaction mixture was filtered through filter earth, concentrated, and the solvent residues were then extracted with toluene. Purification was carried out by column chromatography on silica gel (DCM/7 N NH$_3$ in methanol, 95:5)

| No. | R$^1$ | Method | Stationary phase | Solvent |
|---|---|---|---|---|
| A1 | Ethyl | —* | — | — |
| A2 | 4-methoxyphenyl | —* | — | — |
| A3 | Phenyl | A | Al$_2$O$_3$ | Gradient hexane → hexane:ethyl acetate 8:2 |
| A4 | 3,4-difluorophenyl | B | Al$_2$O$_3$ | Gradient hexane → hexane:ethyl acetate 95:5 |
| A5 | 3,4-dimethylphenyl | B | Al$_2$O$_3$ | Gradient hexane → hexane:ethyl acetate 8:2 |
| A6 | 3-fluorophenyl | B | —** | — |
| A7 | 2-thiophenyl | B | Al$_2$O$_3$ | Hexane |
| A8 | 3-(trifluoro-methyl)phenyl | B | —** | — |
| A9 | 3-methoxyphenyl | B | —** | — |
| A10 | 2-fluoro-4-(trifluoro-methyl)phenyl | B | Al$_2$O$_3$ | Gradient hexane → hexane:ethyl acetate 9:1 |
| A11 | Phenethyl | B | —** | — |
| A12 | n-propyl | —* | — | — |
| A13 | Isopropyl | —* | — | — |
| A14 | Ethyl | —* | — | — |
| A15 | Isopropyl | —* | — | — |
| A16 | t-butyl | B | Silica gel | DCM:methanol 98:2 |
| A17 | Methyl | B | Silica gel | DCM:methanol 9:1 |
| A27 | 3-pyridyl | C | Al$_2$O$_3$ | Gradient hexane → hexane:ethyl acetate 7:3 → ethyl acetate |
| A28 | 6-chloropyridin-3-yl | B | Al$_2$O$_3$ | Gradient hexane → hexane:ethyl acetate 8:2 |

*The amine is commercially obtainable.
**The crude product was used without further purification.

5,6,7,8-tetrahydro-[1,2,4]triazolo[1,5-a]pyrazine A35

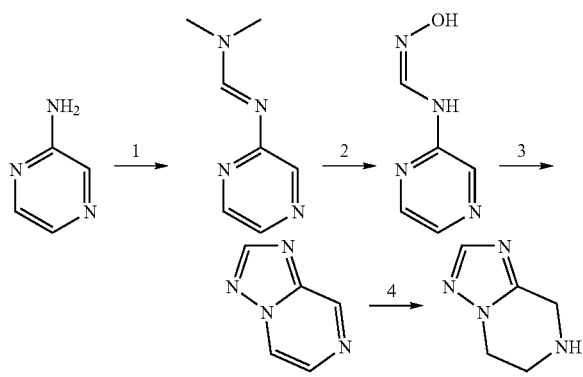

Stage 1. N—N-dimethylformamide dimethyl acetal (29.5 ml, 220 mmole) was added to a solution of the aminopyrazine (18.98 g, 200 mmole) in toluene (110 ml) and heated for 135 minutes under reflux. The reaction solution was then first of all cooled to RT and concentrated by evaporation to dryness. Impurities were removed by evaporation with toluene.

Stage 2. A solution of hydroxylamine hydrochloride (17.0 g, 245 mmole) in methanol (150 ml) was added dropwise to an ice-cooled suspension of N,N-dimethyl-N'-(pyrazin-2-yl)formimidamide (38.27 g, 233 mmole) and sodium acetate (20.1 g, 245 mmole) in methanol (450 ml). The reaction mixture was stirred for 4 hours while cooling with ice, and after heating to room temperature was concentrated. The residue was taken up in a mixture of DCM/7 M $NH_3$ solution in methanol (~9:1). The solid product formed was filtered out, washed with a mixture of DCM/7 M $NH_3$ solution in methanol (~9:1), and the filtrate was concentrated by evaporation to dryness. Impurities were removed with ethanol. The product was crystallized from ethanol. The residue of the mother liquor was washed with hot dioxane, and after concentration by evaporation the product was likewise crystallized from ethanol.

Stage 3. Polyphosphoric acid (250 g) was added to the N'-hydroxy-N-(pyrazin-2-yl)formimidamide (25.07 g, 181 mmole), whereupon the temperature rose to 90° C. The reaction mixture was stirred for 4 hours. The hot reaction solution was then added to iced water and adjusted alkaline with sodium hydrogen carbonate solution. The aqueous phase was extracted with DCM (1 litre, 2×0.5 litre) and the combined organic phases were dried over sodium sulfate. The organic phase was concentrated by evaporation to dryness and the product was crystallised from ethanol. The mother liquor was again concentrated by evaporation and the product was crystallised once more from ethanol.

Stage 4. Platinum(IV) oxide (2.75 g, 12.1 mmole) was added to a suspension, saturated with nitrogen, of CaO (9.30 g, 166 mmole) and [1,2,4]-triazolo[1,5-a]pyrazine (18.1 g, 151 mmole) in methoxyethanol (150 ml). The reaction mixture was stirred for 21.5 hours under a hydrogen atmosphere. The catalyst was filtered off through filter earth and washed with DCM/ethanol (9:1). The filtrate was concentrated, and the solvent was removed firstly with toluene and then with 2-propanol. The residue was taken up in ethyl acetate, filtered again through filter earth, washed with ethyl acetate, and concentrated. The residue was washed with hot 2-propanol and concentrated in vacuo.

Synthesis of the Amine Building Blocks A18-26, A30-A32

Synthesis of the Aminals

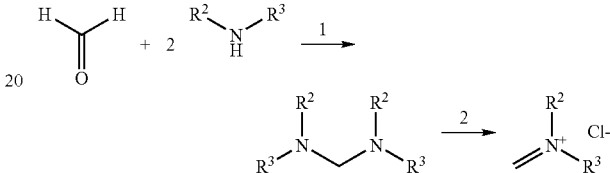

Stage 1. Method A. The formaldehyde solution (37% in water, 119 ml, 1.6 mole) was placed in a reaction vessel, dimethylamine solution (40% in water, 405 ml, 3.2 mole) was added, and the mixture was then stirred overnight at RT.

After completion of the reaction $K_2CO_3$ was added to the reaction mixture until phase separation occurred. The phases were separated and dried over $K_2CO_3$. The product was purified by means of fractional distillation (b.p. 80-84° C.).

$^1$H NMR (300 MHz, $CDCl_3$) δ ppm 2.23 (s, 12H) 2.73 (s, 2H).

Literature: M. Gaudry, Y. Jasor, B. T. Khac, *Org. Synth.* 59, 153-158

Stage 1. Method B. The formaldehyde solution (37% in water, 59.5 ml, 0.8 mole) was placed in a reaction vessel and the corresponding amine (1.6 mole) was added. The mixture was then stirred overnight at RT. The reaction mixture was worked up by adding water (100 ml) and was extracted four times with 200 ml of ethyl acetate each time. The combined organic phases were dried over $MgSO_4$ and concentrated. The crude product could be used without further purification.

Stage 2. A reaction flask was heated and the aminal (60 mmole) was added and dissolved or suspended in diethyl ether (70 ml). Acetyl chloride (72 mmole) dissolved in diethyl ether (20 ml) was added dropwise while cooling with ice. The reaction mixture was then stirred overnight at RT. The precipitate that had formed was filtered off through a glass frit, quickly transferred to a round-bottomed flask and dried under an oil pump vacuum. The crude product was used without further purification.

Literature: G. Kienast, L. F. Tietze, *Angew. Chemie* 1976, 88, 8, 261-262

| $NR^2R^3$ | Aminal name | Aminal preparation method (Stage 1) | Iminium salt name |
|---|---|---|---|
| $NMe_2$ | N,N,N',N'-tetramethyl-methanediamine | A | N-methyl-N-methylene-methaniminium chloride |

| NR²R³ | Aminal name | Aminal preparation method (Stage 1) | Iminium salt name |
|---|---|---|---|
|  | Dipyrrolidin-1-ylmethane | B | 1-methylene-pyrrolidinium chloride |
| 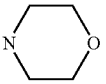 | Dimorpholinomethane | B | 1-methylene-morpholinium chloride |
|  | Dipiperidin-1-ylmethane | B | 1-methylene-piperidinium chloride |
| 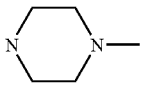 | Bis-(4-methylpiperazin-1-yl)methane | B | 4-methyl-1-methylene-piperazin-1-ium chloride |

1,2,3,4-tetrahydropyrrolo[1,2-a]pyrazine

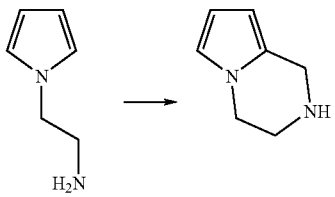

TFA (0.5 ml) was added to a solution of 1-(2-aminoethyl) pyrrole (9 mmole) in ethanol (20 ml) and 37% formaldehyde (9 mmole). The reaction mixture was stirred for 15 minutes at 50° C. The reaction solution was then cooled to 25° C. and stirred for 4 hours at this temperature. The reaction solution was concentrated by evaporation under reduced pressure. The residue was taken up in ethyl acetate and washed with aqueous sodium carbonate solution. The organic phase was separated, dried over sodium sulfate and concentrated by evaporation to dryness. The product was used without further purification.

Aminoalkylation

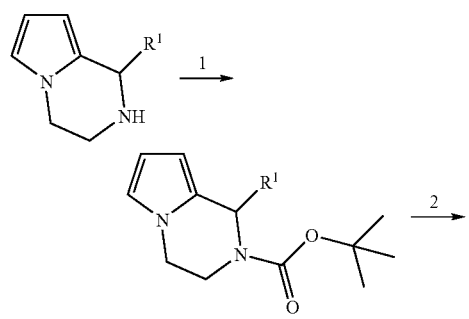

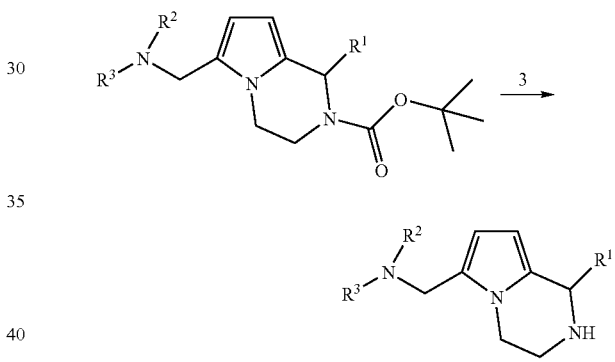

Stage 1, Method A. The corresponding 1-substituted 1,2,3,4-tetrahydropyrrolo[1,2-a]pyrazine (1 equiv.) was dissolved in 2.5 ml/mmole DCM in a heated three-necked flask. Di-tert-butyl dicarbonate (0.5 equiv.) was dissolved in 1.5 ml/mmole DCM and added dropwise within 30 minutes. The suspension was stirred overnight at RT. The reaction mixture was worked up by adding saturated sodium carbonate solution and the organic phase was separated. The aqueous phase was then extracted twice with DCM. The organic phases were combined, dried over magnesium sulfate and concentrated by evaporation. The products were purified by column chromatography on silica gel.

Stage 1, Method B. Diisopropylethylamine (12.15 mmole) and di-tert-butyl dicarbonate (8.9 mmole) were added to a solution of the correspondingly 1-substituted 1,2,3,4-tetrahydropyrrolo[1,2-a]pyrazine (8.1 mmole) in DCM. The reaction mixture was stirred for 16 hours at 25° C. The organic phase was then washed with sodium carbonate solution, water and saturated NaCl solution, dried over sodium sulfate and concentrated by evaporation. The crude product was purified by column chromatography (silica gel, ethyl acetate/DCM, 99:1)

| R¹ | Method | Name |
|---|---|---|
| Ethyl | A | tert-butyl 1-ethyl-3,4-dihydropyrrolo[1,2-]]pyrazine-2(1H)-carboxylate |
| Butyl | A | tert-butyl 1-butyl-3,4-dihydropyrrolo[1,2-a]pyrazine-2(1H)-carboxylate |
| Phenyl | A | tert-butyl-1-phenyl-3,4-dihydropyrrolo[1,2-a]pyrazine-2(1H)-carboxylate |
| Benzyl | A | tert-butyl-1-benzyl-3,4-dihydropyrrolo[1,2-a]pyrazine-2(1H)-carboxylate |
| Phenethyl | A | tert-butyl 1-phenethyl-3,4-dihydroppyrrolo[1,2-a]pyrazine-2(1H)-carboxylate |
| 2-thiophenyl | A | tert-butyl-1-(thiophen-2-yl)-3,4-dihydroppyrrolo[1,2-a]pyrazine-2(1H)-carboxylate |
| H | B | tert-butyl 3,4-dihydroppyrrolo[1,2-a]pyrazine-2(1H)-carboxylate |

Stage 2. Methods for the Aminoalkylation

Method A

The BOC-protected 1-substituted 1,2,3,4-tetrahydropyrrolo[1,2-a]pyrazine (1 equiv.) was dissolved in acetonitrile (5 ml/mmole), the corresponding iminium salt (1 equiv.) was added and the reaction mixture was stirred overnight at RT. For the working-up the reaction mixture was first adjusted to pH 1 with 1N HCl and then extracted three times with diethyl ether. The aqueous phase was then made alkaline with sodium hydrogen carbonate solution and extracted three times with diethyl ether. The combined organic phases were dried over magnesium sulfate and concentrated by evaporation on a rotary evaporator. The crude product was purified if necessary by column chromatography on silica gel (solvent: gradient: DCM/methanol 99:1→95:5).

Method B

The BOC-protected 1-substituted 1,2,3,4-tetrahydropyrrolo[1,2-a]pyrazine (1 equiv.) was dissolved in acetonitrile (10 ml/mmole), the corresponding iminium salt (1 equiv.) was added, and the reaction mixture was stirred overnight at RT. For the working-up the reaction mixture was diluted with ethyl acetate and then washed with sodium hydrogen carbonate solution, water and saturated sodium chloride solution, dried over sodium sulfate and concentrated by evaporation.

The crude product was purified by column chromatography (silica gel, DCM/methanol 95:5)

Stage 3: Methods for Cleavage of the Protective Groups

Method A

The aminoalkylated Boc-protected 1-substituted 1,2,3,4-tetrahydropyrrolo[1,2-a]pyrazine was dissolved in DCM (7 ml/mmole), TFA (10 equiv.) was added, and the reaction mixture was stirred overnight at RT. After completion of the reaction (DC check) the reaction mixture was made alkaline with sodium carbonate solution. The phases were separated and the aqueous phase was extracted three times with DCM. The combined organic phases were dried over magnesium sulfate and the solvent was removed on a rotary evaporator. The crude product could be used without further purification.

Method B

The aminoalkylated Boc-protected 1-substituted 1,2,3,4-tetrahydropyrrolo[1,2-a]pyrazine was dissolved in ethyl acetate (1 ml/mmole) and a saturated solution of HCl in ethyl acetate (3 ml/mmole) was added at 0° C. The reaction mixture was then heated to RT and stirred for 2 hours. The solvent was removed and the product was used without further purification.

| No. | R¹ | NR²R³ | Aminoalkylation method (Stage 2) | Method for removal of protective groups (Stage 3) | Name |
|---|---|---|---|---|---|
| A18 | Phenyl | NMe₂ | A | A | N,N-dimethyl-1-(1-phenyl-1,2,3,4-tetrahydropyrrolo[1,2-a]pyrazin-6-yl)methanamine |
| A19 | Phenyl |  | A | A | 1-phenyl-6-(pyrrolidin-1-ylmethyl)-1,2,3,4-tetrahydropyrrolo[1,2-a]pyrazine |
| A20 | Phenyl |  | A | A | 1-phenyl-6-(piperidin-1-ylmethyl)-1,2,3,4-tetrahydropyrrolo[1,2-a]pyrazine |
| A21 | Phenyl |  | A | A | 4-((1-phenyl-1,2,3,4-tetrahydropyrrolo[1,2-a]pyrazin-6-yl)methyl)morpholine |
| A22 | Benzyl | NMe₂ | A | A | 1-(1-benzyl-1,2,3,4-tetrahydropyrrolo[1,2-a]pyrazin-6-yl)-N,N-dimethylmethanamine |

-continued

| No. | R¹ | NR²R³ | Amino-alkylation method (Stage 2) | Method for removal of protective groups (Stage 3) | Name |
|---|---|---|---|---|---|
| A23 | Phenethyl | NMe₂ | A | A | N,N-dimethyl-1-(1-phenethyl-1,2,3,4-tetrahydropyrrolo[1,2-a]pyrazin-6-yl)methanamine |
| A24 | Butyl | NMe₂ | A | A | 1-(1-butyl-1,2,3,4-tetrahydropyrrolo[1,2-a]pyrazin-6-yl)-N,N-dimethylmethanamine |
| A25 | 2-thienyl | NMe₂ | A | A | N,N-dimethyl-1(1-(thiophen-2-yl)-1,2,3,4-tetrahydro-pyrrolo[1,2-a]pyrazin-6-yl)methanamine |
| A26 | Ethyl | NMe₂ | A | A | 1-(1-ethyl-1,2,3,4-tetrahydropyrrolo[1,2-a]pyrazin-6-yl)-N,N-dimethylmethanamine |
| A30 | H | N-methylpiperazinyl | B | B | 6-((4-methylpiperazin-1-yl)methyl-1,2,3,4-tetrahydropyrrolo[1,2-a]pyrazine |
| A31 | H | morpholinyl | B | B | 4-((1,2,3,4-tetrahydropyrrolo[1,2-a]pyrazin-6-yl)methyl)morpholine |
| A32 | H | pyrrolidinyl | B | B | 6-(pyrrolidin-1-ylmethyl)-1,2,3,4-tetrahydropyrrolo[1,2-a]pyrazine |

Preparation of the Amine Building Blocks A33, A34

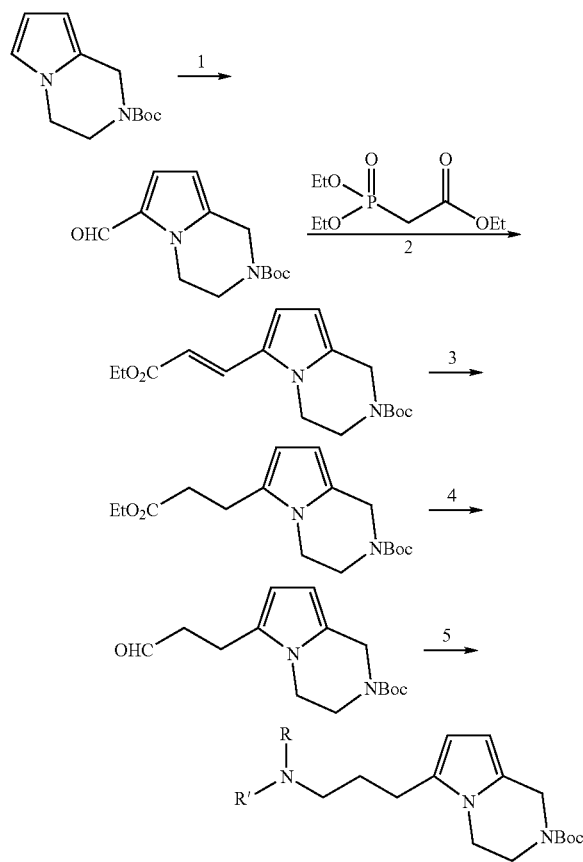

Stage 1. A solution of oxalyl chloride (1 equiv.) in DCE (15 ml) was added to an ice-cooled solution of dry DCE (15 ml) and dry DMF (1 equiv.) and stirred for 15 minutes at RT. The solution was re-cooled to 0° C. and a solution of tert-butyl 3,4-dihydropyrrolo[1,2-]pyrazine-2(1H)-carboxylate (5 g, 22.25 mmole) in DCE (15 ml) was added. The reaction solution was stirred for 30 minutes at this temperature (DC check). Ice was then added, followed by aqueous NaOH solution (50%). The aqueous phase was extracted with DCM and the organic phase was then washed in succession with water and saturated sodium chloride solution. After drying over sodium sulfate, the solvent was removed on a rotary evaporator. The crude product obtained was used without further purification in the next stage.

Stage 2. A solution of triethylphosphonium acetate (48.9 mmole) in dry THF (160 ml) was slowly added to a suspension of NaH (60%, 48.9 mmole) in dry THF (160 ml), cooled to 0° C., and then stirred for 60 minutes at 25° C. The reaction mixture was then cooled to 0° C. and the aldehyde (from Stage 1, 22.25 mmole) in dry THF (160 ml) was added dropwise, the temperature being maintained constant. The reaction mixture was then heated to 25° C. and stirred for 16 hours at this temperature until the reaction had gone to completion. The reaction mixture was hydrolysed first with ice and then with saturated sodium chloride solution. The aqueous phase was extracted with ethyl acetate. The organic phase was then washed with water and saturated sodium chloride solution. The organic phase was dried over sodium sulfate and the solvent was removed on a rotary evaporator. The crude product was purified by column chromatography on silica gel (solvent: DCM/ethyl acetate, 95:5).

Stage 3. A solution of the ester (from Stage 2, 9.37 mmole) in methanol (150 ml) was firstly deoxygenated with argon over a period of 15 minutes and Pd/C (10%, 20 wt. %) was added. The reaction mixture was hydrogenolysed for 45 minutes under atmospheric pressure (LCMS check). After completion of the reaction the reaction mixture was filtered through filter earth and washed with methanol. The combined organic phases were concentrated and the product obtained was used without further purification in the next stage.

Stage 4. DIBAL-H (1 equiv., 1.5 M in toluene) was added dropwise at −70° C. and under an argon atmosphere to a solution of the tert-butyl 6-(2-ethoxycarbonylethyl)-3,4-dihydro-1H-pyrrolo[1,2-a]pyrazine-2-carbonate (from Stage 3, 1 equiv.) in dry toluene (7 ml/mmole). The reaction mixture was stirred for 1 hour at this temperature, after which the educt had completely reacted (DC check). Methanol (30 ml) was added at −70° C. and the reaction mixture was heated to 25° C. Saturated sodium chloride solution (30 ml) was added. The reaction mixture was stirred for 30 minutes at this temperature and then filtered through filter earth. The reaction mixture was washed several times with ethyl acetate. The combined organic phases were washed with saturated sodium chloride solution and then dried over sodium sulfate, and the solvent was removed on a rotary evaporator. The product obtained was used without further purification in the next stage.

Stage 5. The corresponding amine (1 equiv.) and glacial acetic acid (170 μl/mmole) were added to a solution of the aldehyde (from Stage 4, 1.5 equiv.) in DCM (20 ml/mmole) at 25° C. and stirred for 30 minutes at this temperature. Sodium triacetoxy boron hydride (4 equiv.) was added to the reaction mixture and stirred for 20 hours at 25° C. (DC check). The reaction mixture was then diluted with DCM and washed with saturated, aqueous sodium hydrogen carbonate solution. The reaction mixture was then dried over sodium sulfate and the solvent was removed on a rotary evaporator. The crude product was purified by column chromatography on silica gel (solvent: DCM/methanol, 9:1).

Preparation of the Amine Building Blocks A36 and A37

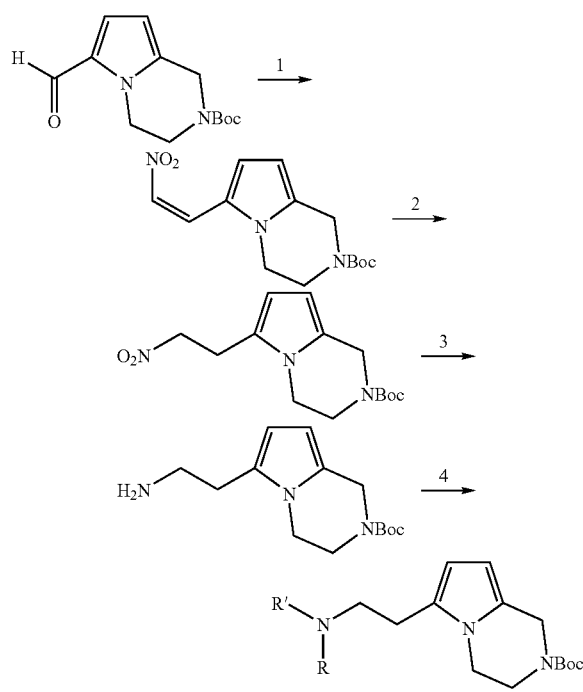

The preparation of the aldehyde reacted in Stage 1 was carried out according to Stage 1 of the synthesis of the building blocks A33 and A34.

Stage 1. Ammonium acetate (0.45 equiv.) was added to a solution of the aldehyde (10.4 mmole) in nitromethane (14.5 ml). The reaction mixture was then heated under reflux for 2 hours (DC check). After completion of the reaction the nitromethane was carefully removed under reduced pressure. The residue was taken up in ethyl acetate and washed successively with water and saturated sodium chloride solution. The organic phase was dried over sodium sulfate and the solvent was removed on a rotary evaporator. The crude product was purified by column chromatography on silica gel (solvent: hexane/ethyl acetate 9:1).

Stage 2. The nitro compound from Stage 1 (32 mmole) was added to a mixture of methanol and DMF (2:1, 17.5 ml/mmole) and cooled to 0° C. NaBH$_4$ (48 mmole) was added in portions to this mixture. The reaction mixture was stirred for 30 minutes at 0° C. (DC check). Water (14 ml/mmole) and 1 drop of acetic acid were then added. The product was extracted with DCM. The organic phase was washed with saturated sodium chloride solution, dried over sodium sulfate, and the solvent was removed on a rotary evaporator. The crude product was purified by column chromatography on silica gel (solvent: hexane/ethyl acetate 9:1).

Stage 3. A solution of the nitro compound (3.5 g, 12 mmole) from Stage 2 in ethanol (60 ml) was cooled to 0° C. and zinc dust (10 equiv.) was added in portions. The reaction mixture was stirred at 0° C. for 12 hours and then filtered through Celite. The filtrate was washed several times with ethanol. The combined organic phases were concentrated by evaporation. The brown residue was taken up in DCM and washed in succession with sodium carbonate solution and saturated sodium chloride solution. The residue was then dried over sodium sulfate and the solvent was removed on a rotary evaporator. The crude product was used without further purification.

Stage 4. The tert-butyl-6-(2-aminoethyl)-3,4-dihydropyrrolo[1,2-a]pyrazine-2(1H)-carboxylate (1 equiv.) was dissolved in toluene (5 ml/mmole) and potassium carbonate (5 equiv.) was added. 1-chloro-2-(2-chloroethoxy)ethane or 2-chloro-N-(2-chloroethyl)-N-methyl-ethanamine (1.5 equiv.) was then added at RT. The reaction mixture was heated for 16 hours at 100° C. in a closed tube (DC check). After completion of the reaction the mixture was cooled to RT, diluted with ethyl acetate, and washed in succession with water and saturated sodium chloride solution. The organic phase was dried over sodium sulfate and the solvent was removed on a rotary evaporator. The crude product was purified by column chromatography on silica gel (solvent: DCM/methanol, NRR'=morpholine: 98:2, NRR'=methylpiperazine: 94:6).

Preparation of the Amine Building Block A38

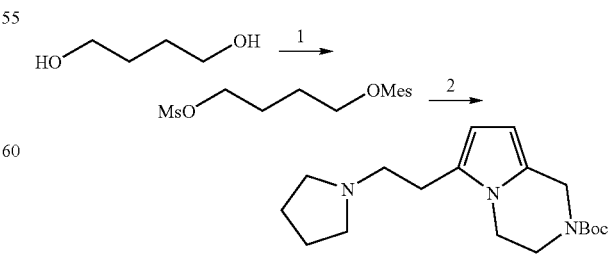

Stage 1. Butanediol (5 g, 56 mmole) was dissolved in DCM, triethylamine (280 mmole) was added and the mixture was cooled to 0° C. Methanesulfonic acid chloride (140 mmole) was added at this temperature and stirred for 1 hour at 0° C. After completion of the reaction the mixture was diluted with DCM and washed in succession with water and saturated sodium chloride solution. The organic phase was dried over sodium sulfate and the solvent was removed on a rotary evaporator. The crude product was used without further purification.

Stage 2. The tert-butyl-6-(2-aminoethyl)-3,4-dihydropyrrolo[1,2-a]pyrazine-2(1H)-carboxylate (1 equiv.) was dissolved in toluene (5 ml/mmole) and potassium carbonate (5 equiv.) was added. Butane-1,4-diyldimethanesulfonate (1.5 equiv.) was then added at RT. The reaction mixture was heated for 16 hours at 100° C. in a closed tube (DC check). After completion of the reaction the mixture was cooled to RT, diluted with ethyl acetate, and washed in succession with water and saturated sodium chloride solution. The organic phase was dried over sodium sulfate and the solvent was removed on a rotary evaporator. The crude product was purified by column chromatography on silica gel (solvent: DCM/methanol).

Preparation of Amine Building Block A39 tert-Butyl 6-(pyridin-4-yl)-3,4-dihydropyrrolo[1,2-a]pyrazine-2(1H)-carboxylate

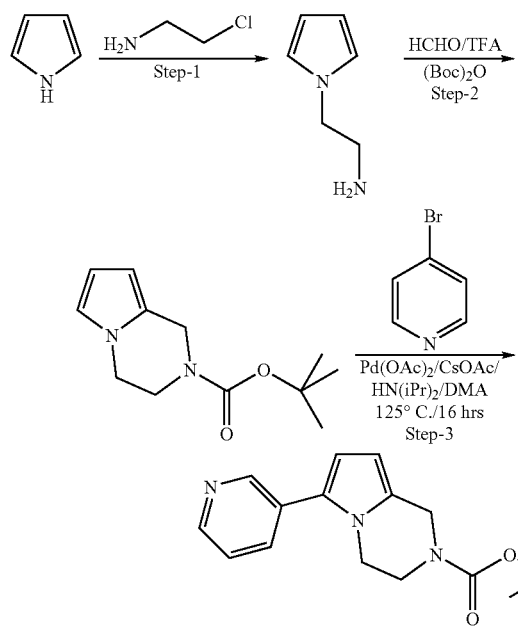

Procedure for Step-1:

To a solution containing 4 g (0.06 mol) of pyrrole in 33 ml of acetonitrile were added 9.4 g (0.23 mol) of powdered sodium hydroxide and 0.8 g (2.36 mmol) of tetrabutylammonium hydrogensulfate. After the mixture was stirred at 25° C. for 30 minutes, 2-chloroethylamine hydrochloride (8.2 g, 0.07 mol) was added. The reaction mixture was refluxed for 24 hrs, inorganic solid was filtered off and the solvent was removed under reduced pressure to get crude 1-(2-aminoethyl)pyrrole. This was distilled under vacuum to get a colorless liquid that was used in the next step directly. Yield: 30% (crude)

Procedure for Step-2:

To a ethanol solution (20 ml) of 1-(2-aminoethyl)pyrrole (9 mmol) and 37% formaldehyde (9 mmol) was added TFA (0.5 ml) and the resulting reaction mixture was stirred at 50° C. for 15 minutes. It was then cooled to come to 25° C. and stirred at this temperature for 4 hrs. Solvent was removed under reduced pressure, residue was dissolved in ethyl acetate, basified with aqueous sodium carbonate solution, organic layer was separated and dried over sodium sulfate. Evaporation of the organic layer gave the crude 1,2,3,4-Tetrahydro-pyrrolo[1,2-a]pyrazine which was dissolved in dichloromethane (90 ml) at to it DIPEA (12.15 mmol) and boc anhydride (8.9 mmol) were added at 0° C. The resulting reaction mixture was stirred for 16 hrs at 25° C. Organic layer was washed with sodium carbonate, water and brine and finally dried over sodium sulfate. Evaporation of the organic layer gave the crude product which was purified by column chromatography (1% ethyl acetate in dichloromethane). (10% ethyl acetate in hexane).

Procedure for Step-3

To a solution of 3,4-Dihydro-1H-pyrrolo[1,2-a]pyrazine-2-carboxylic acid tert-butyl ester (200 mg, 0.9 mmol) obtained from step-2 in dry dimethyl acetamide (200 μL) was added cesium acetate (3 eqv), diisopropyl amine (4 eqv) and 4-bromopyridine hydrochloride (2 eqv) under argon atmosphere. To this reaction mixture was then added Pd(OAc)$_2$ (0.15 eqv) under inert atmosphere and the reaction was heated at 130° C. for 16 hrs. It was then diluted with ethyl acetate, filtered through celite bed and the organic layer was washed successively with water and brine. Evaporation of organic layer under reduced pressure gave the crude product which was purified by column chromatography. Yield: 40%

Preparation of Amine Building Block A40 tert-Butyl 6-(pyridin-4-ylmethyl)-3,4-dihydropyrrolo[1,2-a]pyrazine-2(11H)-carboxylate

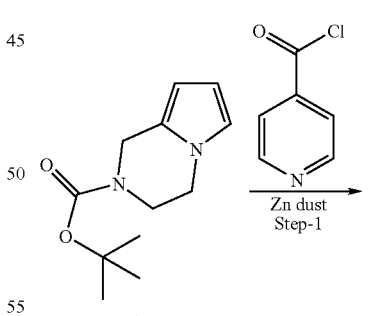

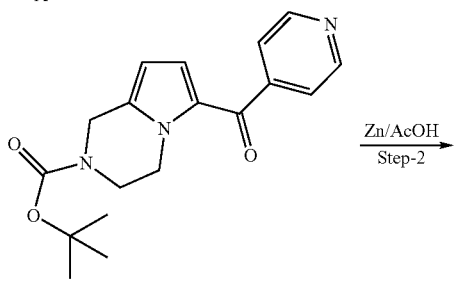

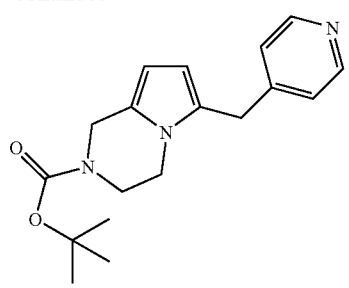

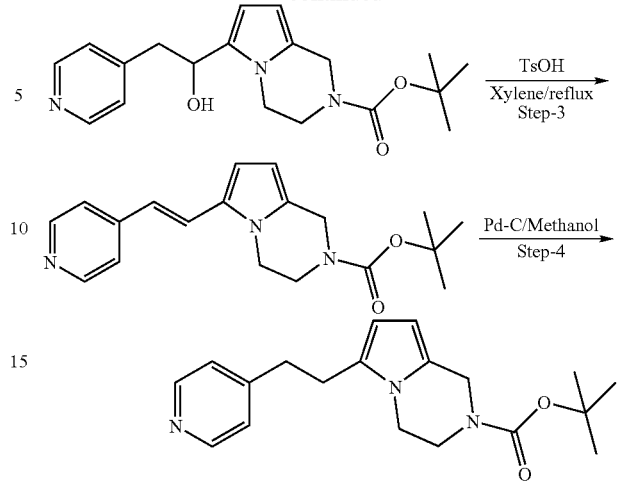

Procedure for Step-1:

Compound A (3 g, 13.5 mmol) was taken in dry toluene (30 ml) and to it was added zinc dust (3 eqv) under inert atmosphere. The resulting reaction mixture was stirred at 25° C. for 5 minutes and then isonicotinoyl chloride hydrochloride (1.5 eqv) was added under stirring. Stirring was continued for further 16 hrs. Reaction mixture was filtered through celite bed, diluted with ethyl acetate, organic layer was washed successively with water and brine and finally dried over sodium sulfate. Evaporation of organic layer under reduced pressure gave the crude product that was purified by column chromatography (5% methanol in dichloromethane). Yield: 40%

Procedure for Step-2:

A 2:1 mixture of AcOH-MeOH (36 ml) was added to the keto compound (3.6 mmol) and to it zinc dust (50 eqv) was added under stirring. The resulting reaction mixture was stirred at 25° C. for 16 hrs (monitored by LCMS) and filtered through celite bed. Solvent was completely evaporated, residue was taken in ethyl acetate, organic layer was washed successively with sodium bicarbonate and brine and finally dried over sodium sulfate. Evaporation of organic layer under reduced pressure gave the crude product which was purified by column chromatography (5% methanol in dichloromethane). Yield: 26%

Preparation of amine building block A41 tert-Butyl 6-(2-(pyridin-4-yl)ethyl)-3,4-dihydropyrrolo[1,2-a]pyrazine-2(1H)-carboxylate

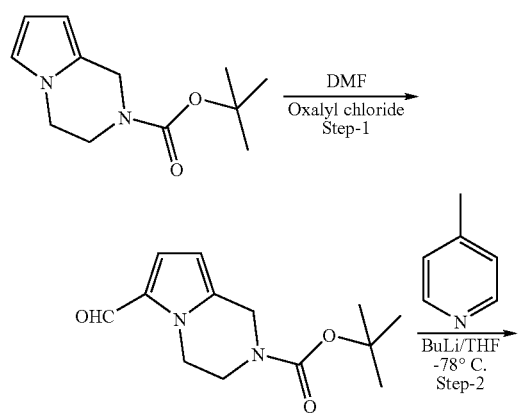

Procedure for Step-1:

To an ice cold solution of dry DCE (15 ml) and dry DMF (1 eqv) was added a solution of oxalyl chloride (1 eqv) in dry DCE (15 ml) and the resulting reaction mixture was stirred at 25° C. for 15 minutes. Reaction was again cooled to 0° C. and to it was added a solution of 3,4-Dihydro-1H-pyrrolo[1,2-a]pyrazine-2-carboxylic acid tert-butyl ester (5 gm, 22.25 mmol) in dry DCE (15 ml) and the reaction was stirred at the same temperature for 30 minutes (monitored by TLC). It was quenched with ice, 50% aqueous NaOH solution was then added, aqueous layer was extracted with DCM and the organic layer was washed successively with water and brine. After drying over sodium sulfate, organic layer was evaporated under reduced pressure to get the crude product which was used immediately in the next step without any further purification. Yield: 60% (crude)

Procedure for Step-2:

To a solution of 4-picoline (4 mmol) in dry THF (10 ml) was added n-BuLi (1.57M, 2.5 ml, 4 mmol) at −78° C. and the resulting reaction mixture was stirred at 25° C. for 1 hr. It was again cooled to 0° C. and the aldehyde obtained from step-1 (1 g, 4 mmol) was added to the reaction mixture drop wise. After stirring at 25° C. for 3 hrs, reaction mixture was quenched with water (5 ml), extracted with ethyl acetate and the combined organic layer was washed with brine. After drying over sodium sulfate, organic layer was evaporated under reduced pressure to get the crude alcohol that was purified by column chromatography (2% methanol in dichloromethane). Yield: 48%

Procedure for Step-3:

To a solution of the alcohol obtained from step-2 (1 g, 2.91 mmol) in xylene (15 ml) wadded p-toluene sulfonic acid (0.05 eqv) and the resulting reaction mixture was refluxed using a dean-stark apparatus for 5 hrs (monitored by TLC). Reaction mixture was cooled to room temperature, diluted with ethyl acetate and washed successively with saturated sodium bicarbonate solution, water and brine. Organic layer was dried over sodium sulfate evaporated under reduced pressure to get the crude product that was purified by column chromatography (2% methanol in dichloromethane). Yield: 56%

Procedure for Step-4:

A solution of the compound obtained from step-3 was taken in methanol (15 ml) and deoxygenated with argon. To it was added 10% Pd—C (150 mg) and the resulting reaction mixture was hydrogenated under atmospheric pressure for 3 hrs. It was filtered through celite bed, residue washed with methanol and the combined organic layer was evaporated to dryness to get the crude product which was used directly in the next step without any further purification. Yield: 80% (crude)

Preparation of Amine Building Block A42 tert-Butyl 6-(pyridin-3-yl)-3,4-dihydropyrrolo[1,2-a]pyrazine-2(11H)-carboxylate

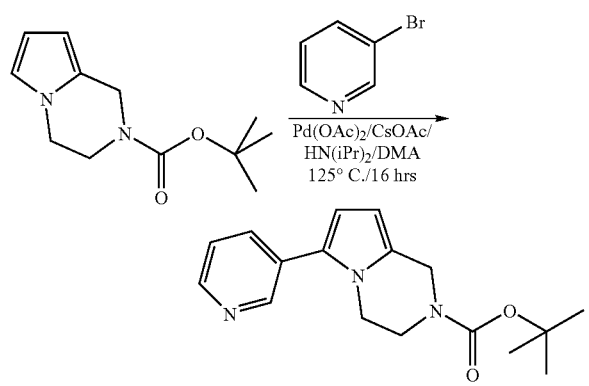

Procedure:

To a solution of 3,4-Dihydro-1H-pyrrolo[1,2-a]pyrazine-2-carboxylic acid tert-butyl ester (2 g, 9 mmol) in dry dimethyl acetamide (2 ml) was added cesium acetate (3 eqv), diisopropyl amine (4 eqv) and 3-bromopyridine (2 eqv) under argon atmosphere. To this reaction mixture was then added Pd(OAc)$_2$ (0.15 eqv) under inert atmosphere and the reaction was heated at 130° C. for 16 hrs. It was then diluted with ethyl acetate, filtered through celite bed and the organic layer was washed successively with water and brine. Evaporation of organic layer under reduced pressure gave the crude product that was purified by column chromatography. Yield: 40%

Preparation of Amine Building Block A43 tert-Butyl 6-(pyridin-3-ylmethyl)-3,4-dihydropyrrolo[1,2-a]pyrazine-2(1H)-carboxylate

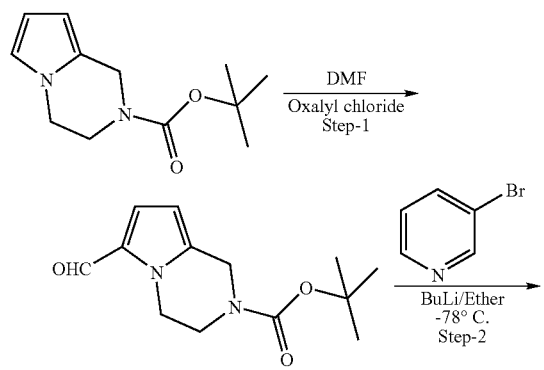

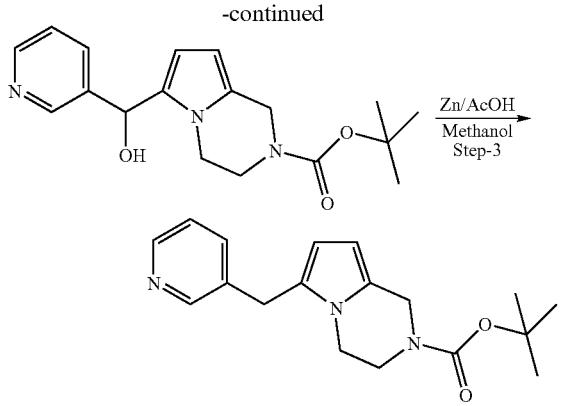

Procedure for Step-1: Same as Step-1 of A41

Procedure for Step-2:

To a solution of n-BuLi (1.57 M, 2.54 ml, 4 mmol) in dry ether (5 ml) at −78° C. was added 3-bromo pyridine (4 mmol) and the reaction mixture was stirred at the same temperature for 30 minutes. To it aldehyde (4 mmol) obtained from step-1 in dry ether (10 ml) was added drop wise and the resulting reaction mixture was stirred at 25° C. for 16 hrs (monitored by TLC). Reaction was quenched with water, extracted with ethyl acetate, combined organic layer was washed with brine and finally dried over sodium sulfate. Evaporation of organic layer under reduced pressure gave the crude product which was purified by column chromatography (3% methanol in dichlormethane). Yield: 30%

Procedure for Step-3:

A 2:1 mixture of AcOH-MeOH (16 ml) was added to the keto compound (3.6 mmol) and to it zinc dust (50 eqv) was added under stirring. The resulting reaction mixture was stirred at 25° C. for 16 hrs (monitored by LCMS) and filtered through celite bed. Solvent was completely evaporated, residue was taken in ethyl acetate, organic layer was washed successively with sodium bicarbonate and brine and finally dried over sodium sulfate. Evaporation of organic layer under reduced pressure gave the crude product that was purified by column chromatography (5% methanol in dichloromethane). Yield: 35%

Preparation of Amine Building Block A44 tert-Butyl 6-(2-(pyridin-3-yl)ethyl)-3,4-dihydropyrrolo[1,2-a]pyrazine-2(1H)-carboxylate

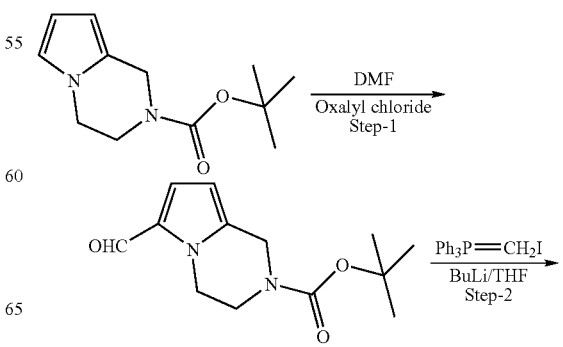

-continued

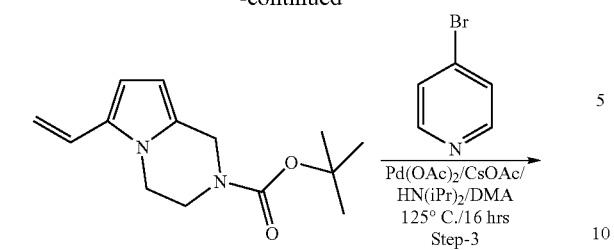

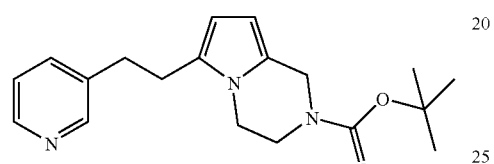

Procedure for Step-1: Same as Step-1 of A41

Procedure for Step-2

To an ice cold suspension of the wittig salt (4 mmol) in dry THF (25 ml) was slowly added n-BuLi (5 mmol) and the resulting reaction mixture was stirred at that temperature for 30 minutes. To it aldehyde B (2 mmol) in dry THF (10 ml) was added at 0° C. and stirred for further 1 hr. Reaction was quenched with saturated ammonium chloride solution and extracted with ethyl acetate. Organic layer was washed with water and brine and finally dried over sodium sulfate. Evaporation of organic layer under reduced pressure gave the crude product that was unstable and used immediately without any further purification.

Procedure for Step-3

To a DMA solution (2 ml) of the crude compound obtained from step-2 (9.12 mmol) was added cesium acetate (3 eqv), diisopropyl amine (4 eqv) and 3-bromopyridine (2 eqv) under argon atmosphere. To this reaction mixture was then added Pd(OAc)$_2$ (0.15 eqv) under inert atmosphere and the reaction was heated at 130° C. for 16 hrs. It was then diluted with ethyl acetate, filtered through celite bed and the organic layer was washed successively with water and brine. Evaporation of organic layer under reduced pressure gave the crude product that was purified by column chromatography (5% methanol in dichloromethane) Yield: 15%

Procedure for Step-4:

A solution of the compound obtained from step-3 (400 mg) was taken in methanol (10 ml) and deoxygenated with argon. To it was added 10% Pd—C (200 mg) and the resulting reaction mixture was hydrogenated under atmospheric pressure for 3 hrs. It was filtered through celite bed, residue washed with methanol and the combined organic layer was evaporated to dryness to get the crude product which was used directly in the next step without any further purification. Yield: 80% (crude)

Preparation of Amine Building Block A45 tert-Butyl 2-(pyridin-4-yl)-5,6-dihydroimidazo[1,2-a]pyrazine-7(8H)-carboxylate

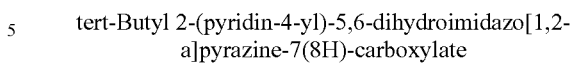

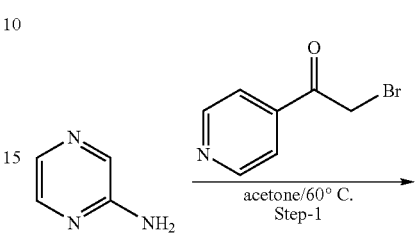

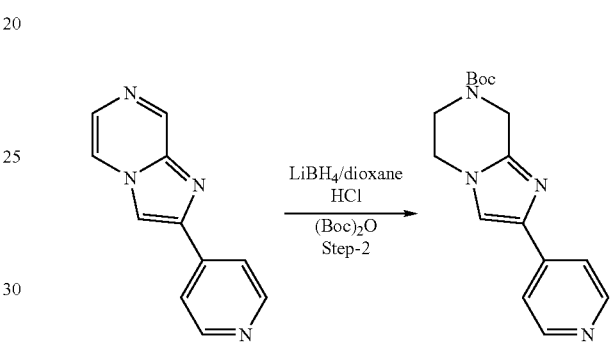

Procedure for Step-1:

To a solution of 2-aminopyrazine (1.87 g) in dry acetone (30 ml) was added potassium carbonate (3 eqv), 4-bromoacetyl pyridine (2 eqv) and the resulting reaction mixture was heated at 60° C. for 20 hrs. Reaction mixture was filtered through a celite bed, residue washed with DCM and combined organic layer was evaporated completely to get a brown residue. It was again dissolved in ethyl acetate, washed with water and brine and finally dried over sodium sulfate. Evaporation of organic layer gave the crude product which was purified by column chromatography (1% methanol in dichloromethane). Yield: 12%, 30% Starting material recovered.

Procedure for Step-2:

To a dry dioxane solution (22 ml) of the compound obtained from step-1 (2.55 mmol) was added lithium borohydride (2 eqv) portion wise at 25° C. and the resulting reaction mixture was stirred at this temperature for 10 minutes. It was then warmed to 60° C. and kept at that temperature for 30 minutes (monitored by TLC). Reaction was cooled to 0° C. and acidified with 1 (N)HCl. Dioaxane was completely evaporated, dichloromethane (5 ml), diisopropyl ethyl amine (2.5 eqv) and boc-anhydride (1.5 eqv) was added to the residue and the resulting reaction mixture was stirred at 25° C. for 16 hrs. It was diluted with dichloromethane, organic layer was washed with water and brine and finally dried over sodium sulfate. Evaporation of the organic layer gave the crude product which was purified by column chromatography (5% methanol in dichloromethane). Yield: 58%

Preparation of Amine Building Block A46 tert-Butyl 2-(pyridin-4-ylmethyl)-5,6-dihydroimidazo[1,2-a]pyrazine-7(8H)-carboxylate

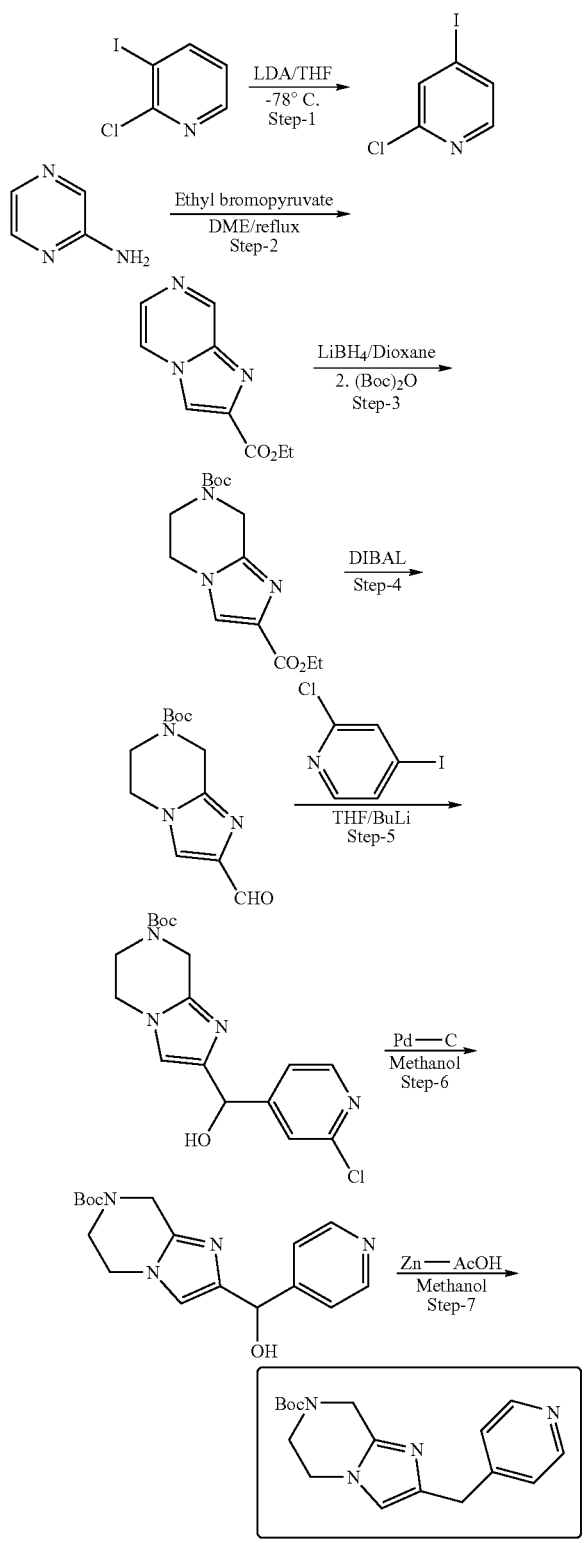

Procedure for Step-1

To a THF solution (40 ml) of Diisopropyl amine (4.46 ml, 1.5 eqv) was added BuLi (1.88 M, 1.5 eqv) at −15° C. and the resulting reaction mixture was stirred at same temperature for 20 minutes. It was then cooled to −78° C., and 2-chloro-3-iodopyridine (5 g, 20.92 mmol) in THF (10 ml) was added dropwise at the same temperature and stirred for 1 hr at −78° C. Reaction was quenched with water (10 ml), stirred at ambient temperature for 15 minutes and extracted with ethyl acetate. Organic layer was washed successively with brine and finally dried over sodium sulfate. Evaporation of organic layer under reduced pressure gave the crude product which was immediately used in the next step without any further purification. Yield: 80% (Crude)

Procedure for Step-2:

To a solution of 2-amino pyrazine (20 g, 210 mmol) in dimethoxy ethane (400 ml) was added ethyl bromopyruvate (32.8 ml) at 25° C. and the resulting reaction mixture was stirred at the same temperature for 4 hrs. It was then cooled to 0° C. and stirred for 30 minutes. The separated solid was filtered and washed with ether. Solid residue was taken in ethanol (1000 ml) and refluxed for 4 hrs. The solvent was removed completely, residue taken up in chloroform (1000 ml), saturated sodium bicarbonate solution (700 ml) was added to it and the mixture was stirred for 45 minutes. The mixture was filtered through a celite bed, washed several times with chloroform and the filtrate was dried over sodium sulfate. Evaporation of the organic layer under reduced pressure gave the crude mass, which was purified by crystallization using ether-methanol mixture. Yield: 20%

Procedure for Step-3:

To a well stirred suspension of the ester obtained from step-1 (10 g, 52.3 mmol) in dioxane (400 ml) was added lithium borohydride (2 eqv) at 25° C. and the resulting reaction mixture was stirred at the same temperature for 10 minutes. It was then warmed to 60° C. and kept at this temperature for 20 minutes (! Higher temperature and more reaction time reduce the yield and quality of reaction). The reaction mixture was then cooled to 0° C., acidified with 1N HCl and dioxane was completely evaporated under reduced pressure. Residue was taken in dichloromethane (200 ml), TEA (4-eqv) and Boc-anhydride (1.2 eqv) was added to it and the resulting reaction mixture was stirred at 25° C. for 16 hrs. The organic layer was washed with water and brine and finally dried over sodium sulfate. Evaporation of organic layer gave the crude product which was purified by column chromatography (70% ethyl acetate in hexane). Yield: 27%

Procedure for Step-4:

To a solution of the BOC-ester (1 g, 3.38 mmol) obtained from step-3 in dry toluene (40 ml) was added DIBAL (1M, 3.7 mmol) at −78° C. and the reaction mixture was stirred at this temperature for 5 hrs (monitored by TLC). Reaction was quenched with methanol (3.7 ml) and was slowly brought to 25° C. Brine (10 ml) was added to it and filtered through celite bed. Residue was washed with dichloromethane and combined organic layer was evaporated to get the crude aldehyde, which was used directly in the next step without any further purification. Yield: 800 mg (crude)

Procedure for Step-5:

To a ether solution (17 ml) of 2-chloro-4-iodo pyridine (1 eqv) was added BuLi (1.2 eqv) at −78° C. and the resulting reaction mixture was stirred at the same temperature for 1 hr. To it was added the aldehyde (1 eqv) obtained from step-4 at −78° C. and stirred for 1 hr at the same temperature. It was quenched with water, extracted with ethyl acetate and the organic layer was washed successively with brine and finally dried over sodium sulfate. Evaporation of organic layer under reduced pressure gave the crude product which was purified by column chromatography. Yield: 35%

Procedure for Step-6:

A solution of the compound obtained from step-5 was taken in methanol (10 ml/mmol) and deoxygenated with argon. To it was added 10% Pd—C (50% by wt of the alcohol) and the resulting reaction mixture was hydrogenated under atmospheric pressure for 16 hrs. It was then filtered through celite bed, residue washed with methanol and the combined organic layer was evaporated to dryness to get the crude product which was used directly in the next step without any further purification. Yield: 44% (crude)

Procedure for Step-7:

To a solution of the alcohol (1 eqv) obtained from step-6 in methanol (5 ml/mmol) was added glacial acetic acid (10 ml/mmol), Zn dust (50 eqv) and the resulting reaction mixture was stirred at ambient temperature for 16 hrs. Reaction mixture was filtered through celite bed, washed with methanol and combined organic layer was evaporated completely. It was then taken in ethyl acetate, washed with sodium bicarbonate, water and brine and finally dried over sodium sulfate. Evaporation of organic layer under reduced pressure gave the crude product which was purified by column chromatography (2% methanol in dichloromethane). Yield: 26%

Preparation of the Amine Building Block A47 tert-Butyl 2-(2-(pyridin-4-yl)ethyl)-5,6-dihydroimidazo[1,2-a]pyrazine-7(8H)-carboxylate

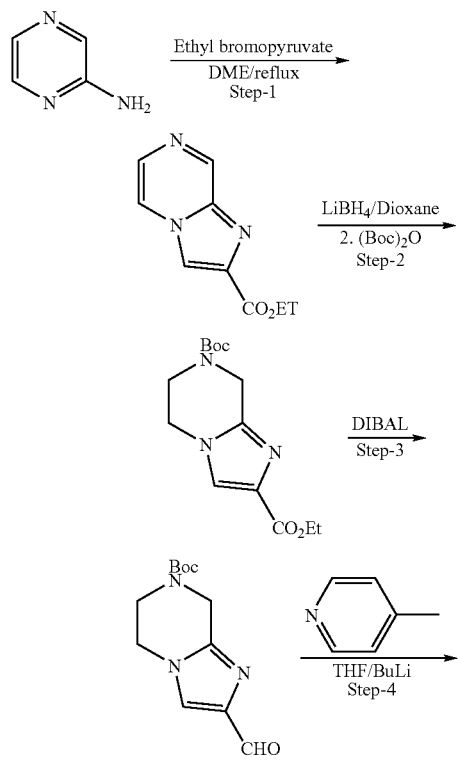

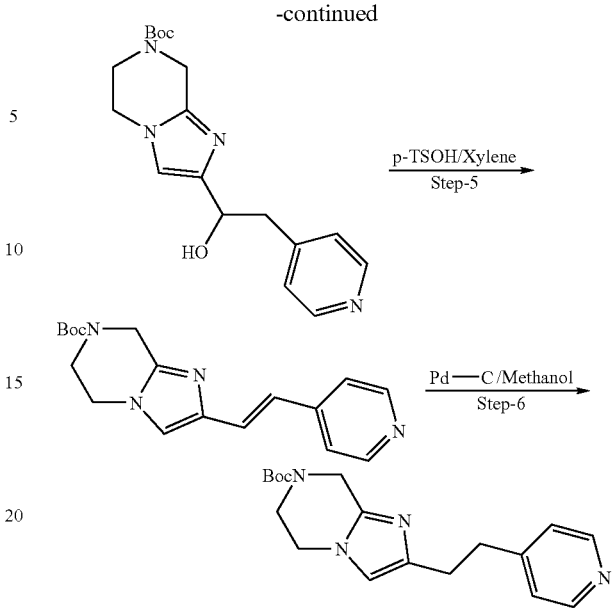

Procedure for Step-1:

To a solution of 2-amino pyrazine (20 g, 210 mmol) in dimethoxy ethane (400 ml) was added ethyl bromopyruvate (32.8 ml) at 25° C. and the resulting reaction mixture was stirred at the same temperature for 4 hrs. It was then cooled to 0° C. and stirred for 30 minutes. The separated solid was filtered and washed with ether. Solid residue was taken in ethanol (1000 ml) and refluxed for 4 hrs. Solvent was removed completely, the residue taken up in chloroform (1000 ml), saturated sodium bicarbonate solution (700 ml) was added to it and the mixture was stirred for 45 minutes. The mixture was filtered through a celite bed, washed several times with chloroform and the filtrate was dried over sodium sulfate. Evaporation of the organic layer under reduced pressure gave the crude mass, which was purified by crystallization using ether-methanol mixture. Yield: 20%

Procedure for Step-2:

To a well stirred suspension of the ester obtained from step-1 (10 g, 52.3 mmol) in dioxane (400 ml) was added lithium borohydride (2 eqv) at 25° C., and the resulting reaction mixture was stirred at the same temperature for 10 minutes. It was then warmed to 60° C. and kept at this temperature for 20 minutes (! Higher temperature and more reaction time reduce the yield and quality of reaction). Reaction mixture was then cooled to 0° C., acidified with 1N HCl and dioxane was completely evaporated under reduced pressure. Residue was taken in dichloromethane (200 ml), TEA (4-eqv) and Boc-anhydride (1.2 eqv) was added to it and the resulting reaction mixture was stirred at 25° C. for 16 hrs. The organic layer was washed with water and brine and finally dried over sodium sulfate. Evaporation of organic layer gave the crude product which was purified by column chromatography (70% ethyl acetate in hexane). Yield: 27%

Procedure for Step-3:

To a solution of the boc-ester (1 g, 3.38 mmol) obtained from step-2 in dry DCM (40 ml) was added DIBAL (1M, 3.7 mmol) at −78° C. and the reaction mixture was stirred at this temperature for 5 hrs (monitored by TLC). Reaction was quenched with methanol (3.7 ml) and was slowly brought to 25° C. Brine (10 ml) was added to it, and filtered through a celite bed. The residue was washed with dichloromethane and the combined organic layer was evaporated to get the crude aldehyde, which was used directly in the next step without any further purification. Yield: 800 mg (crude)

Procedure for Step-4:

To a solution of 4-picoline (3 mmol) in dry THF (10 ml) was added n-BuLi (1.57M, 3 mmol) at −78° C. and the resulting reaction mixture was stirred at 25° C. for 1 hr. It was again cooled to 0° C. and the aldehyde obtained from step-3 (3 mmol) was added to the reaction mixture drop wise. After stirring at 25° C., reaction mixture was quenched with water (5 ml), extracted with ethyl acetate and the combined organic layer was washed with brine. After drying over sodium sulfate, the organic layer was evaporated under reduced pressure to get the crude alcohol, which was purified by column chromatography (3% methanol in dichloromethane). Yield: 36%

Procedure for Step-5:

To a solution of the alcohol obtained from step-4 (2.3 mmol) in xylene (12 ml) wadded p-toluene sulfonic acid (0.05 eqv) and the resulting reaction mixture was refluxed using a dean-stark apparatus for 5 hrs (monitored by TLC). Reaction mixture was cooled to room temperature, diluted with ethyl acetate and washed successively with saturated sodium bicarbonate solution, water and brine. The organic layer was dried over sodium sulfate evaporated under reduced pressure to get the crude product that was purified by column chromatography (2% methanol in dichloromethane). Yield: 59%

Procedure for Step-6:

A solution of the compound (1.38 mmol) obtained from step-5 was taken in methanol (15 ml) and deoxygenated with argon. To it was added 10% Pd—C (225 mg) and the resulting reaction mixture was hydrogenated under atmospheric pressure for 3 hrs. It was filtered through celite bed, residue washed with methanol and the combined organic layer was evaporated to dryness to get the crude product which was used directly in the next step without any further purification. Yield: 80% (crude)

Preparation of the Amine Building Block A48

3-(Piperidin-1-ylmethyl)-5,6,7,8-tetrahydro-[1,2,4]triazolo[4,3-a]pyrazine

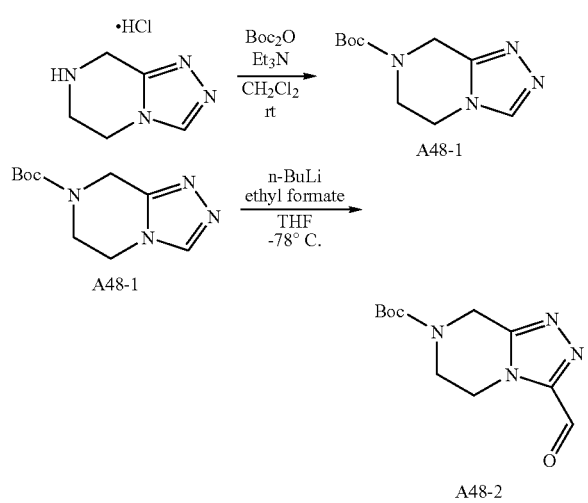

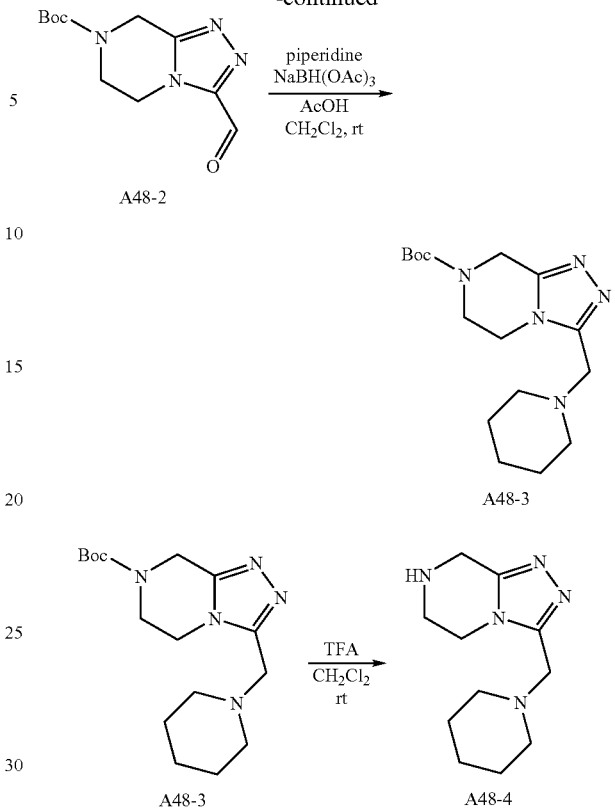

Procedure for Step-1:

To a solution of 5,6,7,8-tetrahydro-[1,2,4]triazolo[4,3-a]pyrazine hydrochloride (1.0 g, 6.23 mmol) in $CH_2Cl_2$ (25 mL) were added $Et_3N$ (2.17 mL, 15.57 mmol) and $Boc_2O$ (1.52 mL, 6.54 mmol) and the reaction was stirred at room temperature overnight. The mixture was extracted with aqueous 0.25 M $KHSO_4$ (50 mL). The organic layer was dried ($Na_2SO_4$) and evaporated to dryness to afford compound A48-1 (1.29 g, 92%).

Procedure for Step-2:

To a solution of compound A48-1 (1.29 g, 5.75 mmol) in dry THF (50 mL) was added a solution of 2.5 M n-BuLi in hexane (2.53 mL, 6.33 mmol) at −78° C. under argon. After 15 min ethyl formate (702 μL, 8.63 mmol) was added and the reaction mixture was stirred for 15 min at −78° C. Saturated aqueous $NH_4Cl$ (150 mL) was added and the mixture was extracted with $CH_2Cl_2$ (3×100 mL). The combined organic layer was dried ($Na_2SO_4$) and evaporated to dryness to afford aldehyde A48-2 (1.21 g, 83%).

Procedure for Step-3:

To a solution of aldehyde A48-2 (1.21 g, 4.80 mmol), piperidine (522 μL, 5.28 mmol) and AcOH (329 μL, 5.76 mmol) in $CH_2Cl_2$ (50 mL) was added $NaBH(OAc)_3$ (1.53 g, 7.19 mmol) and the reaction mixture was stirred at room temperature overnight. The mixture was diluted with $CH_2Cl_2$ (50 mL) and washed with brine (50 mL). The organic layer was dried ($Na_2SO_4$) and evaporated to dryness to afford amine A48-3 (1.53 g, 99%).

Procedure for Step-4:

To a solution of compound A48-3 (1.53 g, 4.76 mmol) in $CH_2Cl_2$ (30 mL) was added TFA (18.3 mL, 238 mmol) and the mixture was stirred at room temperature overnight. The mixture was concentrated in vacuo and co-evaporated twice with $CH_2Cl_2$ (50 mL) to afford amine A48 (3.18 g, '302%').

Process for Preparing Substituted Sulfonamide Compounds According to the Invention

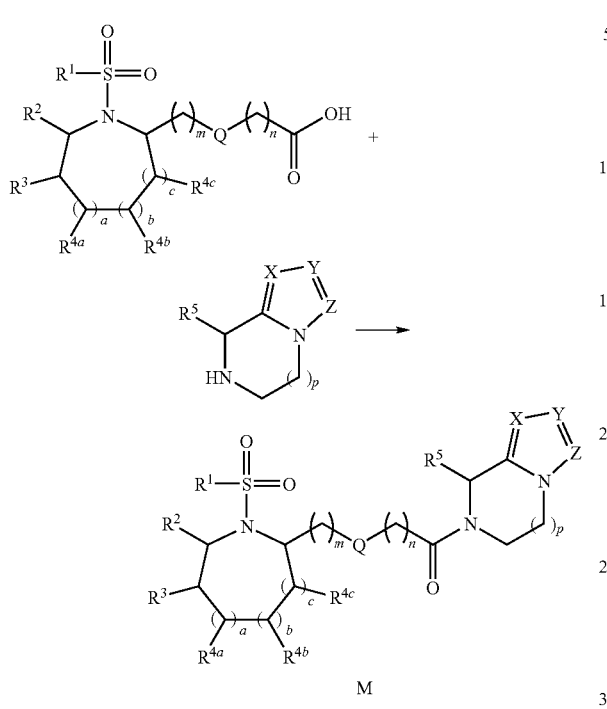

The carboxylic acids are converted in an amide formation process using primary or secondary amines in the presence of water-removing agents such as sodium or magnesium sulfate, phosphorus oxide or reagents such as, for example, CDI, DCC (optionally polymer-bound), TBTU, EDCI, PyBOP or PFPTFA also in the presence of HOAt or HOBt and an organic base, for example, DIPEA or pyridine in an organic solvent such as THF, dichloromethane, diethyl ether, dioxane, DMF or acetonitrile, at a temperature from 0° C. to the reflux temperature, to yield the final products of formula M.

Parallel Syntheses

Parallel Synthesis Method 1

An acid solution (0.05 M in DCM, 2 ml) was added to 105 μmole of CDI solution (0.105 M in DCM, 1 ml) and shaken for 1 hour at RT. 100 μmole of the amine solution (0.1 M in DCM) were then added at RT and shaken for a further 12 hours at RT. 3 ml of water were next added to the reaction mixture, shaken for 15 minutes, and the organic phase was separated. After distilling of the solvent the crude products were analysed by means of LC-MS and purified by HPLC.

Parallel Synthesis Method 2

EDCI (1.5 equiv.), HOBt (1 equiv.) and diisopropylethylamine (1.5 equiv.) were first of all added to a solution of the corresponding acid (1 equiv.) in DCM (3 ml/mmole) and stirred for 15 minutes at 25° C. The corresponding amine was dissolved in DCM (1 ml/mmole) in another reaction vessel, cooled to 0° C., and diisopropylethylamine (4 equiv.) was added. The cooled solution was added to the acid solution and stirred for 16 hours at RT. For working-up, the mixture was first of all diluted with DCM and then washed in succession with ammonium chloride solution, sodium carbonate solution and saturated sodium chloride solution, and dried over sodium sulfate. The solution was concentrated by evaporation to dryness. The product was purified using a purification system from Biotage operating in parallel.

Parallel Synthesis Method 3

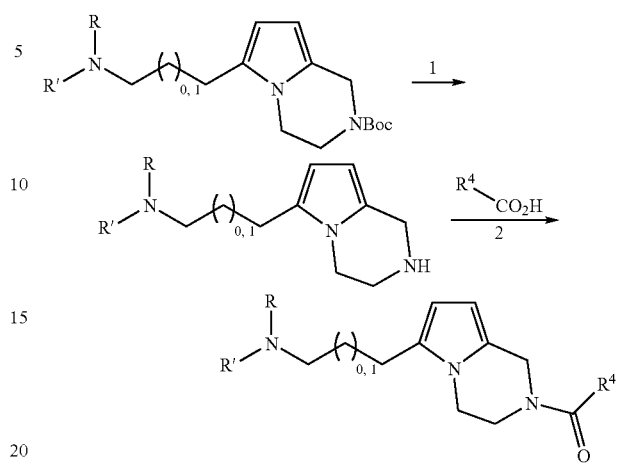

Stage 1. TFA (20% in DCM, 3 ml/mole mmole) was added at 0° C. to the Boc-protected amine (1 equiv.). The reaction mixture was heated to 25° C. and stirred at this temperature for 2 hours (DC check). The solvent was completely removed and the product was carefully dried in order to remove traces of TFA. The crude product was used without further purification.

Stage 2. EDCI (1.5 equiv.), HOBt (1 equiv.) and DIPEA (2.5 equiv.) were added to a solution of the acid building block (1 equiv.) in DCM (3 ml/mmole) and stirred for 15 minutes at 25° C. The Boc-deprotected amine (1.5 equiv.) in DCM (1 ml/mmole) was cooled to 0° C. in another reaction vessel and DIPEA (4 equiv.) was added. The solution thereby obtained was added to the solution of the acid building block. The reaction mixture was stirred for 16 hours at 25° C. and then diluted with DCM. The organic phase was washed in succession with aqueous ammonium chloride solution, aqueous sodium hydrogen carbonate solution and saturated sodium chloride solution. The organic phase was dried over sodium sulfate and concentrated by evaporation. The crude product was purified using a parallel purification system from Biotage.

Biotage Purification of Library Compounds

Step-1: Before purification all the crude compounds were analyzed to get LCMS data of each compound. Thus, it is possible to determine the polarity of compounds.

Step-2: Each compound was dissolved in minimum quantity of dichloromethane and loaded onto a Biotage column (Biotage Si 12+M) and it was then placed in the 12 channel Biotage Quad-3 parallel purification system. At a time 12 compounds were purified.

Step-3: Depending on the polarity of the compound (TLC was used to determine the eluent) specific solvent mixtures were run in 12 channel Biotage Quad-3 purification system and the fractions were collected in test tubes. Pure fractions were combined after checking the TLC of all the fractions.

Step-4: Combined pure fractions from each column were evaporated under reduced pressure, transferred to pre-tared glass vials using acetonitrile as solvent and dried in Speed Vac Thermo explorer to get dry pure compound. These were then submitted for final analysis.

LCMS Method for MONITORING

1. LC Parameters

Column=phenomenex GEMINI 5 μm C18 110A (50*4.6 mm)

U.V wavelength=220 nm, 260 nm

Shimadzu LC system injection volume=1.00 to 5.00 μl
(Depending on Concentration)
Flow rate=1.2 ml/min
Time Program:
A: 0.05% TFA (pH 2.3)
B: Acetonitrile

| TIME | MODULE | EVENTS | PARAMETER |
|---|---|---|---|
| 0.01 | Pumps | % B | 10 |
| 1.50 | Pumps | % B | 30 |
| 3.00 | Pumps | % B | 90 |
| 4.00 | Pumps | % B | 90 |
| 5.00 | Pumps | % B | 10 |
| 5.10 | System Controller | Stop | |

2. MS Parameters

Scan Type: Q1 MS (Q1)

Polarity: Positive

Scan Mode Profile

Ion Source Turbo Spray

Source Temperature (at setpoint): 200° C.

| Start (amu) | Stop (amu) | Time (sec) | Param | Start | Stop |
|---|---|---|---|---|---|
| 100.00 | 800.00 | 2.00 | CEP | 26.51 | 41.21 |

Detector Parameters):

IS (Ion Spray Voltage): 5500

Detector CEM: 2200.0

DP (Declustering Potential): 50.00

EP (Entrance Potential): 10.00

HPLC: Schimadzu Prominance integrated with MS of API 2000 LCMS/MS of Applied Biosystems, and ELS Detector of Polymer labs (temperature 50° C.)

Example 1

Preparation of 1-(5,6-dihydro-[1,2,4]triazolo[4,3-a]pyrazin-7(8H)-yl)-2-((1-(4-methoxy-2,6-dim ethylphenylsulfonyl)piperidin-2-yl)methoxy)ethanone

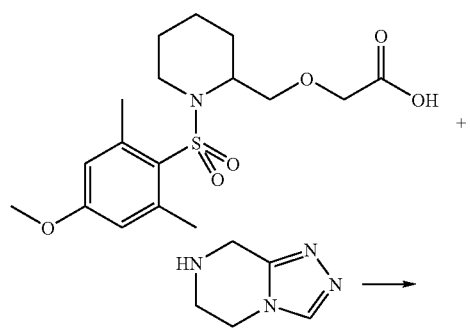

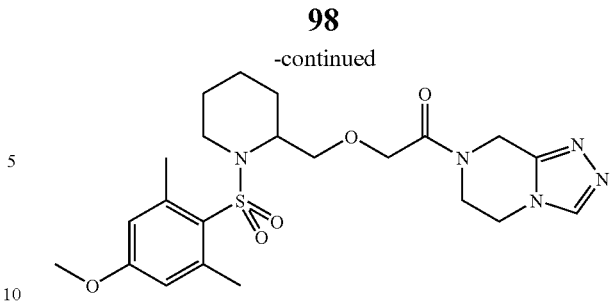

EDCI (506 mg, 2.64 mmole) was added to a solution of the acid S2 (654 mg, 1.76 mmole), 5,6,7,8-tetrahydro-[1,2,4]triazolo[4,3-a]pyrazine hydrochloride (311 mg, 1.94 mmole), HOAt (35.9 mg, 0.26 mmole) and DIPEA (922 μl, 5.28 mmole) in DCM (10 ml) and the reaction mixture was stirred overnight at RT. After removing the solvent in vacuo the residue was purified by column chromatography (flash, silica DCM/(7 M NH$_3$ in MeOH), 99:1 to 95:5). The product was dissolved in DCM (10 ml) and washed with aqueous 0.5 M HCl (10 ml). The organic phase was dried over sodium sulfate and after filtration the solvent was removed. Yield: 623 mg, 74%. 5,6,7,8-tetrahydro-[1,2,4]triazolo[4,3-a]pyrazine is commercially available.

Example 2

Preparation of 2-((1-(4-methoxy-2,6-dimethylphenylsulfonyl)piperidin-2-yl)methoxy)-1-(2-(piperidin-1-ylmethyl)-5,6-dihydroimidazo[1,2-a]pyrazin-7(8H)-yl)ethanone Preparation of 2-(piperidin-1-ylmethyl)-5,6,7,8-tetrahydroimidazo[1,2-a]pyrazine

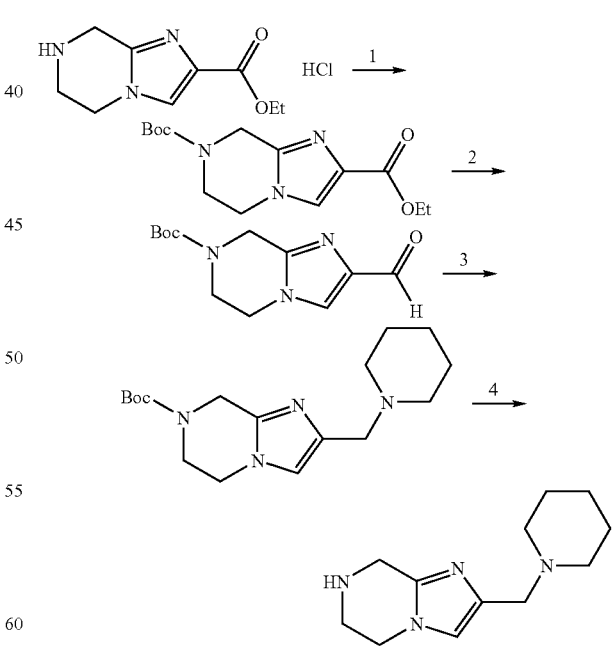

Stage 1. First DMAP (0.75 g, 6.12 mmole) and then Boc$_2$O (1.34 g, 6.12 mmole) were added to a solution of the ethyl 5,6,7,8-tetrahydroimidazo[1,2-a]pyrazine-2-carboxylate hydrochloride (1.09 g, 4.70 mmole) in DCM (100 ml). The reaction mixture was stirred for 18 hours at RT. Since the reaction had not yet gone to completion further Boc$_2$O (0.12 g, 0.53 mmole) was added and the mixture was again stirred overnight. After completion of the reaction the mixture was washed with aqueous HCl solution (1 M, 100 ml), and the organic phase was dried over sodium sulfate and concentrated by evaporation in vacuo. The crude product was purified by column chromatography (silica gel, ethyl acetate). Yield: 300 mg, 21%.

Stage 2. A solution of 7-tert-butyl 2-ethyl 5,6-dihydroimidazo[1,2-a]pyrazine-2,7(8H)-dicarboxylate (300 mg, 1.02 mmole) in THF (15 ml) was cooled to −78° C. and DIBAL-H (1 M in hexane, 2.0 ml, 2.0 mmole) was slowly added under a N$_2$ atmosphere. The reaction mixture was stirred for 1 hour at this temperature and Na$_2$SO$_4$×10H$_2$O was then added until the evolution of gas could no longer be detected. Further sodium sulfate was added, the mixture was filtered, and the residue was washed with DCM (25 ml). The filtrate was concentrated and the crude product obtained (450 mg) was used without further purification in the next stage.

Stage 3. The tert-butyl 2-formyl-5,6-dihydroimidazo[1,2-a]pyrazine-7(8H)-carboxylate (400 mg, max. 0.91 mmole) and piperidine (158 μl, 1.59 mmole) were dissolved in DCM (8 ml) and NaBH(OAc)$_3$ (506 mg, 2.39 mmole) was added in portions. The reaction mixture was stirred for 2 hours at RT and then hydrolyzed with saturated sodium hydrogen carbonate solution (25 ml). The phases were separated and the aqueous phase was re-extracted with DCM (25 ml). The combined organic phases were washed with saturated sodium chloride solution, dried over sodium sulfate, and concentrated by evaporation in vacuo. Yield: 260 mg, 90% over 2 stages.

Stage 4. TFA (2.83 ml, 36.7 mmole) was added to a solution of the tert-butyl 2-(piperidin-1-ylmethyl)-5,6-dihydroimidazo[1,2-a]pyrazine-7(8H)-carboxylate (235 mg, 0.73 mmole) in DCM (10 ml) and stirred for 3-4 hours at RT (DC check). After completion of the reaction the solvent was first of all removed, DCM was added, and the mixture was concentrated again by evaporation to dryness. The product was used without further purification for further reactions.

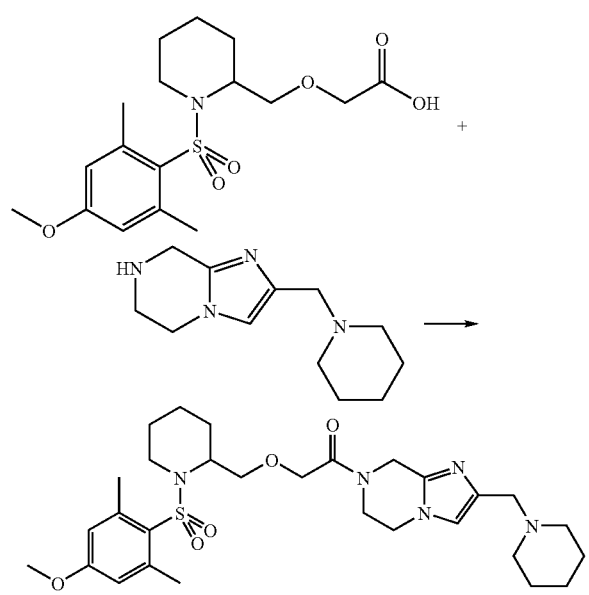

The acid (1.88 g, 5.06 mmole), HOAt (69 mg, 0.51 mmole), DIPEA (5.30 ml, 30.4 mmole) and EDCI (1.46 g, 7.59 mmole) were added to a solution of the amine (3.17 g, max. 3.48 mmole) in DCM (50 ml) and the reaction mixture was stirred overnight at RT. After removing the solvent in vacuo, the residue was purified by column chromatography (flash, silica, DCM/(7 M NH$_3$ in MeOH). The product was dissolved in DCM (35 ml) and washed with aqueous 0.1 M HCl (25 ml). The organic phase was dried over sodium sulfate and after filtration the solvent was evaporated. Yield: 610 mg, 31%.

Example 3

Preparation of 1-(3-chloro-2-(piperidin-1-ylmethyl)-5,6-dihydro-imidazo[1,2-a]pyrazin-7(8H)-yl-2-((−1-(4-methoxy-2,6-dimethylphenylsulfonyl)-piperidin-2-yl)methoxy)ethanone Preparation of 3-chloro-2-(piperidin-1-ylmethyl)-5,6,7,8-tetrahydroimidazo[1,2-a]pyrazine

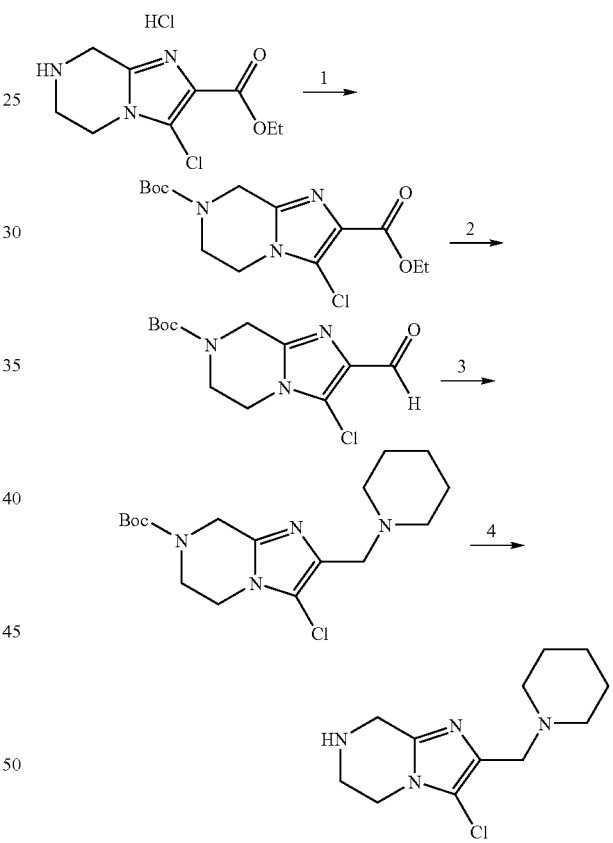

Stage 1. Triethylamine (1.34 ml, 9.58 mmole) and Boc$_2$O (0.92 g, 4.22 mmole) were added to a solution of the ethyl-3-chloro-5,6,7,8-tetrahydroimidazo[1,2-a]pyrazin-2-carboxylate hydrochloride (1.02 g, 3.83 mmole) in DCM (100 ml) and stirred for 18 hours at RT. After completion of the reaction (DC check) the reaction mixture was diluted with DCM and washed with aqueous 0.5 M KHSO$_4$ solution (100 ml). The organic phase was dried over sodium sulfate and the solvent was evaporated after filtration.

Stage 2. A solution of the BOC-protected ethyl-3-chloro-5,6,7,8-tetrahydroimidazo[1,2-a]pyrazin-2-carboxylate (1.19 g, 3.62 mmole) in THF (25 ml) was cooled to −78° C. and DIBAL-H (1 M in hexane, 7.24 ml, 7.24 mmole) was slowly added under a $N_2$ atmosphere. The reaction mixture was stirred for 1 hour at −78° C. and hydrolysed with sodium sulfate×10H$_2$O until the evolution of gas could no longer be detected. An excess of Na$_2$SO$_4$×10H$_2$O was added and the mixture was then filtered. The solid was washed with DCM (2×25 ml) and the filtrate was then concentrated by evaporation to dryness. The crude product obtained was used further without further purification.

Stage 3. The aldehyde (720 mg, 2.52 mmole) and piperidine (249 µl, 2.52 mmole) were dissolved in DCM (15 ml) and sodium triacetoxy boron hydride (822 mg, 3.88 mmole) was added in portions. The reaction mixture was stirred for 4 hours at RT (LCMS check). The reaction mixture was hydrolysed with saturated aqueous sodium hydrogen carbonate solution. The phases were separated and the aqueous phase was extracted once more with DCM (25 ml). The combined organic phases were washed with saturated sodium chloride solution (25 ml), dried over sodium sulfate, and concentrated by evaporation to dryness.

Stage 4. TFA (2.61 ml, 33.8 mmole) was added to a solution of the Boc-protected amine (240 mg, 0.68 mmole) in DCM (10 ml) and stirred for 4 hours at RT. After completion of the reaction (DC check) the reaction mixture was concentrated by evaporation to dryness, taken up in DCM (20 ml), concentrated by evaporation to dryness, taken up again in DCM (20 ml) and then concentrated by evaporation to dryness. The crude product was used further without further purification.

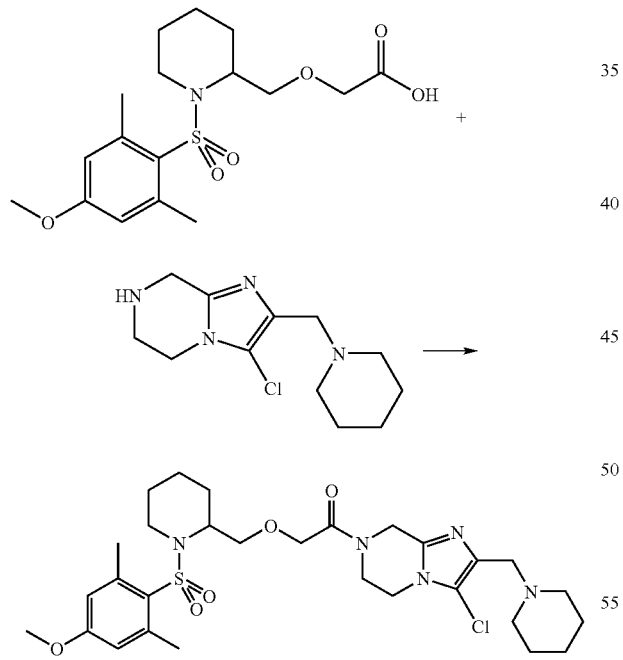

The acid (244 mg, 657 µmole), HOAt (8.9 mg, 66 µmmole), DIPEA (573 µl, 3.28 mmole) and EDCI (189 mg, 985 µmole) were added to a solution of the amine (695 mg, max. 722 µmole) in DCM (25 ml) and the reaction mixture was stirred overnight at RT. After removing the solvent in vacuo the residue was purified by column chromatography (flash, silica, DCM/(7 M NH$_3$ in MeOH, 99:1). Yield 340 mg.

Example 85

Preparation of 1-(1-ethyl-3,4-dihydropyrrolo[1,2-a]pyrazin-2(1H)-yl)-3-(1-(4-methoxy-2,6-dimethylphenylsulfonyl)piperidin-2-yl)propan-1-one

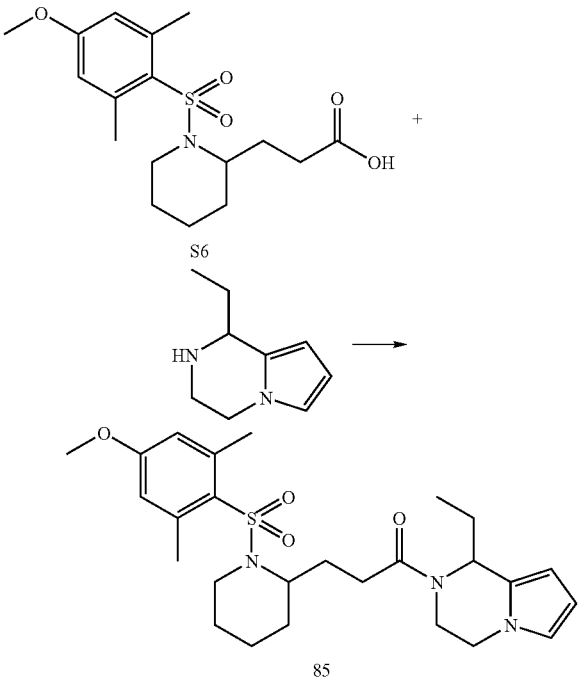

Carboxylic acid S6 (120 mg, 0.338 mmol) and N-ethyl-N'-(3-dimethylamino propyl) carbodiimide hydrochloride (EDCI) (96 mg, 0.507 mmol) were dissolved in CH$_2$Cl$_2$ (8 mL). HOBt (49 mg, 0.372 mmol), 1-ethyl-1,2,3,4-tetrahydropyrrolo[1,2-a]pyrazine (76 mg, 0.507 mmol) and DIPEA (146 µL, 0.845 mmol) were added and the mixture stirred overnight at room temperature. The reaction mixture was diluted with sat. sodium hydrogen carbonate solution and the aqueous layer extracted with CH$_2$Cl$_2$ (2×). The combined organics fractions were dried (MgSO$_4$) and concentrated in vacuo. The crude product was purified by column chromatography (silica, hexane/ethylacetate, 2:1) to afford screening compound 85 (180 mg, >99%).

LC/MS: R$_t$=5.4 min; m/z=488.3 [MH]$^+$

Example 86

Preparation of 1-(1-ethyl-3,4-dihydropyrrolo[1,2-a]pyrazin-2(11H)-yl)-2-(((S)-1-(4-methoxy-2,6-dimethylphenylsulfonyl)piperidin-2-yl)methoxy)ethanone

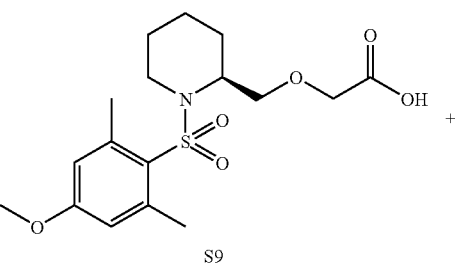

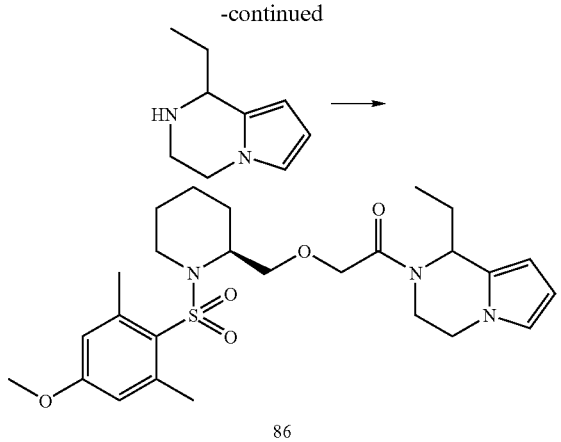

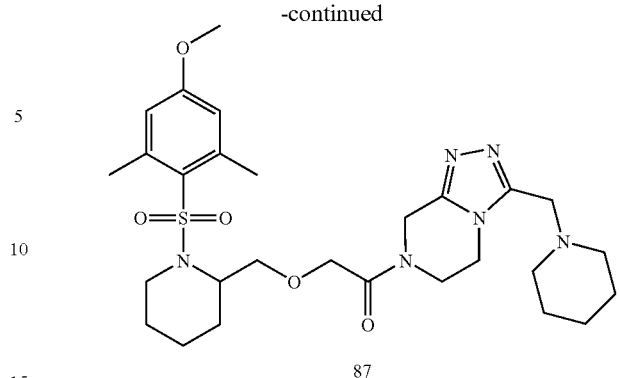

Carboxylic acid S9 (100 mg, 0.27 mmol) and N-ethyl-N'-(3-dimethylamino propyl) carbodiimide hydrochloride (EDCI) (77 mg, 0.404 mmol) were dissolved in CH$_2$Cl$_2$ (6 mL). HOBt (39 mg, 0.296 mmol), 1-ethyl-1,2,3,4-tetrahydropyrrolo[1,2-a]pyrazine (61 mg, 0.404 mmol) and DIPEA (86 µL, 0.674 mmol) were added and the mixture stirred overnight at room temperature. The reaction mixture was diluted with sat. sodium hydrogen carbonate solution and the aqueous layer extracted with CH$_2$Cl$_2$ (2×). The combined organics fractions were dried (MgSO$_4$) and concentrated in vacuo. The crude product was purified by column chromatography (silica, ethylacetate/hexane, 2:1) to afford screening compound 86 (100 mg, 74%).

LC/MS: R$_t$=5.26 min; m/z=504.3 [MH]+

Example No. 87

Preparation of 2-((1-(4-Methoxy-2,6-dimethylphenylsulfonyl)-piperidin-2-yl)methoxy)-1-(3-(piperidin-1-ylmethyl)-5,6-dihydro-[1,2,4]triazolo[4,3-a]pyrazin-7(8H)-yl)ethanone

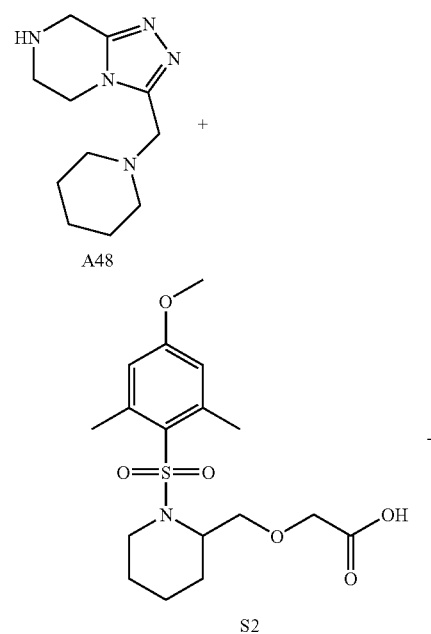

To a solution of amine A48 (795 mg, max. 1.19 mmol), carboxylic acid S2$^i$ (442 mg, 1.19 mmol) and DIPEA (1.66 mL, 9.52 mmol) in CH$_2$Cl$_2$ (20 mL) was added HATU (498 mg, 1.31 mmol) and the mixture was stirred overnight at room temperature. The mixture was evaporated to dryness and subjected to column chromatography (flash, silica, CH$_2$Cl$_2$/(7 M NH$_3$ in MeOH), 99:1 to 97:3). The product was then purified further by preparative LCMS three times to afford compound 87 (20 mg, 2.9%).

The method used for the synthesis of the example compounds can be found in the following table. The synthesised example compounds (1) to (84) were analyzed inter alia according to their molecular weight. The molecular weights measured by means of ESI-MS are summarised in the following table:

| Example | Method | Mol. wt. (ESI-MS) |
|---|---|---|
| 1 | | 477.2 |
| 2 | | 573.3 |
| 3 | | 607.3 |
| 4 | | 587.3 |
| 5 | 2 | 575.3 |
| 6 | 2 | 574.3 |
| 7 | 2 | 567.3 |
| 8 | 2 | 538.2 |
| 9 | 2 | 546.2 |
| 10 | 2 | 616.17 |
| 11 | 2 | 645.19 |
| 12 | 2 | 562.24 |
| 13 | 2 | 558.29 |
| 14 | 3 | 615.84 |
| 15 | 3 | 595.73 |
| 16 | 3 | 674.69 |
| 17 | 3 | 566.69 |
| 18 | 3 | 575.23 |
| 19 | 1 | 531.3 |
| 20 | 1 | 489.2 |
| 21 | 1 | 552.2 |
| 22 | 1 | 586.2 |
| 23 | 1 | 476.2 |
| 24 | 1 | 581.3 |
| 25 | 1 | 551.3 |
| 26 | 1 | 587.2 |
| 27 | 1 | 579.3 |
| 28 | 1 | 569.2 |
| 29 | 1 | 557.2 |
| 30 | 1 | 619.2 |
| 31 | 1 | 581.3 |
| 32 | 1 | 637.2 |
| 33 | 1 | 515.3 |
| 34 | 1 | 473.2 |
| 35 | 1 | 536.3 |
| 36 | 1 | 570.2 |
| 37 | 1 | 460.2 |

| Example | Method | Mol. wt. (ESI-MS) |
|---|---|---|
| 38 | 1 | 565.3 |
| 39 | 1 | 535.3 |
| 40 | 1 | 571.2 |
| 41 | 1 | 563.3 |
| 42 | 1 | 553.2 |
| 43 | 1 | 541.2 |
| 44 | 1 | 603.2 |
| 45 | 1 | 563.3 |
| 46 | 1 | 592.3 |
| 47 | 1 | 618.3 |
| 48 | 1 | 632.3 |
| 49 | 1 | 634.3 |
| 50 | 1 | 606.3 |
| 51 | 1 | 620.3 |
| 52 | 1 | 572.3 |
| 53 | 1 | 598.3 |
| 54 | 1 | 544.3 |
| 55 | 1 | 487.3 |
| 56 | 1 | 501.3 |
| 57 | 1 | 501.3 |
| 58 | 1 | 501.3 |
| 59 | 1 | 515.3 |
| 60 | 1 | 579.3 |
| 61 | 1 | 608.3 |
| 62 | 1 | 634.3 |
| 63 | 1 | 648.3 |
| 64 | 1 | 650.3 |
| 65 | 1 | 622.3 |
| 66 | 1 | 636.3 |
| 67 | 1 | 588.3 |
| 68 | 1 | 614.3 |
| 69 | 1 | 560.3 |
| 70 | 1 | 503.3 |
| 71 | 1 | 517.3 |
| 72 | 1 | 517.3 |
| 73 | 1 | 477.2 |
| 74 | 3 | 601.3 |
| 75 | 3 | 581.2 |
| 76 | 3 | 568.2 |
| 77 | 3 | 577.2 |
| 78 | 3 | 646.2 |
| 79 | 3 | 560.26 |
| 80 | 3 | 572.3 |
| 81 | 3 | 552.2 |
| 82 | 3 | 610.2 |
| 83 | 3 | 589.3 |
| 84 | 3 | 588.3 |

Parallel Synthesis Method 4
Generalized Synthetic Scheme

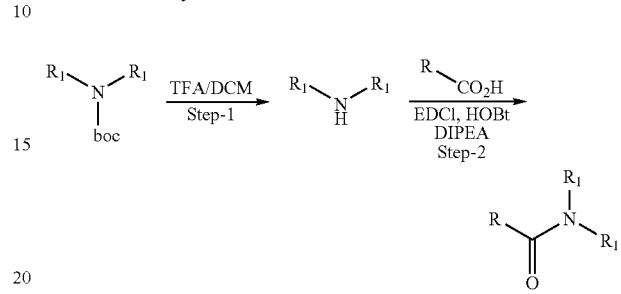

Procedure for step-1: Boc-protected amine BB (1 eqv) was treated with 20% TFA in DCM (10 ml/mol) at 0° C. and the resulting reaction mixture was stirred at 25° C. for 4 hrs (monitored by TLC). Solvent was completely evaporated, dried properly to remove traces of TFA and the residue was directly used in library synthesis.

Procedure for step-2: To a dichloromethane solution (3 ml/mmol) of acid BBs (1 eqv) was added EDCI (1.5 eqv), HOBT (1 eqv), DIPEA (2.5 eqv) and the resulting reaction mixture was stirred for 15 minutes at 25° C. In another R.B flask, Boc deprotected amine BB (1.5 eqv) in dichloromethane (1 ml/mmol) was cooled in ice bath, treated with DIPEA (4 eqv) and it was added to the reaction mixture. Reaction mixture was stirred at 25° C. for 16 hrs and diluted with dichloromethane. Organic layer was successively washed with aqueous ammonium chloride, sodium bicarbonate and brine and finally dried over sodium sulfate. Evaporation of organic layer under reduced pressure gave the crude product, which was purified by Biotage parallel purification system. Yield: 20-25%

Example Compounds 88-121 were Obtained According to Parallel Synthesis Method 4:

| Example No. | Structure | Name |
|---|---|---|
| 88 | 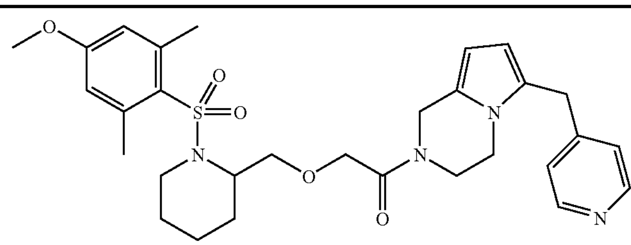 | 2-((1-(4-Methoxy-2,6-dimethylphenylsulfonyl)piperidin-2-yl)methoxy)-1-(6-(pyridin-4-ylmethyl)-3,4-dihydropyrrolo[1,2-a]pyrazin-2(1H)-yl)ethanone |
| 89 | 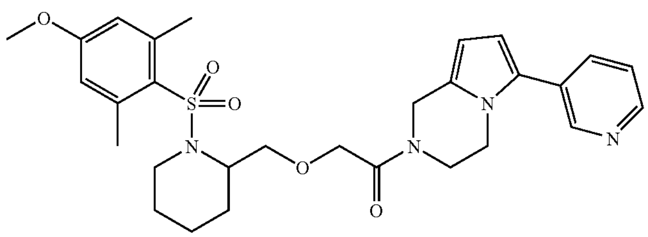 | 2-((1-(4-Methoxy-2,6-dimethylphenylsulfonyl)piperidin-2-yl)methoxy)-1-(6-(pyridin-3-yl)-3,4-dihydropyrrolo[1,2-a]pyrazin-2(1H)-yl)ethanone |

| Example No. | Structure | Name |
|---|---|---|
| 90 | 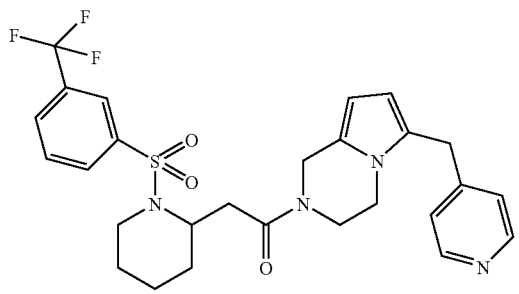 | 1-(6-(Pyridin-4-ylmethyl)-3,4-dihydropyrrolo[1,2-a]pyrazin-2(1H)-yl)-2-(1-(3-(trifluoromethyl)phenylsulfonyl)piperidin-2-yl)ethanone |
| 91 | 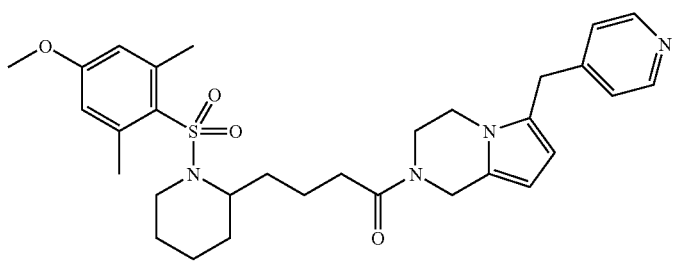 | 4-(1-(4-Methoxy-2,6-dimethylphenylsulfonyl)piperidin-2-yl)-1-(6-(pyridin-4-ylmethyl)-3,4-dihydropyrrolo[1,2-a]pyrazin-2(1H)-yl)butan-1-one |
| 92 | 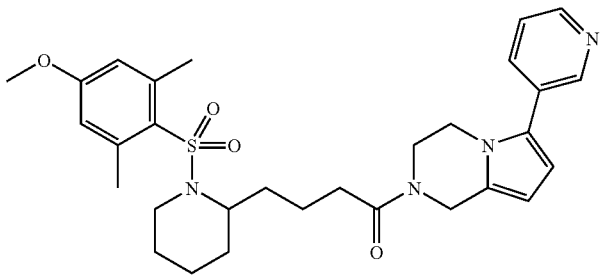 | 4-(1-(4-Methoxy-2,6-dimethylphenylsulfonyl)piperidin-2-yl)-1-(6-(pyridin-3-yl)-3,4-dihydropyrrolo[1,2-a]pyrazin-2(1H)-yl)butan-1-one |
| 93 | 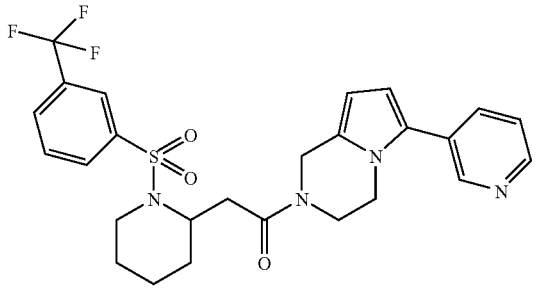 | 1-(6-(Pyridin-3-yl)-3,4-dihydropyrrolo[1,2-a]pyrazin-2(1H)-yl)-2-(1-(3-(trifluoromethyl)phenylsulfonyl)piperidin-2-yl)ethanone |
| 94 | 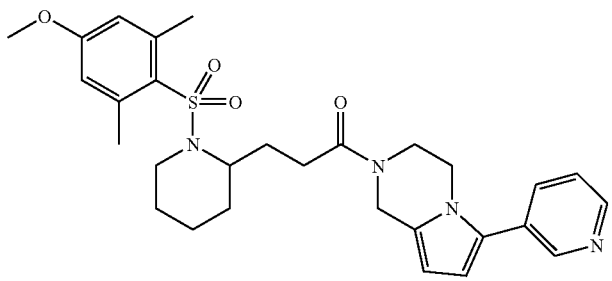 | 3-(1-(4-Methoxy-2,6-dimethylphenylsulfonyl)piperidin-2-yl)-1-(6-(pyridin-3-yl)-3,4-dihydropyrrolo[1,2-a]pyrazin-2(1H)-yl)propan-1-one |

| Example No. | Structure | Name |
|---|---|---|
| 95 | 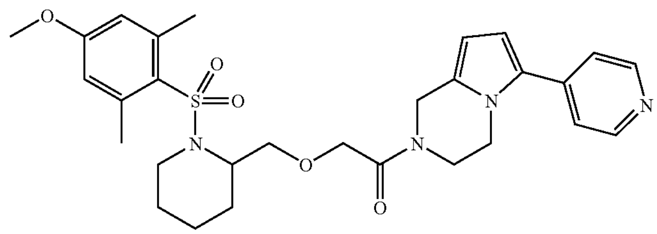 | 2-((1-(4-Methoxy-2,6-dimethylphenylsulfonyl)piperidin-2-yl)methoxy)-1-(6-(pyridin-4-yl)-3,4-dihydropyrrolo[1,2-a]pyrazin-2(1H)-yl)ethanone |
| 96 | 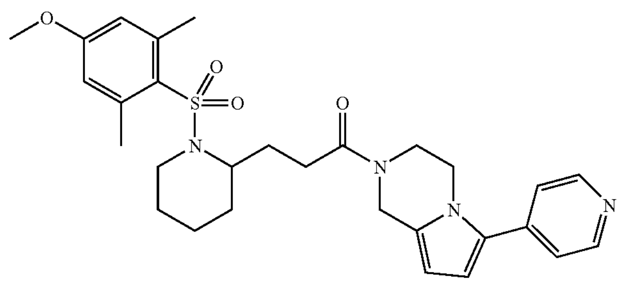 | 3-(1-(4-Methoxy-2,6-dimethylphenylsulfonyl)piperidin-2-yl)-1-(6-(pyridin-4-yl)-3,4-dihydropyrrolo[1,2-a]pyrazin-2(1H)-yl)propan-1-one |
| 97 | 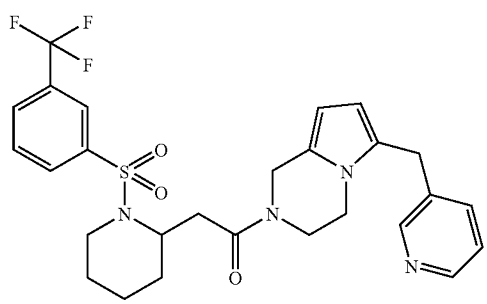 | 1-(6-(Pyridin-3-ylmethyl)-3,4-dihydropyrrolo[1,2-a]pyrazin-2(1H)-yl)-2-(1-(3-(trifluoromethyl)phenylsulfonyl)piperidin-2-yl)ethanone |
| 98 | 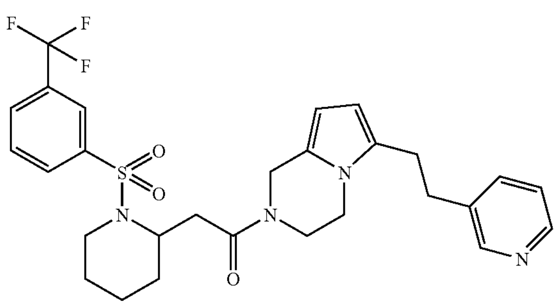 | 1-(6-(2-(Pyridin-3-yl)ethyl)-3,4-dihydropyrrolo[1,2-a]pyrazin-2(1H)-yl)-2-(1-(3-(trifluoromethyl)phenylsulfonyl)piperidin-2-yl)ethanone |
| 99 | 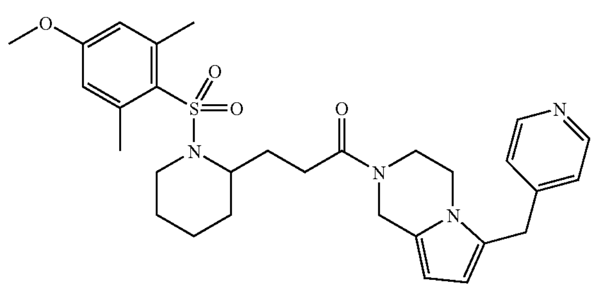 | 3-(1-(4-Methoxy-2,6-dimethylphenylsulfonyl)piperidin-2-yl)-1-(6-(pyridin-4-ylmethyl)-3,4-dihydropyrrolo[1,2-a]pyrazin-2(1H)-yl)propan-1-one |

| Example No. | Structure | Name |
|---|---|---|
| 100 | 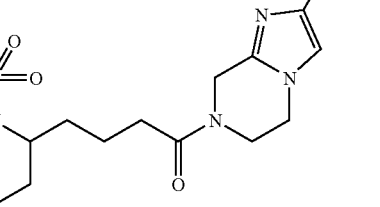 | 4-(1-(4-Methoxy-2,6-dimethylphenylsulfonyl)piperidin-2-yl)-1-(2-(pyridin-4-yl)-5,6-dihydroimidazo[1,2-a]pyrazin-7(8H)-yl)butan-1-one |
| 101 | 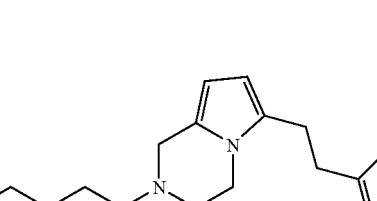 | 2-((1-(4-Methoxy-2,6-dimethylphenylsulfonyl)piperidin-2-yl)methoxy)-1-(6-(2-(pyridin-3-yl)ethyl)-3,4-dihydropyrrolo[1,2-a]pyrazin-2(1H)-yl)ethanone |
| 102 | 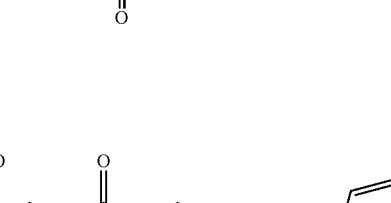 | 3-(1-(4-Methoxy-2,6-dimethylphenylsulfonyl)piperidin-2-yl)-1-(6-(2-(pyridin-3-yl)ethyl)-3,4-dihydropyrrolo[1,2-a]pyrazin-2(1H)-yl)propan-1-one |
| 103 | 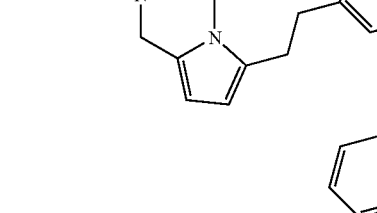 | 4-(1-(4-Methoxy-2,6-dimethylphenylsulfonyl)piperidin-2-yl)-1-(6-(2-(pyridin-3-yl)ethyl)-3,4-dihydropyrrolo[1,2-a]pyrazin-2(1H)-yl)butan-1-one |
| 104 | 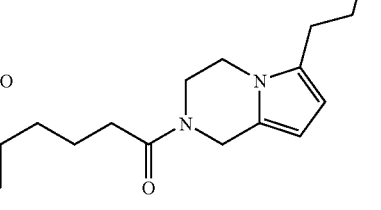 | 1-(2-(Pyridin-4-yl)-5,6-dihydroimidazo[1,2-a]pyrazin-7(8H)-yl)-2-(1-(3-(trifluoromethyl)phenylsulfonyl)piperidin-2-yl)ethanone |

-continued

| Example No. | Structure | Name |
|---|---|---|
| 105 | 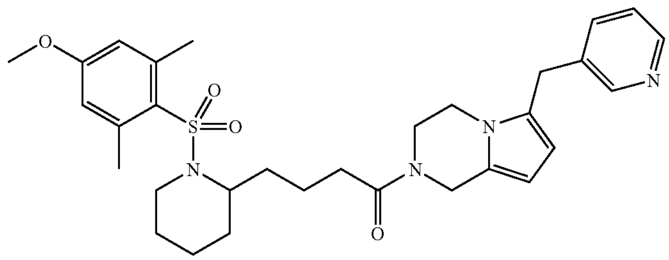 | 4-(1-(4-Methoxy-2,6-dimethylphenylsulfonyl)piperidin-2-yl)-1-(6-(pyridin-3-ylmethyl)-3,4-dihydropyrrolo[1,2-a]pyrazin-2(1H)-yl)butan-1-one |
| 106 | 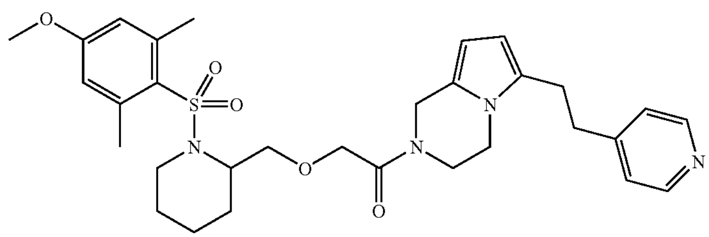 | 2-((1-(4-Methoxy-2,6-dimethylphenylsulfonyl)piperidin-2-yl)methoxy)-1-(6-(2-(pyridin-4-yl)ethyl)-3,4-dihydropyrrolo[1,2-a]pyrazin-2(1H)-yl)ethanone |
| 107 | 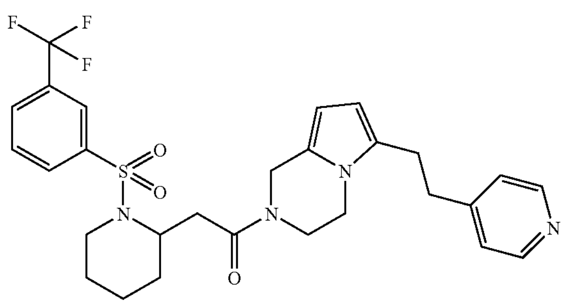 | 1-(6-(2-(Pyridin-4-yl)ethyl)-3,4-dihydropyrrolo[1,2-a]pyrazin-2(1H)-yl)-2-(1-(3-(trifluoromethyl)phenylsulfonyl)piperidin-2-yl)ethanone |
| 108 | 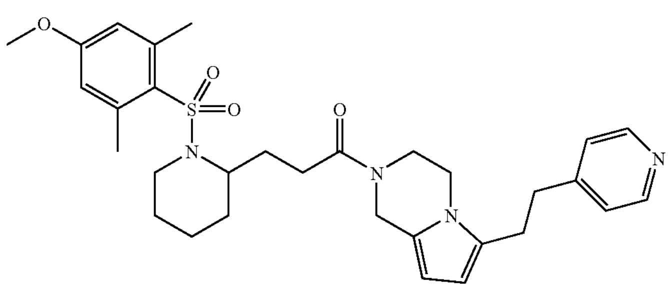 | 3-(1-(4-Methoxy-2,6-dimethylphenylsulfonyl)piperidin-2-yl)-1-(6-(2-(pyridin-4-yl)ethyl)-3,4-dihydropyrrolo[1,2-a]pyrazin-2(1H)-yl)propan-1-one |
| 109 | 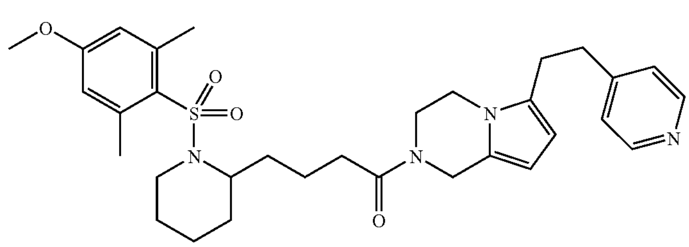 | 4-(1-(4-Methoxy-2,6-dimethylphenylsulfonyl)piperidin-2-yl)-1-(6-(2-(pyridin-4-yl)ethyl)-3,4-dihydropyrrolo[1,2-a]pyrazin-2(1H)-yl)butan-1-one |

-continued

| Example No. | Structure | Name |
|---|---|---|
| 110 | 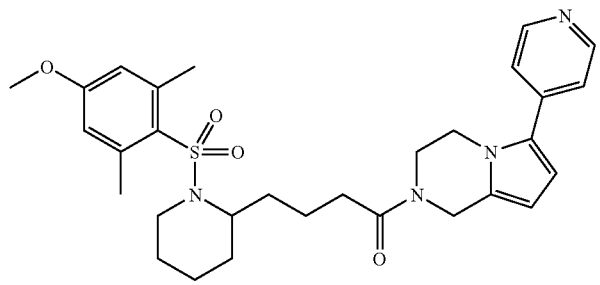 | 4-(1-(4-Methoxy-2,6-dimethylphenylsulfonyl)piperidin-2-yl)-1-(6-(pyridin-4-yl)-3,4-dihydropyrrolo[1,2-a]pyrazin-2(1H)-yl)butan-1-one |
| 111 | 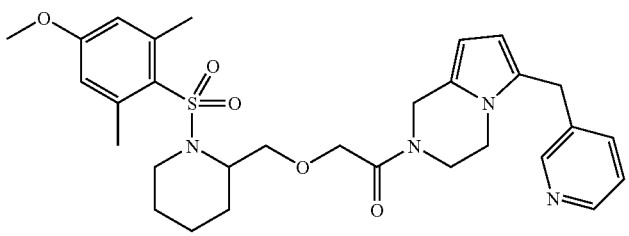 | 2-((1-(4-Methoxy-2,6-dimethylphenylsulfonyl)piperidin-2-yl)methoxy)-1-(6-(pyridin-3-ylmethyl)-3,4-dihydropyrrolo[1,2-a]pyrazin-2(1H)-yl)ethanone |
| 112 | 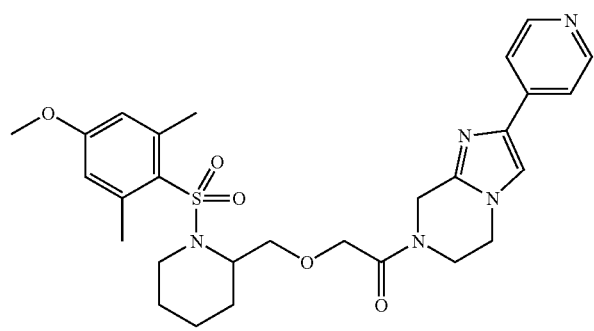 | 2-((1-(4-Methoxy-2,6-dimethylphenylsulfonyl)piperidin-2-yl)methoxy)-1-(2-(pyridin-4-yl)-5,6-dihydroimidazo[1,2-a]pyrazin-7(8H)-yl)ethanone |
| 113 | 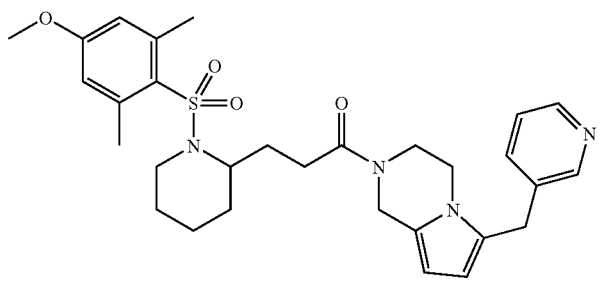 | 3-(1-(4-Methoxy-2,6-dimethylphenylsulfonyl)piperidin-2-yl)-1-(6-(pyridin-3-ylmethyl)-3,4-dihydropyrrolo[1,2-a]pyrazin-2(1H)-yl)propan-1-one |
| 114 | 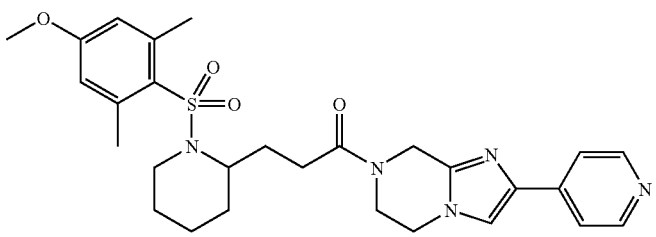 | 3-(1-(4-Methoxy-2,6-dimethylphenylsulfonyl)piperidin-2-yl)-1-(2-(pyridin-4-yl)-5,6-dihydroimidazo[1,2-a]pyrazin-7(8H)-yl)propan-1-one |

-continued

| Example No. | Structure | Name |
| --- | --- | --- |
| 115 | 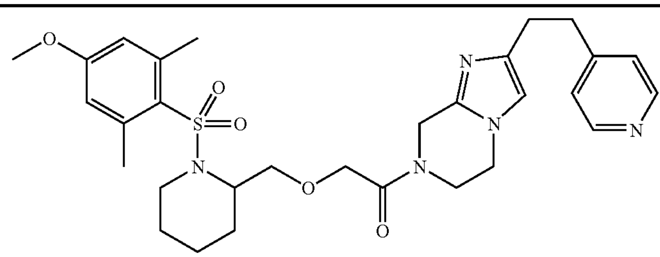 | 2-((1-(4-Methoxy-2,6-dimethylphenylsulfonyl)piperidin-2-yl)methoxy)-1-(2-(2-(pyridin-4-yl)ethyl)-5,6-dihydroimidazo[1,2-a]pyrazin-7(8H)-yl)ethanone |
| 116 | 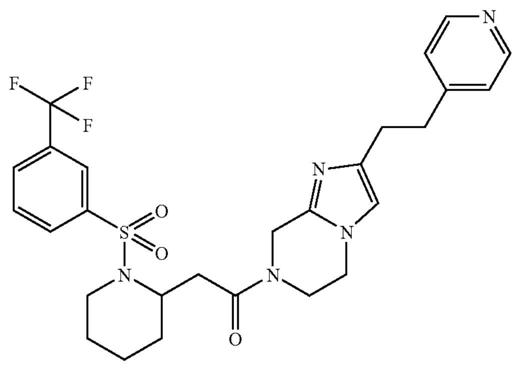 | 1-(2-(2-(pyridin-4-yl)ethyl)-5,6-dihydroimidazo[1,2-a]pyrazin-7(8H)-yl)-2-(1-(3-(trifluoromethyl)phenylsulfonyl)piperidin-2-yl)ethanone |
| 117 | 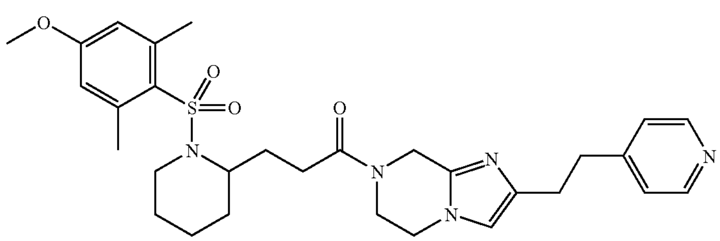 | 3-(1-(4-Methoxy-2,6-dimethylphenylsulfonyl)piperidin-2-yl)-1-(2-(2-(pyridin-4-yl)ethyl)-5,6-dihydroimidazo[1,2-a]pyrazin-7(8H)-yl)propan-1-one |
| 118 | 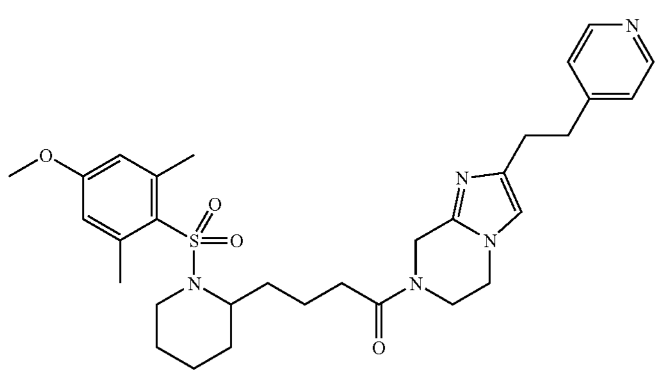 | 4-(1-(4-Methoxy-2,6-dimethylphenylsulfonyl)piperidin-2-yl)-1-(2-(2-(pyridin-4-yl)ethyl)-5,6-dihydroimidazo[1,2-a]pyrazin-7(8H)-yl)butan-1-one |
| 119 | 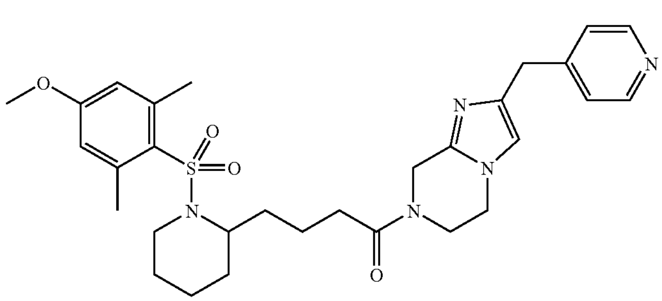 | 4-(1-(4-Methoxy-2,6-dimethylphenylsulfonyl)piperidin-2-yl)-1-(2-(pyridin-4-ylmethyl)-5,6-dihydroimidazo[1,2-a]pyrazin-7(8H)-yl)butan-1-one |

| Example No. | Structure | Name |
|---|---|---|
| 120 | 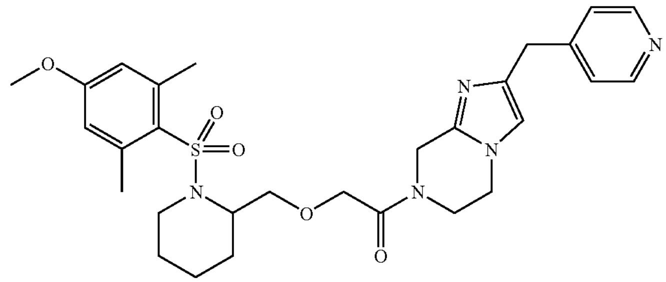 | 2-((1-(4-Methoxy-2,6-dimethylphenylsulfonyl)piperidin-2-yl)methoxy)-1-(2-(pyridin-4-ylmethyl)-5,6-dihydroimidazo[1,2-a]pyrazin-7(8H)-yl)ethanone |
| 121 | 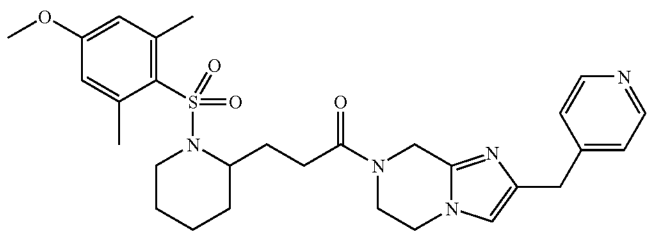 | 3-(1-(4-Methoxy-2,6-dimethylphenylsulfonyl)piperidin-2-yl)-1-(2-(pyridin-4-ylmethyl)-5,6-dihydroimidazo[1,2-a]pyrazin-7(8H)-yl)propan-1-one |

The following building blocks were used in the synthesis of example compounds 88-121:

| Example No. | Amine No. | Amine Name | Acid No. | Acid Name |
|---|---|---|---|---|
| 88 | A40 | 6-(Pyridin-4-ylmethyl)-1,2,3,4-tetrahydro-pyrrolo[1,2-a]pyrazine | S2 | 2-((1-(4-Methoxy-2,6-dimethylphenylsulfonyl)-piperidin-2-yl)methoxy)-acetic acid |
| 89 | A42 | 6-(Pyridin-3-yl)-1,2,3,4-tetrahydropyrrolo[1,2-a]pyrazine | S2 | 2-((1-(4-Methoxy-2,6-dimethylphenylsulfonyl)-piperidin-2-yl)methoxy)-acetic acid |
| 90 | A40 | 6-(Pyridin-4-ylmethyl)-1,2,3,4-tetrahydro-pyrrolo[1,2-a]pyrazine | S4 | 2-(1-(3-(Trifluoromethyl)-phenylsulfonyl)piperidin-2-yl)acetic acid |
| 91 | A40 | 6-(Pyridin-4-ylmethyl)-1,2,3,4-tetrahydro-pyrrolo[1,2-a]pyrazine | S7 | 4-(1-(4-Methoxy-2,6-dimethylphenylsulfonyl)piperidin-2-yl)butanoic acid |
| 92 | A42 | 6-(Pyridin-3-yl)-1,2,3,4-tetrahydropyrrolo[1,2-a]pyrazine | S7 | 4-(1-(4-Methoxy-2,6-dimethylphenylsulfonyl)piperidin-2-yl)butanoic acid |
| 93 | A42 | 6-(Pyridin-3-yl)-1,2,3,4-tetrahydropyrrolo[1,2-a]pyrazine | S4 | 2-(1-(3-(Trifluoromethyl)-phenylsulfonyl)piperidin-2-yl)acetic acid |
| 94 | A42 | 6-(Pyridin-3-yl)-1,2,3,4-tetrahydropyrrolo[1,2-a]pyrazine | S6 | 3-(1-(4-Methoxy-2,6-dimethylphenylsulfonyl)piperidin-2-yl)propanoic acid |
| 95 | A39 | 6-(Pyridin-4-yl)-1,2,3,4-tetrahydropyrrolo[1,2-a]pyrazine | S2 | 2-((1-(4-Methoxy-2,6-dimethylphenylsulfonyl)-piperidin-2-yl)methoxy)-acetic acid |
| 96 | A39 | 6-(Pyridin-4-yl)-1,2,3,4-tetrahydropyrrolo[1,2-a]pyrazine | S6 | 3-(1-(4-Methoxy-2,6-dimethylphenylsulfonyl)piperidin-2-yl)propanoic acid |
| 97 | A43 | 6-(Pyridin-3-ylmethyl)-1,2,3,4-tetrahydro-pyrrolo[1,2-a]pyrazine | S4 | 2-(1-(3-(Trifluoromethyl)-phenylsulfonyl)piperidin-2-yl)acetic acid |
| 98 | A44 | 6-(2-(Pyridin-3-yl)ethyl)-1,2,3,4-tetrahydro-pyrrolo[1,2-a]pyrazine | S4 | 2-(1-(3-(Trifluoromethyl)-phenylsulfonyl)piperidin-2-yl)acetic acid |
| 99 | A40 | 6-(Pyridin-4-ylmethyl)-1,2,3,4-tetrahydro-pyrrolo[1,2-a]pyrazine | S6 | 3-(1-(4-Methoxy-2,6-dimethylphenylsulfonyl)piperidin-2-yl)propanoic acid |

-continued

| Example No. | Amine No. | Amine Name | Acid No. | Acid Name |
|---|---|---|---|---|
| 100 | A45 | 2-(Pyridin-4-yl)-5,6,7,8-tetrahydroimidazo[1,2-a]pyrazine | S7 | 4-(1-(4-Methoxy-2,6-dimethylphenylsulfonyl)piperidin-2-yl)butanoic acid |
| 101 | A44 | 6-(2-(Pyridin-3-yl)ethyl)-1,2,3,4-tetrahydro-pyrrolo[1,2-a]pyrazine | S2 | 2-((1-(4-Methoxy-2,6-dimethylphenylsulfonyl)-piperidin-2-yl)methoxy)-acetic acid |
| 102 | A44 | 6-(2-(Pyridin-3-yl)ethyl)-1,2,3,4-tetrahydro-pyrrolo[1,2-a]pyrazine | S6 | 3-(1-(4-Methoxy-2,6-dimethylphenylsulfonyl)piperidin-2-yl)propanoic acid |
| 103 | A44 | 6-(2-(Pyridin-3-yl)ethyl)-1,2,3,4-tetrahydro-pyrrolo[1,2-a]pyrazine | S7 | 4-(1-(4-Methoxy-2,6-dimethylphenylsulfonyl)-piperidin-2-yl)butanoic acid |
| 104 | A45 | 2-(Pyridin-4-yl)-5,6,7,8-tetrahydroimidazo[1,2-a]pyrazine | S4 | 2-(1-(3-(Trifluoromethyl)-phenylsulfonyl)piperidin-2-yl)acetic acid |
| 105 | A43 | 6-(Pyridin-3-ylmethyl)-1,2,3,4-tetrahydro-pyrrolo[1,2-a]pyrazine | S7 | 4-(1-(4-Methoxy-2,6-dimethylphenylsulfonyl)piperidin-2-yl)butanoic acid |
| 106 | A41 | 6-(2-(Pyridin-4-yl)ethyl)-1,2,3,4-tetrahydro-pyrrolo[1,2-a]pyrazine | S2 | 2-((1-(4-Methoxy-2,6-dimethylphenylsulfonyl)-piperidin-2-yl)methoxy)-acetic acid |
| 107 | A41 | 6-(2-(Pyridin-4-yl)ethyl)-1,2,3,4-tetrahydro-pyrrolo[1,2-a]pyrazine | S4 | 2-(1-(3-(Trifluoromethyl)-phenylsulfonyl)piperidin-2-yl)acetic acid |
| 108 | A41 | 6-(2-(Pyridin-4-yl)ethyl)-1,2,3,4-tetrahydro-pyrrolo[1,2-a]pyrazine | S6 | 3-(1-(4-Methoxy-2,6-dimethylphenylsulfonyl)piperidin-2-yl)propanoic acid |
| 109 | A41 | 6-(2-(Pyridin-4-yl)ethyl)-1,2,3,4-tetrahydro-pyrrolo[1,2-a]pyrazine | S7 | 4-(1-(4-Methoxy-2,6-dimethylphenylsulfonyl)piperidin-2-yl)butanoic acid |
| 110 | A39 | 6-(Pyridin-4-yl)-1,2,3,4-tetrahydropyrrolo[1,2-a]pyrazine | S7 | 4-(1-(4-Methoxy-2,6-dimethylphenylsulfonyl)piperidin-2-yl)butanoic acid |
| 111 | A43 | 6-(Pyridin-3-ylmethyl)-1,2,3,4-tetrahydro-pyrrolo[1,2-a]pyrazine | S2 | 2-((1-(4-Methoxy-2,6-dimethylphenylsulfonyl)-piperidin-2-yl)methoxy)-acetic acid |
| 112 | A45 | 2-(Pyridin-4-yl)-5,6,7,8-tetrahydroimidazo[1,2-a]pyrazine | S2 | 2-((1-(4-Methoxy-2,6-dimethylphenylsulfonyl)-piperidin-2-yl)methoxy)-acetic acid |
| 113 | A43 | 6-(Pyridin-3-ylmethyl)-1,2,3,4-tetrahydro-pyrrolo[1,2-a]pyrazine | S6 | 3-(1-(4-Methoxy-2,6-dimethylphenylsulfonyl)piperidin-2-yl)propanoic acid |
| 114 | A45 | 2-(Pyridin-4-yl)-5,6,7,8-tetrahydroimidazo[1,2-a]pyrazine | S6 | 3-(1-(4-Methoxy-2,6-dimethylphenylsulfonyl)piperidin-2-yl)propanoic acid |
| 115 | A47 | 2-(2-(Pyridin-4-yl)ethyl)-5,6,7,8-tetrahydro-imidazo[1,2-a]pyrazine | S2 | 2-((1-(4-Methoxy-2,6-dimethylphenylsulfonyl)-piperidin-2-yl)methoxy)-acetic acid |
| 116 | A47 | 2-(2-(Pyridin-4-yl)ethyl)-5,6,7,8-tetrahydro-imidazo[1,2-a]pyrazine | S4 | 2-(1-(3-(Trifluoromethyl)-phenylsulfonyl)piperidin-2-yl)acetic acid |
| 117 | A47 | 2-(2-(Pyridin-4-yl)ethyl)-5,6,7,8-tetrahydro-imidazo[1,2-a]pyrazine | S6 | 3-(1-(4-Methoxy-2,6-dimethylphenylsulfonyl)piperidin-2-yl)propanoic acid |
| 118 | A47 | 2-(2-(Pyridin-4-yl)ethyl)-5,6,7,8-tetrahydro-imidazo[1,2-a]pyrazine | S7 | 4-(1-(4-Methoxy-2,6-dimethylphenylsulfonyl)piperidin-2-yl)butanoic acid |
| 119 | A46 | 2-(Pyridin-4-ylmethyl)-5,6,7,8-tetrahydro-imidazo[1,2-a]pyrazine | S7 | 4-(1-(4-Methoxy-2,6-dimethylphenylsulfonyl)piperidin-2-yl)butanoic acid |
| 120 | A46 | 2-(Pyridin-4-ylmethyl)-5,6,7,8-tetrahydro-imidazo[1,2-a]pyrazine | S2 | 2-((1-(4-Methoxy-2,6-dimethylphenylsulfonyl)-piperidin-2-yl)methoxy)-acetic acid |
| 121 | A46 | 2-(Pyridin-4-ylmethyl)-5,6,7,8-tetrahydro-imidazo[1,2-a]pyrazine | S6 | 3-(1-(4-Methoxy-2,6-dimethylphenylsulfonyl)piperidin-2-yl)propanoic acid |

The purity (determined by UV), the ESI-MS Results as well as the retention times are given in the following table:

| Example No. | Purity [UV] | MS-Found | Rt [min] |
|---|---|---|---|
| 88 | 100.0 | 567.3 | 2.891 |
| 89 | 100.0 | 553.2 | 2.958 |
| 90 | 100.0 | 547.2 | 2.911 |
| 91 | 100.0 | 565.3 | 2.954 |
| 92 | 100.0 | 551.2 | 3.027 |
| 93 | 98.6 | 533.2 | 2.969 |
| 94 | 100.0 | 537.3 | 2.980 |
| 95 | 100.0 | 553.3 | 4.811 |
| 96 | 94.4 | 537.2 | 9.762 |
| 97 | 96.0 | 547.1 | 2.925 |
| 98 | 92.8 | 561.2 | 9.884 |
| 99 | 95.2 | 551.2 | 2.916 |
| 100 | 100.0 | 552.4 | 2.808 |
| 101 | 99.9 | 581.1 | 2.933 |
| 102 | 100.0 | 565.1 | 2.950 |
| 103 | 96.4 | 579.2 | 2.990 |
| 104 | 94.8 | 534.2 | 2.798 |
| 105 | 100.0 | 565.5 | 9.932 |
| 106 | 100.0 | 581.2 | 2.927 |
| 107 | 99.4 | 561.1 | 2.934 |
| 108 | 99.2 | 565.1 | 2.935 |
| 109 | 96.4 | 579.1 | 2.985 |
| 110 | 90.4 | 551.1 | 9.764 |
| 111 | 97.0 | 567.5 | 2.931 |
| 112 | 100.0 | 554.4 | 2.806 |
| 113 | 100.0 | 551.4 | 2.956 |
| 114 | 100.0 | 538.4 | 2.826 |
| 115 | 99.3 | 582.3 | 2.581 |
| 116 | 91.6 | 562.3 | 2.596 |
| 117 | 100.0 | 566.4 | 5.592 |
| 118 | 100.0 | 580.3 | 2.680 |
| 119 | 90.3 | 566.2 | 2.690 |
| 120 | 94.1 | 568.3 | 2.580 |
| 121 | 95.3 | 552.3 | 2.640 |

Pharmacological Investigations:

The agonistic and antagonistic action of the compounds according to the invention on the bradykinin 1 receptor (B1R) of humans and rats were determined as described above. Antagonists lead to a suppression of the $Ca^{2+}$ inflow. The % inhibition compared to the maximum achievable inhibition was calculated. The compounds according to the invention are highly effective on the human and rat receptor.

| Example | hB1R [10 µM] % Inhibition | rB1R [10 µM] % Inhibition | Example | hB1R [10 µM] % Inhibition | rB1R [10 µM] % Inhibition |
|---|---|---|---|---|---|
| (1) | 56 | 100 | (2) | 105 | 106 |
| (3) | — | — | (4) | 105 | 101 |
| (5) | 100 | 51 | (6) | 100 | 101 |
| (7) | 87 | 52 | (8) | 99 | 96 |
| (9) | 104 | 48 | (10) | 101 | 91 |
| (11) | 100 | 56 | (12) | 103 | 57 |
| (13) | 102 | 102 | (14) | 97 | 99 |
| (14) | 97 | 99 | (15) | 46 | 100 |
| (15) | 46 | 100 | (16) | 48 | 92 |
| (17) | 50 | 75 | (18) | 90 | 99 |
| (19) | 102 | 96 | (20) | 101 | 99 |
| (21) | 100 | 98 | (22) | 102 | 99 |
| (23) | 70 | 99 | (24) | 101 | 98 |
| (25) | 99 | 97 | (26) | 86 | 98 |
| (27) | 66 | 97 | (28) | 98 | 98 |
| (29) | 102 | 98 | (30) | 58 | 98 |
| (31) | 96 | 98 | (32) | 61 | 99 |
| (33) | 98 | 100 | (34) | 76 | 99 |
| (35) | 100 | 97 | (36) | 99 | 99 |
| (37) | 18 | 91 | (38) | 90 | 99 |
| (39) | 77 | 99 | (40) | 38 | 100 |
| (41) | 35 | 98 | (42) | 73 | 99 |
| (43) | 96 | 98 | (44) | 10 | 79 |
| (45) | 45 | 98 | (46) | 102 | 102 |
| (47) | 101 | 103 | (48) | 103 | 103 |
| (49) | 103 | 103 | (50) | 100 | 102 |
| (51) | 101 | 101 | (52) | 103 | 100 |
| (53) | 92 | 102 | (54) | 102 | 100 |
| (55) | 98 | 103 | (56) | 95 | 102 |
| (57) | 102 | 103 | (58) | 97 | 103 |
| (59) | 85 | 103 | (60) | 87 | 102 |
| (61) | 102 | 101 | (62) | 102 | 101 |
| (63) | 104 | 103 | (64) | 103 | 102 |
| (65) | 102 | 100 | (66) | 102 | 101 |
| (67) | 102 | 100 | (68) | 102 | 103 |
| (69) | 104 | 102 | (70) | 102 | 103 |
| (71) | 103 | 102 | (72) | 102 | 102 |
| (73) | 36 | 102 | | | |
| (85) | 95 | 98 | (86) | 99 | 99 |
| (87) | | 103 | (88) | 99 | 100 |
| (89) | 99 | 96 | (90) | 25 | 47 |
| (91) | 95 | 100 | (92) | 91 | 99 |
| (93) | 18 | 55 | (94) | 45 | 99 |
| (95) | 99 | 97 | (96) | 61 | 96 |
| (97) | 80 | 103 | (98) | 90 | 90 |
| (99) | 72 | 102 | (100) | 85 | 101 |
| (101) | 100 | 98 | (102) | 86 | 101 |
| (103) | 95 | 100 | (104) | 43 | 49 |
| (105) | 64 | 103 | (106) | 99 | 99 |
| (107) | 26 | 75 | (108) | 92 | 99 |
| (109) | 95 | 99 | (110) | 84 | 101 |
| (111) | 100 | 98 | (112) | 100 | 101 |
| (113) | 97 | 100 | (114) | 79 | 98 |
| (115) | 100 | 98 | (116) | 78 | 102 |
| (117) | 82 | 98 | (118) | 98 | 102 |
| (119) | 90 | 107 | (120) | 99 | 105 |
| (121) | 66 | 51 | | | |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:
1. A compound corresponding to formula I':

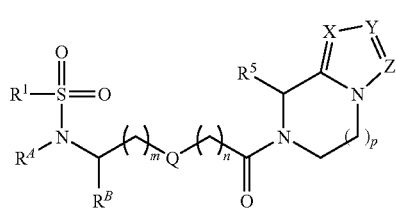

wherein
m and n, each independently denote 0, 1 or 2;
p denotes 1 or 2;
Q denotes —O— or —$CH_2$—;
X denotes $CR^6$;
Y denotes $CR^7$;
Z denotes $CR^8$;
$R^A$ and $R^B$ together with their linking group —N—CH— form a heterocycle, wherein said heterocycle may be substituted on one or more of its carbon ring members with one or more substituents independently selected from the group consisting of halogen, O—CF$_3$, methyl, ethyl, n-propyl, iso-propyl, and cyclopropyl, wherein methyl, ethyl, n-propyl, iso-propyl, and cyclopropyl are unsubstituted or substituted with one or more halogen which are identical or different and/or wherein said heterocycle may be annelated with at least one ring, and wherein said heterocycle is saturated or at least mono-unsaturated, but not aromatic, and wherein said heterocycle is 4-, 5-, 6- or 7-membered, and may comprise one or more heteroatoms or heteroatom groups independently selected from the group consisting of N, NR$^{50}$, O, S, S=O and S(=O)$_2$ in addition to the nitrogen atom to which R$^4$ is attached, and wherein:

said ring is 4-, 5-, 6- or 7-membered and saturated, unsaturated or aromatic and unsubstituted or monosubstituted or polysubstituted with identical or different substituents independently selected from the group consisting of C$_{1-6}$-alkyl, —O—C$_{1-6}$-alkyl, CF$_3$, OCF$_3$ and halogen;

R$^{50}$ represents H, C$_{1-6}$-alkyl, —C(=O)—R$^{51}$, C$_{3-8}$-cycloalkyl, aryl, heteroaryl or C$_{3-8}$-cycloalkyl, aryl or heteroaryl bonded via a C$_{1-6}$-alkylene group, and R$^{51}$ represents C$_{1-6}$-alkyl, C$_{3-8}$-cycloalkyl, aryl, heteroaryl or C$_{3-8}$-cycloalkyl, aryl or heteroaryl bonded via a C$_{1-6}$-alkylene group;

R$^1$ denotes aryl or heteroaryl; or denotes an aryl or heteroaryl bonded via a C$_{1-6}$-alkylene group;

R$^5$ denotes H, halogen, CN, NO$_2$, C$_{1-6}$-alkyl, C$_{2-6}$-alkenyl, aryl or heteroaryl; or denotes an aryl or heteroaryl bonded via a C$_{1-6}$-alkylene group, C$_{2-6}$-alkenylene group or C$_{2-6}$-alkynylene group;

R$^6$, R$^7$ and R$^8$ each independently denote H, halogen, CN, C$_{1-6}$-alkyl, —NH(C$_{1-6}$-alkyl), —N(C$_{1-6}$-alkyl)$_2$, —C$_{1-6}$-alkylene-NH(C$_{1-6}$-alkyl), —C$_{1-6}$-alkylene-N(C$_{1-6}$-alkyl)$_2$, C$_{3-8}$-cycloalkyl, heterocyclyl, aryl or heteroaryl; or denote a C$_{3-8}$-cycloalkyl, heterocyclyl, aryl or heteroaryl bonded via a C$_{1-6}$-alkylene group, C$_{2-6}$-alkenylene group or C$_{2-6}$-alkynylene group;

wherein:
said C$_{1-6}$-alkyl, C$_{1-6}$-alkylene, C$_{2-6}$-alkenyl, C$_{2-6}$-alkenylene, C$_{2-6}$-alkynylene, C$_{3-8}$-cycloalkyl, heterocyclyl, aryl and heteroaryl groups each may be unsubstituted or monosubstituted or polysubstituted with identical or different substituents, and said C$_{1-6}$-alkyl, C$_{1-6}$-alkylene, C$_{2-6}$-alkenyl, C$_{2-6}$-alkenylene, and C$_{2-6}$-alkynylene groups each may be branched or unbranched;

or a physiologically compatible salt thereof;

wherein:
in connection with "alkyl", "alkenyl", "alkylene", "alkenylene", "alkynylene" and "cycloalkyl" the term "substituted" denotes replacement of a hydrogen atom by F, Cl, Br, I, CN, NH$_2$, NH—C$_{1-6}$-alkyl, NHC$_{1-6}$-alkylene-OH, C$_{1-6}$-alkyl, N(C$_{1-6}$-alkyl)$_2$, N(C$_{1-6}$-alkylene-OH)$_2$, NO$_2$, SH, S—C$_{1-6}$-alkyl, S-benzyl, O—C$_{1-6}$-alkyl, OH, O—C$_{1-6}$-alkylene-OH, =O, O-benzyl, C(=O)C$_{1-6}$-alkyl, CO$_2$H, CO$_2$—C$_{1-6}$-alkyl, or benzyl;

in connection with "heterocyclyl" the term "substituted" denotes replacement of a hydrogen atom on one or more ring members by F, Cl, Br, I, —CN, NH$_2$, NH—C$_{1-6}$-alkyl, NH—C$_{1-6}$-alkylene-OH, C$_{1-6}$-alkyl, N(C$_{1-6}$-alkyl)$_2$, N(C$_{1-6}$-alkylene-OH)$_2$, pyrrolinyl, piperazinyl, morpholinyl, NO$_2$, SH, S—C$_{1-6}$-alkyl, S-benzyl, O—C$_{1-6}$-alkyl, OH, O—C$_{1-6}$-alkylene-OH, =O, O-benzyl, C(=O)C$_{1-6}$-alkyl, CO$_2$H, CO$_2$—C$_{1-6}$-alkyl or benzyl; and in connection with "aryl" and "heteroaryl" the term "substituted" denotes replacement of one or more hydrogen atoms of the aryl or heteroaryl ring system by F, Cl, Br, I, CN, NH$_2$, NH—C$_{1-6}$-alkyl, NH—C$_{1-6}$-alkylene-OH, N(C$_{1-6}$-alkyl)$_2$, N(C$_{1-6}$-alkylene-OH)$_2$, NH-aryl$^1$, N(aryl$^1$)$_2$, N(C$_{1-6}$-alkyl)aryl$^1$, pyrrolinyl, piperazinyl, morpholinyl, NO$_2$, SH, S—C$_{1-6}$-alkyl, OH, O—C$_{1-6}$-alkyl, O—C$_{1-6}$-alkyl-OH, C(=O)C$_{1-6}$-alkyl, NHSO$_2$C$_{1-6}$-alkyl, NHCOC$_{1-6}$-alkyl, CO$_2$H, CH$_2$SO$_2$-phenyl, CO$_2$—C$_{1-6}$-alkyl, OCF$_3$, CF$_3$, —O—CH$_2$—O—, —O—CH$_2$—CH$_2$—O—, —O—C(CH$_3$)$_2$—CH$_2$—, unsubstituted C$_{1-6}$-alkyl, pyrrolidinyl, imidazolyl, piperidinyl, benzyloxy, phenoxy, phenyl, naphthyl, pyridinyl, —C$_{1-3}$-alkylene-aryl$^1$, benzyl, thienyl, furyl, wherein aryl$^1$ denotes phenyl, furyl, thienyl or pyridinyl.

2. A compound as claimed in claim 1, corresponding to formula Ia:

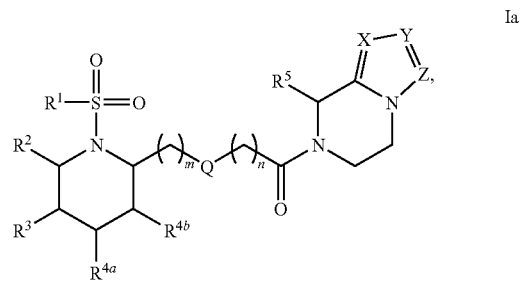

wherein
m and n each independently denote 0, 1 or 2;
Q denotes —O— or —CH$_2$—;
X denotes CR$^6$;
Y denotes CR$^7$;
Z denotes CR$^8$;
R$^1$ denotes an aryl or heteroaryl group; or an aryl or heteroaryl group bonded via a C$_{1-6}$-alkylene group;
R$^2$, R$^3$, R$^{4a}$ and R$^{4b}$ each independently denote H, or two adjacent groups selected from the group consisting of R$^2$, R$^3$, R$^{4a}$ and R$^{4b}$ form a 5- or 6-membered ring which may be saturated, unsaturated or aromatic and may be unsubstituted or monosubstituted or polysubstituted with identical or different groups;
R$^5$ denotes H, halogen, CN, NO$_2$, C$_{1-6}$-alkyl, C$_{2-6}$-alkenyl, or an aryl or heteroaryl group; or an aryl or heteroaryl group bonded via C$_{1-6}$-alkylene group, C$_{2-6}$-alkenylene group or C$_{2-6}$-alkynylene group;
R$^6$, R$^7$ and R$^8$ each independently denote H, halogen, CN, C$_{1-6}$-alkyl, —NH(C$_{1-6}$-alkyl), —N(C$_{1-6}$-alkyl)$_2$, —C$_{1-6}$-alkylene-NH(C$_{1-6}$-alkyl), —C$_{1-6}$-alkylene-N(C$_{1-6}$-alkyl)$_2$, C$_{3-8}$-cycloalkyl, heterocyclyl, aryl or heteroaryl group; or a C$_{3-8}$-cycloalkyl, heterocyclyl, aryl or heteroaryl group bonded via a C$_{1-6}$-alkylene group, C$_{2-6}$-alkenylene group or C$_{2-6}$-alkynylene group;
wherein
said C$_{1-6}$-alkyl, C$_{1-6}$-alkylene, C$_{2-6}$-alkenyl, C$_{2-6}$-alkenylene, C$_{2-6}$-alkynylene, C$_{3-8}$-cycloalkyl, heterocyclyl, aryl and heteroaryl groups each may be unsubstituted or monosubstituted or polysubstituted with identical or different substituents, and said $C_{1-6}$-alkyl, $C_{1-6}$-alkylene, $C_{2-6}$-alkenyl, $C_{2-6}$-alkenylene and $C_{2-6}$-alkynylene groups each may be branched or unbranched;

the substituted alkyl, alkenyl, alkylene, alkenylene, alkynylene or cycloalkyl groups may be mono- or poly-substituted with identical or different substituents selected from the group consisting of F, Cl, Br, I, CN, $NH_2$, $NH$—$C_{1-6}$-alkyl, $NH$—$C_{1-6}$-alkylene-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl and benzyl;

the substituted heterocyclyl groups may be mono- or poly-substituted with identical or different substituents selected from the group consisting of F, Cl, Br, I, —CN, $NH_2$, $NH$—$C_{1-6}$-alkyl, $NH$—$C_{1-6}$-alkylene-OH, $C_{1-6}$-alkyl, $N(C_{1-6}$-alkyl$)_2$, $N(C_{1-6}$-alkylene-OH$)_2$, pyrrolinyl, piperazinyl, morpholinyl, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$ alkyl, $CO_2H$, $CO_2$—$C_{1-6}$-alkyl and benzyl; and the substituted aryl or heteroaryl groups may be mono- or poly-substituted with identical or different substituents selected from the group consisting of F, Cl, Br, I, CN, $NH_2$, $NH$—$C_{1-6}$-alkyl, $NH$—$C_{1-6}$-alkylene-OH, $N(C_{1-6}$-alkyl$)_2$, $N(C_{1-6}$-alkylene-OH$)_2$, $NH$-$aryl^1$, $N(aryl^1)_2$, $N(C_{1-6}$-alkyl$)aryl^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—$C(CH_3)_2$—$CH_2$—, unsubstituted $C_{1-6}$-alkyl pyrrolidinyl, imidazolyl, piperidinyl, benzyloxy, phenoxy, phenyl, pyridinyl, —$C_{1-3}$-alkylene-$aryl^1$, benzyl, thienyl and furyl; wherein $aryl^1$ denotes phenyl, furyl, thienyl or pyridinyl.

3. A compound as claimed in claim 2, wherein
m and n each independently denote 0 or 1;
Q denotes —O— or —$CH_2$—;
X denotes $CR^6$;
Y denotes $CR^7$;
Z denotes $CR^8$;
$R^1$ denotes a phenyl, naphthyl, indolyl, benzofuranyl, benzothiophenyl, benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl or dibenzothiophenyl group, which may be unsubstituted or mono- or poly-substituted with substituents independently selected from the group consisting of —O—$C_{1-3}$-alkyl, $C_{1-6}$-alkyl, F, Cl, Br, I, $CF_3$, $OCF_3$, OH, SH, phenyl, naphthyl, furyl, thienyl and pyridinyl;
$R^2$, $R^3$, $R^{4a}$ and $R^{4b}$ each independently denote H, or two adjacent groups selected from the group consisting of $R^2$, $R^3$, $R^{4a}$ and $R^{4b}$ form a 5- or 6-membered aromatic ring, which may be unsubstituted or mono- or poly-substituted with substituents independently selected from the group consisting of methyl, methoxy, $CF_3$, F, Cl and Br;
$R^5$ denotes H, $C_{1-6}$-alkyl, a 5- or 6-membered aryl or heteroaryl group; or a 5-membered or 6-membered aryl or heteroaryl group bonded via a $C_{1-6}$-alkylene group, $C_{2-6}$-alkenylene group or $C_{2-6}$-alkynylene group; wherein the aryl or heteroaryl group is selected from the group consisting of phenyl, naphthyl, pyridinyl, thienyl and furyl, and may be unsubstituted or mono- or poly-substituted with substituents independently selected from the group consisting of O—$C_{1-3}$-alkyl, unsubstituted $C_{1-6}$-alkyl, F, Cl, Br, I, $CF_3$, $OCF_3$, OH and SH;

$R^6$ denotes H;

$R^7$ denotes H, a 5- or 6-membered heterocyclyl group bonded via a $C_{1-6}$-alkylene group, wherein the heterocyclyl group contains one or two identical or different heteroatoms selected from the group consisting of N and O and may be unsubstituted or mono- or poly-substituted with $C_{1-6}$-alkyl; or $R^7$ denotes a 5- or 6-membered heteroaryl group or a 5- or 6-membered heteroaryl group bonded via a $C_{1-6}$-alkylene group, wherein said heteroaryl group contains 1 or 2 nitrogen atoms and may be unsubstituted or mono- or polysubstituted;

$R^8$ denotes H, halogen, $C_{1-6}$-alkyl, —$N(C_{1-6}$alkyl$)_2$, —$C_{1-6}$-alkylene-$N(C_{1-6}$-alkyl$)_2$, or a 5- or 6-membered heterocyclyl group bonded via a $C_{1-6}$-alkylene group, wherein the heterocyclyl group contains one or two identical or different heteroatoms selected from the group consisting of N and O and may be unsubstituted or mono- or poly-substituted with $C_{1-6}$-alkyl; or $R^8$ denotes a 5- or 6-membered heteroaryl group or a 5- or 6-membered heteroaryl group bonded via a $C_{1-6}$-alkylene group, wherein said heteroaryl group contains 1 or 2 nitrogen atoms and may be unsubstituted or mono- or polysubstituted.

4. A compound as claimed in claim 3, wherein:
$R^1$ is selected from the group consisting of phenyl, naphthyl, benzothiophenyl, benzooxadiazolyl, thiophenyl, pyridinyl, imidazothiazolyl or dibenzofuranyl, and
two adjacent groups selected from the group consisting of $R^2$, $R^3$, $R^{4a}$ and $R^{4b}$ form a 6-membered aromatic ring.

5. A compound as claimed in claim 2, wherein:
m and n each independently denote 0 or 1;
Q denotes —O— or —$CH_2$—;
X denotes $CR^6$;
Y denotes $CR^7$;
Z denotes $CR^8$;
$R^1$ denotes phenyl or naphthyl, in each case unsubstituted or mono- or poly-substituted with substituents independently selected from the group consisting of methyl, methoxy, $CF_3$, F, Cl and Br;
$R^2$, $R^3$, $R^{4a}$ and $R^{4b}$ each independently denote H, or two adjacent groups selected from the group consisting of $R^2$, $R^3$, $R^{4a}$, and $R^{4b}$ form a 6-membered aromatic ring which may be unsubstituted or mono- or poly-substituted with substituents independently selected from the group consisting of methyl, methoxy, $CF_3$, F, Cl, and Br;
$R^5$ denotes H, $C_{1-6}$-alkyl, phenyl, furyl, thienyl, pyridinyl, or a phenyl, furyl, thienyl or pyridinyl group bonded via a $C_{1-3}$-alkylene group, wherein the phenyl, furyl, thienyl or pyridinyl may be unsubstituted or mono- or poly-substituted with substituents independently selected from the group consisting of —O—$C_{1-3}$-alkyl, unsubstituted $C_{1-6}$-alkyl, F, Cl, Br, I, $CF_3$, $OCF_3$, OH, and SH;
$R^6$ denotes H;
$R^7$ denotes H or a group selected from the group consisting of:

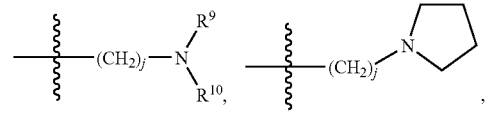

-continued

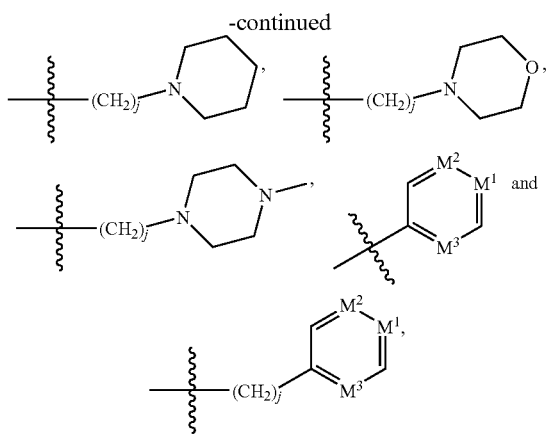

wherein
R⁹ and R¹⁰ each independently denote a $C_{1-6}$-alkyl group,
j is 1, 2 or 3; and
$M^1$, $M^2$ und $M^3$ each independently denote N or CH, wherein one of $M^1$, $M^2$ and $M^3$ represents N, and the other two of $M^1$, $M^2$ and $M^3$ each represent CH;
$R^8$ denotes H, F, Cl, Br, I, $C_{1-6}$-alkyl or a group selected from the group consisting of:

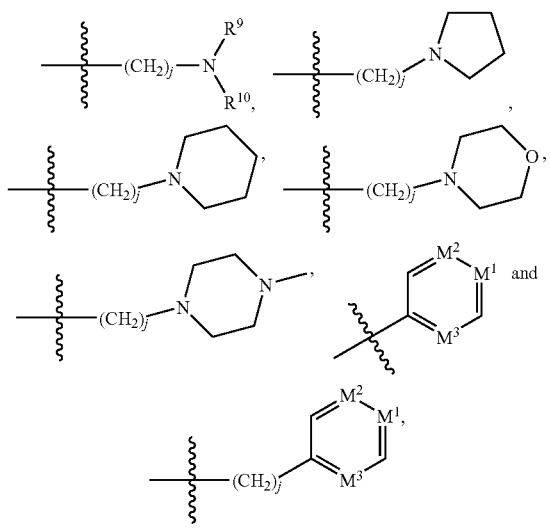

wherein
R⁹ and R¹⁰ each independently denote a $C_{1-6}$ alkyl group;
j is 1, 2 or 3; and
$M^1$, $M^2$ und $M^3$ each independently denote N or CH, wherein one of $M^1$, $M^2$ and $M^3$ represents N, and the other two of $M^1$, $M^2$ and $M^3$ each represent CH.

6. A compound as claimed in claim 2, wherein:
m=1, n=1, and Q denotes —O—; or
m=1, n=1, and Q denotes —CH₂—; or
m=1, n=0, and Q denotes —CH₂—; or
m=0, n=1, and Q denotes —CH₂—; or
m=0, n=0 and Q denotes —CH₂—;
X denotes $CR^6$;
Y denotes $CR^7$;
Z denotes $CR^8$;
$R^1$ denotes phenyl which may be unsubstituted or monosubstituted or identically or differently disubstituted, trisubstituted, tetrasubstituted or pentasubstituted with substituents independently selected from the group consisting of methyl, methoxy, $CF_3$, Cl, Br and F;

$R^2$, $R^3$, $R^{4a}$, and $R^{4b}$ each independently denote H, or two adjacent groups selected from the group consisting of $R^2$, $R^3$, $R^{4a}$ and $R^{4b}$ form a benzo ring;

$R^5$ denotes H, methyl, ethyl, n-propyl, iso-propyl, n-butyl, iso-butyl, sec-butyl, tert-butyl, phenyl, furyl, thienyl, pyridinyl, or a phenyl, furyl, thienyl or pyridinyl group bonded via a —(CH₂)—, —(CH₂)₂— or —(CH₂)₃— group, wherein the phenyl, furyl, thienyl or pyridinyl in each case may be unsubstituted or monosubstituted, disubstituted or trisubstituted with substituents independently selected from the group consisting of methoxy, ethoxy, n-propoxy, iso-propoxy, methyl, ethyl, n-propyl, iso-propyl, n-butyl, iso-butyl, sec-butyl, tert-butyl, F, Cl, Br, I, $CF_3$, $OCF_3$, OH and SH;

$R^6$ denotes H;

$R^7$ denotes H or a group selected from the group consisting of:

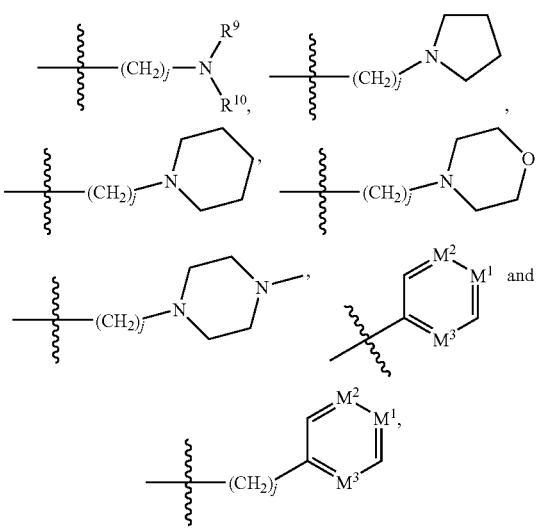

wherein
R⁹ and R¹⁰ each independently denote a methyl group;
j is 1, 2 or 3; and
$M^1$, $M^2$ and $M^3$ each independently denote N or CH, wherein one of $M^1$, $M^2$ and $M^3$ represents N, and the other two of $M^1$, $M^2$ and $M^3$ each represent CH;

$R^8$ denotes H, F, Cl, Br, I, methyl, ethyl, n-propyl, iso-propyl, n-butyl, iso-butyl, sec-butyl, tert-butyl or a group selected from the group consisting of:

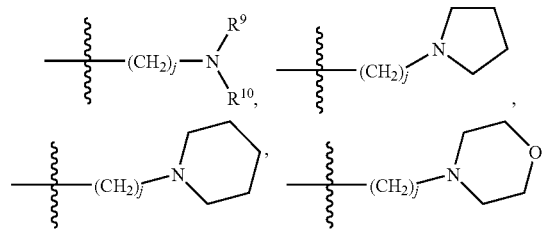

-continued

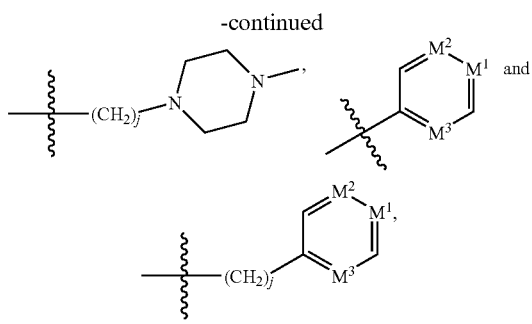

wherein
$R^9$ and $R^{10}$ each independently denote a methyl group;
j is 1, 2 or 3; and
$M^1$, $M^2$ and $M^3$ each independently denote N or CH, wherein one of $M^1$, $M^2$ and $M^3$ represents N, and the other two of $M^1$, $M^2$ and $M^3$ each represent CH.

7. A compound as claimed in claim 1, corresponding to formula I:

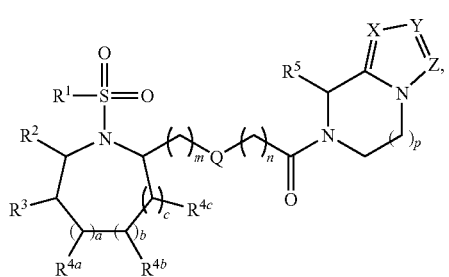

wherein
a, b and c each independently denote 0 or 1;
m and n each independently denote 0, 1 or 2;
p denotes 1 or 2;
Q denotes —O— or —$CH_2$—;
X denotes $CR^6$;
Y denotes $CR^7$;
Z denotes $CR^8$;
$R^1$ denotes aryl, heteroaryl, or an aryl or heteroaryl bonded via a $C_{1-6}$-alkylene group;
$R^2$, $R^3$, $R^{4a}$, $R^{4b}$ and $R^{4c}$ each independently denote H, or two adjacent groups selected from $R^2$, $R^3$, $R^{4a}$, $R^{4b}$ and $R^{4c}$ form a 5- or 6-membered ring, which may be saturated, unsaturated or aromatic and unsubstituted, monosubstituted or polysubstituted with identical or different substituents;
$R^5$ denotes H, halogen, CN, $NO_2$, $C_{1-6}$-alkyl, $C_{2-6}$-alkenyl, aryl, heteroaryl, or an aryl or heteroaryl group bonded via a $C_{1-6}$-alkylene group, $C_{2-6}$-alkenylene group or $C_{2-6}$-alkynylene group;
$R^6$, $R^7$ and $R^8$ each independently denote H, halogen, CN, $C_{1-6}$-alkyl, —$NH(C_{1-6}$-alkyl), —$N(C_{1-6}$-alkyl)$_2$, —$C_{1-6}$-alkylene-NH($C_{1-6}$-alkyl), —$C_{1-6}$-alkylene-N($C_{1-6}$-alkyl)$_2$, $C_{3-8}$-cycloalkyl, heterocyclyl, aryl, heteroaryl, or a $C_{3-8}$-cycloalkyl, heterocyclyl, aryl or heteroaryl group bonded via a $C_{1-6}$-alkylene group, $C_{2-6}$-alkenylene group or $C_{2-6}$-alkynylene group;
wherein:
said $C_{1-6}$-alkyl, $C_{1-6}$-alkylene, $C_{2-6}$-alkenyl, $C_{2-6}$-alkenylene, $C_{2-6}$-alkynylene, $C_{3-8}$-cycloalkyl, heterocyclyl, aryl and heteroaryl groups each may be unsubstituted or monosubstituted or polysubstituted with identical or different substituents, and
said $C_{1-6}$-alkyl, $C_{1-6}$-alkylene, $C_{2-6}$-alkenyl, $C_{2-6}$-alkenylene, and $C_{2-6}$-alkynylene groups each may be branched or unbranched
the substituents of substituted alkyl, alkenyl, alkylene, alkenylene, alkynylene or cycloalkyl groups are independently selected from the group consisting of F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl)$_2$, $N(C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl and benzyl;
the substituents of substituted heterocyclyl groups are independently selected from the group consisting of F, Cl, Br, I, —CN, $NH_2$ NH—$C_{1-6}$-alkyl, NH—$C_{1-6}$-alkylene-OH, $C_{1-6}$-alkyl, $N(C_{1-6}$-alkyl)$_2$, $N(C_{1-6}$-alkylene-OH)$_2$, pyrrolinyl, piperazinyl, morpholinyl, $NO_2$, SH, S—$C_{1-6}$-alkyl, S-benzyl, O—$C_{1-6}$-alkyl, OH, O—$C_{1-6}$ alkylene-OH, =O, O-benzyl, C(=O)$C_{1-6}$-alkyl $CO_2H$, $CO_2$—$C_{1-6}$-alkyl and benzyl; and
the substituents of substituted aryl or heteroaryl groups are independently selected from the group consisting of F, Cl, Br, I, CN, $NH_2$ NH—$C_{1-6}$-alkyl, NH—$C_{1-6}$-alkylene-OH, $N(C_{1-6}$-alkyl)$_2$, $N(C_{1-6}$-alkylene-OH)$_2$, NH-aryl$^1$, N(aryl$^1$)$_2$, $N(C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—$C(CH_3)_2$—$CH_2$—, unsubstituted $C_{1-6}$-alkyl, pyrrolidinyl, imidazolyl, piperidinyl, benzyloxy, phenoxy, phenyl, pyridinyl, —$C_{1-3}$-alkylene-aryl$^1$, benzyl, thienyl and furyl, wherein aryl$^1$ denotes phenyl, furyl, thienyl or pyridinyl.

8. A compound as claimed in claim 7, wherein:
a, b and c each independently denote 0 or 1;
m and n each independently denote 0, 1 or 2;
p denotes 1 or 2;
Q denotes —O— or —$CH_2$—;
X denotes $CR^6$;
Y denotes $CR^7$;
Z denotes $CR^8$;
$R^1$ denotes aryl, heteroaryl, or an aryl or heteroaryl group bonded via a $C_{1-6}$-alkylene group;
$R^2$, $R^3$, $R^{4a}$, $R^{4b}$ and $R^{4c}$ each independently denote H, or two adjacent groups selected from $R^2$, $R^3$, $R^{4a}$, $R^{4b}$ and $R^{4c}$ form a 5- or 6-membered ring, which may be saturated, unsaturated or aromatic, and unsubstituted or monosubstituted or polysubstituted with identical or different substituents;
$R^5$ denotes H, halogen, CN, $NO_2$, $C_{1-6}$-alkyl, $C_{2-6}$-alkenyl, aryl, heteroaryl, or an aryl or heteroaryl group bonded via a $C_{1-6}$-alkylene group, $C_{2-6}$-alkenylene group or $C_{2-6}$-alkynylene group;
$R^6$, $R^7$ and $R^8$ each independently denote H, halogen, CN, $C_{1-6}$-alkyl, —$NH(C_{1-6}$-alkyl), —$N(C_{1-6}$-alkyl)$_2$, —$C_{1-6}$-alkylene-NH($C_{1-6}$-alkyl), —$C_{1-6}$-alkylene-N($C_{1-6}$-alkyl)$_2$, $C_{3-8}$-cycloalkyl, heterocyclyl, aryl, heteroaryl, or a $C_{3-8}$-cycloalkyl, heterocyclyl, aryl or heteroaryl group bonded via a $C_{1-6}$-alkylene group, $C_{2-6}$-alkenylene group or $C_{2-6}$-alkynylene group;
wherein
said $C_{1-6}$-alkyl, $C_{1-6}$-alkylene, $C_{2-6}$-alkenyl, $C_{2-6}$-alkenylene, $C_{2-6}$-alkynylene, $C_{3-8}$-cycloalkyl, heterocyclyl, aryl and heteroaryl groups each may be unsubstituted or monosubstituted or polysubstituted with identical or different substituents;

said $C_{1-6}$-alkyl, $C_{1-6}$-alkylene, $C_{2-6}$-alkenyl, $C_{2-6}$-alkenylene, and $C_{2-6}$-alkynylene groups each may be branched or unbranched;

the substituents of substituted alkyl, alkenyl, alkylene, alkenylene, alkynylene or cycloalkyl groups are independently selected from the group consisting of F, Cl, Br, I, CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl and benzyl;

the substituents of substituted heterocyclyl groups are independently selected from the group consisting of F, Cl, Br, I, —CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, pyrrolinyl, piperazinyl, morpholinyl, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl and benzyl; and the substitutents of substituted aryl or heteroaryl groups are independently selected from the group consisting of F, Cl, Br, I, CN, $NH_2$, NH—$C_{1-6}$-alkyl, NH—$C_{1-6}$alkylene-OH, N($C_{1-6}$-alkyl)$_2$, N($C_{1-6}$-alkylene-OH)$_2$, NH-aryl$^1$, N(aryl$^1$)$_2$, N($C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—$C(CH_3)_2$—$CH_2$—, unsubstituted $C_{1-6}$-alkyl, pyrrolidinyl, imidazolyl, piperidinyl, benzyloxy, phenoxy, phenyl, pyridinyl, —$C_{1-3}$-alkylene-aryl$^1$, benzyl, thienyl and furyl, wherein aryl$^1$ denotes phenyl, furyl, thienyl or pyridinyl.

9. A compound as claimed in claim 7, wherein $R^2$, $R^3$, $R^{4a}$, $R^{4b}$ and $R^{4c}$ each independently denote H, or two adjacent groups selected from the group consisting of $R^2$, $R^3$, $R^{4a}$, $R^{4b}$ and $R^{4c}$ form a 5- or 6-membered aromatic ring which may be unsubstituted or mono- or poly-substituted with substituents independently selected from the group consisting of methyl, methoxy, $CF_3$, F, Cl and Br.

10. A compound as claimed in claim 7, wherein the sum a+b+c=2.

11. A compound as claimed in claim 1, wherein said compound is present in the form of a mixture of stereoisomers in any mixing ratio.

12. A compound as claimed in claim 11, wherein said mixture is a racemic mixture.

13. A compound as claimed in claim 1, wherein $R^1$ denotes phenyl, naphthyl, indolyl, benzofuranyl, benzothiophenyl, benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl or dibenzothiophenyl, each of which may be unsubstituted or mono- or poly-substituted with substituents independently selected from the group consisting of —O—$C_{1-3}$-alkyl, $C_{1-6}$-alkyl, F, Cl, Br, I, $CF_3$, $OCF_3$, OH, SH, phenyl, naphthyl, furyl, thienyl and pyridinyl.

14. A compound as claimed in claim 13, wherein $R^1$ denotes a phenyl or naphthyl group, each of which may be unsubstituted or mono- or polysubstituted with substituents independently selected from the group consisting of methyl, methoxy, $CF_3$, F, Cl, and Br.

15. A compound as claimed in claim 1, wherein said compound is present in the form of an isolated stereoisomer.

16. A compound as claimed in claim 1, wherein if Q=-O—, then m and n each denote 1, and if Q=-$CH_2$—, then the sum m+n equals 0, 1 or 2.

17. A compound as claimed in claim 1, wherein the following partial structures

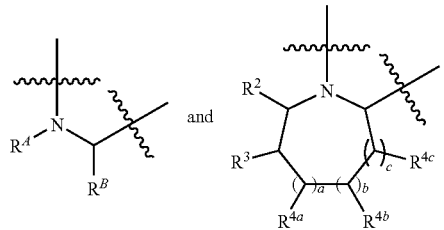

and are selected from the group consisting of

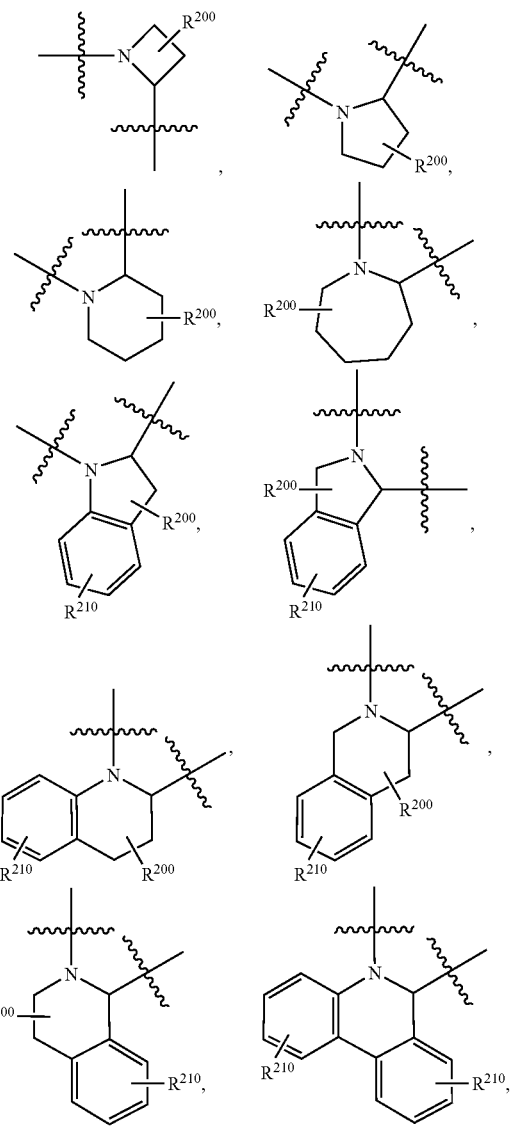

-continued

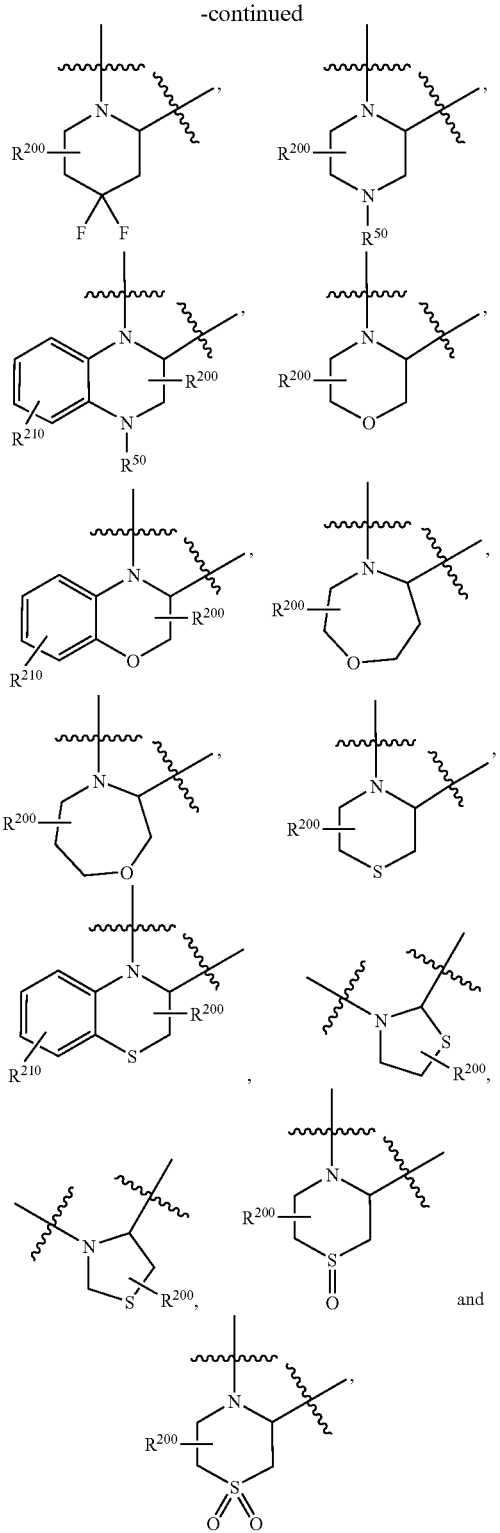

wherein
R$^{200}$ represents 1, 2, 3 or 4 substituents independently selected from the group consisting of H, halogen, O—CF$_3$, CF$_3$, methyl, ethyl, n-propyl, iso-propyl, and cyclopropyl;
R$^{210}$ represents 1, 2, 3 or 4 substituents independently selected from the group consisting of H, methoxy, methyl, ethyl, n-propyl, iso-propyl, halogen, CF$_3$ and OCF$_3$; and R$^{50}$ represents H, methyl, ethyl, n-propyl, iso-propyl, C$_{3-8}$-cycloalkyl, aryl, heteroaryl or a C$_{3-8}$-cycloalkyl, aryl or heteroaryl bonded via a C$_{1-3}$-alkylene group.

18. A compound as claimed in claim 1, wherein p is 1.
19. A compound as claimed in claim 1, wherein
R$^5$ denotes H, C$_{1-6}$-alkyl, 5- or 6-membered aryl or heteroaryl group; or a 5-membered or 6-membered aryl or heteroaryl group bonded via a C$_{1-6}$-alkylene group, C$_{2-6}$-alkenylene group or C$_{2-6}$-alkynylene group;
wherein the aryl or heteroaryl group is selected from the group consisting of phenyl, naphthyl, pyridinyl, thienyl and furyl, and may be unsubstituted or monosubstituted or polysubstituted with substituents independently selected from the group consisting of O—C$_{1-3}$-alkyl, unsubstituted C$_{1-6}$-alkyl, F, Cl, Br, I, CF$_3$, OCF$_3$, OH and SH.

20. A compound as claimed in claim 1, wherein
R$^6$, R$^7$ and R$^8$ each independently denote H, halogen, C$_{1-6}$-alkyl, —N(C$_{1-6}$-alkyl)$_2$, —C$_{1-6}$-alkylene-N(C$_{1-6}$-alkyl)$_2$, 5-, 6- or 7-membered heterocyclyl group, 5- or 6-membered heteroaryl group, or a 5- or 6-membered heteroaryl group or 5-, 6- or 7-membered heterocyclyl group bonded via a C$_{1-6}$-alkylene group;
wherein heterocyclyl comprises 1 or 2 identical or different heteroatoms selected from the group consisting of N and O and may be unsubstituted or monosubstituted or polysubstituted with C$_{1-6}$-alkyl.

21. A compound as claimed in claim 1, selected from the group consisting of:
2-((1-(4-methoxy-2,6-dimethylphenylsulfonyl)piperidin-2-yl)methoxy)-1-(6-((4-methylpiperazin-1-yl)methyl)-3,4-dihydropyrrolo[1,2-a]pyrazin-2(1H)-yl)ethanone;
3-(1-(4-chloro-2,5-dimethylphenylsulfonyl)piperidin-2-yl)-1-(6-((4-methyl-piperazin-1-yl)methyl)-3,4-dihydropyrrolo[1,2-a]pyrazin-2(1H)-yl)propan-1-one;
2-((1-(4-methoxy-2,6-dimethylphenylsulfonyl)piperidin-2-yl)methoxy)-1-(6-(morpholinomethyl)-3,4-dihydropyrrolo[1,2-a]pyrazin-2(1H)-yl)ethanone;
1-(6-((4-methylpiperazin-1-yl)methyl)-3,4-dihydropyrrolo[1,2-a]pyrazin-2(1H)-yl)-2-(1-(3-(trifluoromethyl)phenylsulfonyl)piperidin-2-yl)ethanone;
1-(6-(pyrrolidin-1-ylmethyl)-3,4-dihydropyrrolo[1,2-a]pyrazin-2(1H)-yl)-2-(1-(3-(trifluoromethyl)phenylsulfonyl)piperidin-2-yl)ethanone;
3-(1-(4-chloro-2,5-dimethylphenylsulfonyl)piperidin-2-yl)-1-(6-(pyrrolidin-1-ylmethyl)-3,4-dihydropyrrolo[1,2-a]pyrazin-2(1H)-yl)propan-1-one;
2-((1-(3,4-dichlorophenylsulfonyl)-1,2,3,4-tetrahydroquinolin-2-yl)methoxy)-1-(6-(pyrrolidin-1-ylmethyl)-3,4-dihydropyrrolo[1,2-a]pyrazin-2(1H)-yl)ethanone;
2-((1-(3,4-dichlorophenylsulfonyl)-1,2,3,4-tetrahydroquinolin-2-yl)methoxy)-1-(6-((4-methylpiperazin-1-yl)methyl)-3,4-dihydropyrrolo[1,2-a]pyrazin-2(1H)-yl)ethanone;
3-(1-(4-chloro-2,5-dimethylphenylsulfonyl)piperidin-2-yl)-1-(6-(morpholino-methyl)-3,4-dihydropyrrolo[1,2-a]pyrazin-2(1H)-yl)propan-1-one;
2-((1-(4-methoxy-2,6-dimethylphenylsulfonyl)piperidin-2-yl)methoxy)-1-(6-(pyrrolidin-1-ylmethyl)-3,4-dihydropyrrolo[1,2-a]pyrazin-2(1H)-yl)ethanone;
2-((1-(4-methoxy-2,6-dimethylphenylsulfonyl)piperidin-2-yl)methoxy)-1-(6-(3-(4-methylpiperazin-1-yl)propyl)-3,4-dihydropyrrolo[1,2-a]pyrazin-2(1H)-yl)ethanone;
1-(6-(3-(4-methylpiperazin-1-yl)propyl)-3,4-dihydropyrrolo[1,2-a]pyrazin-2(1H)-yl)-2-(1-(3-(trifluoromethyl)phenylsulfonyl)piperidin-2-yl)ethanone;

2-((1-(3,4-dichlorophenylsulfonyl)-1,2,3,4-tetrahydro-quinolin-2-yl)methoxy)-1-(6-(3-(4-methylpiperazin-1-yl)propyl)-3,4-dihydropyrrolo[1,2-a]pyrazin-2(1H)-yl)ethanone;

1-(6-(3-(pyrrolidin-1-yl)propyl)-3,4-dihydropyrrolo[1,2-a]pyrazin-2(1H)-yl)-2-(1-(3-(trifluoromethyl)phenyl-sulfonyl)piperidin-2-yl)ethanone;

3-(1-(4-chloro-2,5-dimethylphenylsulfonyl)piperidin-2-yl)-1-(6-(3-(pyrrolidin-1-yl)propyl)-3,4-dihydropyrrolo[1,2-a]pyrazin-2(1H)-yl)propan-1-one;

1-(1-tert-butyl-3,4-dihydropyrrolo[1,2-a]pyrazin-2(1H)-yl)-2-((1-(4-methoxy-2,6-dimethyl-phenylsulfonyl)piperidin-2-yl)methoxy)ethanone;

2-((1-(4-methoxy-2,6-dimethylphenylsulfonyl)piperidin-2-yl)methoxy)-1-(1-methyl-3,4-dihydropyrrolo[1,2-a]pyrazin-2(1H)-yl)ethanone;

2-((1-(4-methoxy-2,6-dimethylphenylsulfonyl)piperidin-2-yl)methoxy)-1-(1-(pyridin-3-yl)-3,4-dihydropyrrolo[1,2-a]pyrazin-2(1H)-yl)ethanone;

1-(1-(6-chloropyridin-3-yl)-3,4-dihydropyrrolo[1,2-a]pyrazin-2(1H)-yl)-2-((1-(4-methoxy-2,6-dimethyl phenylsulfonyl)piperidin-2-yl)methoxy)ethanone;

2-((1-(4-methoxy-2,6-dimethylphenylsulfonyl)piperidin-2-yl)methoxy)-1-(1-(4-methoxyphenyl)-3,4-dihydropyrrolo[1,2-a]pyrazin-2(1H)-yl)ethanone;

2-((1-(4-methoxy-2,6-dimethylphenylsulfonyl)piperidin-2-yl)methoxy)-1-(1-phenyl-3,4-dihydropyrrolo[1,2-a]pyrazin-2(1H)-yl)ethanone;

1-(1-(3,4-difluorophenyl)-3,4-dihydropyrrolo[1,2-a]pyrazin-2(1H)-yl)-2-((1-(4-methoxy-2,6-dimethyl phenylsulfonyl)piperidin-2-yl)methoxy)ethanone;

1-(1-(3,4-dimethylphenyl)-3,4-dihydropyrrolo[1,2-a]pyrazin-2(1H)-yl)-2-((1-(4-methoxy-2,6-dimethyl phenylsulfonyl)piperidin-2-yl)methoxy)ethanone;

1-(1-(3-fluorophenyl)-3,4-dihydropyrrolo[1,2-a]pyrazin-2(1H)-yl)-2-((1-(4-methoxy-2,6-dimethylphenylsulfonyl)piperidin-2-yl)methoxy)ethanone;

2-((1-(4-methoxy-2,6-dimethylphenylsulfonyl)piperidin-2-yl)methoxy)-1-(1-(thiophen-2-yl)-3,4-dihydropyrrolo[1,2-a]pyrazin-2(1H)-yl)ethanone;

2-((1-(4-methoxy-2,6-dimethylphenylsulfonyl)piperidin-2-yl)methoxy)-1-(1-(3-(trifluoromethyl)phenyl)-3,4-dihydropyrrolo[1,2-a]pyrazin-2(1H)-yl)ethanone;

2-((1-(4-methoxy-2,6-dimethylphenylsulfonyl)piperidin-2-yl)methoxy)-1-(1-(3-methoxyphenyl)-3,4-dihydropyrrolo[1,2-a]pyrazin-2(1H)-yl)ethanone;

1-(1-(2-fluoro-4-(trifluoromethyl)phenyl)-3,4-dihydropyrrolo[1,2-a]pyrazin-2(1H)-yl)-2-((1-(4-methoxy-2,6-dimethylphenylsulfonyl)piperidin-2-yl)methoxy)ethanone;

1-(1-tert-butyl-3,4-dihydropyrrolo[1,2-a]pyrazin-2(1H)-yl)-2-((1-(mesitylsulfonyl)piperidin-2-yl)methoxy)ethanone;

2-((1-(mesitylsulfonyl)piperidin-2-yl)methoxy)-1-(1-methyl-3,4-dihydropyrrolo[1,2-a]pyrazin-2(1H)-yl)ethanone;

2-((1-(mesitylsulfonyl)piperidin-2-yl)methoxy)-1-(1-(pyridin-3-yl)-3,4-dehydro-pyrrolo[1,2-a]pyrazin-2(1H)-yl)ethanone;

1-(1-(6-chloropyridin-3-yl)-3,4-dihydropyrrolo[1,2-a]pyrazin-2(1H)-yl)-2-((1-(mesitylsulfonyl)piperidin-2-yl)methoxy)ethanone;

2-((1-(mesitylsulfonyl)piperidin-2-yl)methoxy)-1-(4-methoxyphenyl)-3,4-dihydropyrrolo[1,2-a]pyrazin-2(1H)-yl)ethanone;

2-((1-(mesitylsulfonyl)piperidin-2-yl)methoxy)-1-(1-phenyl-3,4-dihydropyrrolo[1,2-a]pyrazin-2(1H)-yl)ethanone;

1-(1-(3,4-difluorophenyl)-3,4-dihydropyrrolo[1,2-a]pyrazin-2(1H)-yl)-2-((1-(mesitylsulfonyl)piperidin-2-yl)methoxy)ethanone;

1-(1-(3,4-dimethylphenyl)-3,4-dihydropyrrolo[1,2-a]pyrazin-2(1H)-yl)-2-((1-(mesitylsulfonyl)piperidin-2-yl)methoxy)ethanone;

1-(1-(3-fluorophenyl)-3,4-dihydropyrrolo[1,2-a]pyrazin-2(1H)-yl)-2-((1-(mesitylsulfonyl)piperidin-2-yl)methoxy)ethanone;

2-((1-(mesitylsulfonyl)piperidin-2-yl)methoxy)-1-(1-(thiophen-2-yl)-3,4-dihydropyrrolo[1,2-a]pyrazin-2(1H)-yl)ethanone;

2-((1-(mesitylsulfonyl)piperidin-2-yl)methoxy)-1-(1-(3-(trifluoromethyl)phenyl)-3,4-dihydropyrrolo[1,2-a]pyrazin-2(1H)-yl)ethanone;

2-((1-(mesitylsulfonyl)piperidin-2-yl)methoxy)-1-(1-phenethyl-3,4-dihydro-pyrrolo[1,2-a]pyrazin-2(1H)-yl)ethanone;

1-(6-((dimethylamino)methyl)-1-phenyl-3,4-dihydropyrrolo[1,2-a]pyrazin-2(1H)-yl)-2-((1-(mesitylsulfonyl)piperidin-2-yl)methoxy)ethanone;

2-((1-(mesitylsulfonyl)piperidin-2-yl)methoxy)-1-(1-phenyl-6-(pyrrolidin-1-yl-methyl)-3,4-dihydropyrrolo[1,2-a]pyrazin-2(1H)-yl)ethanone;

2-((1-(mesitylsulfonyl)piperidin-2-yl)methoxy)-1-(1-phenyl-6-(piperidin-1-yl-methyl)-3,4-dihydropyrrolo[1,2-a]pyrazin-2(1H)-yl)ethanone;

2-((1-(mesitylsulfonyl)piperidin-2-yl)methoxy)-1-(6-(morpholinomethyl)-1-phenyl-3,4-dihydropyrrolo[1,2-a]pyrazin-2(1H)-yl)ethanone;

1-(1-benzyl-6-((dimethylamino)methyl)-3,4-dihydropyrrolo[1,2-a]pyrazin-2(1H)-yl)-2-((1-(mesitylsulfonyl)piperidin-2-yl)methoxy)ethanone;

1-(6-((dimethylamino)methyl)-1-phenethyl-3,4-dihydropyrrolo[1,2-a]pyrazin-2(1H)-yl)-2-((1-(mesitylsulfonyl)piperidin-2-yl)methoxy)ethanone;

1-(1-butyl-6-((dimethylamino)methyl)-3,4-dihydropyrrolo[1,2-a]pyrazin-2(1H)-yl)-2-((1-(mesitylsulfonyl)piperidin-2-yl)methoxy)ethanone;

1-(6-((dimethylamino)methyl)-1-(thiophen-2-yl)-3,4-dihydropyrrolo[1,2-a]pyrazin-2(1H)-yl)-2-((1-(mesitylsulfonyl)piperidin-2-yl)methoxy)ethanone;

1-(6-((dimethylamino)methyl)-1-ethyl-3,4-dihydropyrrolo[1,2-a]pyrazin-2(1H)-yl)-2-((1-(mesitylsulfonyl)piperidin-2-yl)methoxy)ethanone;

1-(1-ethyl-3,4-dihydropyrrolo[1,2-a]pyrazin-2(1H)-yl)-2-((1-(mesitylsulfonyl)piperidin-2-yl)methoxy)ethanone;

2-((1-(mesitylsulfonyl)piperidin-2-yl)methoxy)-1-(1-propyl-3,4-dihydropyrrolo[1,2-a]pyrazin-2(1H)-yl)ethanone;

1-(1-isopropyl-3,4-dihydropyrrolo[1,2-a]pyrazin-2(1H)-yl)-2-((1-(mesitylsulfonyl)piperidin-2-yl)methoxy)ethanone;

1-(1-ethyl-6-methyl-3,4-dihydropyrrolo[1,2-a]pyrazin-2(1H)-yl)-2-((1-(mesitylsulfonyl)piperidin-2-yl)methoxy)ethanone;

1-(1-isopropyl-6-methyl-3,4-dihydropyrrolo[1,2-a]pyrazin-2(1H)-yl)-2-((1-(mesitylsulfonyl)piperidin-2-yl)methoxy)ethanone;

2-((1-(4-methoxy-2,6-dimethylphenylsulfonyl)piperidin-2-yl)methoxy)-1-(1-phenethyl-3,4-dihydropyrrolo[1,2-a]pyrazin-2(1H)-yl)ethanone;

1-(6-((dimethylamino)methyl)-1-phenyl-3,4-dihydropyrrolo[1,2-a]pyrazin-2(1H)-yl)-2-((1-(4-methoxy-2,6-dimethylphenylsulfonyl)piperidin-2-yl)methoxy)ethanone;

2-((1-(4-methoxy-2,6-dimethylphenylsulfonyl)piperidin-2-yl)methoxy)-1-(1-phenyl-6-(pyrrolidin-1-ylmethyl)-3,4-dihydropyrrolo[1,2-a]pyrazin-2(1H)-yl)ethanone;

2-((1-(4-methoxy-2,6-dimethylphenylsulfonyl)piperidin-2-yl)methoxy)-1-(1-phenyl-6-(piperidin-1-ylmethyl)-3,4-dihydropyrrolo[1,2-a]pyrazin-2(1H)-yl)ethanone;

2-((1-(4-methoxy-2,6-dimethylphenylsulfonyl)piperidin-2-yl)methoxy)-1-(6-(morpholinomethyl)-1-phenyl-3,4-dihydropyrrolo[1,2-a]pyrazin-2(1H)-yl)ethanone;

1-(1-benzyl-6-((dimethylamino)methyl)-3,4-dihydropyrrolo[1,2-a]pyrazin-2(1H)-yl)-2-((1-(4-methoxy-2,6-dimethylphenylsulfonyl)piperidin-2-yl)methoxy)ethanone;

1-(6-((dimethylamino)methyl)-1-phenethyl-3,4-dihydropyrrolo[1,2-a]pyrazin-2(1H)-yl)-2-((1-(4-methoxy-2,6-dimethylphenylsulfonyl)piperidin-2-yl)methoxy)ethanone;

1-(1-butyl-6-((dimethylamino)methyl)-3,4-dihydropyrrolo[1,2-a]pyrazin-2(1H)-yl)-2-((1-(4-methoxy-2,6-dimethylphenylsulfonyl)piperidin-2-yl)methoxy)ethanone;

1-(6-((dimethylamino)methyl)-1-(thiophen-2-yl)-3,4-dihydropyrrolo[1,2-a]pyrazin-2(1H)-yl)-2-((1-(4-methoxy-2,6-dimethylphenylsulfonyl)piperidin-2-yl)methoxy)ethanone;

1-(6-((dimethylamino)methyl)-1-ethyl-3,4-dihydropyrrolo[1,2-a]pyrazin-2(1H)-yl)-2-((1-(4-methoxy-2,6-dimethylphenylsulfonyl)piperidin-2-yl)methoxy)ethanone;

1-(1-ethyl-3,4-dihydropyrrolo[1,2-a]pyrazin-2(1H)-yl)-2-((1-(4-methoxy-2,6-dimethylphenylsulfonyl)piperidin-2-yl)methoxy)ethanone;

2-((1-(4-methoxy-2,6-dimethylphenylsulfonyl)piperidin-2-yl)methoxy)-1-(1-propyl-3,4-dihydropyrrolo[1,2-a]pyrazin-2(1H)-yl)ethanone;

1-(1-isopropyl-3,4-dihydropyrrolo[1,2-a]pyrazin-2(1H)-yl)-2-((1-(4-methoxy-2,6-dimethylphenylsulfonyl)piperidin-2-yl)methoxy)ethanone;

2-((1-(4-methoxy-2,6-dimethylphenylsulfonyl)piperidin-2-yl)methoxy)-1-(6-(2-(4-methylpiperazin-1-yl)ethyl)-3,4-dihydropyrrolo[1,2-a]pyrazin-2(1H)-yl)ethanone;

1-(6-(2-(4-methylpiperazin-1-yl)ethyl)-3,4-dihydropyrrolo[1,2-a]pyrazin-2(1H)-yl)-2-(1-(3-(trifluoromethyl)phenylsulfonyl)piperidin-2-yl)ethanone;

1-(6-(2-morpholinoethyl)-3,4-dihydropyrrolo[1,2-a]pyrazin-2(1H)-yl)-2-(1-(3-(trifluoromethyl)phenylsulfonyl)piperidin-2-yl)ethanone;

3-(1-(4-chloro-2,5-dimethylphenylsulfonyl)piperidin-2-yl)-1-(6-(2-morpholinoethyl)-3,4-dihydropyrrolo[1,2-a]pyrazin-2(1H)-yl)propan-1-one;

2-((1-(3,4-dichlorophenylsulfonyl)-1,2,3,4-tetrahydroquinolin-2-yl)methoxy)-1-(6-(2-morpholinoethyl)-3,4-dihydropyrrolo[1,2-a]pyrazin-2(1H)-yl)ethanone;

3-(1-(4-chloro-2,5-dimethylphenylsulfonyl)piperidin-2-yl)-1-(6-(2-(pyrrolidin-1-yl)ethyl)-3,4-dihydropyrrolo[1,2-a]pyrazin-2(1H)-yl)propan-1-one;

2-((1-(4-methoxy-2,6-dimethylphenylsulfonyl)piperidin-2-yl)methoxy)-1-(6-(2-(pyrrolidin-1-yl)ethyl)-3,4-dihydropyrrolo[1,2-a]pyrazin-2(1H)-yl)ethanone;

1-(6-(2-(pyrrolidin-1-yl)ethyl)-3,4-dihydropyrrolo[1,2-a]pyrazin-2(1H)-yl)-2-(1-(3-(trifluoromethyl)phenylsulfonyl)piperidin-2-yl)ethanone;

2-((1-(3,4-dichlorophenylsulfonyl)-1,2,3,4-tetrahydroquinolin-2-yl)methoxy)-1-(6-(2-(pyrrolidin-1-yl)ethyl)-3,4-dihydropyrrolo[1,2-a]pyrazin-2(1H)-yl)ethanone;

3-(1-(4-chloro-2,5-dimethylphenylsulfonyl)piperidin-2-yl)-1-(6-(2-(4-methylpiperazin-1-yl)ethyl)-3,4-dihydropyrrolo[1,2-a]pyrazin-2(1H)-yl)propan-1-one;

2-((1-(4-methoxy-2,6-dimethylphenylsulfonyl)piperidin-2-yl)methoxy)-1-(6-(2-morpholinoethyl)-3,4-dihydropyrrolo[1,2-a]pyrazin-2(1H)-yl)ethanone;

1-(1-ethyl-3,4-dihydropyrrolo[1,2-a]pyrazin-2(1H)-yl)-3-(1-(4-methoxy-2,6-dimethylphenylsulfonyl)piperidin-2-yl)propan-1-one;

1-(1-ethyl-3,4-dihydropyrrolo[1,2-a]pyrazin-2(1H)-yl)-2-(((S)-1-(4-methoxy-2,6-dimethylphenylsulfonyl)piperidin-2-yl)methoxy)ethanone;

2-((1-(4-Methoxy-2,6-dimethylphenylsulfonyl)piperidin-2-yl)methoxy)-1-(6-(pyridin-4-ylmethyl)-3,4-dihydropyrrolo[1,2-a]pyrazin-2(1H)-yl)ethanone;

2-((1-(4-Methoxy-2,6-dimethylphenylsulfonyl)piperidin-2-yl)methoxy)-1-(6-(pyridin-3-yl)-3,4-dihydropyrrolo[1,2-a]pyrazin-2(1H)-yl)ethanone;

1-(6-(Pyridin-4-ylmethyl)-3,4-dihydropyrrolo[1,2-a]pyrazin-2(1H)-yl)-2-(1-(3-(trifluoromethyl)phenylsulfonyl)piperidin-2-yl)ethanone;

4-(1-(4-Methoxy-2,6-dimethylphenylsulfonyl)piperidin-2-yl)-1-(6-(pyridin-4-ylmethyl)-3,4-dihydropyrrolo[1,2-a]pyrazin-2(1H)-yl)butan-1-one;

4-(1-(4-Methoxy-2,6-dimethylphenylsulfonyl)piperidin-2-yl)-1-(6-(pyridin-3-yl)-3,4-dihydropyrrolo[1,2-a]pyrazin-2(1H)-yl)butan-1-one;

1-(6-(Pyridin-3-yl)-3,4-dihydropyrrolo[1,2-a]pyrazin-2(1H)-yl)-2-(1-(3-(trifluoromethyl)phenylsulfonyl)piperidin-2-yl)ethanone;

3-(1-(4-Methoxy-2,6-dimethylphenylsulfonyl)piperidin-2-yl)-1-(6-(pyridin-3-yl)-3,4-dihydropyrrolo[1,2-a]pyrazin-2(1H)-yl)propan-1-one;

2-((1-(4-Methoxy-2,6-dimethylphenylsulfonyl)piperidin-2-yl)methoxy)-1-(6-(pyridin-4-yl)-3,4-dihydropyrrolo[1,2-a]pyrazin-2(1H)-yl)ethanone;

3-(1-(4-Methoxy-2,6-dimethylphenylsulfonyl)piperidin-2-yl)-1-(6-(pyridin-4-yl)-3,4-dihydropyrrolo[1,2-a]pyrazin-2(1H)-yl)propan-1-one;

1-(6-(Pyridin-3-ylmethyl)-3,4-dihydropyrrolo[1,2-a]pyrazin-2(1H)-yl)-2-(1-(3-(trifluoromethyl)phenylsulfonyl)piperidin-2-yl)ethanone;

1-(6-(2-(Pyridin-3-yl)ethyl)-3,4-dihydropyrrolo[1,2-a]pyrazin-2(1H)-yl)-2-(1-(3-(trifluoromethyl)phenylsulfonyl)piperidin-2-yl)ethanone;

3-(1-(4-Methoxy-2,6-dimethylphenylsulfonyl)piperidin-2-yl)-1-(6-(pyridin-4-ylmethyl)-3,4-dihydropyrrolo[1,2-a]pyrazin-2(1H)-yl)propan-1-one;

2-((1-(4-Methoxy-2,6-dimethylphenylsulfonyl)piperidin-2-yl)methoxy)-1-(6-(2-(pyridin-3-yl)ethyl)-3,4-dihydropyrrolo[1,2-a]pyrazin-2(1H)-yl)ethanone;

3-(1-(4-Methoxy-2,6-dimethylphenylsulfonyl)piperidin-2-yl)-1-(6-(2-(pyridin-3-yl)ethyl)-3,4-dihydropyrrolo[1,2-a]pyrazin-2(1H)-yl)propan-1-one;

4-(1-(4-Methoxy-2,6-dimethylphenylsulfonyl)piperidin-2-yl)-1-(6-(2-(pyridin-3-yl)ethyl)-3,4-dihydropyrrolo[1,2-a]pyrazin-2(1H)-yl)butan-1-one;

4-(1-(4-Methoxy-2,6-dimethylphenylsulfonyl)piperidin-2-yl)-1-(6-(pyridin-3-ylmethyl)-3,4-dihydropyrrolo[1,2-a]pyrazin-2(1H)-yl)butan-1-one;

2-((1-(4-Methoxy-2,6-dimethylphenylsulfonyl)piperidin-2-yl)methoxy)-1-(6-(2-(pyridin-4-yl)ethyl)-3,4-dihydropyrrolo[1,2-a]pyrazin-2(1H)-yl)ethanone;

1-(6-(2-(Pyridin-4-yl)ethyl)-3,4-dihydropyrrolo[1,2-a]
pyrazin-2(1H)-yl)-2-(1-(3-(trifluoromethyl)phenylsulfonyl)piperidin-2-yl)ethanone;

3-(1-(4-Methoxy-2,6-dimethylphenylsulfonyl)piperidin-2-yl)-1-(6-(2-(pyridin-4-yl)ethyl)-3,4-dihydropyrrolo[1,2-a]pyrazin-2(1H)-yl)propan-1-one;

4-(1-(4-Methoxy-2,6-dimethylphenylsulfonyl)piperidin-2-yl)-1-(6-(2-(pyridin-4-yl)ethyl)-3,4-dihydropyrrolo[1,2-a]pyrazin-2(1H)-yl)butan-1-one;

4-(1-(4-Methoxy-2,6-dimethylphenylsulfonyl)piperidin-2-yl)-1-(6-(pyridin-4-yl)-3,4-dihydropyrrolo[1,2-a]pyrazin-2(1H)-yl)butan-1-one;

2-((1-(4-Methoxy-2,6-dimethylphenylsulfonyl)piperidin-2-yl)methoxy)-1-(6-(pyridin-3-ylmethyl)-3,4-dihydropyrrolo[1,2-a]pyrazin-2(1H)-yl)ethanone;

3-(1-(4-Methoxy-2,6-dimethylphenylsulfonyl)piperidin-2-yl)-1-(6-(pyridin-3-ylmethyl)-3,4-dihydropyrrolo[1,2-a]pyrazin-2(1H)-yl)propan-1-one;

and physiologically compatible salts thereof.

22. A pharmaceutical composition comprising a compound as claimed in claim 1, and at least one pharmaceutically acceptable carrier or at least one auxiliary substance selected from the group consisting of fillers, solvents, diluents, coloring agents and binders.

23. A method of treating or inhibiting pain mediated via a bradykinin 1 receptor in a subject, said method comprising administering to said subject a pharmacologically effective amount of a compound as claimed in claim 1.

24. A method as claimed in claim 23, wherein said pain is selected from the group consisting of acute pain, neuropathic pain, and chronic pain.

25. A method of treating or inhibiting a condition selected from the group consisting of migraine, bronchial asthma, allergies, chronic obstructive pulmonary disease, ulcerative colitis, Crohn's disease, epilepsy, anxiety, atopic dermatitis, psoriasis, M. Behcet's syndrome, pelvitis and prostatitis, in a subject in need thereof, said method comprising administering to said subject a pharmacologically effective amount of a compound as claimed in claim 1.

26. A process for the preparation of a compound as claimed in claim 7, said process comprising reacting a carboxylic acid of formula L with an amine of formula M according to the following reaction scheme:

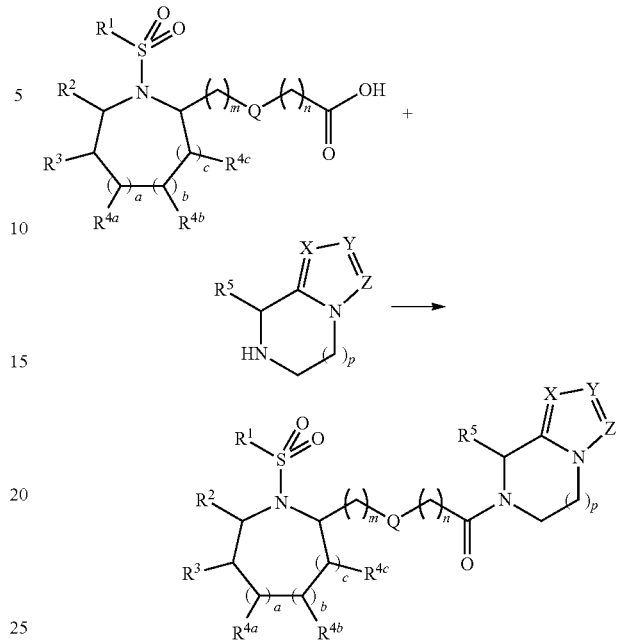

in the presence of a water removing agent, a reagent selected from the group consisting of 1,1'-carbonyl diimidazole, optionally polymer-bound dicyclohexylcarbodiimide, O-benzotriazole-1-yl-1,1,3,3-tetramethyluronium tetrafluoroborate, N-ethyl-N'-(3-dimethylaminopropyl)carbodiimide hydrochloride, benzotriazole-1-yl-oxy-tris-pyrrolidino-phosphonium hexafluorophosphate and pentafluoropropionic-trifluoroacetic acid; 1-hydroxy-7-azabenzotriazole or 1-hydroxy-benzotriazole; and an organic base; and in an organic solvent, at a temperature from 0° C. to reflux temperature, to yield an amide compound corresponding to formula N; wherein a, b, c, m, n, p, $R^1$, $R^2$, $R^3$, $R^{4a}$, $R^{4b}$, $R^{4c}$, $R^5$, X, Y and Z have the respective meanings given in claim 7.

27. A process as claimed in claim 26, wherein said water-removing agent is sodium sulfate, magnesium sulfate, or phosphorus oxide; said organic base is diisopropylethylamine or pyridine; and said organic solvent is selected from the group consisting of tetrahydrofuran, dichloromethane, diethyl ether, dioxane, dimethylformamide and acetonitrile.

* * * * *